US010711062B2

(12) United States Patent
Culp et al.

(10) Patent No.: US 10,711,062 B2
(45) Date of Patent: Jul. 14, 2020

(54) ANTI-CD33 ANTIBODIES AND METHODS OF USE THEREOF

(71) Applicant: ALECTOR LLC, South San Francisco, CA (US)

(72) Inventors: Patricia Culp, Oakland, CA (US); Helen Lam, Union City, CA (US); Arnon Rosenthal, Woodside, CA (US); Seung-Joo Lee, Benicia, CA (US); Nels P. Nielson, Hopkinton, NH (US); Robert Pejchal, Norwich, VT (US)

(73) Assignee: ALECTOR LLC, South San Francisco, CA (US)

( * ) Notice: Subject to any disclaimer, the term of this patent is extended or adjusted under 35 U.S.C. 154(b) by 0 days.

(21) Appl. No.: 16/054,840

(22) Filed: Aug. 3, 2018

(65) Prior Publication Data
US 2019/0040131 A1    Feb. 7, 2019

Related U.S. Application Data

(60) Provisional application No. 62/667,388, filed on May 4, 2018, provisional application No. 62/541,024, filed on Aug. 3, 2017.

(51) Int. Cl.
C07K 16/28 (2006.01)
C07K 16/46 (2006.01)
A61K 39/00 (2006.01)

(52) U.S. Cl.
CPC ........ C07K 16/2803 (2013.01); C07K 16/468 (2013.01); A61K 2039/505 (2013.01); C07K 2317/24 (2013.01); C07K 2317/31 (2013.01); C07K 2317/732 (2013.01); C07K 2317/734 (2013.01); C07K 2317/76 (2013.01); C07K 2317/77 (2013.01); C07K 2317/92 (2013.01)

(58) Field of Classification Search
CPC .............. C07K 16/2803; C07K 16/468; C07K 2317/24; C07K 2317/31; C07K 2317/56; C07K 2317/565; C07K 2317/732; C07K 2317/734; C07K 2317/76; C07K 2317/77; C07K 2317/92; A61K 2039/505
See application file for complete search history.

(56) References Cited

U.S. PATENT DOCUMENTS

| | | |
|---|---|---|
| 4,469,863 A | 9/1984 | Ts'o et al. |
| 4,657,760 A | 4/1987 | Kung et al. |
| 4,676,980 A | 6/1987 | Segal et al. |
| 4,816,567 A | 3/1989 | Cabilly et al. |
| 5,206,344 A | 4/1993 | Katre et al. |
| 5,225,212 A | 7/1993 | Martin et al. |
| 5,229,275 A | 7/1993 | Goroff et al. |
| 5,536,821 A | 7/1996 | Agrawal et al. |
| 5,541,306 A | 7/1996 | Agrawal et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,825 A | 10/1996 | Lonberg et al. |
| 5,571,894 A | 11/1996 | Wels et al. |
| 5,573,905 A | 11/1996 | Lerner et al. |
| 5,587,458 A | 12/1996 | King et al. |
| 5,591,669 A | 1/1997 | Krimpenfort et al. |
| 5,614,622 A | 3/1997 | Iyer et al. |
| 5,625,126 A | 4/1997 | Lonberg et al. |
| 5,633,425 A | 5/1997 | Lonberg et al. |
| 5,637,683 A | 6/1997 | Usher et al. |
| 5,637,684 A | 6/1997 | Cook et al. |
| 5,641,870 A | 6/1997 | Rinderknecht et al. |
| 5,648,237 A | 7/1997 | Carter et al. |
| 5,661,016 A | 8/1997 | Lonberg et al. |
| 5,700,922 A | 12/1997 | Cook |
| 5,717,083 A | 2/1998 | Cook et al. |
| 5,719,262 A | 2/1998 | Buchardt et al. |
| 5,730,982 A | 3/1998 | Scheinberg |
| 5,731,168 A | 3/1998 | Carter et al. |
| 5,739,277 A | 4/1998 | Presta et al. |
| 5,739,308 A | 4/1998 | Kandimalla et al. |
| 5,739,314 A | 4/1998 | Roy et al. |
| 5,773,601 A | 6/1998 | Agrawal |
| 5,789,199 A | 8/1998 | Joly et al. |
| 5,840,523 A | 11/1998 | Simmons et al. |

(Continued)

FOREIGN PATENT DOCUMENTS

| | | |
|---|---|---|
| CN | 102952191 A | 3/2013 |
| EP | 0308936 B1 | 7/1994 |

(Continued)

OTHER PUBLICATIONS

Alegre, M.-L. et al. (Jun. 1, 1994). "A Non-Activating "Humanized" Anti-cd3 Monoclonal Antibody Retains Immunosuppressive Properties in Vivo," Transplantation 57(11):1537-1543.

Almagro, J.C. et al. (2008). "Humanization of Antibodies," Frontiers in Bio-Science 13:1619-1633.

Al-Shawi, R.et al. (2008). "Neurotoxic and Neurotrophic Roles of proNGF and the Receptor Sortilin in the Adult and Ageing Nervous System," European Journal of Neuroscience 27:2103-2114.

Angal, S. et al. (1993). "A Single Amino Acid Substitution Abolishes the Heterogeneity of Chimeric Mouse/Human (IgG4) Antibody," Molecular Immunology 30(1):105-108.

(Continued)

Primary Examiner — Kimberly Ballard
(74) Attorney, Agent, or Firm — Morrison & Foerster LLP

(57) ABSTRACT

The present disclosure is generally directed to compositions that include antibodies, e.g., monoclonal, chimeric, humanized antibodies, antibody fragments, etc., that specifically bind one or more epitopes within a CD33 protein, e.g., human CD33 or a mammalian CD33, and have improved and/or enhanced functional characteristics, and use of such compositions in preventing, reducing risk, or treating an individual in need thereof.

77 Claims, 10 Drawing Sheets
Specification includes a Sequence Listing.

(56) References Cited

U.S. PATENT DOCUMENTS

| | | | |
|---|---|---|---|
| 5,869,046 A | 2/1999 | Presta et al. | |
| 5,886,165 A | 3/1999 | Kandimalla et al. | |
| 5,929,226 A | 7/1999 | Padmapriya et al. | |
| 5,955,599 A | 9/1999 | Iyer et al. | |
| 5,959,177 A | 9/1999 | Hein et al. | |
| 5,962,674 A | 10/1999 | Iyer et al. | |
| 5,977,296 A | 11/1999 | Nielsen et al. | |
| 6,040,498 A | 3/2000 | Stomp et al. | |
| 6,075,181 A | 6/2000 | Kucherlapati et al. | |
| 6,117,992 A | 9/2000 | Iyer | |
| 6,140,482 A | 10/2000 | Iyer et al. | |
| 6,150,584 A | 11/2000 | Kucherlapati et al. | |
| 6,417,429 B1 | 7/2002 | Hein et al. | |
| 6,420,548 B1 | 7/2002 | Vézina et al. | |
| 6,455,308 B1 | 9/2002 | Freier | |
| 6,982,321 B2 | 1/2006 | Winter | |
| 7,087,409 B2 | 8/2006 | Barbas, III et al. | |
| 7,125,978 B1 | 10/2006 | Vézina et al. | |
| 7,342,110 B2 | 3/2008 | Hoffee et al. | |
| 7,557,189 B2 | 7/2009 | Hoffee et al. | |
| 8,119,787 B2 | 2/2012 | Hoffee et al. | |
| 8,124,069 B2 | 2/2012 | Bae et al. | |
| 8,337,855 B2 | 12/2012 | Hoffee et al. | |
| 8,465,741 B2* | 6/2013 | Frey | C07K 16/2809 424/133.1 |
| 8,614,299 B2 | 12/2013 | Baurin et al. | |
| 9,028,830 B2* | 5/2015 | Tso | C07K 16/2866 424/172.1 |
| 9,725,515 B2* | 8/2017 | Anderson | A61K 45/06 |
| 9,845,363 B2* | 12/2017 | Pritsker | C07K 16/38 |
| 9,914,781 B1* | 3/2018 | Bhinder | C07K 16/2863 |
| 2007/0148167 A1 | 6/2007 | Strohl | |
| 2009/0181855 A1 | 7/2009 | Vasquez et al. | |
| 2010/0056386 A1 | 3/2010 | Vasquez et al. | |
| 2010/0280227 A1 | 11/2010 | Ambrose et al. | |
| 2012/0082670 A1 | 4/2012 | Konopitzky et al. | |
| 2013/0309223 A1 | 11/2013 | Sutherland et al. | |
| 2019/0002560 A1 | 1/2019 | Monroe et al. | |
| 2019/0085076 A1 | 3/2019 | Rosenthal et al. | |

FOREIGN PATENT DOCUMENTS

| | | |
|---|---|---|
| EP | 0404097 B1 | 9/1996 |
| WO | WO-1987/04462 A1 | 7/1987 |
| WO | WO-1991/00360 A1 | 1/1991 |
| WO | WO-1991/09058 A1 | 6/1991 |
| WO | WO-1991/10741 A1 | 7/1991 |
| WO | WO-1992/00373 A1 | 1/1992 |
| WO | WO-1993/08829 A1 | 5/1993 |
| WO | WO-1993/11161 A1 | 6/1993 |
| WO | WO-1993/16185 A2 | 8/1993 |
| WO | WO-1993/20848 A1 | 10/1993 |
| WO | WO-1994/04690 A1 | 3/1994 |
| WO | WO-1996/27011 A1 | 9/1996 |
| WO | WO-1996/33735 A1 | 10/1996 |
| WO | WO-1996/34096 A1 | 10/1996 |
| WO | WO-1997/11971 A1 | 4/1997 |
| WO | WO-1997/17852 A1 | 5/1997 |
| WO | WO-1998/24893 A2 | 6/1998 |
| WO | WO-1999/32619 A1 | 7/1999 |
| WO | WO-1999/58572 A1 | 11/1999 |
| WO | WO-2000/44895 A1 | 8/2000 |
| WO | WO-2000/56746 A2 | 9/2000 |
| WO | WO-2000/75372 A1 | 12/2000 |
| WO | WO-2001/14398 A1 | 3/2001 |
| WO | WO-2001/29058 A1 | 4/2001 |
| WO | WO-2001/36646 A1 | 5/2001 |
| WO | WO-2003/093298 A2 | 11/2003 |
| WO | WO-2004/042072 A2 | 5/2004 |
| WO | WO-2004/043344 A2 | 5/2004 |
| WO | WO-2007/014743 A2 | 2/2007 |
| WO | WO-2007/106585 A1 | 9/2007 |
| WO | WO-2008/058021 A2 | 5/2008 |
| WO | WO-2008/079246 A2 | 7/2008 |
| WO | WO-2009/036379 A2 | 3/2009 |
| WO | WO-2010/105256 A1 | 9/2010 |
| WO | WO-2011/036183 A2 | 3/2011 |
| WO | WO-2011/038301 A2 | 3/2011 |
| WO | WO-2012/009568 A2 | 1/2012 |
| WO | WO-2012/045752 A1 | 4/2012 |
| WO | WO-2012/074097 A1 | 6/2012 |
| WO | WO-2013/173496 A2 | 11/2013 |
| WO | WO-2016/201388 A2 | 12/2016 |
| WO | WO-2016/201388 A3 | 12/2016 |
| WO | WO-2016/201389 A2 | 12/2016 |
| WO | WO-2016/201389 A3 | 12/2016 |

OTHER PUBLICATIONS

Armour, K.L. et al. (1999). "Recombinant Human IgG Molecules Lacking FcGamma Receptor I Binding and Monocyte Triggering Activities," *Eur. J. Immunol.* 29:2613-2624.

Armour, K.L. et al. (2003). "Differential Binding to Human Fcγriia and Fcγriib Receptors by Human IgG Wildtype and Mutant Antibodies," *Molecular Immunology* 40:585-593.

Armour, K.L. et al. (Jun. 25-28, 2000). "Mutant IgG Lacking FcγRIII Binding and ADCC Activities," *The Haematology Journal*, poster Session 1, Presented at the 5th Annual Meeting of the European Haematology Association, Birmingham, UK, 1(Suppl. 1):27, 2 pages.

Arnett, M.G. et al. (Dec. 5, 2007; e-published on Oct. 26, 2007). "proNGF, Sortilin, and p75$^{NTR}$: Potential Mediators of Injury-Induced Apoptosis in the Mouse Dorsal Root Ganglion," *Brain Res.* 1183:32-42.

Asquith, D.L. et al. (2009). "Animal Models of Rheumatoid Arthritis," *Eur. J. Immunol.* 39:2040-2044.

Attrill, H. et al. (Oct. 27, 2006; e-published on Aug. 8, 2006). "Siglec-7 Undergoes a Major Conformational Change When Complexed with the α(2,8)-Disialylganglioside GT1b," *J. Biol. Chem.* 281:32774-32783.

Baca, M. et al. (1997). "Antibody Humanization Using Monovalent Phage Display," *The Journal of Biological Chemistry* 272(16):10678-10684.

Balaian, L. et al. (Dec. 2001). "Direct Effect of Bispecific Anti-CD33 X Anti-CD64 Antibody on Proliferation and Signaling in Myeloid Cells," *Leuk Res.* 25(12):1115-1125.

Barbas III, C.F. et al. (Apr. 1994). "In Vitro Evolution of a Neutralizing Human Antibody to Human Immunodeficiency Virus Type 1 to Enhance Affinity and Broaden Strain Cross-Reactivity," *Proc Nat. Acad. Sci. USA* 91:3809-3813.

Bartholomaeus et al. (2014). "Cell Contact-Dependent Priming and Fe Interaction with CD32+ Immune Cells Contribute to the TGN1412-Triggered Cytokine Response," *The Journal of Immunology* 192:2091-2098.

Beattie, M.S. et al. (Oct. 24, 2002). "ProNGF Induces p75-Mediated Death of Oligodendrocytes following Spinal Cord Injury," *Neuron* 36(3):375-386.

Bertram, L. et al. (Nov. 17, 2008). "Genome-wide Association Analysis Reveals Putative Alzheimer's Disease Susceptibility Loci in Addition to APOE," *Am. J. Hum. Genet.* 83(5):623-632.

Boerner, P. et al. (1991). "Production of Antigen-Specific Human Monoclonal Antibodies From In Vitro-Primed Human Splenocytes," *Journal of Immunology* 147(1):86-95.

Bolt, S. et al. (1993). "The Generation of a Humanized, Non-Mitogenic Cd3 Monoclonal Antibody Which Retains In Vitro Immunosuppressive Properties," *European Journal Immunol.* 23:403-411.

Bradshaw, E.M. et al. (Jul. 2013; e-published on May 23, 2013). "CD33 Alzheimer's Disease Locus: Altered Monocyte Function and Amyloid Biology," *Nat. Neurosci.* 16(7):848-850, fourteen pages.

Brehm, M.A. et al. (Apr. 2010). "Humanized Mouse Models to Study Human Diseases," *Curr Opin Endocrinol Diabetes Obes.* 17(2):120-125.

Brennan, M. et al. (Jul. 5, 1985). "Preparation of Bispecific Antibodies by Chemical Recombination of Monoclonal Immunoglobulin G1 Fragments," *Science* 229:81-83.

(56) References Cited

OTHER PUBLICATIONS

Brinkman-Van Der Linden, E.C.M. et al. (Jun. 2003). "CD33/Siglec-3 Binding Specificity, Expression Pattern, and Consequences of Gene Deletion in Mice," *Mol. Cell Biol.* 23(12):4199-4206.

Bross, P.F. et al. (Jun. 2001). "Approval Summary: Gemtuzumab Ozogamicin in Relapsed Acute Myeloid Leukemia," *Clinical Cancer Research* 7:1490-1496.

Bruggemann, M. et al. (1993). "Designer Mice: The Production of Human Antibody Repertoires in Transgenic Animals," *Year in Immunol.* 7:33-40.

Calligé, M. et al. (Jun. 2005). "CSN5/Jab1 is Involved in Ligand-Dependent Degradation of Estrogen Receptor α by the Proteasome," *Mol. Cell Biol.* 25(11):4349-4358.

Cantoni, C. et al. (Mar. 2015). "TREM2 Regulates Microglial Cell Activation in Response to Demyelination In Vivo," *Acta Neuropathol,* 129(3):429-447, thirty three pages.

Cao, X. et al. (Sep. 2011). "Macrophage Polarization in the Maculae of Age-Related Macular Degeneration: A Pilot Study," *Pathology International* 61(9):528-535, fourteen pages.

Capel, P.J.A. et al. (1994). "Heterogeneity of Human IgG Fc Receptors," *Immunomethods* 4:25-34.

Carter, P. et al. (Feb. 1992). "High Level *Escherichia coli* Expression and Production of a Bivalent Humanized Antibody Fragment," *Bio/technology* 10:163-167.

Carter, P. et al. (May 1992). "Humanization of an Anti-p185$^{HER2}$ Antibody for Human Cancer Therapy," *Proc. Natl. Acad. Sci. USA* 89:4285-4289.

Chang et al. (2002). "Retinal Degeneration Mutants in the Mouse," *Vision Research* 42:517-525.

Chothia, C. et al. (1987). "Canonical Structures for the Hypervariable Regions of Immunoglobulins," *J. Mol. Biol,* 196:901-917.

Chu, S.Y. et al. (2008, e-pub. Aug. 8, 2008). "Inhibition of B cell Receptor-Mediated Activation of Primary Human B Cells by Coengagement of CD19 and FcγRIIb with Fe-Engineered Antibodies," *Molecular Immunology* 45:3926-3933.

Clackson, T. et al. (1991). "Making Antibody Fragments Using Phage Display Libraries," *Nature* 352(15):624-628.

Cole, M.S. et al. (Aug. 27, 1999). "HuM291, A Humanized Anti-Cd3 Antibody is Immunosuppressive to T Cells While Exhibiting Reduced Mitogenicity in Vitro," *Transplantation* 68(4):563-571.

Compston, A. et al. (Oct. 25, 2008). "Multiple Sclerosis," *Lancet* 372(9648):1502-1517.

Correale, C. et al. (Feb. 2013). "Bacterial Sensor Triggering Receptor Expressed on Myeloid Cells-2 Regulates the Mucosal Inflammatory Response," *Gastroenterology* 144(2):346-356.

Crocker, P.R. et al. (Apr. 2007). "Siglecs and their Roles in the Immune System," *Nat Rev Immunol.* 7(4):255-266.

Crocker, P.R. et al. (Apr. 2012; e-published on Feb. 21, 2012). "CD33-related Siglecs as Potential Modulators of Inflammatory Responses," *Ann. NY Acad. Sci.* 1253:102-111.

Crocker, P.R. et al. (Jul. 1999). "Molecular Analysis of Sialoside Binding to Sialoadhesin by NMR and Site-Directed Mutagenesis," *Biochem J.* 341(Pt. 2):355-361.

Crocker, P. R. et al. (Jun. 1, 2001). "Siglecs, Sialic Acids and Innate Immunity," *Trends Immunol.* 22(6):337-342.

Cruts, M. et al. (2008, e-pub. Mar. 6, 2008). "Loss of Progranulin Function in Frontotemporal Lobar Degeneration," *Trends Genetics* 24(4):186-194.

Cunningham, B.C. et al. (Jun. 2, 1989). "High-Resolution Epitope Mapping of hGH-Receptor Interactions by Alanine-Scanning Mutagenesis," *Science* 244:1081-1085.

Daëron, M. (1997). "FC Receptor Biology," *Annu. Rev. Immunol.* 15:203-234.

Dall' Acqua, W.F. et al. (Aug. 18, 2006). "Properties of Human IgG1s Engineered for Enhanced Binding to the Neonatal Fc Receptor (FcRn)," *The Journal of Biological Chemistry* 281(33):23514-23524.

Daneman, R. et al. (Oct. 29, 2010). "The Mouse Blood-Brain Barrier Transcriptome: A New Resource for Understanding the Development and Function of Brain Endothelial Cells," *PLoS One* 5(10):e13741, sixteen pages.

Davis, P.M. et al. (2007). "Abatacept Binds to the Fc Receptor Cd64 But Does Not Mediate Complement-Dependent Cytotoxicity or Antibody-Dependent Cellular Cytotoxicity," *The Journal of Rheumatology* 34(11):2204-2210.

De Haas, M. et al. (1995). "Fcγ Receptors of Phagocytes," *J. Lab. Clin. Med.* 126(4):330-341.

Ducry, L. et al. (Jan. 2010; e-published on Sep. 21, 2009). "Antibody-Drug Conjugates: Linking Cytotoxic Payloads to Monoclonal Antibodies," *Bioconjugate Chemistry* 21(1):5-13.

Eksioglu, E.A. et al. (Jan. 1, 2014). "Novel Therapeutic Approach to Improve Hematopoiesis by Targeting Myeloid Derived Suppressor Cells with a Humanized Anti-CD33 Antibody," *Blood* 124(21):4597, located at < http://www.bloodjournal.org/content/124/21/4597>, last visited on Jan. 5, 2017, three pages.

El-Danaf, R.N. et al. (Feb. 11, 2015). "Characteristic Patterns of Dendritic Remodeling in Early-Stage Glaucoma: Evidence from Genetically Identified Retinal Ganglion Cell Types," *The Journal of Neuroscience* 35(6):2329-2343.

Estep, P. et al. (Mar.- Apr. 2013). "High Throughput Solution-Based Measurement of Antibody-Antigen Affinity and Epitope Binning," *mAbs.* 5(2):270-278.

Etemad, S. et al. (2012). "A Novel In Vitro Human Microglia Model: Characterization of Human Monocyte-Derived Microglia," *Journal of Neuroscience Methods* 209:79-89.

Fahnestock, M. et al. (2001). "The Precursor Pro-Nerve Growth Factor Is the Predominant Form of Nerve Growth Factor in Brain and Is Increased in Alzheimer's Disease," *Molecular and Cellular Neuroscience* 18:210-220.

Fan, Y.-J. (2008). "Differential effects of Pro-BDNF on Sensory Neurons after Sciatic Nerve Transection in Neonatal Rats," *European Journal of Neuroscience* 27:2380-2390.

Fasen, K. et al. (Feb. 2008; e-published on Dec. 19, 2007). "Ligand Binding Induces Cbl-Dependent EphB1 Receptor Degradation Through the Lysosomal Pathway," *Traffic* 9(2):251-266.

Feldhaus, M.J. et al. (2004, e-pub. May 31, 2004). "Yeast Display of Antibody Fragments: A Discovery and Characterization Platform," *Journal of Immunological Methods* 290:69-80.

Fellouse, F.A. et al. (Aug. 24, 2004). "Synthetic Antibodies from a Four-Amino-Acid Code: A Dominant Role for Tyrosine in Antigen Recognition," *PNAS* 101(34):12467-12472.

Ferlazzo, G. et al. (2000). "Engagement of CD33 Surface Molecules Prevents the Generation of Dendritic Cells From Both Monocytes and CD34$^+$ Myeloid Precursors," *Eur J Immunol.* 30:827-833.

Fishwild, D.M. et al. (Jul. 1996). "High-Avidity Human Iggk Monoclonal Antibodies from a Novel Strain of Minilocus Transgenic Mice," *Nature Biotechnology* 14:845-851.

Gabathuler, R. (2010, e-pub. Aug. 5, 2009). "Approaches to Transport Therapeutic Drugs across the Blood-Brain Barrier to Treat Brain Diseases," *Neurobiology of Disease* 37:48-57.

Gawish, R. et al. (Apr. 2015; e.pub Dec. 4, 2014). "Triggering Receptor Expressed on Myeloid cells-2 Fine-Tunes Inflammatory Responses in Murine Gram-Negative Sepsis," *The FASEB Journal* 29(4):1247-1257.

Gerngross, T.U. (Nov. 2004, e-pub. Nov. 4, 2004). "Advances in the Production of Human Therapeutic Proteins in Yeasts and Filamentous Fungi," *Nature Biotechnology* 22(11):1409-1414.

Graham, F.L. et al. (1977). "Characteristics of a Human Cell Line Transformed by DNA from Human Adenovirus Type 5," *Journal of General Virology* 36:59-72.

Griciuc, A. et al. (May 22, 2013; e-published on Apr. 25, 2013). "Alzheimer's Disease Risk Gene CD33 Inhibits Microglial Uptake of Amyloid Beta," *Neuron* 78(4):631-643.

Griffin, J.D. et al. (1984). "A Monoclonal Antibody Reactive with Normal and Leukemic Human Myeloid Progenitor Cells," *Leukemia Research* 8(4):521-534.

Griffiths, A.D. et al. (1993). "Human Anti-Self Antibodies with High Specificity from Phage Display Libraries," *The EMBO Journal* 12(2):725-734.

(56) References Cited

OTHER PUBLICATIONS

Grobe, K. et al. (May 1, 2002). "Role of Protein Kinase C in the Phosphorylation of CD33 (Siglec-3) and its Effect on Lectin Activity," *Blood* 99(9):3188-3196.

Gruber, M. et al. (1994). "Efficient Tumor Cell Lysis Mediated by a Bispecific Single Chain Antibody Expressed in *Escherichia coli*," *The Journal of Immunology* 152(11):5368-5374.

Gupta, N. et al. (2003). "Activated Microglia in Human Retinitis Pigmentosa, Late-Onset Retinal Degeneration, and Age-Related Macular Degeneration," *Experimental Eye Research* 76:463-471.

Hamann, P.R. et al. (2002, e-pub. Dec. 19, 2001). "Gemtuzumab Ozogamicin, A Potent and Selective Anti-CD33 Antibody-Calicheamicin Conjugate for Treatment of Acute Myeloid Leukemia," *Bioconjugate Chemistry* 13(1):47-58.

Hamers-Casterman, C. et al. (Jun. 3, 1993). "Naturally Occurring Antibodies Devoid of Light Chains," *Nature* 363:446-448.

Handgretinger, R. et al. (Aug. 1993). "Expression of an Early Myelopoietic Antigen (CD33) of a Subset of Human Umbilical Cord Blood-Derived Natural Killer Cells," *Immunol Lett.* 37(2-3):223-228.

Harrington, A.W. et al. (Apr. 20, 2004). "Secreted proNGF is a Pathophysiological Death-Inducing Ligand After Adult CNS Injury," *Proc. Natl. Acad. Sci USA* 101(16):6226-6230.

Harris, W.J. (Nov. 1, 1995). "Therapeutic Monoclonals—Production of Humanized Monoclonal Antibodies for In Vivo Imaging and Therapy," *Biochem. Soc. Transactions* 23(4):1035-1038.

Hawkins, R.E. et al. (1992). "Selection of Phage Antibodies by Binding Affinity: Mimicking Affinity Maturation," *Journal of Molecular Biology* 226:889-896.

Heider, K. et al. (Jan. 1, 2012). "A Novel Fc-Engineered Antibody to CD33 with Enhanced ADCC Activity for Treatment of AML," *Blood* 120(21):1363, located at <http://www.bloodjournal.org/content/120/21/1363>, last visited on Jan. 5, 2017, five pages.

Hernández-Caselles, T. et al. (Jan. 2006). "A Study of CD33 (SIGLEC-3) Antigen Expression and Function on Activated Human T and NK Cells: Two Isoforms of CD33 are Generated by Alternative Splicing," *J Leukoc Biol.* 79(1):46-58.

Hezareh, M. et al. (Dec. 2001). "Effector Function Activities of a Panel of Mutants of a Broadly Neutralizing Antibody against Human Immunodeficiency Virus Type 1," *Journal of Virology* vol. 75(24):12161-12168.

Holliger, P. et al. (Jul. 1993). ""Diabodies": Small Bivalent and Bispecific Antibody Fragments," *Proceedings of the National Academy of Sciences* 90:6444-6448.

Hollingworth, P. et al. (May 2011; e-published on Apr. 3, 2011). "Common Variants in ABCA7, MS4A6A/MS4A4E, EPHA1, CD33 and CD2AP are Associated with Alzheimer's Disease," *Nat. Genet.* 43(5):429-435.

Hongo, J.S. et al. (1995). "Development and Characterization of Murine Monoclonal Antibodies to the Latency-Associated Peptide of Transforming Growth Factor β1," *Hybridoma* 14(3):253-260.

Hoogenboom, H.R. et al. (1992). "By-Passing Immunisation. Human Antibodies from Synthetic Repertoires of Germline Hh Gene Segments Rearranged in Vitro," *Journal of Molecular Biology* 227:381-388.

Hoyer, J.D. et al. (Feb. 1, 2008). "CD33 Detection by Immunohistochemistry in Paraffin-Embedded Tissues: A New Antibody Shows Excellent Specificity and Sensitivity for Cells of Myelomonocytic Lineage," *Am. J. Clin. Pathol.* 129(2):316-323.

Humphrey, M.B. et al. (2006). "TREM2, a DAP12-Associated Receptor, Regulates Osteoclast Differentiation and Function," *J Bone Miner Res.* 21(2):237-245.

Hurle, M.R. et al. (Aug. 1994)."Protein Engineering Techniques for Antibody Humanization," *Current Opinion in Biotechnology* 5:428-433.

Hutchins, J.T. et al. (Dec. 1995). "Improved Biodistribution, Tumor Targeting, and Reduced Immunogenicity in Mice with a Gamma 4 Variant of Campath-IH," *Proc. Natl. Acad. Sci.* 92:11980-11984.

Hutton, M. et al. (Jun. 18, 1998). "Association of Missense and 5'-Splice-Site Mutations in Tau with the Inherited Dementia FTDP-17," *Nature* 393:702-705.

Ito, M. et al. (2008). "NOD/Shi-scid IL2rγ$^{null}$ (NOG) Mice More Appropriate for Humanized Mouse Models," *Curr Top Microbiol Immunol.* 324:53-76.

Ito, R. et al. (May 2012; e-published on Feb. 13, 2012). "Current Advances in Humanized Mouse Models," *Cellular & Molecular Immunology* 9(3):208-214.

Jackson, J.R. et al. (Apr. 1, 1995). "In Vitro Antibody Maturation. Improvement of a High Affinity, Neutralizing Antibody against IL-1 Beta," *The Journal of Immunology* 157(7):3310-3319.

Jakobovits, A. et al. (Mar. 18, 1993) "Germ-line Transmission and Expression of a Human-derived Yeast Artificial Chromosome," *Nature* 362:255-258.

Jakobovits, A. et al. (Mar. 1993). "Analysis of Homozygous Mutant Chimeric Mice: Deletion of the Immunoglobulin Heavy-chain Joining Region Blocks B-Cell Development and Antibody Production," *Proceedings of the National Academy of Sciences* 90:2551-2555.

Jandus, C. et al. (Aug. 15, 2011; e-published on May 31, 2011). "Targeting Siglecs—A Novel Pharmacological Strategy for Immuno- and Glycotherapy," *Biochem. Pharmacol.* 82(4):323-332.

Jansen, P. et al. (Nov. 2007, e-pub. Oct. 14, 2007). "Roles for the Pro-Neurotrophin Receptor Sortilin in Neuronal Development, Aging and Brain Injury," *Nature Neuroscience* 10(11):1449-1457.

Johnson, K.S. et al. (Aug. 1993). "Human antibody engineering: Current Opinion in Structural Biology," *Current Opinion in Structural Biology* 3(4):564-571.

Jones, P.T. et al. (May 29, 1986). "Replacing the Complementarity-Determining Regions in a Human Antibody with Those from a Mouse," *Nature* 321:522-525.

Jurcic, J.G. (Mar. 2012, e-pub. Nov. 23, 2011). "What Happened to Anti-CD33 Therapy for Acute Myeloid Leukemia?," *Curr Hematol Malig Rep* 7(1):65-73.

Kelm, S. et al. (1994). "Sialoadhesin, Myelin-Associated Glycoprotein and CD22 Define a New Family of Sialic Acid-Dependent Adhesion Molecules of the Immunoglobulin Superfamily," *Current Biology* 4(11):965-972.

Koga, T. et al. (Apr. 15, 2004). "Costimulatory Signals Mediated by the ITAM Motif Cooperate with RANKL for Bone Homeostasis," *Nature* 428:758-763.

Köhler, G. et al. (Aug. 7, 1975). "Continuous Cultures of Fused Cells Secreting Antibody of Predefined Specificity," *Nature* 256:495-497.

Kostelny, S.A. et al. (Mar. 1, 1992). "Formation of a Bispecific Antibody by the Use of Leucine Zippers," *The Journal of Immunology* 148(5):1547-1553.

Kozbor, D. et al. (Dec. 1984). "A Human Hybrid Myeloma for Production of Human Monoclonal Antibodies," *The Journal of Immunology* 133(6):3001-3005.

Laird, A.S. et al. (Oct. 13, 2010). "Progranulin is Neurotrophic in Vivo and Protects against a Mutant TDP-43 Induced Axonopathy," *Plos One* 5(10):e13368, seven pages.

Lajaunias, F. et al. (Jan. 2005; e-published on Dec. 16, 2004). "Constitutive Repressor Activity of CD33 on Human Monocytes Requires Sialic Acid Recognition and Phosphoinositide 3-Kinase-Mediated Intracellular Signaling," *Eur J Immunol.* 35(1):243-251.

Langer, R. (Sep. 28, 1990). "New Methods of Drug Delivery," *Science* 249(4976):1527-1533.

Lavail, M.M. et al. (Jun. 30, 2011). "Retinal Degeneration Rat Model Resource Availability of P23H and S334ter Mutant Rhodopsin Transgenic Rats and RCS Inbred and RCS Congenic Strains of Rats," University of California, pp. 1-12.

Lazar, G.A. et al. (Mar. 14, 2006). "Engineered Antibody Fc variants with Enhanced Effector Function," *PNAS* 103(11):4005-4010.

Lee, C.V. et al. (2004). "Bivalent Antibody Phage Display Mimics Natural Immunoglobulin," *Journal of Immunological Methods* 284:119-132.

Lee, C.V. et al. (2004). "High-affinity Human Antibodies from Phage-displayed Synthetic Fab Libraries with a Single Framework Scaffold," *Journal of Molecular Biology* 340:1073-1093.

(56) References Cited

OTHER PUBLICATIONS

Li, H. et al. (Feb. 2006). "Optimization of Humanized IgGs in Glycoengineered *Pichia pastoris*," *Nature Biotechnology* 24(2):210-215.

Li, J. et al. (Mar. 7, 2006). "Human Antibodies for Immunotherapy Development Generated via a Human B Cell Hybridoma Technology," *PNAS* 103(10):3557-3562.

Lightle, S. et al. (Mar. 24, 2010; e-published on Jan. 29, 2010). "Mutations Within a Human Lgg2 Antibody Form Distinct and Homogeneous Disulfide Isomers but do not Affect Fc Gamma Receptor or C1q Binding," *Protein Science* 19:753-762.

Lipovsek, D. et al. (2004, e-pub. May 31, 2004). "In-vitro protein evolution by ribosome display and mRNA display," *Journal of Immunological Methods* 290:51-67.

Lonberg, N. et al. (1995). "Human Antibodies from Transgenic Mice," *International Reviews of Immunology.* 13:65-93.

Lonberg, N. et al. (Apr. 28, 1994). "Antigen-Specific Human Antibodies from Mice Comprising Four Distinct Genetic Modifications," *Nature* 368:856-859.

Low, D. et al. (2013). "Animal Models of Ulcerative Colitis and their Application in Drug Research," *Drug Design, Development and Therapy* 7:1341-1357.

Lütje, S. et al. (Feb. 19, 2014). "Anti-CEA Antibody Fragments Labeled with [$^{18}$F]AlF for PET Imaging of CEA-Expressing Tumors," *Bioconjugate Chemistry* 25(2):335-341.

MacAuley, M.S. et al. (Oct. 2014; e-published on Sep. 19, 2014). "Siglec Regulation of Immune Cell Function in Disease," *Nature Reviews Immunology* 14(10):653-666, twenty nine pages.

Malik, B.R. et al. (Nov. 1, 2015; e-published on Aug. 6, 2015). "VPS35 Pathogenic Mutations Confer no Dominant Toxicity but Partial Loss of Function in *Drosophila* and Genetically Interact With *Parkin,*" *Human Molecular Genetics* 24(21):6106-6117.

Malik, M. et al. (Aug. 14, 2013). "CD33 Alzheimer's Risk-Altering Polymorphism, CD33 Expression, and Exon 2 Splicing," *J. Neurosci* 33(33):13320-13325.

Marks, J.D. et al. (1991). "By-passing immunization: Human antibodies from V-gene libraries displayed on phage," *Journal of Molecular Biology* 222(3): 581-597.

Marks, J.D. et al. (Jul. 1992)."By-Passing Immunization: Building High Affinity Human Antibodies by Chain Shuffling," *Bio/Technology* 10:779-782.

Martens, L.H. et al. (Nov. 2012). "Progranulin Deficiency Promotes Neuroinflammation and Neuron Loss Following Toxin-Induced Injury," *The Journal of Clinical Investigation* 122(11):3955-3959.

Mather, J.P. (1980). "Establishment and Characterization of Two Distinct Mouse Testicular Epithelial Cell Lines," *Biology of Reproduction* 23:243-252.

Mather, J.P. et al. (1982). "Culture of Testicular Cells in Hormone-Supplemented Serum-Free Medium," *Annals of the New York Academy of Sciences, Testicular Cell Culture* 383:44-68.

May, A.P. et al. (Apr. 1998). "Crystal Structure of the N-Terminal Domain of Sialoadhesin in Complex with 3' Sialyllactose at 1.85 Å Resolution," *Molecular Cell* 1(5):719-728.

McCafferty, J. et al. (Dec. 6, 1990). "Phage Antibodies: Filamentous Phage Displaying Antibody Variable Domains," *Nature* 348:552-554.

McEarchern, J.A. et al. (Feb. 1, 2007, e-pub. Oct. 12, 2006). "Engineered Anti-CD70 Antibody with Multiple Effector Functions Exhibits in Vitro and in Vivo Antitumor Activities," *Blood* 109(3):1185-1192.

McMillan, S.J. et al. (Aug. 11, 2008; e-published on Jan. 17, 2008). "CD33-related Sialic-Acid-Binding Immunoglobulin-Like Lectins in Health and Disease," *Carbohydrate Research* 343(12):2050-2056.

Milstein, C. et al. (Oct. 6, 1983). "Hybrid Hybridomas and their use in Immunohistochemistry," *Nature* 305:537-540.

Mizoguchi, A. (2012). "Animal Models of Inflammatory Bowel Disease," *Progress in Molecular Biology and Translational Science* 105:263-320, fifty eight pages.

Monsonego-Oran, E. et al. (Sep. 25, 2002; e-published on Aug. 28, 2002). "FGF Receptors Ubiquitylation: Dependence on Tyrosine Kinase Activity and Role in Downregulation," *FEBS Letters* 528(1-3):83-89.

Morimoto, K. et al. (1992). "Single-Step Purification of F(ab')2 Fragments of Mouse Monoclonal Antibodies (Immunoglobulins G1) by Hydrophobic Interaction High Performance Liquid Chromatography Using TSKgel Phenyl-5PW," *Journal of Biochemical and Biophysical Methods* 24:107-117.

Morrison, S.L. (Apr. 28, 1994). "Success in Specification," *Nature* 368:812-813.

Morrison, S.L. et al. (Nov. 1984). "Chimeric Human Antibody Molecules: Mouse Antigen-binding Domains with Human Constant Region Domains," *Proc. Nat'l Acad. Sci* 81:6851-6855.

Mortland, L. et al. (Feb. 26, 2013). "Clinical Significance of CD33 Nonsynonymous SingleNucleotide Polymorphisms in Pediatric Patients with Acute Myeloid Leukemia Treated with Gemtuzumab-Ozogamicin- Containing Chemotherapy," *Clin Cancer Res*, pp. 1-8.

Munson, P.J. et al. (1980). "Ligand: A Versatile Computerized Approach for Characterization of Ligand-binding Systems," *Analytical Biochemistry* 107:220-239.

Naito, K. et al. (2000). "Calicheamicin-Conjugated Humanized Anti-CD33 Monoclonal Antibody (gemtuzumab zogamicin, CMA-676) Shows Cytocidal effect on CD33—Positive Leukemia Cell Lines, But is Inactive on P-glycoprotein-Expressing sublines," *Leukemia* 14:1436-1443.

Naj, A.C. et al. (May 2011; e-published on Apr. 3, 2011). "Common Variants in MS4A4/MS4A6E, CD2uAP, CD33, and EPHA1 are Associated with Late-onset Alzheimer's Disease," *Nat Genet.* 43(5):436-441, seventeen pages.

Nakamura, K. et al. (2007)."Intracellular Sortilin Expression Pattern Regulates proNGF-Induced Naturally Occurring Cell Death during Development," *Cell Death and Differentiation* 14:1552-1554.

Neary, D. et al. (Dec. 1998). "Frontotemporal Lobar Degeneration: A Consensus on Clinical Diagnostic Criteria," *Neurology* 51:1546-1554.

Neuberger, M. (Jul. 1996). "Generating high-avidity human Mabs in mice," *Nature Biotechnology* 14:826, one page.

Neumann, M. et al. (Oct. 2007). "TDP-43 Proteinopathy in Frontotemporal Lobar Degeneration and Amyotrophic Lateral Sclerosis," *Arch Neurol.* 64(10):1388-1394.

Novack, D.V. et al. (2008). "The Osteoclast: Friend or Foe?," *Annu. Rev. Pathol. Mech. Dis.* 3:457-484.

Nykjaer, A. et al. (2005, e-pub. Jan. 26, 2005). "p75$^{NTR}$—Live or Let Die," *Current Opinion in Neurobiology* 15:49-57.

Nykjaer, A. et al. (Feb. 26, 2004). "Sortilin is Essential for proNGF Induced Neuronal Cell Death," *Nature* 427:843-848.

Oganesyan, V. et al. (2008). "Structural characterization of a Human Fc Fragment Engineered for Lack of Effector Functions," *Acta Crystallography* 64:700-704.

Ohgidani, M. et al. (May 14, 2014). "Direct induction of ramified microglia-like cells from human monocytes: Dynamic microglial dysfunction in Nasu-Hakola disease," *Scientific Reports* 4(Article No. 4957):1-7.

O'Reilly, M.K. et al. (May 2009; e-published on Apr. 7, 2009). "Siglecs as Targets for Therapy in Immune Cell Mediated Disease," *Trends Pharmacol. Sci.* 30(5):240-248, twenty three pages.

Otero, K. et al. (2012; e-published on Feb. 6, 2012). "TREM2 and β-Catenin Regulate Bone Homeostasis by Controlling the Rate of Osteoclastogenesis," *J Immunol* 188:2612-2621.

Park, M. et al. (Jan. 2015). "Triggering Receptor Expressed on Myeloid Cells 2 (TREM2) Promotes Adipogenesis and Diet-Induced Obesity," *Diabetes* 64:117-127.

Paul, S.P. et al. (Jul. 15, 2000). "Myeloid Specific Human CD33 is an Inhibitory Receptor With Differential ITIM Function in Recruiting the Phosphatases SHP-1 and SHP-2," *Blood* 96(2):483-490.

Peiper, S.C. et al. (Jul. 1988). "Molecular Cloning, Expression, and Chromosomal Localization of a Human Gene Encoding the CD33 Myeloid Differentiation Antigen," *Blood* 72(1):314-321.

Peng, Q. et al. (May 18, 2010). "TREM2- and DAP12-Dependent Activation of PI3K Requires DAP10 and Is Inhibited by SHIP1," *Science Signaling* 3(122):ra38, pp. 1-15.

(56) References Cited

OTHER PUBLICATIONS

Pennesi, M.E. et al. (Aug. 2012). "Animal Models of Age Related Macular Degeneration," *Molecular Aspects of Medicine* 33(4):487-509, forty pages.

Pérez-Oliva, A. et al. (Jun. 1, 2011; e-published on Jan. 28, 2011). "Epitope Mapping, Expression and Post-Translational Modifications of Two Isoforms of CD33 (CD33M and CD33m) on Lymphoid and Myeloid Human Cells," *Glycobiology* 21(6):757-770.

Peters, S.J. et al. (Jul. 13, 2012). "Engineering an Improved IgG4 Molecule with Reduced Disulfide Bond Heterogeneity and Increased Fab Domain Thermal Stability," *The Journal of Biological Chemistry* 287(29):24525-24533.

Pillai, S. et al. (2012; Jan. 3, 2012). "Siglecs and Immune Regulation," *Annu. Rev. Immunol.* 30:357-392.

Plückthun, A. (Dec. 1992). "Mono- and Bivalent Antibody Fragments Produced in *Escherichia coli*: Engineering, Folding and Antigen Binding," *Immunological Reviews* 130:151-188.

Poduslo, J.F. et al. (Jun. 1994). "Macromolecular Permeability Across the Blood-Nerve and Blood-Brain Barriers," *Proc. Natl. Acad. Sci. USA* 91:5705-5709.

Pollenz, R.S. et al. (Dec. 1, 2006, e-pub. Aug. 25, 2006). "Ligand-Dependent and -Independent Degradation of the Human Aryl Hydrocarbon Receptor (hAHR) in Cell Culture Models," *Chemico-Biological Interactions* 164(1-2):49-59.

Presta, L.G. (1992). "Antibody Engineering," *Current Opinion in Structural Biology* 2:593-596.

Presta, L.G. et al. (Sep. 1, 1993). "Humanization of an Antibody Directed Against IgE," *The Journal of Immunology* 151(5):2623-2632.

Provenzano, M.J. (2008). "p75NTR and Sortilin Increase After Facial Nerve Injury," *Laryngoscope* 118:87-93.

Raj, T. et al. (May 15, 2014; e-published on Dec. 30, 2013). "CD33: Increased Inclusion of Exon 2 Implicates the Ig V-Set Domain in Alzheimer's Disease Susceptibility," *Human Molecular Genetics* 23(10):2729-2736.

Ratnavalli, E. et al. (Jun. 2002). "The Prevalence of Frontotemporal Dementia," *Neurology* 58(1 of 2):1615-1621.

Ravetch, J.V. et al. (1991). "Fc Receptors," *Annual Review Immunology* 9:457-492.

Reddy, M.P. et al. (2000). "Elimination of Fc Receptor-Dependent Effector Functions of a Modified IgG4 Monoclonal Antibody to Human CD4," *The Journal of Immunology* 164:1925-1933.

Ricart, A.D. (Oct. 15, 2011). "Antibody-Drug Conjugates of Calicheamicin Derivative: Gemtuzumab Ozogamicin and Inotuzumab Ozogamicin," *Clin Cancer Res* 17(20):6417-6427.

Riechmann, L. et al. (Mar. 24, 1988). "Reshaping Human Antibodies for Therapy," *Nature* 332:323-327.

Roberts, R.W. et al. (Nov. 1997). "RNA-Peptide Fusions for the In Vitro Selection of Peptides and Proteins," *Proc. Natl. Acad. Sci. USA* 94:12297-12302.

Rollins-Raval, M.A et al. (May 2012; e-published on Feb. 20, 2012). "The Value of Immunohistochemistry for CD14, CD123, CD33, Myeloperoxidase and CD68R in the Diagnosis of Acute and Chronic Myelomonocytic Leukaemias," *Histopathology* 60(6):933-942.

Rosok, M.J. et al. (Sep. 13, 1996). "Combinatorial Library Strategy for the Rapid Humanization of Anticarcinoma BR96 Fab," *The Journal of Biological Chemistry* 271(37):22611-22618.

Sazinsky, S.L. et al. (Dec. 23, 2008). "Aglycosylated Immunoglobulin G1 Variants Productively Engage Activating Fc Receptors," *PNAS* 105(51):20167-20172.

Schabbauer, G. et al. (Jul. 2010). "Myeloid PTEN Promotes Inflammation but Impairs Bactericidal Activities During Murine Pneumococcal Pneumonia," *The Journal of Immunology* 185(1):468-476.

Schaffitzel, C. et al. (1999). "Ribosome Display: An In Vitro Method for Selection and Evolution of Antibodies from Libraries," *Journal of Immunological Methods* 231:119-135.

Schier, R. et al. (1996). "Identification of Functional and Structural Amino-Acid Residues by Parsimonious Mutagenesis," *Gene* 169:147-155.

Schymick, J.C. et al. (2007). "Progranulin Mutations and Amyotrophic Lateral Sclerosis or Amyotrophic Lateral Sclerosis—Frontotemporal Dementia Phenotypes," *Journal of Neurology, Neurosurgery and Psychiatry* 78:754-756.

Seno, H. et al. (Jan. 6, 2009). "Efficient Colonic Mucosal Wound Repair Requires Trem2 Signaling," *PNAS* 106(1):256-261.

Shalaby, M.F. et al. (Jan. 1992). "Development of Humanized Bispecific Antibodies Reactive with Cytotoxic Lymphocytes and Tumor Cells Overexpressing the HER2 Protooncogene," *The Journal of Experimental Medicine* 175:217-225.

Sharif, O. et al. (Jun. 12, 2014). "The Triggering Receptor Expressed on Myeloid Cells 2 Inhibits Complement Component 1 q Effector Mechanisms and Exerts Detrimental Effects during Pneumococcal Pneumonia," *PLoS Pathogen* 10(6):e1004167, sixteen pages.

Sheriff, S. et al. (Sep. 1996). "Redefining the Minimal Antigen-binding Fragment," *Nature Structural & Molecular Biology* 3(9):733-736.

Shields, R.L. et al. (Mar. 2, 2001). "High Resolution Mapping of the Binding Site on Human IgG1 for FcγRI, FcγRII, FcγRIII, and FcRn and Design of IgG1 Variants with Improved Binding to the FcγR," *The Journal of Biological Chemistry* 276(9):6591-6604.

Sidhu, S.S. et al. (Apr. 2004). "Phage-displayed Antibody Libraries of Synthetic Heavy Chain Complementarity Determining Regions," *Journal of Molecular Biology* 338(2):299-310.

Sieber, M.W. et al. (Jan. 3, 2013). "Attenuated Inflammatory Response in Triggering Receptor Expressed on Myeloid Cells 2 (TREM2) Knock-Out Mice following Stroke," *PLoS One* 8(1):e52982, ten pages.

Simmons, D. et al. (Oct. 15, 1988). "Isolation of a cDNA Encoding CD33, a Differentiation Antigen of Myeloid Progenitor Cells," *J Immunol.* 141(8):2797-2800.

Sims, M.J. et al. (Aug. 15, 1993). "A Humanized CD18 Antibody Can Block Function Without Cell Destruction," *The Journal of Immunology* 151(4):2296-2308.

Siolas, D. et al. (Sep. 2013). "Patient-Derived Tumor Xenografts: Transforming Clinical Samples into Mouse Models," *Cancer Research* 73(17):5315-5319.

Skerra, A. (1993). "Bacterial Expression of Immunoglobulin Fragments," *Current Opinion in Immunology* 5:256-262.

Sollid, L.M. et al. (Sep. 2008). "Animal Models of Inflammatory Bowel Disease at the Dawn of the New Genetics Era," *PLoS Med* 5(9):1338-1342(e198).

Strohl, W.R. (2009; e-published on Nov. 4, 2009). "Optimization of Fc-mediated Effector Functions of Monoclonal Antibodies," *Current Opinion in Biotechnology* 20:685-691.

Sun, M. et al. (May 2013). "TREM-2 Promotes Host Resistance Against *Pseudomonas aeruginosa* Infection by Suppressing Corneal Inflammation via a PI3K/Akt Signaling Pathway," *Investigative Ophthalmology & Visual Science* 54(5):3451-3462.

Suresh, M.R. et al. (1986). "Bispecific Monoclonal Antibodies from Hybrid Hybridomas," *Methods in Enzymology* 121:210-228.

Sutherland, M.K. et al. (Sep.-Oct. 2009; e-published Sep. 15, 2009). "Anti-Leukemic Activity of Lintuzumab (SGN-33) in Preclinical Models of Acute Myeloid Leukemia," *MABS* 1(5):481-490.

Takahashi, K. et al. (Apr. 10, 2007). "TREM2-Transduced Myeloid Precursors Mediate Nervous Tissue Debris Clearance and Facilitate Recovery in an Animal Model of Multiple Sclerosis," *Plos Med* 4(4):e124, pp. 0675-0689.

Takahashi, K. et al. (Feb. 21, 2005). "Clearance of apoptotic neurons without inflammation by microglial triggering receptor expressed on myeloid cells-2," *Journal of Experimental Medicine* 201(4):647-657.

Tanaka, Y. et al.(2013). "Exacerbated Inflammatory Responses Related to Activated Microglia After Traumatic Brain Injury in Progranulin-Deficient Mice," *Neuroscience* 231:49-60.

Tavaré, R. et al. (Jan. 21, 2014). "Engineered Antibody Fragments for Immuno-PET Imaging of Endogenous CD8+ T Cells in Vivo," *PNAS* 111(3):1108-1113.

Taylor, V.C. et al. (Apr. 23, 1999). "The Myeloid-specific Sialic Acid-binding Receptor, CD33, Associates with the Protein-tyrosine Phosphatases, SHP-1 and SHP-2," *Journal of Biological Chemistry* 274(17):11505-11512.

(56) References Cited

OTHER PUBLICATIONS

Teng, H.K. et al. (Jun. 1, 2005). "ProBDNF Induces Neuronal Apoptosis via Activation of a Receptor Complex of $p75^{NTR}$ and Sortilin," *The Journal of Neuroscience* 25(22):5455-5463.

Traunecker, A. et al. (1991). "Bispecific Single Chain Molecules (Janusins) Target Cytotoxic Lymphocytes on HIV Infected Cells," *The EMBO Journal* 10(12):3655-3659.

Tutt, A. et al. (Jul. 1, 1991). "Trispecific F(ab')3 Derivatives that Use Cooperative Signaling Via the TCR/CD3 Complex and CD2 to Activate and Redirect Resting Cytotoxic T Cells1," *The Journal of Immunology* 147(1):60-69.

Ulyanova, T. et al. (1999). "The Sialoadhesin CD33 is a Myeloid-Specific Inhibitory Receptor," *Eur J Immunol.* 29:3440-3449.

Urlaub, G. et al. (Jul. 1980). "Isolation of Chinese Hamster Cell Mutants Deficient in Dihydrofolate Reductase Activity," *Proc. Natl. Acad. Sci.* 77(7):4216-4220.

Vafa, O. et al.(2014; e-published on Jul. 17, 2013). "An Engineered Fc Variant of an IgG Eliminates All Immune Effector Functions Via Structural Perturbations," *Methods* 65:114-126.

Van Dijk, M.A et al. (2001)."Human Antibodies as Next Generation Therapeutics," *Current Opinion in Chemical Biology* 5:368-374.

Varki, A. et al. (Jan. 1, 2006; e-published on Jul. 13, 2005). "Siglecs—The Major Subfamily of I-Type Lectins," *Glycobiology* 16(1):1R-27R.

Vaswani, S.K. et al. (Aug. 1998). "Humanized Antibodies as Potential Therapeutic Drugs," *Annals of Allergy, Asthma & Immunology* 81:105-119.

Verhoeyen, M. et al. (1988). "Reshaping Human Antibodies: Grafting an Antilysozyme Activity," *Science* 239:1534-1536.

Vetrano, S. et al. (2008). "Unique Role of Junctional Adhesion Molecule-A in Maintaining Mucosal Homeostasis in Inflammatory Bowel Disease," *Gastroenterology* 135(1):173-184.

Vitale, C. et al. (May 8, 2001). "Surface Expression and Function of P75/AIRM-1 or CD33 in Acute Myeloid Leukemias: Engagement of CD33 Induces Apoptosis of Leukemic Cells," *Proc Natl Acad Sci USA* 98(10):5764-5769.

Volosin, M. et al. (Jul. 19, 2006). "Interaction of Survival and Death Signaling in Basal Forebrain Neurons: Roles of Neurotrophins and Proneurotrophins," *The Journal of Neuroscience* 26(29):7756-7766.

Volosin, M. et al. (Sep. 24, 2008). "Induction of Proneurotrophins and Activation of P75ntr-Mediated Apoptosis Via Neurotrophin Receptor-Interacting Factor in Hippocampal Neurons After Seizures," *The Journal of Neuroscience* 28(39):9870-9879, twenty five pages.

Von Gunten, S. et al. (Nov. 2008). "Basic and Clinical Immunology of Siglecs," *Ann. NY Acad. Sci.* 1143:61-82, twenty five pages.

Walker, D.G. et al. (Feb. 2015; e-published on Oct. 2, 2014). "Association of CD33 Polymorphism Rs3865444 With Alzheimer's Disease Pathology and CD33 Expression in Human Cerebral Cortex," *Neurobiology of Aging* 36(2):571-582, thirty two pages.

Wang, Y. et al. (Mar. 12, 2015; e-published on Feb. 26, 2015). "TREM2 Lipid Sensing Sustains the Microglial Response in an Alzheimer's Disease Model," *Cell* 160(6):1061-1071.

Waterhouse, P. et al. (1993). "Combinatorial Infection and In Vivo Recombination: A Strategy for Making Large Phage Antibody Repertoires," *Nucleic Acids Research* 21(9):2265-2266.

Wei, Y. et al. (2007). "Enhanced Protein Expressions of Sortilin and $p75^{NTR}$ in Retina of Rat Following Elevated Intraocular Pressure-Induced Retinal Ischemia," *Neuroscience Letters* 429(2-3):169-174.

White, A.L. et al. (Jan. 12, 2015). "Conformation of the Human Immunoglobulin G2 Hinge Imparts Superagonistic Properties to Immunostimulatory Anticancer Antibodies," *Cancer Cell* 27:138-148.

Wiehr, S. et al. (2014). "Pharmacokinetics and PET Imaging Properties of Two Recombinant Anti-PSMA Antibody Fragments in Comparison to their Parental Antibody," *The Prostate* 74(7):743-755.

Wilkinson, I.C. et al. (2013). "Monovalent IgG4 Molecules: Immunoglobulin Fc Mutations that Result in a Monomeric Structure," *mAbs* 5(3):406-417.

Wilson, N.S. et al. (Jan. 18, 2011). "An Fcγ Receptor-Dependent Mechanism Drives Antibody-Mediated Target-Receptor Signaling in Cancer Cells," *Cancer Cell* 19:101-113.

Xu, D. et al. (2000). "In Vitro Characterization of Five Humanized OKT3 Effector Function Variant Antibodies," *Cellular Immunology* 200(1):16-26.

Xu, J. et al. (Jul. 2000). "Diversity in the CDR3 Region of $V_H$ Is Sufficient for Most Antibody Specificities," *Immunity* 13:37-45.

Xu, Y. et al. (2013). "Addressing Polyspecificity of Antibodies Selected from an in Vitro Yeast presentation system: a FACS-based, high-throughput selection and analytical tool," *Protein Engineering, Design & Selection* 26(10):663-670.

Yano, H. et al. (Nov. 25, 2009)."Proneurotrophin-3 Is a Neuronal Apoptotic Ligand: Evidence for Retrograde-Directed Cell Killing," *The Journal of Neuroscience* 29(47):14790-14802.

Yelton, D.E. et al. (1995). "Affinity maturation of the BR96 anticarcinoma antibody by codon-based mutagenesis," *The Journal of Immunology* 155:1994-2004.

Yin, F. et al. (Dec. 21, 2009). "Exaggerated Inflammation, Impaired Host Defense, and Neuropathology in Progranulin-Deficient Mice," *J. Exp. Med.* 207(1):117-128.

Zapata, G. et al. (1995). "Engineering Linear F(ab')2 Fragments for Efficient Production in *Escherichia coli* and Enhanced Antiproliferative Activity," *Protein Engineering Designs and Selections* 8(10):1057-1062.

Zhou, Q. et al. (Mar. 1, 2014). "Humanized NOD-SCID IL2rg$^{-/-}$ Mice as a Preclinical Model for Cancer Research and its Potential Use for Individualized Cancer Therapies," *Cancer Letters* 344(1):13-19.

Zhu, Y. et al. (Sep. 15, 2014, e-pub. Jul. 31, 2014). "CSF1/CSF1 R Blockade Reprograms Tumor-Infiltrating Macrophages and Improves Response to T Cell Checkpoint Immunotherapy in Pancreatic Cancer Models," *Cancer Research* 74(18):5057-5069.

International Preliminary Report on Patentability dated Dec. 21, 2017 for International Application No. PCT/US2016/037108, filed on Jun. 11, 2016, eleven pages.

International Preliminary Report on Patentability dated Dec. 21, 2017 for International Application No. PCT/US2016/037109, filed on Jun. 11, 2016, fifteen pages.

International Search Report and Written Opinion dated Dec. 6, 2016 for International Application No. PCT/US2016/037108, filed on Jun. 11, 2016, sixteen pages.

International Search Report and Written Opinion dated Dec. 6, 2016 for PCT Application No. PCT/US2016/037109 filed on Jun. 11, 2016, twenty pages.

U.S. Appl. No. 15/735,946, filed Dec. 12, 2017 by Rosenthal et al.

U.S. Appl. No. 15/735,947, filed Dec. 12, 2017 by Monroe et al.

Anonymous, (2019). "EC50," Available online at: <en.wikipedia.org/wiki/EC50>, Sep. 16, 2019, 3 pages.

Edwards et al., (2003). "The remarkable flexibility of the human antibody repertoire; isolation of over one thousand different antibodies to a single protein, BLyS," *J. Mol. Biol.*, 334:103-118.

International Search Report and Written Opinion dated Nov. 13, 2018 for PCT Application No. PCT/US2018/045056 filed on Aug. 2, 2018, 16 pages.

International Search Report and Written Opinion dated Nov. 13, 2019 for PCT Application No. PCT/US2019/048994 filed on Aug. 30, 2019, 383 pages.

International Search Report and Written Opinion dated Oct. 25, 2013 for PCT Application No. PCT/US2013/041209 filed on May 15, 2013, 9 pages.

Li et al. (2011). "Inhibitory Fcgamma Receptor Engagement Drives Adjuvant and Anti-Tumor Activities of Agonistic CD40 Antibodies," *Science*, 333(6045):1030-1034.

Lloyd et al., (2009). "Modelling the human immune response: performance of a 1011 human antibody repertoire against a broad panel of therapeutically relevant antigens," *Protein Eng. Design & Select*, 22(3):159-168.

Vasu et al. (Jun. 9, 2016, e-pub. Mar. 24, 2016). "Decitabine Enhances Anti-CD33 Monoclonal Antibody BI 836858—Mediated Natural Killer ADCC Against AML Blasts," *Blood*, 127(23):2879-2889.

(56) References Cited

OTHER PUBLICATIONS

Vincent et al. (Dec. 2012, e-pub. Nov. 1, 2012). "Current Strategies in Antibody Engineering: Fc Engineering and pH-Dependent Antigen Binding, Bispecific Antibodies and Antibody Drug Conjugates," Biotechnol J., 7(12):1444-1450.

White et al., (Aug. 15, 2011, e-pub. Jul. 8, 2011). "Interaction with FcgammaRIIB is Critical for the Agonistic Activity of Anti-CD40 Monoclonal Antibody," J Immunol., 187(4):1754-1763.

\* cited by examiner

SEQUENCE LISTING

```
<160> NUMBER OF SEQ ID NOS: 205

<210> SEQ ID NO 1
<211> LENGTH: 364
<212> TYPE: PRT
<213> ORGANISM: Homo sapiens

<400> SEQUENCE: 1

Met Pro Leu Leu Leu Leu Pro Leu Leu Trp Ala Gly Ala Leu Ala
1               5                   10                  15

Met Asp Pro Asn Phe Trp Leu Gln Val Gln Glu Ser Val Thr Val Gln
            20                  25                  30

Glu Gly Leu Cys Val Leu Val Pro Cys Thr Phe Phe His Pro Ile Pro
        35                  40                  45

Tyr Tyr Asp Lys Asn Ser Pro Val His Gly Tyr Trp Phe Arg Glu Gly
    50                  55                  60
```

```
Ala Ile Ile Ser Arg Asp Ser Pro Val Ala Thr Asn Lys Leu Asp Gln
 65                  70                  75                  80

Glu Val Gln Glu Glu Thr Gln Gly Arg Phe Arg Leu Leu Gly Asp Pro
                 85                  90                  95

Ser Arg Asn Asn Cys Ser Leu Ser Ile Val Asp Ala Arg Arg Arg Asp
            100                 105                 110

Asn Gly Ser Tyr Phe Phe Arg Met Glu Arg Gly Ser Thr Lys Tyr Ser
        115                 120                 125

Tyr Lys Ser Pro Gln Leu Ser Val His Val Thr Asp Leu Thr His Arg
    130                 135                 140

Pro Lys Ile Leu Ile Pro Gly Thr Leu Glu Pro Gly His Ser Lys Asn
145                 150                 155                 160

Leu Thr Cys Ser Val Ser Trp Ala Cys Glu Gln Gly Thr Pro Pro Ile
                165                 170                 175

Phe Ser Trp Leu Ser Ala Ala Pro Thr Ser Leu Gly Pro Arg Thr Thr
            180                 185                 190

His Ser Ser Val Leu Ile Ile Thr Pro Arg Pro Gln Asp His Gly Thr
        195                 200                 205

Asn Leu Thr Cys Gln Val Lys Phe Ala Gly Ala Gly Val Thr Thr Glu
    210                 215                 220

Arg Thr Ile Gln Leu Asn Val Thr Tyr Val Pro Gln Asn Pro Thr Thr
225                 230                 235                 240

Gly Ile Phe Pro Gly Asp Gly Ser Gly Lys Gln Glu Thr Arg Ala Gly
                245                 250                 255

Val Val His Gly Ala Ile Gly Gly Ala Gly Val Thr Ala Leu Leu Ala
            260                 265                 270

Leu Cys Leu Cys Leu Ile Phe Phe Ile Val Lys Thr His Arg Arg Lys
        275                 280                 285

Ala Ala Arg Thr Ala Val Gly Arg Asn Asp Thr His Pro Thr Thr Gly
    290                 295                 300

Ser Ala Ser Pro Lys His Gln Lys Lys Ser Lys Leu His Gly Pro Thr
305                 310                 315                 320

Glu Thr Ser Ser Cys Ser Gly Ala Ala Pro Thr Val Glu Met Asp Glu
                325                 330                 335

Glu Leu His Tyr Ala Ser Leu Asn Phe His Gly Met Asn Pro Ser Lys
            340                 345                 350

Asp Thr Ser Thr Glu Tyr Ser Glu Val Arg Thr Gln
        355                 360

<210> SEQ ID NO 2
<211> LENGTH: 25
<212> TYPE: PRT
<213> ORGANISM: Artificial Sequence
<220> FEATURE:
<223> OTHER INFORMATION: Synthetic Construct

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 3
<211> LENGTH: 25
<212> TYPE: PRT
<213> ORGANISM: Artificial Sequence
<220> FEATURE:
```

```
<223> OTHER INFORMATION: Synthetic Construct

<400> SEQUENCE: 3

Gln Val Gln Leu Val Gln Ser Gly Ala Glu Val Lys Lys Pro Gly Ser
1               5                   10                  15

Ser Val Lys Val Ser Cys Lys Ala Ser
            20                  25

<210> SEQ ID NO 4
<211> LENGTH: 25
<212> TYPE: PRT
<213> ORGANISM: Artificial Sequence
<220> FEATURE:
<223> OTHER INFORMATION: Synthetic Construct

<400> SEQUENCE: 4

Gln Val Gln Leu Val Gln Ser Gly Ala Glu Val Lys Lys Pro Gly Ala
1               5                   10                  15

Ser Val Lys Ile Ser Cys Lys Ala Ser
            20                  25

<210> SEQ ID NO 5
<211> LENGTH: 14
<212> TYPE: PRT
<213> ORGANISM: Artificial Sequence
<220> FEATURE:
<223> OTHER INFORMATION: Synthetic Construct

<400> SEQUENCE: 5

Trp Val Arg Gln Ala Pro Gly Gln Gly Leu Glu Trp Ile Gly
1               5                   10

<210> SEQ ID NO 6
<211> LENGTH: 39
<212> TYPE: PRT
<213> ORGANISM: Artificial Sequence
<220> FEATURE:
<223> OTHER INFORMATION: Synthetic Construct

<400> SEQUENCE: 6

Tyr Ala Gln Lys Phe Gln Gly Arg Val Thr Met Thr Val Asp Thr Ser
1               5                   10                  15

Thr Ser Thr Val Tyr Met Glu Leu Ser Ser Leu Arg Ser Glu Asp Thr
            20                  25                  30

Ala Val Tyr Tyr Cys Ala Arg
        35

<210> SEQ ID NO 7
<211> LENGTH: 39
<212> TYPE: PRT
<213> ORGANISM: Artificial Sequence
<220> FEATURE:
<223> OTHER INFORMATION: Synthetic Construct

<400> SEQUENCE: 7

Tyr Ala Gln Asp Phe Gln Gly Arg Val Thr Met Thr Val Asp Thr Ser
1               5                   10                  15

Thr Ser Thr Val Tyr Met Glu Leu Ser Ser Leu Arg Ser Glu Asp Thr
            20                  25                  30

Ala Val Tyr Tyr Cys Ala Arg
        35

<210> SEQ ID NO 8
```

```
<211> LENGTH: 39
<212> TYPE: PRT
<213> ORGANISM: Artificial Sequence
<220> FEATURE:
<223> OTHER INFORMATION: Synthetic Construct

<400> SEQUENCE: 8

Tyr Ala Gln Lys Phe Gln Asp Arg Val Thr Met Thr Val Asp Thr Ser
1               5                   10                  15

Thr Ser Thr Val Tyr Met Glu Leu Ser Ser Leu Arg Ser Glu Asp Thr
            20                  25                  30

Ala Val Tyr Tyr Cys Ala Arg
        35

<210> SEQ ID NO 9
<211> LENGTH: 39
<212> TYPE: PRT
<213> ORGANISM: Artificial Sequence
<220> FEATURE:
<223> OTHER INFORMATION: Synthetic Construct

<400> SEQUENCE: 9

Ser Ala Gln Lys Phe Gln Gly Arg Val Thr Met Thr Val Asp Thr Ser
1               5                   10                  15

Thr Ser Thr Val Tyr Met Glu Leu Ser Ser Leu Arg Ser Glu Asp Thr
            20                  25                  30

Ala Val Tyr Tyr Cys Ala Arg
        35

<210> SEQ ID NO 10
<211> LENGTH: 39
<212> TYPE: PRT
<213> ORGANISM: Artificial Sequence
<220> FEATURE:
<223> OTHER INFORMATION: Synthetic Construct

<400> SEQUENCE: 10

Tyr Ala Gln Lys Asp Gln Gly Arg Val Thr Met Thr Val Asp Thr Ser
1               5                   10                  15

Thr Ser Thr Val Tyr Met Glu Leu Ser Ser Leu Arg Ser Glu Asp Thr
            20                  25                  30

Ala Val Tyr Tyr Cys Ala Arg
        35

<210> SEQ ID NO 11
<211> LENGTH: 39
<212> TYPE: PRT
<213> ORGANISM: Artificial Sequence
<220> FEATURE:
<223> OTHER INFORMATION: Synthetic Construct

<400> SEQUENCE: 11

Tyr Ala Gln Lys Phe Thr Gly Arg Val Thr Met Thr Val Asp Thr Ser
1               5                   10                  15

Thr Ser Thr Val Tyr Met Glu Leu Ser Ser Leu Arg Ser Glu Asp Thr
            20                  25                  30

Ala Val Tyr Tyr Cys Ala Arg
        35

<210> SEQ ID NO 12
<211> LENGTH: 39
<212> TYPE: PRT
<213> ORGANISM: Artificial Sequence
```

```
<220> FEATURE:
<223> OTHER INFORMATION: Synthetic Construct

<400> SEQUENCE: 12

Tyr Ala Gln Lys Phe Gln Gly Arg Ala Thr Leu Thr Val Asp Asn Ser
1               5                   10                  15

Thr Ser Thr Ala Tyr Met Glu Leu Ser Ser Leu Arg Ser Glu Asp Thr
            20                  25                  30

Ala Val Tyr Tyr Cys Ala Arg
        35

<210> SEQ ID NO 13
<211> LENGTH: 39
<212> TYPE: PRT
<213> ORGANISM: Artificial Sequence
<220> FEATURE:
<223> OTHER INFORMATION: Synthetic Construct

<400> SEQUENCE: 13

Tyr Ala Glu Lys Phe Glu Gly Arg Ala Thr Leu Thr Val Asp Asn Ser
1               5                   10                  15

Thr Ser Thr Ala Tyr Met Glu Leu Ser Ser Leu Arg Ser Glu Asp Thr
            20                  25                  30

Ala Val Tyr Tyr Cys Ala Arg
        35

<210> SEQ ID NO 14
<211> LENGTH: 39
<212> TYPE: PRT
<213> ORGANISM: Artificial Sequence
<220> FEATURE:
<223> OTHER INFORMATION: Synthetic Construct

<400> SEQUENCE: 14

Tyr Ala Gln Lys Phe Phe Gly Arg Ala Thr Leu Thr Val Asp Asn Ser
1               5                   10                  15

Thr Ser Thr Ala Tyr Met Glu Leu Ser Ser Leu Arg Ser Glu Asp Thr
            20                  25                  30

Ala Val Tyr Tyr Cys Ala Arg
        35

<210> SEQ ID NO 15
<211> LENGTH: 39
<212> TYPE: PRT
<213> ORGANISM: Artificial Sequence
<220> FEATURE:
<223> OTHER INFORMATION: Synthetic Construct

<400> SEQUENCE: 15

Tyr Ala Gln Lys Phe Gln His Arg Ala Thr Leu Thr Val Asp Asn Ser
1               5                   10                  15

Thr Ser Thr Ala Tyr Met Glu Leu Ser Ser Leu Arg Ser Glu Asp Thr
            20                  25                  30

Ala Val Tyr Tyr Cys Ala Arg
        35

<210> SEQ ID NO 16
<211> LENGTH: 39
<212> TYPE: PRT
<213> ORGANISM: Artificial Sequence
<220> FEATURE:
<223> OTHER INFORMATION: Synthetic Construct
```

```
<400> SEQUENCE: 16

Tyr Ala Gln Lys Phe Gln Gly Arg Ala Thr Leu Thr Val Asp Thr Ser
1               5                   10                  15

Thr Ser Thr Ala Tyr Met Glu Leu Ser Ser Leu Arg Ser Glu Asp Thr
            20                  25                  30

Ala Val Tyr Tyr Cys Ala Arg
        35

<210> SEQ ID NO 17
<211> LENGTH: 39
<212> TYPE: PRT
<213> ORGANISM: Artificial Sequence
<220> FEATURE:
<223> OTHER INFORMATION: Synthetic Construct

<400> SEQUENCE: 17

Tyr Ala Gln Lys Phe Gln Gly Arg Ala Thr Leu Thr Val Asp Gln Ser
1               5                   10                  15

Thr Ser Thr Ala Tyr Met Glu Leu Ser Ser Leu Arg Ser Glu Asp Thr
            20                  25                  30

Ala Val Tyr Tyr Cys Ala Arg
        35

<210> SEQ ID NO 18
<211> LENGTH: 39
<212> TYPE: PRT
<213> ORGANISM: Artificial Sequence
<220> FEATURE:
<223> OTHER INFORMATION: Synthetic Construct

<400> SEQUENCE: 18

Tyr Ala Gln Lys Phe Gln Gly Arg Ala Thr Leu Thr Val Asp Asn Ser
1               5                   10                  15

Ala Ser Thr Ala Tyr Met Glu Leu Ser Ser Leu Arg Ser Glu Asp Thr
            20                  25                  30

Ala Val Tyr Tyr Cys Ala Arg
        35

<210> SEQ ID NO 19
<211> LENGTH: 39
<212> TYPE: PRT
<213> ORGANISM: Artificial Sequence
<220> FEATURE:
<223> OTHER INFORMATION: Synthetic Construct

<400> SEQUENCE: 19

Tyr Ala Gln Lys Phe Gln Gly Arg Ala Thr Leu Thr Val Asp Asn Pro
1               5                   10                  15

Thr Ser Thr Ala Tyr Met Glu Leu Ser Ser Leu Arg Ser Glu Asp Thr
            20                  25                  30

Ala Val Tyr Tyr Cys Ala Arg
        35

<210> SEQ ID NO 20
<211> LENGTH: 11
<212> TYPE: PRT
<213> ORGANISM: Artificial Sequence
<220> FEATURE:
<223> OTHER INFORMATION: Synthetic Construct

<400> SEQUENCE: 20

Trp Gly Gln Gly Thr Leu Val Thr Val Ser Ser
```

```
<210> SEQ ID NO 21
<211> LENGTH: 11
<212> TYPE: PRT
<213> ORGANISM: Artificial Sequence
<220> FEATURE:
<223> OTHER INFORMATION: Synthetic Construct

<400> SEQUENCE: 21

Trp Gly Gln Gly Thr Leu Leu Thr Val Ser Ser
1               5                   10

<210> SEQ ID NO 22
<211> LENGTH: 23
<212> TYPE: PRT
<213> ORGANISM: Artificial Sequence
<220> FEATURE:
<223> OTHER INFORMATION: Synthetic Construct

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 23
<211> LENGTH: 23
<212> TYPE: PRT
<213> ORGANISM: Artificial Sequence
<220> FEATURE:
<223> OTHER INFORMATION: Synthetic Construct

<400> SEQUENCE: 23

Asp Ile Gln Met Thr Gln Ser Pro Ser Ser Leu Pro Ala Ser Val Gly
1               5                   10                  15

Asp Arg Val Thr Ile Thr Cys
            20

<210> SEQ ID NO 24
<211> LENGTH: 23
<212> TYPE: PRT
<213> ORGANISM: Artificial Sequence
<220> FEATURE:
<223> OTHER INFORMATION: Synthetic Construct

<400> SEQUENCE: 24

Gly Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 25
<211> LENGTH: 23
<212> TYPE: PRT
<213> ORGANISM: Artificial Sequence
<220> FEATURE:
<223> OTHER INFORMATION: Synthetic Construct

<400> SEQUENCE: 25

Asp Ile Val Leu Thr Gln Ser Pro Asp Ser Leu Ala Val Ser Leu Gly
1               5                   10                  15

Glu Arg Ala Thr Ile Asn Cys
            20
```

```
<210> SEQ ID NO 26
<211> LENGTH: 23
<212> TYPE: PRT
<213> ORGANISM: Artificial Sequence
<220> FEATURE:
<223> OTHER INFORMATION: Synthetic Construct

<400> SEQUENCE: 26

Asp Ile Val Leu Thr Gln Ser Pro Asp Ser Leu Ala Val Ser Leu Gly
1               5                   10                  15

Glu Arg Ala Thr Ile Asp Cys
            20

<210> SEQ ID NO 27
<211> LENGTH: 15
<212> TYPE: PRT
<213> ORGANISM: Artificial Sequence
<220> FEATURE:
<223> OTHER INFORMATION: Synthetic Construct

<400> SEQUENCE: 27

Trp Tyr Gln Gln Lys Pro Gly Lys Ala Pro Lys Leu Leu Ile Lys
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Synthetic Construct

<400> SEQUENCE: 28

Trp Tyr Gln Gln Lys Pro Gly Gln Pro Pro Lys Leu Leu Ile Lys
1               5                   10                  15

<210> SEQ ID NO 29
<211> LENGTH: 32
<212> TYPE: PRT
<213> ORGANISM: Artificial Sequence
<220> FEATURE:
<223> OTHER INFORMATION: Synthetic Construct

<400> SEQUENCE: 29

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 30
<211> LENGTH: 32
<212> TYPE: PRT
<213> ORGANISM: Artificial Sequence
<220> FEATURE:
<223> OTHER INFORMATION: Synthetic Construct

<400> SEQUENCE: 30

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Leu Ala Thr Tyr Tyr Cys
            20                  25                  30

<210> SEQ ID NO 31
<211> LENGTH: 32
<212> TYPE: PRT
<213> ORGANISM: Artificial Sequence
```

<220> FEATURE:
<223> OTHER INFORMATION: Synthetic Construct

<400> SEQUENCE: 31

```
Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30
```

<210> SEQ ID NO 32
<211> LENGTH: 10
<212> TYPE: PRT
<213> ORGANISM: Artificial Sequence
<220> FEATURE:
<223> OTHER INFORMATION: Synthetic Construct

<400> SEQUENCE: 32

```
Phe Gly Gln Gly Thr Lys Leu Glu Ile Lys
1               5                   10
```

<210> SEQ ID NO 33
<211> LENGTH: 10
<212> TYPE: PRT
<213> ORGANISM: Artificial Sequence
<220> FEATURE:
<223> OTHER INFORMATION: Synthetic Construct

<400> SEQUENCE: 33

```
Phe Gly Gln Gly Thr Lys Leu Glu Ile Glu
1               5                   10
```

<210> SEQ ID NO 34
<211> LENGTH: 117
<212> TYPE: PRT
<213> ORGANISM: Artificial Sequence
<220> FEATURE:
<223> OTHER INFORMATION: Synthetic Construct

<400> SEQUENCE: 34

```
Gln Val Gln Leu Val Gln Ser Gly Ala Glu Val Lys Lys Pro Gly Ala
1               5                   10                  15

Ser Val Lys Val Ser Cys Lys Ala Ser Gly Ala Thr Phe Thr Asp Tyr
            20                  25                  30

Asn Phe His Trp Val Arg Gln Ala Pro Gly Gln Gly Leu Glu Trp Ile
        35                  40                  45

Gly Phe Ile Tyr Pro Ser Asn Gly Ile Thr Gly Tyr Ala Gln Asp Phe
    50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
            100                 105                 110

Val Thr Val Ser Ser
        115
```

<210> SEQ ID NO 35
<211> LENGTH: 117
<212> TYPE: PRT
<213> ORGANISM: Artificial Sequence
<220> FEATURE:
<223> OTHER INFORMATION: Synthetic Construct

<400> SEQUENCE: 35

```
Gln Val Gln Leu Val Gln Ser Gly Ala Glu Val Lys Lys Pro Gly Ala
1               5                   10                  15
Ser Val Lys Val Ser Cys Lys Ala Ser Gly Ala Thr Phe Thr Asp Tyr
            20                  25                  30
Asn Tyr His Trp Val Arg Gln Ala Pro Gly Gln Gly Leu Glu Trp Ile
        35                  40                  45
Gly Phe Ile Tyr Pro Ser Asn Gly Ile Thr Gly Tyr Ala Gln Lys Phe
    50                  55                  60
Gln Asp Arg Val Thr Met Thr Val Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Ser Phe Val Asp Tyr Phe Asp Tyr Trp Gly Gln Gly Thr Leu
                100                 105                 110
Val Thr Val Ser Ser
        115
```

<210> SEQ ID NO 36
<211> LENGTH: 117
<212> TYPE: PRT
<213> ORGANISM: Artificial Sequence
<220> FEATURE:
<223> OTHER INFORMATION: Synthetic Construct

<400> SEQUENCE: 36

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
Asn Tyr His Trp Val Arg Gln Ala Pro Gly Gln Gly Leu Glu Trp Ile
        35                  40                  45
Gly Phe Ile Tyr Pro Ser Asn Gly Ile Thr Gly Ser Ala Gln Lys Phe
    50                  55                  60
Gln Gly Arg Val Thr Met Thr Val Asp Thr Ser Thr Ser Thr Val Tyr
65                  70                  75                  80
Met Glu Leu Ser Ser Leu Arg Ser Glu Asp Thr Ala Val Tyr Tyr Cys
                85                  90                  95
Ala Arg Ser Asp Val Asp Tyr Phe Asp Tyr Trp Gly Gln Gly Thr Leu
                100                 105                 110
Val Thr Val Ser Ser
        115
```

<210> SEQ ID NO 37
<211> LENGTH: 117
<212> TYPE: PRT
<213> ORGANISM: Artificial Sequence
<220> FEATURE:
<223> OTHER INFORMATION: Synthetic Construct

<400> SEQUENCE: 37

```
Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr Asp Tyr
            20                  25                  30
Asn Tyr His Trp Val Arg Gln Ala Pro Gly Gln Gly Leu Glu Trp Ile
        35                  40                  45
```

Gly Phe Ile Tyr Pro Ser Asn Gly Ile Thr Gly Tyr Ala Gln Lys Phe
            50                  55                  60

Gln Gly Arg Val Thr Met Thr Val Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Asp Ser Thr Val Asp Tyr Phe Asp Tyr Trp Gly Gln Gly Thr Leu
            100                 105                 110

Val Thr Val Ser Ser
            115

<210> SEQ ID NO 38
<211> LENGTH: 117
<212> TYPE: PRT
<213> ORGANISM: Artificial Sequence
<220> FEATURE:
<223> OTHER INFORMATION: Synthetic Construct

<400> SEQUENCE: 38

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
            20                  25                  30

Asn Tyr His Trp Val Arg Gln Ala Pro Gly Gln Gly Leu Glu Trp Ile
        35                  40                  45

Gly Phe Ile Tyr Pro Ser Asn Gly Ile Thr Gly Tyr Ala Gln Lys Phe
    50                  55                  60

Gln Gly Arg Val Thr Met Thr Val Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Asp Val Asp Tyr Phe Asp Tyr Trp Gly Gln Gly Thr Leu
            100                 105                 110

Val Thr Val Ser Ser
            115

<210> SEQ ID NO 39
<211> LENGTH: 117
<212> TYPE: PRT
<213> ORGANISM: Artificial Sequence
<220> FEATURE:
<223> OTHER INFORMATION: Synthetic Construct

<400> SEQUENCE: 39

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asp Tyr
            20                  25                  30

Asn Tyr His Trp Val Arg Gln Ala Pro Gly Gln Gly Leu Glu Trp Ile
        35                  40                  45

Gly Phe Ile Tyr Pro Ser Asn Gly Ile Thr Gly Tyr Ala Gln Lys Phe
    50                  55                  60

Gln Gly Arg Val Thr Met Thr Val Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Ser Val Asp Tyr Phe Asp Tyr Trp Gly Gln Gly Thr Leu
            100                 105                 110

-continued

Val Thr Val Ser Ser
        115

<210> SEQ ID NO 40
<211> LENGTH: 117
<212> TYPE: PRT
<213> ORGANISM: Artificial Sequence
<220> FEATURE:
<223> OTHER INFORMATION: Synthetic Construct

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Asn Tyr His Trp Val Arg Gln Ala Pro Gly Gln Gly Leu Glu Trp Ile
            35                  40                  45

Gly Phe Ile Tyr Pro Ser Asn Gly Ile Thr Gly Tyr Ala Gln Lys Phe
        50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Thr Val Asp Tyr Phe Asp Tyr Trp Gly Gln Gly Thr Leu
                100                 105                 110

Val Thr Val Ser Ser
        115

<210> SEQ ID NO 41
<211> LENGTH: 117
<212> TYPE: PRT
<213> ORGANISM: Artificial Sequence
<220> FEATURE:
<223> OTHER INFORMATION: Synthetic Construct

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
                20                  25                  30

Asn Asn His Trp Val Arg Gln Ala Pro Gly Gln Gly Leu Glu Trp Ile
            35                  40                  45

Gly Phe Ile Tyr Pro Ser Asn Gly Ile Thr Gly Tyr Ala Gln Lys Phe
        50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
                100                 105                 110

Val Thr Val Ser Ser
        115

<210> SEQ ID NO 42
<211> LENGTH: 117
<212> TYPE: PRT
<213> ORGANISM: Artificial Sequence
<220> FEATURE:
<223> OTHER INFORMATION: Synthetic Construct

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
        35                  40                  45

Gly Phe Ile Tyr Pro Ser Asn Gly Ile Thr Gly Tyr Ala Gln Lys Phe
    50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Thr Val Asp Tyr Phe Asp Tyr Trp Gly Gln Gly Thr Leu
            100                 105                 110

Val Thr Val Ser Ser
        115

<210> SEQ ID NO 43
<211> LENGTH: 117
<212> TYPE: PRT
<213> ORGANISM: Artificial Sequence
<220> FEATURE:
<223> OTHER INFORMATION: Synthetic Construct

<400> SEQUENCE: 43

Gln Val Gln Leu Val Gln Ser Gly Ala Glu Val Lys Lys Pro Gly Ser
1               5                   10                  15

Ser Val Lys Val Ser Cys Lys Ala Ser Gly Val Thr Phe Thr Asp Tyr
            20                  25                  30

Asn Tyr His Trp Val Arg Gln Ala Pro Gly Gln Gly Leu Glu Trp Ile
        35                  40                  45

Gly Phe Ile Tyr Pro Ser Asn Gly Ile Thr Gly Tyr Ala Gln Lys Phe
    50                  55                  60

Gln Asp Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Thr Val Asp Tyr Phe Asp Tyr Trp Gly Gln Gly Thr Leu
            100                 105                 110

Val Thr Val Ser Ser
        115

<210> SEQ ID NO 44
<211> LENGTH: 117
<212> TYPE: PRT
<213> ORGANISM: Artificial Sequence
<220> FEATURE:
<223> OTHER INFORMATION: Synthetic Construct

<400> SEQUENCE: 44

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Ala Phe Thr Asp Tyr
            20                  25                  30

Asn Leu His Trp Val Arg Gln Ala Pro Gly Gln Gly Leu Glu Trp Ile
        35                  40                  45

```
Gly Phe Ile Tyr Pro Ser Asn Gly Ile Thr Gly Tyr Ala Gln Lys Phe
        50                  55                  60

Gln Gly Arg Val Thr Met Thr Val Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Asp Val Asp Tyr Phe Asp Tyr Trp Gly Gln Gly Thr Leu
            100                 105                 110

Val Thr Val Ser Ser
        115
```

<210> SEQ ID NO 45
<211> LENGTH: 117
<212> TYPE: PRT
<213> ORGANISM: Artificial Sequence
<220> FEATURE:
<223> OTHER INFORMATION: Synthetic Construct

<400> SEQUENCE: 45

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Glu Thr Asp Tyr
                20                  25                  30

Asn Leu His Trp Val Arg Gln Ala Pro Gly Gln Gly Leu Glu Trp Ile
            35                  40                  45

Gly Phe Ile Tyr Pro Ser Asn Gly Ile Thr Gly Tyr Ala Gln Lys Phe
        50                  55                  60

Gln Gly Arg Val Thr Met Thr Val Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Asp Val Asp Tyr Phe Asp Tyr Trp Gly Gln Gly Thr Leu
            100                 105                 110

Val Thr Val Ser Ser
        115
```

<210> SEQ ID NO 46
<211> LENGTH: 117
<212> TYPE: PRT
<213> ORGANISM: Artificial Sequence
<220> FEATURE:
<223> OTHER INFORMATION: Synthetic Construct

<400> SEQUENCE: 46

```
Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asp Tyr
                20                  25                  30

Asn Phe His Trp Val Arg Gln Ala Pro Gly Gln Gly Leu Glu Trp Ile
            35                  40                  45

Gly Phe Ile Tyr Pro Ala Asn Gly Ile Thr Gly Tyr Ala Gln Lys Asp
        50                  55                  60

Gln Gly Arg Val Thr Met Thr Val Asp Thr Ser Thr Ser Thr Val Tyr
 65                  70                  75                  80

Met Glu Leu Ser Ser Leu Arg Ser Glu Asp Thr Ala Val Tyr Tyr Cys
                 85                  90                  95

Ala Arg Ser Asp Val Asp Tyr Phe Asp Tyr Trp Gly Gln Gly Thr Leu
```

Val Thr Val Ser Ser
        115

<210> SEQ ID NO 47
<211> LENGTH: 117
<212> TYPE: PRT
<213> ORGANISM: Artificial Sequence
<220> FEATURE:
<223> OTHER INFORMATION: Synthetic Construct

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Phe His Trp Val Arg Gln Ala Pro Gly Gln Gly Leu Glu Trp Ile
        35                  40                  45

Gly Phe Ile Tyr Pro Ser Asn Gly Ile Thr Gly Tyr Ala Gln Lys Phe
    50                  55                  60

Thr Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Thr Val Asp Tyr Phe Asp Asp Trp Gly Gln Gly Thr Leu
            100                 105                 110

Val Thr Val Ser Ser
        115

<210> SEQ ID NO 48
<211> LENGTH: 117
<212> TYPE: PRT
<213> ORGANISM: Artificial Sequence
<220> FEATURE:
<223> OTHER INFORMATION: Synthetic Construct

<400> SEQUENCE: 48

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
        35                  40                  45

Gly Phe Ile Tyr Pro Ser Asn Gly Ile Arg Gly Tyr Ala Gln Lys Phe
    50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
            100                 105                 110

Val Thr Val Ser Ser
        115

<210> SEQ ID NO 49
<211> LENGTH: 117
<212> TYPE: PRT
<213> ORGANISM: Artificial Sequence
<220> FEATURE:

<223> OTHER INFORMATION: Synthetic Construct

<400> SEQUENCE: 49

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
        35                  40                  45

Gly Phe Ile Tyr Pro Ser Asn Gly Ile Thr Gly Tyr Ala Gln Lys Phe
    50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
            100                 105                 110

Val Thr Val Ser Ser
        115

<210> SEQ ID NO 50
<211> LENGTH: 117
<212> TYPE: PRT
<213> ORGANISM: Artificial Sequence
<220> FEATURE:
<223> OTHER INFORMATION: Synthetic Construct

<400> SEQUENCE: 50

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Tyr His Trp Val Arg Gln Ala Pro Gly Gln Gly Leu Glu Trp Ile
        35                  40                  45

Gly Phe Ile Tyr Pro Ser Asn Gly Ile Thr Gly Tyr Ala Gln Lys Phe
    50                  55                  60

Gln Gly Arg Val Thr Met Thr Val Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Leu Trp Gly Gln Gly Thr Leu
            100                 105                 110

Val Thr Val Ser Ser
        115

<210> SEQ ID NO 51
<211> LENGTH: 117
<212> TYPE: PRT
<213> ORGANISM: Artificial Sequence
<220> FEATURE:
<223> OTHER INFORMATION: Synthetic Construct

<400> SEQUENCE: 51

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr His Thr Asp Tyr
            20                  25                  30

Asn Leu His Trp Val Arg Gln Ala Pro Gly Gln Gly Leu Glu Trp Ile

```
                35                  40                  45
Gly Phe Ile Tyr Pro Ser Asn Gly Ile Thr Gly Tyr Ala Gln Lys Phe
         50                  55                  60
Gln Gly Arg Val Thr Met Thr Val Asp Thr Ser Thr Ser Thr Val Tyr
 65                  70                  75                  80
Met Glu Leu Ser Ser Leu Arg Ser Glu Asp Thr Ala Val Tyr Tyr Cys
                 85                  90                  95
Ala Arg Ser Asp Val Asp Tyr Phe Asp Tyr Trp Gly Gln Gly Thr Leu
                100                 105                 110
Val Thr Val Ser Ser
            115

<210> SEQ ID NO 52
<211> LENGTH: 117
<212> TYPE: PRT
<213> ORGANISM: Artificial Sequence
<220> FEATURE:
<223> OTHER INFORMATION: Synthetic Construct

<400> SEQUENCE: 52

Gln Val Gln Leu Val Gln Ser Gly Ala Glu Val Lys Lys Pro Gly Ala
  1               5                  10                  15
Ser Val Lys Ile Ser Cys Lys Ala Ser Gly Tyr Thr Phe Thr Asp Tyr
                 20                  25                  30
Asn Leu His Trp Val Arg Gln Ala Pro Gly Gln Gly Leu Glu Trp Ile
             35                  40                  45
Gly Phe Ile Tyr Pro Ser Asn Gly Ile Thr Gly Tyr Ala Gln Lys Phe
         50                  55                  60
Gln Gly Arg Ala Thr Leu Thr Val Asp Asn Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Ser Asp Val Asp Tyr Phe Asp Tyr Trp Gly Gln Gly Thr Leu
                100                 105                 110
Leu Thr Val Ser Ser
            115

<210> SEQ ID NO 53
<211> LENGTH: 117
<212> TYPE: PRT
<213> ORGANISM: Artificial Sequence
<220> FEATURE:
<223> OTHER INFORMATION: Synthetic Construct

<400> SEQUENCE: 53

Gln Val Gln Leu Val Gln Ser Gly Ala Glu Val Lys Lys Pro Gly Ala
  1               5                  10                  15
Ser Val Lys Ile Ser Cys Lys Ala Ser Gly Tyr Thr Phe Thr Asp Tyr
                 20                  25                  30
Asn Leu His Trp Val Arg Gln Ala Pro Gly Gln Gly Leu Glu Trp Ile
             35                  40                  45
Gly Phe Ile Tyr Pro Ser Asn Gly Ile Thr Gly Tyr Ala Gln Lys Phe
         50                  55                  60
Gln Gly Arg Ala Thr Leu Thr Val Asp Asn Ser Thr Ser Thr Ala Tyr
 65                  70                  75                  80
Met Glu Leu Ser Ser Leu Arg Ser Glu Asp Thr Ala Val Tyr Tyr Cys
                 85                  90                  95
```

-continued

Ala Arg Ser Thr Val Asp Tyr Phe Asp Tyr Trp Gly Gln Gly Thr Leu
            100                 105                 110

Leu Thr Val Ser Ser
        115

<210> SEQ ID NO 54
<211> LENGTH: 117
<212> TYPE: PRT
<213> ORGANISM: Artificial Sequence
<220> FEATURE:
<223> OTHER INFORMATION: Synthetic Construct

<400> SEQUENCE: 54

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
        35                  40                  45

Gly Phe Ile Tyr Pro Ser Asn Gly Ile Thr Gly Tyr Ala Glu Lys Phe
    50                  55                  60

Glu Gly Arg Ala Thr Leu Thr Val Asp Asn Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Phe Val Asp Tyr Phe Asp Tyr Trp Gly Gln Gly Thr Leu
            100                 105                 110

Leu Thr Val Ser Ser
        115

<210> SEQ ID NO 55
<211> LENGTH: 117
<212> TYPE: PRT
<213> ORGANISM: Artificial Sequence
<220> FEATURE:
<223> OTHER INFORMATION: Synthetic Construct

<400> SEQUENCE: 55

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Tyr His Trp Val Arg Gln Ala Pro Gly Gln Gly Leu Glu Trp Ile
        35                  40                  45

Gly Phe Ile Tyr Pro Ser Asn Gly Ile Thr Gly Tyr Ala Gln Lys Phe
    50                  55                  60

Phe Gly Arg Ala Thr Leu Thr Val Asp Asn Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
            100                 105                 110

Leu Thr Val Ser Ser
        115

<210> SEQ ID NO 56
<211> LENGTH: 117
<212> TYPE: PRT
<213> ORGANISM: Artificial Sequence
<220> FEATURE:
<223> OTHER INFORMATION: Synthetic Construct

<400> SEQUENCE: 56

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Tyr His Trp Val Arg Gln Ala Pro Gly Gln Gly Leu Glu Trp Ile
        35                  40                  45

Gly Phe Ile Tyr Pro Ser Asn Gly Ile Thr Gly Tyr Ala Gln Lys Phe
    50                  55                  60

Gln Gly Arg Ala Thr Leu Thr Val Asp Asn Ser Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ser Asp Val Asp Tyr Phe Asp Tyr Trp Gly Gln Gly Thr Leu
            100                 105                 110

Leu Thr Val Ser Ser
        115

<210> SEQ ID NO 57
<211> LENGTH: 117
<212> TYPE: PRT
<213> ORGANISM: Artificial Sequence
<220> FEATURE:
<223> OTHER INFORMATION: Synthetic Construct

<400> SEQUENCE: 57

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Tyr His Trp Val Arg Gln Ala Pro Gly Gln Gly Leu Glu Trp Ile
        35                  40                  45

Gly Phe Ile Tyr Pro Ser Asn Gly Ile Thr Gly Tyr Ala Gln Lys Phe
    50                  55                  60

Gln His Arg Ala Thr Leu Thr Val Asp Asn Ser Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ser Asp Val Asp Tyr Phe Asp Tyr Trp Gly Gln Gly Thr Leu
            100                 105                 110

Leu Thr Val Ser Ser
        115

<210> SEQ ID NO 58
<211> LENGTH: 117
<212> TYPE: PRT
<213> ORGANISM: Artificial Sequence
<220> FEATURE:
<223> OTHER INFORMATION: Synthetic Construct

<400> SEQUENCE: 58

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
            35                  40                  45

Gly Phe Ile Tyr Pro Ser Asn Gln Ile Thr Gly Tyr Ala Gln Lys Phe
    50                  55                  60

Gln Gly Arg Ala Thr Leu Thr Val Asp Asn Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
            100                 105                 110

Leu Thr Val Ser Ser
        115

<210> SEQ ID NO 59
<211> LENGTH: 117
<212> TYPE: PRT
<213> ORGANISM: Artificial Sequence
<220> FEATURE:
<223> OTHER INFORMATION: Synthetic Construct

<400> SEQUENCE: 59

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
            35                  40                  45

Gly Phe Ile Tyr Pro Ser Asn Arg Ile Thr Gly Tyr Ala Gln Lys Phe
    50                  55                  60

Gln Gly Arg Ala Thr Leu Thr Val Asp Asn Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
            100                 105                 110

Leu Thr Val Ser Ser
        115

<210> SEQ ID NO 60
<211> LENGTH: 117
<212> TYPE: PRT
<213> ORGANISM: Artificial Sequence
<220> FEATURE:
<223> OTHER INFORMATION: Synthetic Construct

<400> SEQUENCE: 60

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
            35                  40                  45

Gly Phe Ile Tyr Pro Ser Asn Val Ile Thr Gly Tyr Ala Gln Lys Phe
    50                  55                  60

Gln Gly Arg Ala Thr Leu Thr Val Asp Asn Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
            100                 105                 110

Leu Thr Val Ser Ser
        115

<210> SEQ ID NO 61
<211> LENGTH: 117
<212> TYPE: PRT
<213> ORGANISM: Artificial Sequence
<220> FEATURE:
<223> OTHER INFORMATION: Synthetic Construct

<400> SEQUENCE: 61

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
        35                  40                  45

Gly Phe Ile Tyr Pro Ser Asn Gly Ile Thr Gly Tyr Ala Gln Lys Phe
    50                  55                  60

Gln Gly Arg Ala Thr Leu Thr Val Asp Thr Ser Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ser Asp Val Asp Tyr Phe Asp Tyr Trp Gly Gln Gly Thr Leu
            100                 105                 110

Leu Thr Val Ser Ser
        115

<210> SEQ ID NO 62
<211> LENGTH: 117
<212> TYPE: PRT
<213> ORGANISM: Artificial Sequence
<220> FEATURE:
<223> OTHER INFORMATION: Synthetic Construct

<400> SEQUENCE: 62

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
        35                  40                  45

Gly Phe Ile Tyr Pro Ser Asn Gly Ile Thr Gly Tyr Ala Gln Lys Phe
    50                  55                  60

Gln Gly Arg Ala Thr Leu Thr Val Asp Gln Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Arg Ser Asp Val Asp Tyr Phe Asp Tyr Trp Gly Gln Gly Thr Leu
            100                 105                 110

Leu Thr Val Ser Ser
        115

<210> SEQ ID NO 63
<211> LENGTH: 117
<212> TYPE: PRT

```
<213> ORGANISM: Artificial Sequence
<220> FEATURE:
<223> OTHER INFORMATION: Synthetic Construct

<400> SEQUENCE: 63

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
        35                  40                  45

Gly Phe Ile Tyr Pro Ser Asn Gly Ile Thr Gly Tyr Ala Gln Lys Phe
    50                  55                  60

Gln Gly Arg Ala Thr Leu Thr Val Asp Asn Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
            100                 105                 110

Leu Thr Val Ser Ser
        115

<210> SEQ ID NO 64
<211> LENGTH: 117
<212> TYPE: PRT
<213> ORGANISM: Artificial Sequence
<220> FEATURE:
<223> OTHER INFORMATION: Synthetic Construct

<400> SEQUENCE: 64

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
        35                  40                  45

Gly Phe Ile Tyr Pro Ser Asn Gly Ile Thr Gly Tyr Ala Gln Lys Phe
    50                  55                  60

Gln Gly Arg Ala Thr Leu Thr Val Asp Asn Pro Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
            100                 105                 110

Leu Thr Val Ser Ser
        115

<210> SEQ ID NO 65
<211> LENGTH: 117
<212> TYPE: PRT
<213> ORGANISM: Artificial Sequence
<220> FEATURE:
<223> OTHER INFORMATION: Synthetic Construct

<400> SEQUENCE: 65

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30
```

```
Asn Leu His Trp Val Arg Gln Ala Pro Gly Gln Gly Leu Glu Trp Ile
        35                  40                  45

Gly Phe Ile Tyr Pro Ser Asn Gln Ile Thr Gly Tyr Ala Gln Lys Phe
    50                  55                  60

Gln Gly Arg Ala Thr Leu Thr Val Asp Asn Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
                100                 105                 110

Leu Thr Val Ser Ser
        115
```

<210> SEQ ID NO 66
<211> LENGTH: 117
<212> TYPE: PRT
<213> ORGANISM: Artificial Sequence
<220> FEATURE:
<223> OTHER INFORMATION: Synthetic Construct

<400> SEQUENCE: 66

```
Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
                20                  25                  30

Asn Leu His Trp Val Arg Gln Ala Pro Gly Gln Gly Leu Glu Trp Ile
        35                  40                  45

Gly Phe Ile Tyr Pro Ser Asn Gln Ile Thr Gly Tyr Ala Gln Lys Phe
    50                  55                  60

Gln Gly Arg Ala Thr Leu Thr Val Asp Asn Pro Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
                100                 105                 110

Leu Thr Val Ser Ser
        115
```

<210> SEQ ID NO 67
<211> LENGTH: 117
<212> TYPE: PRT
<213> ORGANISM: Artificial Sequence
<220> FEATURE:
<223> OTHER INFORMATION: Synthetic Construct

<400> SEQUENCE: 67

```
Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
                20                  25                  30

Asn Leu His Trp Val Arg Gln Ala Pro Gly Gln Gly Leu Glu Trp Ile
        35                  40                  45

Gly Phe Ile Tyr Pro Ser Asn Arg Ile Thr Gly Tyr Ala Gln Lys Phe
    50                  55                  60

Gln Gly Arg Ala Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
```

```
                    85                  90                  95
Ala Arg Ser Asp Val Asp Tyr Phe Asp Tyr Trp Gly Gln Gly Thr Leu
                100                 105                 110

Leu Thr Val Ser Ser
        115

<210> SEQ ID NO 68
<211> LENGTH: 117
<212> TYPE: PRT
<213> ORGANISM: Artificial Sequence
<220> FEATURE:
<223> OTHER INFORMATION: Synthetic Construct

<400> SEQUENCE: 68

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
                20                  25                  30

Asn Leu His Trp Val Arg Gln Ala Pro Gly Gln Gly Leu Glu Trp Ile
            35                  40                  45

Gly Phe Ile Tyr Pro Ser Asn Arg Ile Thr Gly Tyr Ala Gln Lys Phe
    50                  55                  60

Gln Gly Arg Ala Thr Leu Thr Val Asp Gln Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
                100                 105                 110

Leu Thr Val Ser Ser
        115

<210> SEQ ID NO 69
<211> LENGTH: 117
<212> TYPE: PRT
<213> ORGANISM: Artificial Sequence
<220> FEATURE:
<223> OTHER INFORMATION: Synthetic Construct

<400> SEQUENCE: 69

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
                20                  25                  30

Asn Leu His Trp Val Arg Gln Ala Pro Gly Gln Gly Leu Glu Trp Ile
            35                  40                  45

Gly Phe Ile Tyr Pro Ser Asn Arg Ile Thr Gly Tyr Ala Gln Lys Phe
    50                  55                  60

Gln Gly Arg Ala Thr Leu Thr Val Asp Asn Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
                100                 105                 110

Leu Thr Val Ser Ser
        115

<210> SEQ ID NO 70
<211> LENGTH: 117
```

<212> TYPE: PRT
<213> ORGANISM: Artificial Sequence
<220> FEATURE:
<223> OTHER INFORMATION: Synthetic Construct

<400> SEQUENCE: 70

Gln Val Gln Leu Val Gln Ser Gly Ala Glu Val Lys Lys Pro Gly Ala
1               5                   10                  15
Ser Val Lys Ile Ser Cys Lys Ala Ser Gly Tyr Thr Phe Thr Asp Tyr
            20                  25                  30
Asn Leu His Trp Val Arg Gln Ala Pro Gly Gln Gly Leu Glu Trp Ile
        35                  40                  45
Gly Phe Ile Tyr Pro Ser Asn Val Ile Thr Gly Tyr Ala Gln Lys Phe
    50                  55                  60
Gln Gly Arg Ala Thr Leu Thr Val Asp Thr Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Asp Val Asp Tyr Phe Asp Tyr Trp Gly Gln Gly Thr Leu
            100                 105                 110
Leu Thr Val Ser Ser
        115

<210> SEQ ID NO 71
<211> LENGTH: 117
<212> TYPE: PRT
<213> ORGANISM: Artificial Sequence
<220> FEATURE:
<223> OTHER INFORMATION: Synthetic Construct

<400> SEQUENCE: 71

Gln Val Gln Leu Val Gln Ser Gly Ala Glu Val Lys Lys Pro Gly Ala
1               5                   10                  15
Ser Val Lys Ile Ser Cys Lys Ala Ser Gly Tyr Thr Phe Thr Asp Tyr
            20                  25                  30
Asn Leu His Trp Val Arg Gln Ala Pro Gly Gln Gly Leu Glu Trp Ile
        35                  40                  45
Gly Phe Ile Tyr Pro Ser Asn Val Ile Thr Gly Tyr Ala Gln Lys Phe
    50                  55                  60
Gln Gly Arg Ala Thr Leu Thr Val Asp Gln Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Asp Val Asp Tyr Phe Asp Tyr Trp Gly Gln Gly Thr Leu
            100                 105                 110
Leu Thr Val Ser Ser
        115

<210> SEQ ID NO 72
<211> LENGTH: 117
<212> TYPE: PRT
<213> ORGANISM: Artificial Sequence
<220> FEATURE:
<223> OTHER INFORMATION: Synthetic Construct

<400> SEQUENCE: 72

Gln Val Gln Leu Val Gln Ser Gly Ala Glu Val Lys Lys Pro Gly Ala
1               5                   10                  15
Ser Val Lys Ile Ser Cys Lys Ala Ser Gly Tyr Thr Phe Thr Asp Tyr

```
            20                  25                  30
Asn Leu His Trp Val Arg Gln Ala Pro Gly Gln Gly Leu Glu Trp Ile
        35                  40                  45

Gly Phe Ile Tyr Pro Ser Asn Val Ile Thr Gly Tyr Ala Gln Lys Phe
    50                  55                  60

Gln Gly Arg Ala Thr Leu Thr Val Asp Asn Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
            100                 105                 110

Leu Thr Val Ser Ser
        115

<210> SEQ ID NO 73
<211> LENGTH: 117
<212> TYPE: PRT
<213> ORGANISM: Artificial Sequence
<220> FEATURE:
<223> OTHER INFORMATION: Synthetic Construct

<400> SEQUENCE: 73

Gln Val Gln Leu Val Gln Ser Gly Ala Glu Leu Lys Lys Pro Gly Ala
1               5                   10                  15

Ser Val Lys Val Ser Cys Lys Ala Ser Gly Tyr Thr Phe Thr Asp Tyr
            20                  25                  30

Asn Leu His Trp Val Arg Gln Ala Pro Gly Gln Arg Leu Glu Trp Ile
        35                  40                  45

Gly Phe Ile Tyr Pro Ser Asn Gly Ile Thr Gly Tyr Ser Gln Lys Phe
    50                  55                  60

Gln Gly Lys Ala Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Val Asp Tyr Phe Asp Tyr Trp Gly Gln Gly Thr Thr
            100                 105                 110

Val Thr Val Ser Ser
        115

<210> SEQ ID NO 74
<211> LENGTH: 117
<212> TYPE: PRT
<213> ORGANISM: Artificial Sequence
<220> FEATURE:
<223> OTHER INFORMATION: Synthetic Construct

<400> SEQUENCE: 74

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
        35                  40                  45

Gly Phe Ile Tyr Pro Ser Asn Gly Ile Thr Gly Tyr Ala Gln Lys Phe
    50                  55                  60

Gln Gly Arg Ala Thr Leu Thr Val Asp Thr Ser Thr Ser Thr Ala Tyr
65                  70                  75                  80
```

-continued

Met Glu Leu Ser Ser Leu Arg Ser Glu Asp Thr Ala Val Tyr Tyr Cys
                85                  90                  95

Ala Arg Ser Thr Val Asp Tyr Phe Asp Tyr Trp Gly Gln Gly Thr Leu
            100                 105                 110

Leu Thr Val Ser Ser
        115

<210> SEQ ID NO 75
<211> LENGTH: 117
<212> TYPE: PRT
<213> ORGANISM: Artificial Sequence
<220> FEATURE:
<223> OTHER INFORMATION: Synthetic Construct

<400> SEQUENCE: 75

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Met
        35                  40                  45

Gly Phe Ile Tyr Pro Ser Asn Gly Ile Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Thr Val Asp Tyr Phe Asp Tyr Trp Gly Gln Gly Thr Thr
            100                 105                 110

Val Thr Val Ser Ser
        115

<210> SEQ ID NO 76
<211> LENGTH: 117
<212> TYPE: PRT
<213> ORGANISM: Artificial Sequence
<220> FEATURE:
<223> OTHER INFORMATION: Synthetic Construct

<400> SEQUENCE: 76

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
        35                  40                  45

Gly Phe Ile Tyr Pro Ser Asn Gly Ile Thr Gly Tyr Ala Gln Lys Phe
    50                  55                  60

Gln Gly Arg Ala Thr Leu Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Val Asp Tyr Phe Asp Tyr Trp Gly Gln Gly Thr Thr
            100                 105                 110

Val Thr Val Ser Ser
        115

<210> SEQ ID NO 77

```
<211> LENGTH: 111
<212> TYPE: PRT
<213> ORGANISM: Artificial Sequence
<220> FEATURE:
<223> OTHER INFORMATION: Synthetic Construct

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Thr Ser
            20                  25                  30

Thr Tyr Ser Tyr Met His Trp Tyr Gln Gln Lys Pro Gly Lys Ala Pro
        35                  40                  45

Lys Leu Leu Ile Lys Tyr Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Trp
                85                  90                  95

Glu Ile Pro Leu Thr Phe Gly Gln Gly Thr Lys Leu Glu Ile Lys
            100                 105                 110

<210> SEQ ID NO 78
<211> LENGTH: 111
<212> TYPE: PRT
<213> ORGANISM: Artificial Sequence
<220> FEATURE:
<223> OTHER INFORMATION: Synthetic Construct

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ser
            20                  25                  30

Thr Tyr Ser Tyr Met His Trp Tyr Gln Gln Lys Pro Gly Lys Ala Pro
        35                  40                  45

Lys Leu Leu Ile Lys Tyr Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Trp
                85                  90                  95

Glu Ile Pro Leu Thr Phe Gly Gln Gly Thr Lys Leu Glu Ile Lys
            100                 105                 110

<210> SEQ ID NO 79
<211> LENGTH: 111
<212> TYPE: PRT
<213> ORGANISM: Artificial Sequence
<220> FEATURE:
<223> OTHER INFORMATION: Synthetic Construct

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ser
            20                  25                  30

Thr Tyr Ser Tyr Met His Trp Tyr Gln Gln Lys Pro Gly Lys Ala Pro
        35                  40                  45
```

```
Lys Leu Leu Ile Lys Tyr Val Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln His Ser Trp
                 85                  90                  95

Glu Ile Pro Leu Thr Phe Gly Gln Gly Thr Lys Leu Glu Ile Lys
            100                 105                 110

<210> SEQ ID NO 80
<211> LENGTH: 111
<212> TYPE: PRT
<213> ORGANISM: Artificial Sequence
<220> FEATURE:
<223> OTHER INFORMATION: Synthetic Construct

<400> SEQUENCE: 80

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Ser Thr Ser
                 20                  25                  30

Thr Tyr Ser Tyr Met His Trp Tyr Gln Arg Lys Pro Gly Lys Ala Pro
             35                  40                  45

Lys Leu Leu Ile Lys Tyr Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln His Ser Trp
                 85                  90                  95

Glu Ile Pro Leu Thr Phe Gly Gln Gly Thr Lys Leu Glu Ile Lys
            100                 105                 110

<210> SEQ ID NO 81
<211> LENGTH: 111
<212> TYPE: PRT
<213> ORGANISM: Artificial Sequence
<220> FEATURE:
<223> OTHER INFORMATION: Synthetic Construct

<400> SEQUENCE: 81

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Gly Thr Ser
                 20                  25                  30

Thr Tyr Ser Tyr Met His Trp Tyr Gln Gln Lys Pro Gly Lys Ala Pro
             35                  40                  45

Lys Leu Leu Ile Lys Tyr Ala Ser Ala Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln His Ser Trp
                 85                  90                  95

Glu Ile Pro Leu Thr Phe Gly Gln Gly Thr Lys Leu Glu Ile Lys
            100                 105                 110

<210> SEQ ID NO 82
<211> LENGTH: 111
<212> TYPE: PRT
<213> ORGANISM: Artificial Sequence
```

```
<220> FEATURE:
<223> OTHER INFORMATION: Synthetic Construct

<400> SEQUENCE: 82

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Gly Thr Ser
            20                  25                  30

Thr Tyr Ser Tyr Met His Trp Tyr Gln Gln Lys Pro Gly Lys Ala Pro
        35                  40                  45

Lys Leu Leu Ile Lys Tyr Ala Ser Asn Leu Glu Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Trp
                85                  90                  95

Glu Ile Pro Leu Thr Phe Gly Gln Gly Thr Lys Leu Glu Ile Lys
            100                 105                 110

<210> SEQ ID NO 83
<211> LENGTH: 111
<212> TYPE: PRT
<213> ORGANISM: Artificial Sequence
<220> FEATURE:
<223> OTHER INFORMATION: Synthetic Construct

<400> SEQUENCE: 83

Asp Ile Gln Met Thr Gln Ser Pro Ser Ser Leu Pro Ala Ser Val Gly
1               5                   10                  15

Asp Arg Val Thr Ile Thr Cys Arg Ala Ser Gln Ser Val Gly Thr Ser
            20                  25                  30

Thr Tyr Ser Tyr Met His Trp Tyr Gln Gln Lys Pro Gly Lys Ala Pro
        35                  40                  45

Lys Leu Leu Ile Lys Tyr Ala Ser Asn Leu Gly Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln His Ser Trp
                85                  90                  95

Glu Ile Pro Leu Thr Phe Gly Gln Gly Thr Lys Leu Glu Ile Lys
            100                 105                 110

<210> SEQ ID NO 84
<211> LENGTH: 111
<212> TYPE: PRT
<213> ORGANISM: Artificial Sequence
<220> FEATURE:
<223> OTHER INFORMATION: Synthetic Construct

<400> SEQUENCE: 84

Gly Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Gly Thr Ser
            20                  25                  30

Thr Tyr Ser Tyr Met His Trp Tyr Gln Gln Lys Pro Gly Lys Ala Pro
        35                  40                  45

Lys Leu Leu Ile Lys Tyr Ala Val Asn Leu Glu Ser Gly Val Pro Ser
    50                  55                  60
```

```
Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln His Ser Trp
                 85                  90                  95

Glu Ile Pro Leu Thr Phe Gly Gln Gly Thr Lys Leu Glu Ile Lys
                100                 105                 110

<210> SEQ ID NO 85
<211> LENGTH: 111
<212> TYPE: PRT
<213> ORGANISM: Artificial Sequence
<220> FEATURE:
<223> OTHER INFORMATION: Synthetic Construct

<400> SEQUENCE: 85

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Val Ser Ala Ser
                 20                  25                  30

Thr Tyr Ser Tyr Met His Trp Tyr Gln Gln Lys Pro Gly Lys Ala Pro
             35                  40                  45

Lys Leu Leu Ile Lys Tyr Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Leu Ala Thr Tyr Tyr Cys Gln His Ser Trp
                 85                  90                  95

Glu Ile Pro Leu Thr Phe Gly Gln Gly Thr Lys Leu Glu Ile Lys
                100                 105                 110

<210> SEQ ID NO 86
<211> LENGTH: 111
<212> TYPE: PRT
<213> ORGANISM: Artificial Sequence
<220> FEATURE:
<223> OTHER INFORMATION: Synthetic Construct

<400> SEQUENCE: 86

Asp Ile Val Leu Thr Gln Ser Pro Asp Ser Leu Ala Val Ser Leu Gly
 1               5                  10                  15

Glu Arg Ala Thr Ile Asn Cys Arg Ala Ser Gln Ser Val Ser Thr Ser
                 20                  25                  30

Thr Tyr Ser Tyr Met His Trp Tyr Gln Gln Lys Pro Gly Gln Pro Pro
             35                  40                  45

Lys Leu Leu Ile Lys Tyr Ala Ser Asn Leu Glu Ser Gly Val Pro Asp
 50                  55                  60

Arg Phe Ser Gly Ser Gly Ser Gly Thr Asp Phe Thr Leu Thr Ile Ser
 65                  70                  75                  80

Ser Leu Gln Ala Glu Asp Val Ala Val Tyr Tyr Cys Gln His Ser Trp
                 85                  90                  95

Glu Ile Pro Leu Thr Phe Gly Gln Gly Thr Lys Leu Glu Ile Lys
                100                 105                 110

<210> SEQ ID NO 87
<211> LENGTH: 111
<212> TYPE: PRT
<213> ORGANISM: Artificial Sequence
<220> FEATURE:
<223> OTHER INFORMATION: Synthetic Construct
```

<400> SEQUENCE: 87

Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Asp Val Ser Thr Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Leu Thr Phe Gly Gln Gly Thr Lys Leu Glu Ile Lys
            100                 105                 110

<210> SEQ ID NO 88
<211> LENGTH: 111
<212> TYPE: PRT
<213> ORGANISM: Artificial Sequence
<220> FEATURE:
<223> OTHER INFORMATION: Synthetic Construct

<400> SEQUENCE: 88

Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Asp Val Ser Thr Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Phe Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Leu Glu Phe Gly Gln Gly Thr Lys Leu Glu Ile Lys
            100                 105                 110

<210> SEQ ID NO 89
<211> LENGTH: 111
<212> TYPE: PRT
<213> ORGANISM: Artificial Sequence
<220> FEATURE:
<223> OTHER INFORMATION: Synthetic Construct

<400> SEQUENCE: 89

Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Asp Val Ser Thr Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Tyr Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

```
Ser Leu Gln Ala Glu Asp Val Ala Val Tyr Tyr Cys Glu His Ser Trp
                85                  90                  95

Glu Ile Pro Leu Thr Phe Gly Gln Gly Thr Lys Leu Glu Ile Lys
            100                 105                 110
```

<210> SEQ ID NO 90
<211> LENGTH: 111
<212> TYPE: PRT
<213> ORGANISM: Artificial Sequence
<220> FEATURE:
<223> OTHER INFORMATION: Synthetic Construct

<400> SEQUENCE: 90

```
Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Asp Val Ser Thr Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Leu Pro Leu Thr Phe Gly Gln Gly Thr Lys Leu Glu Ile Lys
            100                 105                 110
```

<210> SEQ ID NO 91
<211> LENGTH: 111
<212> TYPE: PRT
<213> ORGANISM: Artificial Sequence
<220> FEATURE:
<223> OTHER INFORMATION: Synthetic Construct

<400> SEQUENCE: 91

```
Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Asp Val Ser Thr Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Ala Ile Pro Leu Thr Phe Gly Gln Gly Thr Lys Leu Glu Ile Lys
            100                 105                 110
```

<210> SEQ ID NO 92
<211> LENGTH: 111
<212> TYPE: PRT
<213> ORGANISM: Artificial Sequence
<220> FEATURE:
<223> OTHER INFORMATION: Synthetic Construct

<400> SEQUENCE: 92

```
Asp Ile Val Leu Thr Gln Ser Pro Asp Ser Leu Ala Val Ser Leu Gly
```

-continued

```
                1               5                  10                 15
Glu Arg Ala Thr Ile Asn Cys Arg Ala Ser Gln Ser Val Ser Thr Ser
                20                  25                 30

Thr Tyr Ser Tyr Met His Trp Tyr Gln Gln Lys Pro Gly Gln Pro Pro
            35                  40                 45

Lys Leu Leu Ile Lys Tyr Ala Ser Asn Leu Glu Ser Gly Val Pro Asp
        50                  55                 60

Arg Phe Ser Gly Ser Gly Ser Gly Thr Asp Phe Thr Leu Thr Ile Ser
65                  70                 75                  80

Ser Leu Gln Ala Glu Asp Val Ala Val Tyr Tyr Cys Gln His Ser Glu
                85                  90                 95

Glu Ile Pro Leu Thr Phe Gly Gln Gly Thr Lys Leu Glu Ile Lys
                100                 105                110
```

<210> SEQ ID NO 93
<211> LENGTH: 111
<212> TYPE: PRT
<213> ORGANISM: Artificial Sequence
<220> FEATURE:
<223> OTHER INFORMATION: Synthetic Construct

<400> SEQUENCE: 93

```
Asp Ile Val Leu Thr Gln Ser Pro Asp Ser Leu Ala Val Ser Leu Gly
1               5                  10                 15

Glu Arg Ala Thr Ile Asp Cys Lys Ala Ser Gln Asp Val Ser Thr Ser
                20                  25                 30

Thr Tyr Ser Tyr Met His Trp Tyr Gln Gln Lys Pro Gly Gln Pro Pro
            35                  40                 45

Lys Leu Leu Ile Lys Tyr Ala Ser Asn Leu Glu Ser Gly Val Pro Asp
        50                  55                 60

Arg Phe Ser Gly Ser Gly Ser Gly Thr Asp Phe Thr Leu Thr Ile Ser
65                  70                 75                  80

Ser Leu Gln Ala Glu Asp Val Ala Val Tyr Tyr Cys Gln His Ser Trp
                85                  90                 95

Glu Ile Pro Leu Thr Phe Gly Gln Gly Thr Lys Leu Glu Ile Lys
                100                 105                110
```

<210> SEQ ID NO 94
<211> LENGTH: 111
<212> TYPE: PRT
<213> ORGANISM: Artificial Sequence
<220> FEATURE:
<223> OTHER INFORMATION: Synthetic Construct

<400> SEQUENCE: 94

```
Asp Ile Val Leu Thr Gln Ser Pro Asp Ser Leu Ala Val Ser Leu Gly
1               5                  10                 15

Glu Arg Ala Thr Ile Asn Cys Arg Ala Ser Gln Asp Val Ser Thr Ser
                20                  25                 30

Thr Tyr Ser Tyr Met His Trp Tyr Gln Gln Lys Pro Gly Gln Pro Pro
            35                  40                 45

Lys Leu Leu Ile Lys Tyr Ala Ser Asn Val Glu Ser Gly Val Pro Asp
        50                  55                 60

Arg Phe Ser Gly Ser Gly Ser Gly Thr Asp Phe Thr Leu Thr Ile Ser
65                  70                 75                  80

Ser Leu Gln Ala Glu Asp Val Ala Val Tyr Tyr Cys Gln His Ser Trp
                85                  90                 95
```

```
Glu Ile Pro Leu Thr Phe Gly Gln Gly Thr Lys Leu Glu Ile Glu
            100                 105                 110
```

<210> SEQ ID NO 95
<211> LENGTH: 111
<212> TYPE: PRT
<213> ORGANISM: Artificial Sequence
<220> FEATURE:
<223> OTHER INFORMATION: Synthetic Construct

<400> SEQUENCE: 95

```
Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Ser Val His Thr Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Leu Thr Phe Gly Gln Gly Thr Lys Leu Glu Ile Lys
            100                 105                 110
```

<210> SEQ ID NO 96
<211> LENGTH: 111
<212> TYPE: PRT
<213> ORGANISM: Artificial Sequence
<220> FEATURE:
<223> OTHER INFORMATION: Synthetic Construct

<400> SEQUENCE: 96

```
Asp Ile Val Leu Thr Gln Ser Pro Asp Ser Leu Ala Val Ser Leu Gly
1               5                   10                  15

Glu Arg Ala Thr Ile Asn Cys Arg Gly Ser Gln Ser Val Ser Thr Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Glu Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Leu Thr Phe Gly Gln Gly Thr Lys Leu Glu Ile Lys
            100                 105                 110
```

<210> SEQ ID NO 97
<211> LENGTH: 111
<212> TYPE: PRT
<213> ORGANISM: Artificial Sequence
<220> FEATURE:
<223> OTHER INFORMATION: Synthetic Construct

<400> SEQUENCE: 97

```
Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Ser Val Ser Thr Ser
```

```
                    20                  25                  30

Thr Tyr Ser Tyr Met His Trp Tyr Gln Gln Lys Pro Gly Gln Pro Pro
            35                  40                  45

Lys Leu Leu Ile Lys Tyr Glu Ser Asn Leu Glu Ser Gly Val Pro Asp
        50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Leu Thr Phe Gly Gln Gly Thr Lys Leu Glu Ile Lys
            100                 105                 110

<210> SEQ ID NO 98
<211> LENGTH: 111
<212> TYPE: PRT
<213> ORGANISM: Artificial Sequence
<220> FEATURE:
<223> OTHER INFORMATION: Synthetic Construct

<400> SEQUENCE: 98

Asp Ile Val Leu Thr Gln Ser Pro Asp Ser Leu Ala Val Ser Leu Gly
1               5                   10                  15

Glu Arg Ala Thr Ile Asn Cys Arg Val Ser Gln Asp Val Ser Thr Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Leu Thr Phe Gly Gln Gly Thr Lys Leu Glu Ile Lys
            100                 105                 110

<210> SEQ ID NO 99
<211> LENGTH: 111
<212> TYPE: PRT
<213> ORGANISM: Artificial Sequence
<220> FEATURE:
<223> OTHER INFORMATION: Synthetic Construct

<400> SEQUENCE: 99

Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Ser Val Gly Thr Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Leu Thr Phe Gly Gln Gly Thr Lys Leu Glu Ile Lys
            100                 105                 110
```

```
<210> SEQ ID NO 100
<211> LENGTH: 111
<212> TYPE: PRT
<213> ORGANISM: Artificial Sequence
<220> FEATURE:
<223> OTHER INFORMATION: Synthetic Construct

<400> SEQUENCE: 100

Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Asp Val Ser Thr Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Phe Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Leu Thr Phe Gly Gln Gly Thr Lys Leu Glu Ile Lys
            100                 105                 110

<210> SEQ ID NO 101
<211> LENGTH: 111
<212> TYPE: PRT
<213> ORGANISM: Artificial Sequence
<220> FEATURE:
<223> OTHER INFORMATION: Synthetic Construct

<400> SEQUENCE: 101

Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Ser Val Gly Thr Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Asn Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Glu
                85                  90                  95

Glu Ile Pro Leu Thr Phe Gly Gln Gly Thr Lys Leu Glu Ile Lys
            100                 105                 110

<210> SEQ ID NO 102
<211> LENGTH: 111
<212> TYPE: PRT
<213> ORGANISM: Artificial Sequence
<220> FEATURE:
<223> OTHER INFORMATION: Synthetic Construct

<400> SEQUENCE: 102

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Val Ser Thr Ser
            20                  25                  30

Thr Tyr Ser Tyr Met His Trp Tyr Gln Gln Lys Pro Gly Lys Ala Pro
```

35                  40                  45

Lys Leu Leu Ile Tyr Tyr Ala Ser Asn Leu Glu Ser Gly Val Pro Ser
 50                  55                  60

Arg Phe Ser Gly Ser Gly Ser Gly Thr Asp Phe Thr Leu Thr Ile Ser
 65                  70                  75                  80

Ser Leu Gln Pro Glu Asp Phe Ala Thr Tyr Tyr Cys Gln His Ser Trp
                 85                  90                  95

Glu Ile Pro Leu Thr Phe Gly Gln Gly Thr Lys Leu Glu Ile Lys
            100                 105                 110

<210> SEQ ID NO 103
<211> LENGTH: 117
<212> TYPE: PRT
<213> ORGANISM: Mus musculus

<400> SEQUENCE: 103

Glu Val Gln Leu Gln Gln Ser Gly Pro Glu Leu Val Lys Pro Gly Ala
 1               5                  10                  15

Ser Val Lys Ile Ser Cys Lys Ala Ser Gly Tyr Thr Phe Thr Asp Tyr
                 20                  25                  30

Asn Leu His Trp Val Lys Leu Ser His Gly Lys Ser Leu Glu Trp Ile
             35                  40                  45

Gly Phe Ile Tyr Pro Ser Asn Gly Ile Thr Gly Tyr Asn Gln Lys Phe
 50                  55                  60

Lys Asn Lys Ala Thr Leu Thr Val Asp Asn Ser Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Arg Ser Thr Val Asp Tyr Phe Asp Tyr Trp Gly Gln Gly Thr Thr
            100                 105                 110

Leu Thr Val Ser Ser
        115

<210> SEQ ID NO 104
<211> LENGTH: 111
<212> TYPE: PRT
<213> ORGANISM: Mus musculus

<400> SEQUENCE: 104

Asp Ile Val Leu Thr Gln Ser Pro Ala Ser Leu Ala Val Ser Leu Gly
 1               5                  10                  15

Gln Arg Ala Thr Met Ser Cys Arg Ala Ser Gln Ser Val Ser Thr Ser
                 20                  25                  30

Thr Tyr Ser Tyr Met His Trp Tyr Gln Gln Lys Pro Gly Gln Pro Pro
             35                  40                  45

Lys Leu Leu Ile Lys Tyr Ala Ser Asn Leu Glu Ser Gly Val Pro Ala
 50                  55                  60

Arg Phe Ser Gly Ser Gly Ser Gly Thr Asp Phe Thr Leu Asn Ile His
 65                  70                  75                  80

Pro Val Glu Glu Glu Asp Thr Ala Thr Tyr Tyr Cys Gln His Ser Trp
                 85                  90                  95

Glu Ile Pro Leu Thr Phe Gly Ala Gly Thr Lys Leu Glu Leu Lys
            100                 105                 110

<210> SEQ ID NO 105
<211> LENGTH: 10
<212> TYPE: PRT

```
<213> ORGANISM: Artificial Sequence
<220> FEATURE:
<223> OTHER INFORMATION: Synthetic Construct

<400> SEQUENCE: 105

Gly Tyr Thr Phe Thr Asp Tyr Asn Leu His
1               5                   10

<210> SEQ ID NO 106
<211> LENGTH: 10
<212> TYPE: PRT
<213> ORGANISM: Artificial Sequence
<220> FEATURE:
<223> OTHER INFORMATION: Synthetic Construct

<400> SEQUENCE: 106

Gly Ala Thr Phe Thr Asp Tyr Asn Phe His
1               5                   10

<210> SEQ ID NO 107
<211> LENGTH: 10
<212> TYPE: PRT
<213> ORGANISM: Artificial Sequence
<220> FEATURE:
<223> OTHER INFORMATION: Synthetic Construct

<400> SEQUENCE: 107

Gly Ala Thr Phe Thr Asp Tyr Asn Tyr His
1               5                   10

<210> SEQ ID NO 108
<211> LENGTH: 10
<212> TYPE: PRT
<213> ORGANISM: Artificial Sequence
<220> FEATURE:
<223> OTHER INFORMATION: Synthetic Construct

<400> SEQUENCE: 108

Gly Tyr Thr Phe Thr Asp Tyr Asn Tyr His
1               5                   10

<210> SEQ ID NO 109
<211> LENGTH: 10
<212> TYPE: PRT
<213> ORGANISM: Artificial Sequence
<220> FEATURE:
<223> OTHER INFORMATION: Synthetic Construct

<400> SEQUENCE: 109

Gly Tyr Thr Phe Thr Asp Tyr Asn Asn His
1               5                   10

<210> SEQ ID NO 110
<211> LENGTH: 10
<212> TYPE: PRT
<213> ORGANISM: Artificial Sequence
<220> FEATURE:
<223> OTHER INFORMATION: Synthetic Construct

<400> SEQUENCE: 110

Gly Val Thr Phe Thr Asp Tyr Asn Tyr His
1               5                   10

<210> SEQ ID NO 111
<211> LENGTH: 10
<212> TYPE: PRT
<213> ORGANISM: Artificial Sequence
```

```
<220> FEATURE:
<223> OTHER INFORMATION: Synthetic Construct

<400> SEQUENCE: 111

Gly Tyr Ala Phe Thr Asp Tyr Asn Leu His
1               5                   10

<210> SEQ ID NO 112
<211> LENGTH: 10
<212> TYPE: PRT
<213> ORGANISM: Artificial Sequence
<220> FEATURE:
<223> OTHER INFORMATION: Synthetic Construct

<400> SEQUENCE: 112

Gly Tyr Thr Glu Thr Asp Tyr Asn Leu His
1               5                   10

<210> SEQ ID NO 113
<211> LENGTH: 10
<212> TYPE: PRT
<213> ORGANISM: Artificial Sequence
<220> FEATURE:
<223> OTHER INFORMATION: Synthetic Construct

<400> SEQUENCE: 113

Gly Tyr Thr Phe Thr Asp Tyr Asn Phe His
1               5                   10

<210> SEQ ID NO 114
<211> LENGTH: 10
<212> TYPE: PRT
<213> ORGANISM: Artificial Sequence
<220> FEATURE:
<223> OTHER INFORMATION: Synthetic Construct

<400> SEQUENCE: 114

Gly Tyr Thr His Thr Asp Tyr Asn Leu His
1               5                   10

<210> SEQ ID NO 115
<211> LENGTH: 10
<212> TYPE: PRT
<213> ORGANISM: Artificial Sequence
<220> FEATURE:
<223> OTHER INFORMATION: Synthetic Construct

<400> SEQUENCE: 115

Phe Ile Tyr Pro Ser Asn Gly Ile Thr Gly
1               5                   10

<210> SEQ ID NO 116
<211> LENGTH: 10
<212> TYPE: PRT
<213> ORGANISM: Artificial Sequence
<220> FEATURE:
<223> OTHER INFORMATION: Synthetic Construct

<400> SEQUENCE: 116

Phe Ile Tyr Pro Ala Asn Gly Ile Thr Gly
1               5                   10

<210> SEQ ID NO 117
<211> LENGTH: 10
<212> TYPE: PRT
<213> ORGANISM: Artificial Sequence
<220> FEATURE:
```

```
<223> OTHER INFORMATION: Synthetic Construct

<400> SEQUENCE: 117

Phe Ile Tyr Pro Ser Asn Gly Ile Arg Gly
1               5                   10

<210> SEQ ID NO 118
<211> LENGTH: 10
<212> TYPE: PRT
<213> ORGANISM: Artificial Sequence
<220> FEATURE:
<223> OTHER INFORMATION: Synthetic Construct

<400> SEQUENCE: 118

Phe Ile Tyr Pro Ser Asn Gln Ile Thr Gly
1               5                   10

<210> SEQ ID NO 119
<211> LENGTH: 10
<212> TYPE: PRT
<213> ORGANISM: Artificial Sequence
<220> FEATURE:
<223> OTHER INFORMATION: Synthetic Construct

<400> SEQUENCE: 119

Phe Ile Tyr Pro Ser Asn Arg Ile Thr Gly
1               5                   10

<210> SEQ ID NO 120
<211> LENGTH: 10
<212> TYPE: PRT
<213> ORGANISM: Artificial Sequence
<220> FEATURE:
<223> OTHER INFORMATION: Synthetic Construct

<400> SEQUENCE: 120

Phe Ile Tyr Pro Ser Asn Val Ile Thr Gly
1               5                   10

<210> SEQ ID NO 121
<211> LENGTH: 8
<212> TYPE: PRT
<213> ORGANISM: Artificial Sequence
<220> FEATURE:
<223> OTHER INFORMATION: Synthetic Construct

<400> SEQUENCE: 121

Ser Thr Val Asp Tyr Phe Asp Tyr
1               5

<210> SEQ ID NO 122
<211> LENGTH: 8
<212> TYPE: PRT
<213> ORGANISM: Artificial Sequence
<220> FEATURE:
<223> OTHER INFORMATION: Synthetic Construct

<400> SEQUENCE: 122

Ser Asp Val Asp Tyr Phe Asp Tyr
1               5

<210> SEQ ID NO 123
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 123

Ser Phe Val Asp Tyr Phe Asp Tyr
1               5

<210> SEQ ID NO 124
<211> LENGTH: 8
<212> TYPE: PRT
<213> ORGANISM: Artificial Sequence
<220> FEATURE:
<223> OTHER INFORMATION: Synthetic Construct

<400> SEQUENCE: 124

Ser Ser Val Asp Tyr Phe Asp Tyr
1               5

<210> SEQ ID NO 125
<211> LENGTH: 8
<212> TYPE: PRT
<213> ORGANISM: Artificial Sequence
<220> FEATURE:
<223> OTHER INFORMATION: Synthetic Construct

<400> SEQUENCE: 125

Ser Thr Val Asp Tyr Phe Asp Asp
1               5

<210> SEQ ID NO 126
<211> LENGTH: 8
<212> TYPE: PRT
<213> ORGANISM: Artificial Sequence
<220> FEATURE:
<223> OTHER INFORMATION: Synthetic Construct

<400> SEQUENCE: 126

Ser Asp Val Asp Tyr Phe Asp Leu
1               5

<210> SEQ ID NO 127
<211> LENGTH: 15
<212> TYPE: PRT
<213> ORGANISM: Artificial Sequence
<220> FEATURE:
<223> OTHER INFORMATION: Synthetic Construct

<400> SEQUENCE: 127

Arg Ala Ser Gln Ser Val Ser Thr Ser Thr Tyr Ser Tyr Met His
1               5                   10                  15

<210> SEQ ID NO 128
<211> LENGTH: 15
<212> TYPE: PRT
<213> ORGANISM: Artificial Sequence
<220> FEATURE:
<223> OTHER INFORMATION: Synthetic Construct

<400> SEQUENCE: 128

Arg Ala Ser Gln Ser Val Gly Thr Ser Thr Tyr Ser Tyr Met His
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: Synthetic Construct
```

```
<400> SEQUENCE: 129

Arg Ala Ser Gln Ser Val Ser Ala Ser Thr Tyr Ser Tyr Met His
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: Synthetic Construct

<400> SEQUENCE: 130

Arg Ala Ser Gln Asp Val Ser Thr Ser Thr Tyr Ser Tyr Met His
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: Synthetic Construct

<400> SEQUENCE: 131

Lys Ala Ser Gln Asp Val Ser Thr Ser Thr Tyr Ser Tyr Met His
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: Synthetic Construct

<400> SEQUENCE: 132

Arg Ala Ser Gln Ser Val His Thr Ser Thr Tyr Ser Tyr Met His
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: Synthetic Construct

<400> SEQUENCE: 133

Arg Gly Ser Gln Ser Val Ser Thr Ser Thr Tyr Ser Tyr Met His
1               5                   10                  15

<210> SEQ ID NO 134
<211> LENGTH: 15
<212> TYPE: PRT
<213> ORGANISM: Artificial Sequence
<220> FEATURE:
<223> OTHER INFORMATION: Synthetic Construct

<400> SEQUENCE: 134

Arg Val Ser Gln Asp Val Ser Thr Ser Thr Tyr Ser Tyr Met His
1               5                   10                  15

<210> SEQ ID NO 135
<211> LENGTH: 7
<212> TYPE: PRT
<213> ORGANISM: Artificial Sequence
<220> FEATURE:
<223> OTHER INFORMATION: Synthetic Construct

<400> SEQUENCE: 135
```

```
Tyr Ala Ser Asn Leu Glu Ser
1               5

<210> SEQ ID NO 136
<211> LENGTH: 7
<212> TYPE: PRT
<213> ORGANISM: Artificial Sequence
<220> FEATURE:
<223> OTHER INFORMATION: Synthetic Construct

<400> SEQUENCE: 136

Tyr Val Ser Asn Leu Glu Ser
1               5

<210> SEQ ID NO 137
<211> LENGTH: 7
<212> TYPE: PRT
<213> ORGANISM: Artificial Sequence
<220> FEATURE:
<223> OTHER INFORMATION: Synthetic Construct

<400> SEQUENCE: 137

Tyr Ala Ser Ala Leu Glu Ser
1               5

<210> SEQ ID NO 138
<211> LENGTH: 7
<212> TYPE: PRT
<213> ORGANISM: Artificial Sequence
<220> FEATURE:
<223> OTHER INFORMATION: Synthetic Construct

<400> SEQUENCE: 138

Tyr Ala Ser Asn Leu Gly Ser
1               5

<210> SEQ ID NO 139
<211> LENGTH: 7
<212> TYPE: PRT
<213> ORGANISM: Artificial Sequence
<220> FEATURE:
<223> OTHER INFORMATION: Synthetic Construct

<400> SEQUENCE: 139

Tyr Ala Val Asn Leu Glu Ser
1               5

<210> SEQ ID NO 140
<211> LENGTH: 7
<212> TYPE: PRT
<213> ORGANISM: Artificial Sequence
<220> FEATURE:
<223> OTHER INFORMATION: Synthetic Construct

<400> SEQUENCE: 140

Tyr Ala Phe Asn Leu Glu Ser
1               5

<210> SEQ ID NO 141
<211> LENGTH: 7
<212> TYPE: PRT
<213> ORGANISM: Artificial Sequence
<220> FEATURE:
<223> OTHER INFORMATION: Synthetic Construct

<400> SEQUENCE: 141
```

Tyr Ala Ser Tyr Leu Glu Ser
1               5

<210> SEQ ID NO 142
<211> LENGTH: 7
<212> TYPE: PRT
<213> ORGANISM: Artificial Sequence
<220> FEATURE:
<223> OTHER INFORMATION: Synthetic Construct

<400> SEQUENCE: 142

Tyr Ala Ser Asn Val Glu Ser
1               5

<210> SEQ ID NO 143
<211> LENGTH: 7
<212> TYPE: PRT
<213> ORGANISM: Artificial Sequence
<220> FEATURE:
<223> OTHER INFORMATION: Synthetic Construct

<400> SEQUENCE: 143

Tyr Glu Ser Asn Leu Glu Ser
1               5

<210> SEQ ID NO 144
<211> LENGTH: 7
<212> TYPE: PRT
<213> ORGANISM: Artificial Sequence
<220> FEATURE:
<223> OTHER INFORMATION: Synthetic Construct

<400> SEQUENCE: 144

Tyr Ala Ser Phe Leu Glu Ser
1               5

<210> SEQ ID NO 145
<211> LENGTH: 7
<212> TYPE: PRT
<213> ORGANISM: Artificial Sequence
<220> FEATURE:
<223> OTHER INFORMATION: Synthetic Construct

<400> SEQUENCE: 145

Tyr Ala Ser Asn Leu Asn Ser
1               5

<210> SEQ ID NO 146
<211> LENGTH: 9
<212> TYPE: PRT
<213> ORGANISM: Artificial Sequence
<220> FEATURE:
<223> OTHER INFORMATION: Synthetic Construct

<400> SEQUENCE: 146

Gln His Ser Trp Glu Ile Pro Leu Thr
1               5

<210> SEQ ID NO 147
<211> LENGTH: 9
<212> TYPE: PRT
<213> ORGANISM: Artificial Sequence
<220> FEATURE:
<223> OTHER INFORMATION: Synthetic Construct

<400> SEQUENCE: 147

Gln His Ser Trp Glu Ile Pro Leu Glu

```
1               5
```

<210> SEQ ID NO 148
<211> LENGTH: 9
<212> TYPE: PRT
<213> ORGANISM: Artificial Sequence
<220> FEATURE:
<223> OTHER INFORMATION: Synthetic Construct

<400> SEQUENCE: 148

```
Glu His Ser Trp Glu Ile Pro Leu Thr
1               5
```

<210> SEQ ID NO 149
<211> LENGTH: 9
<212> TYPE: PRT
<213> ORGANISM: Artificial Sequence
<220> FEATURE:
<223> OTHER INFORMATION: Synthetic Construct

<400> SEQUENCE: 149

```
Gln His Ser Trp Glu Leu Pro Leu Thr
1               5
```

<210> SEQ ID NO 150
<211> LENGTH: 9
<212> TYPE: PRT
<213> ORGANISM: Artificial Sequence
<220> FEATURE:
<223> OTHER INFORMATION: Synthetic Construct

<400> SEQUENCE: 150

```
Gln His Ser Trp Ala Ile Pro Leu Thr
1               5
```

<210> SEQ ID NO 151
<211> LENGTH: 9
<212> TYPE: PRT
<213> ORGANISM: Artificial Sequence
<220> FEATURE:
<223> OTHER INFORMATION: Synthetic Construct

<400> SEQUENCE: 151

```
Gln His Ser Glu Glu Ile Pro Leu Thr
1               5
```

<210> SEQ ID NO 152
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Tyr, Ala, or Val
<220> FEATURE:
<221> NAME/KEY: VARIANT
<222> LOCATION: 3
<223> OTHER INFORMATION: Xaa = Thr or Ala
<220> FEATURE:
<221> NAME/KEY: VARIANT
<222> LOCATION: 4
<223> OTHER INFORMATION: Xaa = Phe, Glu, or His
<220> FEATURE:
<221> NAME/KEY: VARIANT
<222> LOCATION: 9
<223> OTHER INFORMATION: Xaa = Leu, Phe, Tyr, or Asn

<400> SEQUENCE: 152

```
Gly Xaa Xaa Xaa Thr Asp Tyr Asn Xaa His
1               5                   10
```

<210> SEQ ID NO 153
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 5
<223> OTHER INFORMATION: Xaa = Ser or Ala
<220> FEATURE:
<221> NAME/KEY: VARIANT
<222> LOCATION: 7
<223> OTHER INFORMATION: Xaa = Gly, Gln, Arg, or Val
<220> FEATURE:
<221> NAME/KEY: VARIANT
<222> LOCATION: 9
<223> OTHER INFORMATION: Xaa = Thr or Arg

<400> SEQUENCE: 153

```
Phe Ile Tyr Pro Xaa Asn Xaa Ile Xaa Gly
1               5                   10
```

<210> SEQ ID NO 154
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Thr, Asp, Phe, or Ser
<220> FEATURE:
<221> NAME/KEY: VARIANT
<222> LOCATION: 8
<223> OTHER INFORMATION: Xaa = Tyr, Asp, or Leu

<400> SEQUENCE: 154

```
Ser Xaa Val Asp Tyr Phe Asp Xaa
1               5
```

<210> SEQ ID NO 155
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Arg or Lys
<220> FEATURE:
<221> NAME/KEY: VARIANT
<222> LOCATION: 2
<223> OTHER INFORMATION: Xaa = Ala, Gly, or Val
<220> FEATURE:
<221> NAME/KEY: VARIANT
<222> LOCATION: 5
<223> OTHER INFORMATION: Xaa = Ser or Asp
<220> FEATURE:
<221> NAME/KEY: VARIANT
<222> LOCATION: 7
<223> OTHER INFORMATION: Xaa = Ser, Gly, or His
<220> FEATURE:
<221> NAME/KEY: VARIANT
<222> LOCATION: 8
<223> OTHER INFORMATION: Xaa = Thr or Ala

<400> SEQUENCE: 155

```
Xaa Xaa Ser Gln Xaa Val Xaa Xaa Ser Thr Tyr Ser Tyr Met His
1               5                   10                  15
```

<210> SEQ ID NO 156
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Ala, Val, or Glu
<220> FEATURE:
<221> NAME/KEY: VARIANT
<222> LOCATION: 3
<223> OTHER INFORMATION: Xaa = Ser, Val, or Phe
<220> FEATURE:
<221> NAME/KEY: VARIANT
<222> LOCATION: 4
<223> OTHER INFORMATION: Xaa = Asn, Ala, Tyr, or Phe
<220> FEATURE:
<221> NAME/KEY: VARIANT
<222> LOCATION: 5
<223> OTHER INFORMATION: Xaa = Leu or Val
<220> FEATURE:
<221> NAME/KEY: VARIANT
<222> LOCATION: 6
<223> OTHER INFORMATION: Xaa = Glu, Gly, or Asn

<400> SEQUENCE: 156

```
Tyr Xaa Xaa Xaa Xaa Xaa Ser
1               5
```

<210> SEQ ID NO 157
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Gln or Glu
<220> FEATURE:
<221> NAME/KEY: VARIANT
<222> LOCATION: 4
<223> OTHER INFORMATION: Xaa = Trp or Glu
<220> FEATURE:
<221> NAME/KEY: VARIANT
<222> LOCATION: 5
<223> OTHER INFORMATION: Xaa = Glu or Ala
<220> FEATURE:
<221> NAME/KEY: VARIANT
<222> LOCATION: 6
<223> OTHER INFORMATION: Xaa = Ile or Leu
<220> FEATURE:
<221> NAME/KEY: VARIANT
<222> LOCATION: 9
<223> OTHER INFORMATION: Xaa = Thr or Glu

<400> SEQUENCE: 157

```
Xaa His Ser Xaa Xaa Xaa Pro Leu Xaa
1               5
```

<210> SEQ ID NO 158
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT

```
<222> LOCATION: 16
<223> OTHER INFORMATION: Xaa = Ala or Ser
<220> FEATURE:
<221> NAME/KEY: VARIANT
<222> LOCATION: 20
<223> OTHER INFORMATION: Xaa = Val or Ile

<400> SEQUENCE: 158

Gln Val Gln Leu Val Gln Ser Gly Ala Glu Val Lys Lys Pro Gly Xaa
1               5                   10                  15

Ser Val Lys Xaa Ser Cys Lys Ala Ser
            20                  25

<210> SEQ ID NO 159
<211> LENGTH: 39
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Tyr or Ser
<220> FEATURE:
<221> NAME/KEY: VARIANT
<222> LOCATION: 3
<223> OTHER INFORMATION: Xaa = Gln or Glu
<220> FEATURE:
<221> NAME/KEY: VARIANT
<222> LOCATION: 4
<223> OTHER INFORMATION: Xaa = Lys or Asp
<220> FEATURE:
<221> NAME/KEY: VARIANT
<222> LOCATION: 5
<223> OTHER INFORMATION: Xaa = Phe or Asp
<220> FEATURE:
<221> NAME/KEY: VARIANT
<222> LOCATION: 6
<223> OTHER INFORMATION: Xaa = Gln, Phe, Glu, or Thr
<220> FEATURE:
<221> NAME/KEY: VARIANT
<222> LOCATION: 7
<223> OTHER INFORMATION: Xaa = Gly, Asp, or His
<220> FEATURE:
<221> NAME/KEY: VARIANT
<222> LOCATION: 9
<223> OTHER INFORMATION: Xaa = Val or Ala
<220> FEATURE:
<221> NAME/KEY: VARIANT
<222> LOCATION: 11
<223> OTHER INFORMATION: Xaa = Met or Leu
<220> FEATURE:
<221> NAME/KEY: VARIANT
<222> LOCATION: 15
<223> OTHER INFORMATION: Xaa = Thr, Asn, or Gln
<220> FEATURE:
<221> NAME/KEY: VARIANT
<222> LOCATION: 16
<223> OTHER INFORMATION: Xaa = Ser or Pro
<220> FEATURE:
<221> NAME/KEY: VARIANT
<222> LOCATION: 17
<223> OTHER INFORMATION: Xaa = Thr or Ala
<220> FEATURE:
<221> NAME/KEY: VARIANT
<222> LOCATION: 20
<223> OTHER INFORMATION: Xaa = Val or Ala

<400> SEQUENCE: 159

Xaa Ala Xaa Xaa Xaa Xaa Xaa Arg Xaa Thr Xaa Thr Val Asp Xaa Xaa
1               5                   10                  15

Xaa Ser Thr Xaa Tyr Met Glu Leu Ser Ser Leu Arg Ser Glu Asp Thr
            20                  25                  30
```

Ala Val Tyr Tyr Cys Ala Arg
            35

<210> SEQ ID NO 160
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 7
<223> OTHER INFORMATION: Xaa = Val or Leu

<400> SEQUENCE: 160

Trp Gly Gln Gly Thr Leu Xaa Thr Val Ser Ser
1               5                   10

<210> SEQ ID NO 161
<211> LENGTH: 23
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Asp or Gly
<220> FEATURE:
<221> NAME/KEY: VARIANT
<222> LOCATION: 3
<223> OTHER INFORMATION: Xaa = Gln or Val
<220> FEATURE:
<221> NAME/KEY: VARIANT
<222> LOCATION: 4
<223> OTHER INFORMATION: Xaa = Met or Leu
<220> FEATURE:
<221> NAME/KEY: VARIANT
<222> LOCATION: 9
<223> OTHER INFORMATION: Xaa = Ser or Asp
<220> FEATURE:
<221> NAME/KEY: VARIANT
<222> LOCATION: 12
<223> OTHER INFORMATION: Xaa = Ser, Pro, or Ala
<220> FEATURE:
<221> NAME/KEY: VARIANT
<222> LOCATION: 13
<223> OTHER INFORMATION: Xaa = Ala or Val
<220> FEATURE:
<221> NAME/KEY: VARIANT
<222> LOCATION: 15
<223> OTHER INFORMATION: Xaa = Val or Leu
<220> FEATURE:
<221> NAME/KEY: VARIANT
<222> LOCATION: 17
<223> OTHER INFORMATION: Xaa = Asp or Glu
<220> FEATURE:
<221> NAME/KEY: VARIANT
<222> LOCATION: 19
<223> OTHER INFORMATION: Xaa = Val or Ala
<220> FEATURE:
<221> NAME/KEY: VARIANT
<222> LOCATION: 22
<223> OTHER INFORMATION: Xaa = Thr, Asn, or Asp

<400> SEQUENCE: 161

Xaa Ile Xaa Xaa Thr Gln Ser Pro Xaa Ser Leu Xaa Xaa Ser Xaa Gly
1               5                   10                  15

Xaa Arg Xaa Thr Ile Xaa Cys
            20

<210> SEQ ID NO 162
<211> LENGTH: 15

```
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 8
<223> OTHER INFORMATION: Xaa = Lys or Gln
<220> FEATURE:
<221> NAME/KEY: VARIANT
<222> LOCATION: 9
<223> OTHER INFORMATION: Xaa = Ala or Pro

<400> SEQUENCE: 162

Trp Tyr Gln Gln Lys Pro Gly Xaa Xaa Pro Lys Leu Leu Ile Lys
1               5                   10                  15

<210> SEQ ID NO 163
<211> LENGTH: 32
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Ser or Asp
<220> FEATURE:
<221> NAME/KEY: VARIANT
<222> LOCATION: 24
<223> OTHER INFORMATION: Xaa = Pro or Ala
<220> FEATURE:
<221> NAME/KEY: VARIANT
<222> LOCATION: 27
<223> OTHER INFORMATION: Xaa = Phe, Leu, or Val
<220> FEATURE:
<221> NAME/KEY: VARIANT
<222> LOCATION: 29
<223> OTHER INFORMATION: Xaa = Thr or Val

<400> SEQUENCE: 163

Gly Val Pro Xaa Arg Phe Ser Gly Ser Gly Ser Gly Thr Asp Phe Thr
1               5                   10                  15

Leu Thr Ile Ser Ser Leu Gln Xaa Glu Asp Xaa Ala Xaa Tyr Tyr Cys
                20                  25                  30

<210> SEQ ID NO 164
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 10
<223> OTHER INFORMATION: Xaa = Lys or Glu

<400> SEQUENCE: 164

Phe Gly Gln Gly Thr Lys Leu Glu Ile Xaa
1               5                   10

<210> SEQ ID NO 165
<211> LENGTH: 19
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Asp or Glu
<220> FEATURE:
```

```
<221> NAME/KEY: VARIANT
<222> LOCATION: 2, 3
<223> OTHER INFORMATION: Xaa = Any Amino Acid and up to 2 of them can be
      present or absent
<220> FEATURE:
<221> NAME/KEY: VARIANT
<222> LOCATION: 5, 6
<223> OTHER INFORMATION: Xaa = Any Amino Acid
<220> FEATURE:
<221> NAME/KEY: VARIANT
<222> LOCATION: 7
<223> OTHER INFORMATION: Xaa = Leu or Ile
<220> FEATURE:
<221> NAME/KEY: VARIANT
<222> LOCATION: 8, 9, 10, 11, 12, 13, 14, 15
<223> OTHER INFORMATION: Xaa = Any Amino Acid and up to 2 can be
      present or absent
<220> FEATURE:
<221> NAME/KEY: VARIANT
<222> LOCATION: 17, 18
<223> OTHER INFORMATION: Xaa = Any Amino Acid
<220> FEATURE:
<221> NAME/KEY: VARIANT
<222> LOCATION: 19
<223> OTHER INFORMATION: Xaa = Leu or Ile

<400> SEQUENCE: 165

Xaa Xaa Xaa Tyr Xaa Xaa Xaa Xaa Xaa Xaa Xaa Xaa Xaa Xaa Xaa Tyr
1               5                   10                  15

Xaa Xaa Xaa

<210> SEQ ID NO 166
<211> LENGTH: 110
<212> TYPE: PRT
<213> ORGANISM: Artificial Sequence
<220> FEATURE:
<223> OTHER INFORMATION: Synthetic Construct

<400> SEQUENCE: 166

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro
            100                 105                 110

<210> SEQ ID NO 167
<211> LENGTH: 117
<212> TYPE: PRT
<213> ORGANISM: Artificial Sequence
<220> FEATURE:
<223> OTHER INFORMATION: Synthetic Construct

<400> SEQUENCE: 167

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Tyr
                20                  25                  30
```

Asn Leu His Trp Val Lys Leu Ser His Gly Lys Ser Leu Glu Trp Ile
            35                  40                  45

Gly Phe Ile Tyr Pro Ser Asn Gly Ile Thr Gly Tyr Asn Gln Lys Phe
        50                  55                  60

Lys Asn Lys Ala Thr Leu Thr Val Asp Thr Ser Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Ser Thr Val Asp Tyr Phe Asp Tyr Trp Gly Gln Gly Thr Thr
            100                 105                 110

Leu Thr Val Ser Ser
        115

<210> SEQ ID NO 168
<211> LENGTH: 15
<212> TYPE: PRT
<213> ORGANISM: Artificial Sequence
<220> FEATURE:
<223> OTHER INFORMATION: Synthetic Construct

<400> SEQUENCE: 168

Trp Tyr Gln Arg Lys Pro Gly Lys Ala Pro Lys Leu Leu Ile Lys
1               5                   10                  15

<210> SEQ ID NO 169
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Gln or Arg
<220> FEATURE:
<221> NAME/KEY: VARIANT
<222> LOCATION: 8
<223> OTHER INFORMATION: Xaa = Lys or Gln
<220> FEATURE:
<221> NAME/KEY: VARIANT
<222> LOCATION: 9
<223> OTHER INFORMATION: Xaa = Ala or Pro

<400> SEQUENCE: 169

Trp Tyr Gln Xaa Lys Pro Gly Xaa Xaa Pro Lys Leu Leu Ile Lys
1               5                   10                  15

<210> SEQ ID NO 170
<211> LENGTH: 117
<212> TYPE: PRT
<213> ORGANISM: Artificial Sequence
<220> FEATURE:
<223> OTHER INFORMATION: Synthetic Construct

<400> SEQUENCE: 170

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Met
        35                  40                  45

Gly Phe Ile Tyr Pro Ser Asn Gly Ile Thr Gly Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Ser Thr Val Asp Tyr Phe Asp Tyr Trp Gly Gln Gly Thr Leu
            100                 105                 110

Val Thr Val Ser Ser
        115

<210> SEQ ID NO 171
<211> LENGTH: 117
<212> TYPE: PRT
<213> ORGANISM: Artificial Sequence
<220> FEATURE:
<223> OTHER INFORMATION: Synthetic Construct

<400> SEQUENCE: 171

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Met
        35                  40                  45

Gly Phe Ile Tyr Pro Ser Asn Gly Ile Thr Gly Tyr Ala Gln Lys Phe
    50                  55                  60

Gln Gly Arg Val Thr Met Thr Val Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Val Asp Tyr Phe Asp Tyr Trp Gly Gln Gly Thr Thr
            100                 105                 110

Val Thr Val Ser Ser
        115

<210> SEQ ID NO 172
<211> LENGTH: 117
<212> TYPE: PRT
<213> ORGANISM: Artificial Sequence
<220> FEATURE:
<223> OTHER INFORMATION: Synthetic Construct

<400> SEQUENCE: 172

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Leu His Trp Val Arg Gln Ala Pro Gly Gln Ser Leu Glu Trp Ile
        35                  40                  45

Gly Phe Ile Tyr Pro Ser Asn Gly Ile Thr Gly Tyr Ser Gln Lys Phe
    50                  55                  60

Gln Gly Lys Ala Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Val Asp Tyr Phe Asp Tyr Trp Gly Gln Gly Thr Thr
            100                 105                 110

Val Thr Val Ser Ser
        115

<210> SEQ ID NO 173
<211> LENGTH: 117
<212> TYPE: PRT
<213> ORGANISM: Artificial Sequence
<220> FEATURE:
<223> OTHER INFORMATION: Synthetic Construct

<400> SEQUENCE: 173

```
Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Arg Gln Ala Pro Gly Gln Arg Leu Glu Trp Ile
        35                  40                  45

Gly Phe Ile Tyr Pro Ser Asn Gly Ile Thr Gly Tyr Asn Gln Lys Phe
    50                  55                  60

Lys Asn Lys Ala Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Val Asp Tyr Phe Asp Tyr Trp Gly Gln Gly Thr Thr
            100                 105                 110

Val Thr Val Ser Ser
        115
```

<210> SEQ ID NO 174
<211> LENGTH: 117
<212> TYPE: PRT
<213> ORGANISM: Artificial Sequence
<220> FEATURE:
<223> OTHER INFORMATION: Synthetic Construct

<400> SEQUENCE: 174

```
Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Arg Gln Ala Pro Gly Gln Arg Leu Glu Trp Ile
        35                  40                  45

Gly Phe Ile Tyr Pro Ser Asn Gly Ile Thr Gly Tyr Ser Gln Lys Phe
    50                  55                  60

Gln Gly Lys Ala Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Val Asp Tyr Phe Asp Tyr Trp Gly Gln Gly Thr Thr
            100                 105                 110

Val Thr Val Ser Ser
        115
```

<210> SEQ ID NO 175
<211> LENGTH: 117
<212> TYPE: PRT
<213> ORGANISM: Artificial Sequence
<220> FEATURE:
<223> OTHER INFORMATION: Synthetic Construct

<400> SEQUENCE: 175

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Leu His Trp Val Arg Gln Ala Pro Gly Gln Arg Leu Glu Trp Ile
        35                  40                  45

Gly Phe Ile Tyr Pro Ser Asn Gly Ile Thr Gly Tyr Ser Gln Lys Phe
    50                  55                  60

Gln Gly Arg Ala Thr Leu Thr Val Asp Thr Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Val Asp Tyr Phe Asp Tyr Trp Gly Gln Gly Thr Thr
            100                 105                 110

Val Thr Val Ser Ser
            115

<210> SEQ ID NO 176
<211> LENGTH: 447
<212> TYPE: PRT
<213> ORGANISM: Artificial Sequence
<220> FEATURE:
<223> OTHER INFORMATION: Synthetic Construct

<400> SEQUENCE: 176

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
        35                  40                  45

Gly Phe Ile Tyr Pro Ser Asn Gly Ile Thr Gly Tyr Ala Gln Lys Phe
    50                  55                  60

Gln Gly Arg Ala Thr Leu Thr Val Asp Asn Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
            100                 105                 110

Leu Thr Val Ser Ser Ala Ser Thr Lys Gly Pro Ser Val Phe Pro Leu
    115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

```
Phe Leu Phe Pro Pro Lys Pro Lys Asp Thr Leu Met Ile Ser Arg Thr
                245                 250                 255

Pro Glu Val Thr Cys Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 177
<211> LENGTH: 447
<212> TYPE: PRT
<213> ORGANISM: Artificial Sequence
<220> FEATURE:
<223> OTHER INFORMATION: Synthetic Construct

<400> SEQUENCE: 177

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
        35                  40                  45

Gly Phe Ile Tyr Pro Ser Asn Arg Ile Thr Gly Tyr Ala Gln Lys Phe
    50                  55                  60

Gln Gly Arg Ala Thr Leu Thr Val Asp Asn Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160
```

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
        180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 178
<211> LENGTH: 447
<212> TYPE: PRT
<213> ORGANISM: Artificial Sequence
<220> FEATURE:
<223> OTHER INFORMATION: Synthetic Construct

<400> SEQUENCE: 178

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
        35                  40                  45

Gly Phe Ile Tyr Pro Ser Asn Gln Ile Thr Gly Tyr Ala Gln Lys Phe
    50                  55                  60

Gln Gly Arg Ala Thr Leu Thr Val Asp Asn Ser Ala Ser Thr Ala Tyr
65                  70                  75                  80

```
Met Glu Leu Ser Ser Leu Arg Ser Glu Asp Thr Ala Val Tyr Tyr Cys
                 85                  90                  95

Ala Arg Ser Asp Val Asp Tyr Phe Asp Tyr Trp Gly Gln Gly Thr Leu
            100                 105                 110

Leu Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
        210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445

<210> SEQ ID NO 179
<211> LENGTH: 443
<212> TYPE: PRT
<213> ORGANISM: Artificial Sequence
<220> FEATURE:
<223> OTHER INFORMATION: Synthetic Construct

<400> SEQUENCE: 179
```

```
Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
        35                  40                  45

Gly Phe Ile Tyr Pro Ser Asn Gly Ile Thr Gly Tyr Ala Gln Lys Phe
    50                  55                  60

Gln Gly Arg Ala Thr Leu Thr Val Asp Asn Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
            100                 105                 110

Leu Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
```

Thr Gln Lys Ser Leu Ser Leu Ser Pro Gly Lys
            435                 440

<210> SEQ ID NO 180
<211> LENGTH: 443
<212> TYPE: PRT
<213> ORGANISM: Artificial Sequence
<220> FEATURE:
<223> OTHER INFORMATION: Synthetic Construct

<400> SEQUENCE: 180

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
        35                  40                  45

Gly Phe Ile Tyr Pro Ser Asn Arg Ile Thr Gly Tyr Ala Gln Lys Phe
    50                  55                  60

Gln Gly Arg Ala Thr Leu Thr Val Asp Asn Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
            100                 105                 110

Leu Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu

```
                    340                 345                 350
Glu Met Thr Lys Asn Gln Val Ser Leu Thr Cys Leu Val Lys Gly Phe
            355                 360                 365

Tyr Pro Ser Asp Ile Ala Val Glu Trp Glu Ser Asn Gly Gln Pro Glu
        370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
            435                 440

<210> SEQ ID NO 181
<211> LENGTH: 443
<212> TYPE: PRT
<213> ORGANISM: Artificial Sequence
<220> FEATURE:
<223> OTHER INFORMATION: Synthetic Construct

<400> SEQUENCE: 181

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
        35                  40                  45

Gly Phe Ile Tyr Pro Ser Asn Gln Ile Thr Gly Tyr Ala Gln Lys Phe
    50                  55                  60

Gln Gly Arg Ala Thr Leu Thr Val Asp Asn Ser Ala Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
            100                 105                 110

Leu Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
```

```
                260                 265                 270
Trp Tyr Val Asp Gly Val Glu Val His Asn Ala Lys Thr Lys Pro Arg
            275                 280                 285

Glu Glu Gln Phe Asn Ser Thr Phe Arg Val Val Ser Val Leu Thr Val
        290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430

Thr Gln Lys Ser Leu Ser Leu Ser Pro Gly Lys
        435                 440

<210> SEQ ID NO 182
<211> LENGTH: 447
<212> TYPE: PRT
<213> ORGANISM: Artificial Sequence
<220> FEATURE:
<223> OTHER INFORMATION: Synthetic Construct

<400> SEQUENCE: 182

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
        35                  40                  45

Gly Phe Ile Tyr Pro Ser Asn Gly Ile Thr Gly Tyr Ala Gln Lys Phe
    50                  55                  60

Gln Gly Arg Ala Thr Leu Thr Val Asp Asn Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
```

```
            180             185             190
Leu Gly Thr Gln Thr Tyr Ile Cys Asn Val Asn His Lys Pro Ser Asn
        195                 200                 205

Thr Lys Val Asp Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 183
<211> LENGTH: 447
<212> TYPE: PRT
<213> ORGANISM: Artificial Sequence
<220> FEATURE:
<223> OTHER INFORMATION: Synthetic Construct

<400> SEQUENCE: 183

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
        35                  40                  45

Gly Phe Ile Tyr Pro Ser Asn Arg Ile Thr Gly Tyr Ala Gln Lys Phe
    50                  55                  60

Gln Gly Arg Ala Thr Leu Thr Val Asp Asn Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
```

100                 105                 110
Leu Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 184
<211> LENGTH: 447
<212> TYPE: PRT
<213> ORGANISM: Artificial Sequence
<220> FEATURE:
<223> OTHER INFORMATION: Synthetic Construct

<400> SEQUENCE: 184

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr

-continued

```
             20                  25                  30
Asn Leu His Trp Val Arg Gln Ala Pro Gly Gln Gly Leu Glu Trp Ile
             35                  40                  45

Gly Phe Ile Tyr Pro Ser Asn Gln Ile Thr Gly Tyr Ala Gln Lys Phe
 50                  55                  60

Gln Gly Arg Ala Thr Leu Thr Val Asp Asn Ser Ala Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Asp Val Asp Tyr Phe Asp Tyr Trp Gly Gln Gly Thr Leu
                100                 105                 110

Leu Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
            195                 200                 205

Thr Lys Val Asp Lys Lys Val Glu Pro Lys Ser Cys Asp Lys Thr His
            210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
            435                 440                 445
```

<210> SEQ ID NO 185
<211> LENGTH: 218
<212> TYPE: PRT
<213> ORGANISM: Artificial Sequence
<220> FEATURE:
<223> OTHER INFORMATION: Synthetic Construct

<400> SEQUENCE: 185

Asp Ile Val Leu Thr Gln Ser Pro Asp Ser Leu Ala Val Ser Leu Gly
1               5                   10                  15

Glu Arg Ala Thr Ile Asn Cys Arg Ala Ser Gln Ser Val Ser Thr Ser
            20                  25                  30

Thr Tyr Ser Tyr Met His Trp Tyr Gln Gln Lys Pro Gly Gln Pro Pro
        35                  40                  45

Lys Leu Leu Ile Lys Tyr Ala Ser Asn Leu Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Trp
                85                  90                  95

Glu Ile Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 186
<211> LENGTH: 10
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Tyr or Val
<220> FEATURE:
<221> NAME/KEY: VARIANT
<222> LOCATION: 3
<223> OTHER INFORMATION: Xaa = Thr or Ala
<220> FEATURE:
<221> NAME/KEY: VARIANT
<222> LOCATION: 4
<223> OTHER INFORMATION: Xaa = Phe, Glu, or His
<220> FEATURE:
<221> NAME/KEY: VARIANT
<222> LOCATION: 9
<223> OTHER INFORMATION: Xaa = Leu, Phe, Tyr, or Asn

<400> SEQUENCE: 186

Gly Xaa Xaa Xaa Thr Asp Tyr Asn Xaa His
1               5                   10

<210> SEQ ID NO 187
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Thr, Asp, or Phe
<220> FEATURE:
<221> NAME/KEY: VARIANT
<222> LOCATION: 8
<223> OTHER INFORMATION: Xaa = Tyr, Asp, or Leu

<400> SEQUENCE: 187

Ser Xaa Val Asp Tyr Phe Asp Xaa
1               5

<210> SEQ ID NO 188
<211> LENGTH: 15
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Arg or Lys
<220> FEATURE:
<221> NAME/KEY: VARIANT
<222> LOCATION: 2
<223> OTHER INFORMATION: Xaa = Ala, Gly, or Val
<220> FEATURE:
<221> NAME/KEY: VARIANT
<222> LOCATION: 5
<223> OTHER INFORMATION: Xaa = Ser or Asp
<220> FEATURE:
<221> NAME/KEY: VARIANT
<222> LOCATION: 7
<223> OTHER INFORMATION: Xaa = Ser, Gly, or His
<220> FEATURE:
<221> NAME/KEY: VARIANT
<222> LOCATION: 8
<223> OTHER INFORMATION: Xaa = Thr

<400> SEQUENCE: 188

Xaa Xaa Ser Gln Xaa Val Xaa Xaa Ser Thr Tyr Ser Tyr Met His
1               5                   10                  15

<210> SEQ ID NO 189
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Ala or Glu
<220> FEATURE:
<221> NAME/KEY: VARIANT
<222> LOCATION: 3
<223> OTHER INFORMATION: Xaa = Ser or Phe
<220> FEATURE:
<221> NAME/KEY: VARIANT
<222> LOCATION: 4
<223> OTHER INFORMATION: Xaa = Asn, Tyr, or Phe
<220> FEATURE:
<221> NAME/KEY: VARIANT
<222> LOCATION: 5

```
<223> OTHER INFORMATION: Xaa = Leu or Val
<220> FEATURE:
<221> NAME/KEY: VARIANT
<222> LOCATION: 6
<223> OTHER INFORMATION: Xaa = Glu or Asn

<400> SEQUENCE: 189

Tyr Xaa Xaa Xaa Xaa Xaa Ser
1               5

<210> SEQ ID NO 190
<211> LENGTH: 5
<212> TYPE: PRT
<213> ORGANISM: Artificial Sequence
<220> FEATURE:
<223> OTHER INFORMATION: Synthetic Construct

<400> SEQUENCE: 190

Asp Tyr Asn Leu His
1               5

<210> SEQ ID NO 191
<211> LENGTH: 8
<212> TYPE: PRT
<213> ORGANISM: Artificial Sequence
<220> FEATURE:
<223> OTHER INFORMATION: Synthetic Construct

<400> SEQUENCE: 191

Tyr Cys Ala Arg Ser Asp Val Asp
1               5

<210> SEQ ID NO 192
<211> LENGTH: 7
<212> TYPE: PRT
<213> ORGANISM: Artificial Sequence
<220> FEATURE:
<223> OTHER INFORMATION: Synthetic Construct

<400> SEQUENCE: 192

Leu Leu Ile Lys Tyr Ala Ser
1               5

<210> SEQ ID NO 193
<211> LENGTH: 9
<212> TYPE: PRT
<213> ORGANISM: Artificial Sequence
<220> FEATURE:
<223> OTHER INFORMATION: Synthetic Construct

<400> SEQUENCE: 193

Val Tyr Tyr Cys Gln His Ser Trp Glu
1               5

<210> SEQ ID NO 194
<211> LENGTH: 16
<212> TYPE: PRT
<213> ORGANISM: Artificial Sequence
<220> FEATURE:
<223> OTHER INFORMATION: Synthetic Construct

<400> SEQUENCE: 194

Phe Ile Tyr Pro Ser Asn Gly Ile Thr Gly Tyr Ala Gln Lys Phe Gln
1               5                   10                  15

<210> SEQ ID NO 195
<211> LENGTH: 16
```

```
<212> TYPE: PRT
<213> ORGANISM: Artificial Sequence
<220> FEATURE:
<223> OTHER INFORMATION: Synthetic Construct

<400> SEQUENCE: 195

Phe Ile Tyr Pro Ser Asn Arg Ile Thr Gly Tyr Ala Gln Lys Phe Gln
1               5                   10                  15

<210> SEQ ID NO 196
<211> LENGTH: 16
<212> TYPE: PRT
<213> ORGANISM: Artificial Sequence
<220> FEATURE:
<223> OTHER INFORMATION: Synthetic Construct

<400> SEQUENCE: 196

Phe Ile Tyr Pro Ser Asn Gln Ile Thr Gly Tyr Ala Gln Lys Phe Gln
1               5                   10                  15

<210> SEQ ID NO 197
<211> LENGTH: 446
<212> TYPE: PRT
<213> ORGANISM: Artificial Sequence
<220> FEATURE:
<223> OTHER INFORMATION: Synthetic Construct

<400> SEQUENCE: 197

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
                20                  25                  30

Asn Leu His Trp Val Arg Gln Ala Pro Gly Gln Gly Leu Glu Trp Ile
            35                  40                  45

Gly Phe Ile Tyr Pro Ser Asn Gly Ile Thr Gly Tyr Ala Gln Lys Phe
        50                  55                  60

Gln Gly Arg Ala Thr Leu Thr Val Asp Asn Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
                100                 105                 110

Leu Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
```

```
                        245                 250                 255
Pro Glu Val Thr Cys Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
        290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 198
<211> LENGTH: 446
<212> TYPE: PRT
<213> ORGANISM: Artificial Sequence
<220> FEATURE:
<223> OTHER INFORMATION: Synthetic Construct

<400> SEQUENCE: 198

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
        35                  40                  45

Gly Phe Ile Tyr Pro Ser Asn Arg Ile Thr Gly Tyr Ala Gln Lys Phe
    50                  55                  60

Gln Gly Arg Ala Thr Leu Thr Val Asp Asn Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
```

```
            165                 170                 175
Ser Gly Leu Tyr Ser Leu Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 199
<211> LENGTH: 446
<212> TYPE: PRT
<213> ORGANISM: Artificial Sequence
<220> FEATURE:
<223> OTHER INFORMATION: Synthetic Construct

<400> SEQUENCE: 199

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
        35                  40                  45

Gly Phe Ile Tyr Pro Ser Asn Gln Ile Thr Gly Tyr Ala Gln Lys Phe
    50                  55                  60

Gln Gly Arg Ala Thr Leu Thr Val Asp Asn Ser Ala Ser Thr Ala Tyr
65                  70                  75                  80

Met Glu Leu Ser Ser Leu Arg Ser Glu Asp Thr Ala Val Tyr Tyr Cys
```

85                  90                  95
Ala Arg Ser Asp Val Asp Tyr Phe Asp Tyr Trp Gly Gln Gly Thr Leu
            100                 105                 110

Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 200
<211> LENGTH: 442
<212> TYPE: PRT
<213> ORGANISM: Artificial Sequence
<220> FEATURE:
<223> OTHER INFORMATION: Synthetic Construct

<400> SEQUENCE: 200

Gln Val Gln Leu Val Gln Ser Gly Ala Glu Val Lys Lys Pro Gly Ala

```
1               5                   10                  15
Ser Val Lys Ile Ser Cys Lys Ala Ser Gly Tyr Thr Phe Thr Asp Tyr
                20                  25                  30

Asn Leu His Trp Val Arg Gln Ala Pro Gly Gln Gly Leu Glu Trp Ile
            35                  40                  45

Gly Phe Ile Tyr Pro Ser Asn Gly Ile Thr Gly Tyr Ala Gln Lys Phe
        50                  55                  60

Gln Gly Arg Ala Thr Leu Thr Val Asp Asn Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
            100                 105                 110

Leu Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

Glu Met Thr Lys Asn Gln Val Ser Leu Thr Cys Leu Val Lys Gly Phe
        355                 360                 365

Tyr Pro Ser Asp Ile Ala Val Glu Trp Glu Ser Asn Gly Gln Pro Glu
    370                 375                 380

Asn Asn Tyr Lys Thr Thr Pro Pro Met Leu Asp Ser Asp Gly Ser Phe
385                 390                 395                 400

Phe Leu Tyr Ser Lys Leu Thr Val Asp Lys Ser Arg Trp Gln Gln Gly
                405                 410                 415

Asn Val Phe Ser Cys Ser Val Met His Glu Ala Leu His Asn His Tyr
            420                 425                 430
```

Thr Gln Lys Ser Leu Ser Leu Ser Pro Gly
        435                 440

<210> SEQ ID NO 201
<211> LENGTH: 442
<212> TYPE: PRT
<213> ORGANISM: Artificial Sequence
<220> FEATURE:
<223> OTHER INFORMATION: Synthetic Construct

<400> SEQUENCE: 201

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
        35                  40                  45

Gly Phe Ile Tyr Pro Ser Asn Arg Ile Thr Gly Tyr Ala Gln Lys Phe
    50                  55                  60

Gln Gly Arg Ala Thr Leu Thr Val Asp Asn Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
            100                 105                 110

Leu Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Asn
            180                 185                 190

Phe Gly Thr Gln Thr Tyr Thr Cys Asn Val Asp His Lys Pro Ser Asn
        195                 200                 205

Thr Lys Val Asp Lys Thr Val Glu Arg Lys Cys Cys Val Glu Cys Pro
    210                 215                 220

Pro Cys Pro Ala Pro Pro Val Ala Gly Pro Ser Val Phe Leu Phe Pro
225                 230                 235                 240

Pro Lys Pro Lys Asp Thr Leu Met Ile Ser Arg Thr Pro Glu Val Thr
                245                 250                 255

Cys Val Val Val Asp Val Ser His Glu Asp Pro Glu Val Gln Phe Asn
            260                 265                 270

Trp Tyr Val Asp Gly Val Glu Val His Asn Ala Lys Thr Lys Pro Arg
        275                 280                 285

Glu Glu Gln Phe Asn Ser Thr Phe Arg Val Val Ser Val Leu Thr Val
    290                 295                 300

Val His Gln Asp Trp Leu Asn Gly Lys Glu Tyr Lys Cys Lys Val Ser
305                 310                 315                 320

Asn Lys Gly Leu Pro Ala Pro Ile Glu Lys Thr Ile Ser Lys Thr Lys
                325                 330                 335

Gly Gln Pro Arg Glu Pro Gln Val Tyr Thr Leu Pro Pro Ser Arg Glu
            340                 345                 350

```
Glu Met Thr Lys Asn Gln Val Ser Leu Thr Cys Leu Val Lys Gly Phe
            355                 360                 365
Tyr Pro Ser Asp Ile Ala Val Glu Trp Glu Ser Asn Gly Gln Pro Glu
        370                 375                 380
Asn Asn Tyr Lys Thr Thr Pro Pro Met Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly
            435                 440

<210> SEQ ID NO 202
<211> LENGTH: 442
<212> TYPE: PRT
<213> ORGANISM: Artificial Sequence
<220> FEATURE:
<223> OTHER INFORMATION: Synthetic Construct

<400> SEQUENCE: 202

Gln Val Gln Leu Val Gln Ser Gly Ala Glu Val Lys Lys Pro Gly Ala
1               5                   10                  15
Ser Val Lys Ile Ser Cys Lys Ala Ser Gly Tyr Thr Phe Thr Asp Tyr
            20                  25                  30
Asn Leu His Trp Val Arg Gln Ala Pro Gly Gln Gly Leu Glu Trp Ile
        35                  40                  45
Gly Phe Ile Tyr Pro Ser Asn Gln Ile Thr Gly Tyr Ala Gln Lys Phe
    50                  55                  60
Gln Gly Arg Ala Thr Leu Thr Val Asp Asn Ser Ala Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Asp Val Asp Tyr Phe Asp Tyr Trp Gly Gln Gly Thr Leu
            100                 105                 110
Leu Thr Val Ser Ser Ala Ser Thr Lys Gly Pro Ser Val Phe Pro Leu
        115                 120                 125
Ala Pro Cys Ser Arg Ser Thr Ser Glu Ser Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Asn
            180                 185                 190
Phe Gly Thr Gln Thr Tyr Thr Cys Asn Val Asp His Lys Pro Ser Asn
        195                 200                 205
Thr Lys Val Asp Lys Thr Val Glu Arg Lys Cys Cys Val Glu Cys Pro
    210                 215                 220
Pro Cys Pro Ala Pro Pro Val Ala Gly Pro Ser Val Phe Leu Phe Pro
225                 230                 235                 240
Pro Lys Pro Lys Asp Thr Leu Met Ile Ser Arg Thr Pro Glu Val Thr
                245                 250                 255
Cys Val Val Val Asp Val Ser His Glu Asp Pro Glu Val Gln Phe Asn
            260                 265                 270
```

```
Trp Tyr Val Asp Gly Val Glu Val His Asn Ala Lys Thr Lys Pro Arg
            275                 280                 285
Glu Glu Gln Phe Asn Ser Thr Phe Arg Val Val Ser Val Leu Thr Val
290                 295                 300
Val His Gln Asp Trp Leu Asn Gly Lys Glu Tyr Lys Cys Lys Val Ser
305                 310                 315                 320
Asn Lys Gly Leu Pro Ala Pro Ile Glu Lys Thr Ile Ser Lys Thr Lys
                325                 330                 335
Gly Gln Pro Arg Glu Pro Gln Val Tyr Thr Leu Pro Pro Ser Arg Glu
            340                 345                 350
Glu Met Thr Lys Asn Gln Val Ser Leu Thr Cys Leu Val Lys Gly Phe
        355                 360                 365
Tyr Pro Ser Asp Ile Ala Val Glu Trp Glu Ser Asn Gly Gln Pro Glu
    370                 375                 380
Asn Asn Tyr Lys Thr Thr Pro Pro Met Leu Asp Ser Asp Gly Ser Phe
385                 390                 395                 400
Phe Leu Tyr Ser Lys Leu Thr Val Asp Lys Ser Arg Trp Gln Gln Gly
                405                 410                 415
Asn Val Phe Ser Cys Ser Val Met His Glu Ala Leu His Asn His Tyr
            420                 425                 430
Thr Gln Lys Ser Leu Ser Leu Ser Pro Gly
        435                 440

<210> SEQ ID NO 203
<211> LENGTH: 446
<212> TYPE: PRT
<213> ORGANISM: Artificial Sequence
<220> FEATURE:
<223> OTHER INFORMATION: Synthetic Construct

<400> SEQUENCE: 203

Gln Val Gln Leu Val Gln Ser Gly Ala Glu Val Lys Lys Pro Gly Ala
1               5                   10                  15
Ser Val Lys Ile Ser Cys Lys Ala Ser Gly Tyr Thr Phe Thr Asp Tyr
            20                  25                  30
Asn Leu His Trp Val Arg Gln Ala Pro Gly Gln Gly Leu Glu Trp Ile
        35                  40                  45
Gly Phe Ile Tyr Pro Ser Asn Gly Ile Thr Gly Tyr Ala Gln Lys Phe
    50                  55                  60
Gln Gly Arg Ala Thr Leu Thr Val Asp Asn Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Ser Asp Val Asp Tyr Phe Asp Tyr Trp Gly Gln Gly Thr Leu
            100                 105                 110
Leu Thr Val Ser Ser Ala Ser Thr Lys Gly Pro Ser Val Phe Pro Leu
        115                 120                 125
Ala Pro Ser Ser Lys Ser Thr Ser Gly Gly Thr Ala Ala Leu Gly Cys
    130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
```

-continued

```
Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 204
<211> LENGTH: 446
<212> TYPE: PRT
<213> ORGANISM: Artificial Sequence
<220> FEATURE:
<223> OTHER INFORMATION: Synthetic Construct

<400> SEQUENCE: 204

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30

Asn Leu His Trp Val Arg Gln Ala Pro Gly Gln Gly Leu Glu Trp Ile
        35                  40                  45

Gly Phe Ile Tyr Pro Ser Asn Arg Ile Thr Gly Tyr Ala Gln Lys Phe
    50                  55                  60

Gln Gly Arg Ala Thr Leu Thr Val Asp Asn Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asp Val Asp Tyr Phe Asp Tyr Trp Gly Gln Gly Thr Leu
            100                 105                 110
```

```
Leu Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
        435                 440                 445

<210> SEQ ID NO 205
<211> LENGTH: 446
<212> TYPE: PRT
<213> ORGANISM: Artificial Sequence
<220> FEATURE:
<223> OTHER INFORMATION: Synthetic Construct

<400> SEQUENCE: 205

Gln Val Gln Leu Val Gln Ser Gly Ala Glu Val Lys Lys Pro Gly Ala
1               5                   10                  15

Ser Val Lys Ile Ser Cys Lys Ala Ser Gly Tyr Thr Phe Thr Asp Tyr
            20                  25                  30
```

Asn Leu His Trp Val Arg Gln Ala Pro Gly Gln Gly Leu Glu Trp Ile
                35                  40                  45
Gly Phe Ile Tyr Pro Ser Asn Gln Ile Thr Gly Tyr Ala Gln Lys Phe
         50                  55                  60
Gln Gly Arg Ala Thr Leu Thr Val Asp Asn Ser Ala Ser Thr Ala Tyr
 65                  70                  75                  80
Met Glu Leu Ser Ser Leu Arg Ser Glu Asp Thr Ala Val Tyr Tyr Cys
                 85                  90                  95
Ala Arg Ser Asp Val Asp Tyr Phe Asp Tyr Trp Gly Gln Gly Thr Leu
                100                 105                 110
Leu Thr Val Ser Ser Ala Ser Thr Lys Gly Pro Ser Val Phe Pro Leu
                115                 120                 125
Ala Pro Ser Ser Lys Ser Thr Ser Gly Gly Thr Ala Ala Leu Gly Cys
            130                 135                 140
Leu Val Lys Asp Tyr Phe Pro Glu Pro Val Thr Val Ser Trp Asn Ser
145                 150                 155                 160
Gly Ala Leu Thr Ser Gly Val His Thr Phe Pro Ala Val Leu Gln Ser
                165                 170                 175
Ser Gly Leu Tyr Ser Leu Ser Ser Val Val Thr Val Pro Ser Ser Ser
            180                 185                 190
Leu Gly Thr Gln Thr Tyr Ile Cys Asn Val Asn His Lys Pro Ser Asn
        195                 200                 205
Thr Lys Val Asp Lys Lys Val Glu Pro Lys Ser Cys Asp Lys Thr His
    210                 215                 220
Thr Cys Pro Pro Cys Pro Ala Pro Glu Ala Ala Gly Gly Pro Ser Val
225                 230                 235                 240
Phe Leu Phe Pro Pro Lys Pro Lys Asp Thr Leu Met Ile Ser Arg Thr
                245                 250                 255
Pro Glu Val Thr Cys Val Val Val Asp Val Ser His Glu Asp Pro Glu
            260                 265                 270
Val Lys Phe Asn Trp Tyr Val Asp Gly Val Glu Val His Asn Ala Lys
        275                 280                 285
Thr Lys Pro Arg Glu Glu Gln Tyr Asn Ser Thr Tyr Arg Val Val Ser
    290                 295                 300
Val Leu Thr Val Leu His Gln Asp Trp Leu Asn Gly Lys Glu Tyr Lys
305                 310                 315                 320
Cys Lys Val Ser Asn Lys Ala Leu Pro Ala Ser Ile Glu Lys Thr Ile
                325                 330                 335
Ser Lys Ala Lys Gly Gln Pro Arg Glu Pro Gln Val Tyr Thr Leu Pro
            340                 345                 350
Pro Ser Arg Asp Glu Leu Thr Lys Asn Gln Val Ser Leu Thr Cys Leu
        355                 360                 365
Val Lys Gly Phe Tyr Pro Ser Asp Ile Ala Val Glu Trp Glu Ser Asn
    370                 375                 380
Gly Gln Pro Glu Asn Asn Tyr Lys Thr Thr Pro Pro Val Leu Asp Ser
385                 390                 395                 400
Asp Gly Ser Phe Phe Leu Tyr Ser Lys Leu Thr Val Asp Lys Ser Arg
                405                 410                 415
Trp Gln Gln Gly Asn Val Phe Ser Cys Ser Val Met His Glu Ala Leu
            420                 425                 430
His Asn His Tyr Thr Gln Lys Ser Leu Ser Leu Ser Pro Gly
        435                 440                 445

ANTI-CD33 ANTIBODIES AND METHODS OF USE THEREOF

CROSS-REFERENCE TO RELATED APPLICATIONS

This application claims the benefit of U.S. Provisional Application No. 62/541,024, filed Aug. 3, 2017 and 62/667,388 filed May 4, 2018, which are hereby incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 735022001700SEQLIST.TXT, date recorded: Aug. 2, 2018, size: 185 KB).

FIELD OF THE INVENTION

This present disclosure relates to anti-CD33 antibodies, and therapeutic uses of such antibodies.

BACKGROUND

Myeloid cell surface antigen CD33 precursor (CD33), also known as Siglec-3, is a type 1, immunoglobulin-like, transmembrane protein expressed on immune and hematopoietic cells, including immature and mature myeloid cells, dendritic cells, and microglial cells. (Crocker et al. (2007) Nat Rev Immunol. 7:255-266; McMillan and Crocker (2008) Carbohydr Res. 343:2050-2056; Von Gunten and Bochner (2008) Ann NY Acad Sci. 1143:61-82; Handgretinger et al. (1993) Immunol Lett. 37:223-228; and Hernandez-Caselles et al. (2006) J Leukoc Biol. 79:46-58). CD33 contains an Ig-like C2-type (immunoglobulin-like) and an Ig-like V-type (immunoglobulin-like) extracellular domain, as well as two ITIM-like motifs in its cytoplasmic domain Three alternatively spliced forms (isoforms) of CD33 have been identified, including a higher molecular weight variant, named CD33M and a smaller isoform CD33m that lacks the Ig-like V-type domain (the ligand-binding site), and the disulfide bond linking the V and C domains.

Genome-wide association studies (GWAS) performed on extended cohorts (e.g., thousands of individuals) have identified single nucleotide polymorphisms (SNPs) rs3865444$^{CC}$ (AKA rs3826656) and rs3865444$^{AA}$ in CD33 as genetic modulators of risk for late onset Alzheimer's disease (AD). In oncology, CD33 variants that lead to decreased expression of CD33 have been shown to be associated with improved survival rate from pediatric acute myeloid leukemia (AML). The 3-year overall survival rate from remission is 84%+/−8% for those carrying the variant rs35112940$^{GG}$, which is in strong linkage disequilibrium with the rs3865444$^{AA}$ variant, associated with lower full-length expression of CD33. The remission rate for the non-protective allele is 68%+/−15%. Carriers of the protective allele also have a lower relapse risk and superior disease-free survival. Likewise, patients homozygous for the minor variant allele (TT) of rs12459419, which is associated with over 46% lower expression of the full-length CD33, are more likely to have favorable disease outcome than carriers of the variants CC and CT (52% vs. 31%) and have significantly lower diagnostic blast CD33 expression than other genotypes. This is the case even in patients undergoing treatment with anti-CD33 antibody and a toxic calicheamicin-gamma derivative (Mortland et al., (2013) Clin Cancer Res; 1-8). Carriers of the 2459419$^{TT}$ allele, as well as carriers of the rs12459419$^{CT}$ allele, which show over 25% reduction in expression of full-length CD33, also display reduced Alzheimer's disease risk (Malik M. et al. (2015) Human Molecular Genetics, 1-14). This suggests that reduced expression or functionality of CD33 may be beneficial in Alzheimer's disease and cancer.

Accordingly, there is a need for therapeutic anti-CD33 antibodies to treat diseases, disorders, and conditions associated with undesired CD33 activity.

All references cited herein, including patents, patent applications and publications, are hereby incorporated by reference in their entirety.

SUMMARY

The present disclosure is generally directed to compositions that include antibodies, e.g., monoclonal, chimeric, humanized antibodies, antibody fragments, etc., that specifically bind human CD33, and to methods of using such compositions.

Certain aspects of the present disclosure are based, at least in part, on the identification of anti-CD33 antibodies with improved and/or enhanced functional characteristics (e.g., relative to an anti-CD33 antibody with a heavy chain variable region comprising the sequence of SEQ ID NO: 103 and a light chain variable region comprising the sequence SEQ ID NO: 104), including, for example, improved and/or enhanced capabilities of decreasing cell surface levels of CD33 on human primary immune cells, and/or have improved and/or enhanced binding kinetics. In some embodiments, anti-CD33 antibodies of the present disclosure have a $K_D$ for human CD33 that is at least 9-fold lower than an anti-CD33 antibody having a heavy chain variable region comprising the amino acid sequence of SEQ ID NO: 34 and a light chain variable region comprising the amino acid sequence of SEQ ID NO: 77. In some embodiments, anti-CD33 antibodies of the present disclosure have a $K_D$ for human CD33 that is at least 3-fold lower than an anti-CD33 antibody having a heavy chain variable region comprising the amino acid sequence of SEQ ID NO: 40 and a light chain variable region comprising the amino acid sequence of SEQ ID NO: 86. In some embodiments, anti-CD33 antibodies of the present disclosure have a $K_D$ for human CD33 that is at least 3-fold lower than an anti-CD33 antibody having a heavy chain variable region comprising the amino acid sequence of SEQ ID NO: 52 and a light chain variable region comprising the amino acid sequence of SEQ ID NO: 86. In some embodiments, anti-CD33 antibodies of the present disclosure reduce cell surface levels of CD33 in vitro with an $EC_{50}$ that is at least about 50% lower than an anti-CD33 antibody having a heavy chain variable region comprising the amino acid sequence of SEQ ID NO: 34 and a light chain variable region comprising the amino acid sequence of SEQ ID NO: 77. In some embodiments, anti-CD33 antibodies of the present disclosure reduce cell surface levels of CD33 in vitro with an $EC_{50}$ that is at least about 10% lower than an anti-CD33 antibody having a heavy chain variable region comprising the amino acid sequence of SEQ ID NO: 40 and a light chain variable region comprising the amino acid sequence of SEQ ID NO: 86. In some embodiments, anti-CD33 antibodies of the present disclosure reduce cell surface levels of CD33 in vitro with an $EC_{50}$ that is at least about 10% lower than an anti-CD33 antibody having a heavy chain variable region comprising the amino acid sequence of SEQ ID NO: 52 and a light chain variable region comprising the amino acid sequence of SEQ ID NO: 86. In some embodiments, anti-CD33 antibodies of the present disclosure reduce cell surface levels of CD33 in vitro with an $EC_{50}$ that is at least about 10-fold lower than an anti-CD33 antibody having a heavy chain variable region comprising the amino acid sequence of SEQ ID NO: 103 and a light chain variable region comprising the amino acid sequence of SEQ ID NO: 104, as measured by flow cytometry. Advantageously, the anti-CD33 antibodies decrease cellular levels of CD33 in vitro with a half-maximal effective concentration ($EC_{50}$) that ranges from about 151.1 pM to about 4.1 pM, bind to human cells (such as human primary dendritic cells), and have a dissociation constant ($K_D$) for human CD33 that ranges from about 8.57 nM to about 202 pM.

Accordingly, in one aspect, the present disclosure relates to an antibody that binds to a CD33 protein, wherein the antibody comprises a heavy chain variable region and a light chain variable region, wherein the heavy chain variable region comprises: an HVR-H1 comprising a sequence according to Formula I: $GX_1X_2X_3TDYNX_4H$ (SEQ ID NO: 152), wherein $X_1$ is Y, A, or V, $X_2$ is T or A, $X_3$ is F, E, or H, and $X_4$ is L, F, Y, or N; an HVR-H2 comprising a sequence according to Formula II: $FIYPX_1NX_2IX_3G$ (SEQ ID NO: 153), wherein $X_1$ is S or A, $X_2$ is G, Q, R, or V, and $X_3$ is T or R; and an HVR-H3 comprising a sequence according to Formula III: $SX_1VDYFDX_2$ (SEQ ID NO: 154), wherein $X_1$ is T, D, F, or S, and $X_2$ is Y, D, or L; and wherein the antibody is not an antibody comprising a heavy chain variable region comprising an HVR-H1 comprising the sequence of GYTFTDYNLH (SEQ ID NO: 105), an HVR-H2 comprising the sequence of FIYPSNGITG (SEQ ID NO: 115), and an HVR-H3 comprising the sequence of STVDYFDY (SEQ ID NO: 121).

In another aspect, the present disclosure relates to an antibody that binds to a CD33 protein, wherein the antibody comprises a heavy chain variable region and a light chain variable region, wherein the light chain variable region comprises: an HVR-L1 comprising a sequence according to Formula IV: $X_1X_2SQX_3VX_4X_5STYSYMH$ (SEQ ID NO: 155), wherein $X_1$ is R or K, $X_2$ is A, G, or V, $X_3$ is S or D, $X_4$ is S, G, or H, and $X_5$ is T or A; an HVR-L2 comprising a sequence according to Formula V: $YX_1X_2X_3X_4X_5S$ (SEQ ID NO: 156), wherein $X_1$ is A, V, or E, $X_2$ is S, V, or F, $X_3$ is N, A, Y, or F, $X_4$ is L or V, and $X_5$ is E, G, or N; and an HVR-L3 comprising a sequence according to Formula VI: $X_1HSX_2X_3X_4PLX_5$ (SEQ ID NO: 157), wherein $X_1$ is Q or E, $X_2$ is W or E, $X_3$ is E or A, $X_4$ is I or L, and $X_5$ is T or E; and wherein the antibody is not an antibody comprising a light chain variable region comprising an HVR-L1 comprising the sequence of RASQSVSTSTYSYMH (SEQ ID NO: 127), an HVR-L2 comprising the sequence of YASNLES (SEQ ID NO: 135), and an HVR-L3 comprising the sequence of QHSWEIPLT (SEQ ID NO: 146).

In another aspect, the present disclosure relates to an antibody that binds to a CD33 protein, wherein the antibody comprises a heavy chain variable region and a light chain variable region, wherein the heavy chain variable region comprises: an HVR-H1 comprising a sequence according to Formula I: $GX_1X_2X_3TDYNX_4H$ (SEQ ID NO: 152), wherein $X_1$ is Y, A, or V, $X_2$ is T or A, $X_3$ is F, E, or H, and $X_4$ is L, F, Y, or N; an HVR-H2 comprising a sequence according to Formula II: $FIYPX_1NX_2IX_3G$ (SEQ ID NO: 153), wherein $X_1$ is S or A, $X_2$ is G, Q, R, or V, and $X_3$ is T or R; and an HVR-H3 comprising a sequence according to Formula III: $SX_1VDYFDX_2$ (SEQ ID NO: 154), wherein $X_1$ is T, D, F, or S, and $X_2$ is Y, D, or L; and the light chain variable region comprises: an HVR-L1 comprising a sequence according to Formula IV: $X_1X_2SQX_3VX_4X_5STYSYMH$ (SEQ ID NO: 155), wherein $X_1$ is R or K, $X_2$ is A, G, or V, $X_3$ is S or D, $X_4$ is S, G, or H, and $X_5$ is T or A; an HVR-L2 comprising a sequence according to Formula V: $YX_1X_2X_3X_4X_5S$ (SEQ ID NO: 156), wherein X1 is A, V, or E, $X_2$ is S, V, or F, $X_3$ is N, A, Y, or F, $X_4$ is L or V, and $X_5$ is E, G, or N; and an HVR-L3 comprising a sequence according to Formula VI: $X_1HSX_2X_3X_4PLX_5$ (SEQ ID NO: 157), wherein $X_1$ is Q or E, $X_2$ is W or E, $X_3$ is E or A, $X_4$ is I or L, and $X_5$ is T or E; and wherein the antibody is not an antibody comprising a heavy chain variable region comprising an HVR-H1 comprising the sequence of GYTFTDYNLH (SEQ ID NO: 105), an HVR-H2 comprising the sequence of FIYPSN-GITG (SEQ ID NO: 115), and an HVR-H3 comprising the sequence of STVDYFDY (SEQ ID NO: 121), and a light chain variable region comprising an HVR-L1 comprising the sequence of RASQSVSTSTYSYMH (SEQ ID NO: 127), an HVR-L2 comprising the sequence of YASNLES (SEQ ID NO: 135), and an HVR-L3 comprising the sequence of QHSWEIPLT (SEQ ID NO: 146).

In another aspect, the present disclosure relates to an that binds to a CD33 protein, wherein the antibody comprises a heavy chain variable region and a light chain variable region, wherein the heavy chain variable region comprises the HVR-H1, HVR-H2, and HVR-H3 of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15 (as shown in Tables 3A to 3C).

In another aspect, the present disclosure relates to an antibody that binds to a CD33 protein, wherein the antibody comprises a heavy chain variable region and a light chain variable region, wherein the light chain variable region comprises the HVR-L1, HVR-L2, and HVR-L3 of antibody AB-14.3, AB-14.4, AB-14.6, AB-14.7, AB-14.8, AB-14.9, AB-14.10, AB-14.11, AB-63.6, AB-63.7, AB-63.8, AB-63.9, AB-63.10, AB-63.11, AB-63.12, AB-63.14, AB-63.15, AB-63.16, AB-63.17, AB-63.18, AB-64.2, AB-64.3, AB-64.4, AB-64.5, AB-64.6, AB-64.7, or AB-64.8 (as shown in Tables 4A to 4C).

In another aspect, the present disclosure relates to an antibody that binds to a CD33 protein, wherein the antibody comprises a heavy chain variable region and a light chain variable region, wherein the heavy chain variable region comprises the HVR-H1, HVR-H2, and HVR-H3 of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15 (as shown in Tables 3A to 3C); and the light chain variable region comprises the HVR-L1, HVR-L2, and HVR-L3 of antibody AB-14.3, AB-14.4, AB-14.6, AB-14.7, AB-14.8, AB-14.9, AB-14.10, AB-14.11, AB-63.6, AB-63.7, AB-63.8, AB-63.9, AB-63.10, AB-63.11, AB-63.12, AB-63.14, AB-63.15, AB-63.16, AB-63.17, AB-63.18, AB-64.2, AB-64.3, AB-64.4, AB-64.5, AB-64.6, AB-64.7, or AB-64.8 (as shown in Tables 4A to 4C).

In another aspect, the present disclosure relates to an antibody that binds to a CD33 protein, wherein the antibody comprises a heavy chain variable region comprising an HVR-H1, HVR-H2, and HVR-H3 and a light chain variable region comprising an HVR-L1, HVR-L2, and HVR-L3, wherein the antibody comprises the HVR-H1, HVR-H2, HVR-H3, HVR-L1, HVR-L2, and HVR-L3 of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15 (as shown in Tables 3A to 3C and 4A to 4C).

Other aspects of the present disclosure relate to an antibody that binds to a CD33 protein, wherein the antibody comprises a heavy chain variable region and a light chain variable region, wherein the heavy chain variable region comprises Kabat CDRs; and/or the light chain variable region comprises Kabat CDRs. In some embodiments, the heavy chain variable region comprises a CDR-H1 comprising the sequence of DYNLH (SEQ ID NO: 190), a CDR-H2 comprising the sequence of FIYPSNGITGYAQKFQ (SEQ ID NO: 194); and a CDR-H3 comprising the sequence of YCARSDVD (SEQ ID NO: 191). In some embodiments, the light chain variable region comprises a CDR-L1 comprising the sequence of RASQSVSTSTYSYMH (SEQ ID NO: 127), a CDR-L2 comprising the sequence of LLIKYAS (SEQ ID NO: 192); and a CDR-L3 comprising the sequence of VYYCQHSWE (SEQ ID NO: 193). In some embodiments, the heavy chain variable region comprises a CDR-H1 comprising the sequence of DYNLH (SEQ ID NO: 190), a CDR-H2 comprising the sequence of FIYPSNGITGYAQKFQ (SEQ ID NO: 194); and a CDR-H3 comprising the sequence of YCARSDVD (SEQ ID NO: 191); and the light chain variable region comprises a CDR-L1 comprising the sequence of RASQSVSTSTYSYMH (SEQ ID NO: 127), a CDR-L2 comprising the sequence of LLIKYAS (SEQ ID NO: 192); and a CDR-L3 comprising the sequence of VYYCQHSWE (SEQ ID NO: 193).

Other aspects of the present disclosure relate to an antibody that binds to a CD33 protein, wherein the antibody comprises a heavy chain variable region and a light chain variable region, wherein the heavy chain variable region comprises Kabat CDRs; and/or the light chain variable region comprises Kabat CDRs. In some embodiments, the heavy chain variable region comprises a CDR-H1 comprising the sequence of DYNLH (SEQ ID NO: 190), a CDR-H2 comprising the sequence of FIYPSNRITGYAQKFQ (SEQ ID NO: 195); and a CDR-H3 comprising the sequence of YCARSDVD (SEQ ID NO: 191). In some embodiments, the light chain variable region comprises a CDR-L1 comprising the sequence of RASQSVSTSTYSYMH (SEQ ID NO: 127), a CDR-L2 comprising the sequence of LLIKYAS (SEQ ID NO: 192); and a CDR-L3 comprising the sequence of VYYCQHSWE (SEQ ID NO: 193). In some embodiments, the heavy chain variable region comprises a CDR-H1 comprising the sequence of DYNLH (SEQ ID NO: 190), a CDR-H2 comprising the sequence of FIYPSNRITGYAQKFQ (SEQ ID NO: 195); and a CDR-H3 comprising the sequence of YCARSDVD (SEQ ID NO: 191); and the light chain variable region comprises a CDR-L1 comprising the sequence of RASQSVSTSTYSYMH (SEQ ID NO: 127), a CDR-L2 comprising the sequence of LLIKYAS (SEQ ID NO: 192); and a CDR-L3 comprising the sequence of VYYCQHSWE (SEQ ID NO: 193).

Other aspects of the present disclosure relate to an antibody that binds to a CD33 protein, wherein the antibody comprises a heavy chain variable region and a light chain variable region, wherein the heavy chain variable region comprises Kabat CDRs; and/or the light chain variable region comprises Kabat CDRs. In some embodiments, the heavy chain variable region comprises a CDR-H1 comprising the sequence of DYNLH (SEQ ID NO: 190), a CDR-H2 comprising the sequence of FIYPSNQITGYAQKFQ (SEQ ID NO: 196); and a CDR-H3 comprising the sequence of YCARSDVD (SEQ ID NO: 191). In some embodiments, the light chain variable region comprises a CDR-L1 comprising the sequence of RASQSVSTSTYSYMH (SEQ ID NO: 127), a CDR-L2 comprising the sequence of LLIKYAS (SEQ ID NO: 192); and a CDR-L3 comprising the sequence of VYYCQHSWE (SEQ ID NO: 193). In some embodiments, the heavy chain variable region comprises a CDR-H1 comprising the sequence of DYNLH (SEQ ID NO: 190), a CDR-H2 comprising the sequence of FIYPSNQITGYAQKFQ (SEQ ID NO: 196); and a CDR-H3 comprising the sequence of YCARSDVD (SEQ ID NO: 191); and the light chain variable region comprises a CDR-L1 comprising the sequence of RASQSVSTSTYSYMH (SEQ ID NO: 127), a CDR-L2 comprising the sequence of LLIKYAS (SEQ ID NO: 192); and a CDR-L3 comprising the sequence of VYYCQHSWE (SEQ ID NO: 193).

In some embodiments that may be combined with any of the preceding embodiments, the heavy chain variable region comprises one, two, three, or four framework regions selected from VH FR1, VH FR2, VH FR3, and VH FR4, wherein: VH FR1 comprises a sequence according to Formula VII: QVQLVQSGAEVKKPGX$_1$SVKX$_2$SCKAS (SEQ ID NO: 158), wherein X$_1$ is A or S, and X$_2$ is V or I; VH FR2 comprises the sequence of SEQ ID NO: 5; VH FR3 comprises a sequence according to Formula VIII: X$_1$AX$_2$X$_3$X$_4$X$_5$X$_6$RX$_7$TX$_8$TVDX$_9$X$_{10}$X$_{11}$STX$_{12}$YMELS-SLRSEDTAVYYCAR (SEQ ID NO: 159), wherein X$_1$ is Y or S, X$_2$ is Q or E, X$_3$ is K or D, X$_4$ is F or D, X$_5$ is Q, F, E, or T, X$_6$ is G, D, or H, X$_7$ is V or A, X$_8$ is M or L, X$_9$ is T, N, or Q, X$_{10}$ is S or P, X$_{11}$ is T or A, and X$_{12}$ is V or A; and VH FR4 comprises a sequence according to Formula IX: WGQGTLX$_1$TVSS (SEQ ID NO: 160), wherein X$_1$ is V or L; and/or the light chain comprises one, two, three, or four framework regions selected from VL FR1, VL FR2, VL FR3, and VL FR4, wherein: VL FR1 comprises a sequence according to Formula X: X$_1$IX$_2$X$_3$TQSPX$_4$SLX$_5$X$_6$SX$_7$GX$_8$RX$_9$TIX$_{10}$C (SEQ ID NO: 161), wherein X$_1$ is D or G, X$_2$ is Q or V, X$_3$ is M or L, X$_4$ is S or D, X$_5$ is S, P, or A, X$_6$ is A or V, X$_7$ is V or L, X$_8$ is D or E, X$_9$ is V or A, and X$_{10}$ is T, N, or D; VL FR2 comprises a sequence according to Formula XI: WYQQKPGX$_1$X$_2$PKLLIK (SEQ ID NO: 162), wherein X$_1$ is K or Q, and X$_2$ is A or P; VL FR3 comprises a sequence according to Formula XII: GVPX$_1$RFSGSGSGTDFTLTISSLQX$_2$EDX$_3$AX$_4$YYC (SEQ ID NO: 163), wherein X$_1$ is S or D, X$_2$ is P or A, X$_3$ is F, L, or V, and X$_4$ is T or V; and VL FR4 comprises a sequence according to Formula XIII: FGQGTKLEIX$_1$ (SEQ ID NO: 164), wherein X$_1$ is K or E. In some embodiments that may be combined with any of the preceding embodiments, the heavy chain variable region comprises one, two, three, or four framework regions selected from VH FR1, VH FR2, VH FR3, and VH FR4, wherein: VH FR1 comprises a sequence selected from the group consisting of SEQ ID NOs: 2-4; VH FR2 comprises the sequence of SEQ ID NO: 5; VH FR3 comprises a sequence selected from the group consisting of SEQ ID NOs: 6-19; and VH FR4 comprises a sequence selected from the group consisting of SEQ ID NOs: 20-21; and/or the light chain comprises one, two, three, or four framework regions selected from VL FR1, VL FR2, VL FR3, and VL FR4, wherein: VL FR1 comprises a sequence selected from the group consisting of SEQ ID NOs: 22-26; VL FR2 comprises a sequence selected from the group consisting of SEQ ID NOs: 27-28; VL FR3 comprises a sequence selected from the group consisting of SEQ ID NOs: 29-31; and VL FR4 comprises a sequence selected from the group consisting of SEQ ID NOs: 32-33.

In some embodiments that may be combined with any of the preceding embodiments, the antibody comprises a heavy chain variable region comprising an amino acid sequence selected from the group consisting of SEQ ID NOs: 34-72; and/or a light chain variable region comprises an amino acid sequence selected from the group consisting of SEQ ID NOs: 77-101. In some embodiments, the antibody comprises the heavy chain variable region of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15 (as shown in Table 7); and/or the antibody comprises the light chain variable region of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15 (as shown in Table 8). In some embodiments that may be combined with any of the preceding embodiments, the HVR-H1 comprises the amino acid sequence GYTFTDYNLH (SEQ ID NO: 105), the HVR-H2 comprises the amino acid sequence FIYPSNRITG (SEQ ID NO: 119), the HVR-H3 comprises the amino acid sequence SDVDYFDY (SEQ ID NO: 122), the HVR-L1 comprises the amino acid sequence RASQSVSTSTYSYMH (SEQ ID NO: 127), the HVR-L2 comprises the amino acid sequence YASNLES (SEQ ID NO: 135), and the HVR-L3 comprises the amino acid sequence QHSWEIPLT (SEQ ID NO: 146); or the HVR-H1 comprises the amino acid sequence GYTFTDYNLH (SEQ ID NO: 105), the HVR-H2 comprises the amino acid sequence FIYPSNQITG (SEQ ID NO: 118), the HVR-H3 comprises the amino acid sequence SDVDYFDY (SEQ ID NO: 122), the HVR-L1 comprises the amino acid sequence RASQSVSTSTYSYMH (SEQ ID NO: 127), the HVR-L2 comprises the amino acid sequence YASNLES (SEQ ID NO: 135), and the HVR-L3 comprises the amino acid sequence QHSWEIPLT (SEQ ID NO: 146).

In another aspect, the present disclosure relates to an antibody that binds to a CD33 protein, wherein the antibody comprises a heavy chain variable region and a light chain variable region, wherein: the heavy chain variable region comprises an HVR-H1 comprising the amino acid sequence GYTFTDYNLH (SEQ ID NO: 105), an HVR-H2 comprising the amino acid sequence FIYPSNRITG (SEQ ID NO: 119), and an HVR-H3 comprising the amino acid sequence SDVDYFDY (SEQ ID NO: 122), and the light chain variable region comprises an HVR-L1 comprising the amino acid sequence RASQSVSTSTYSYMH (SEQ ID NO: 127), an HVR-L2 comprising the amino acid sequence YASNLES (SEQ ID NO: 135), and an HVR-L3 comprising the amino acid sequence QHSWEIPLT (SEQ ID NO: 146); or the heavy chain comprises an HVR-H1 comprising the amino acid sequence GYTFTDYNLH (SEQ ID NO: 105), an HVR-H2 comprising the amino acid sequence FIYPSNQITG (SEQ ID NO: 118), and an HVR-H3 comprising the amino acid sequence SDVDYFDY (SEQ ID NO: 122), and the light chain variable region comprises an HVR-L1 comprising the amino acid sequence RASQSVSTSTYSYMH (SEQ ID NO: 127), an HVR-L2 comprising the amino acid sequence YASNLES (SEQ ID NO: 135), and an HVR-L3 comprising the amino acid sequence QHSWEIPLT (SEQ ID NO: 146).

In another aspect, the present disclosure relates to an antibody that binds to a CD33 protein, wherein the antibody comprises a heavy chain variable region comprising an amino acid sequence selected from the group consisting of SEQ ID NOs: 34-72; and/or a light chain variable region comprising an amino acid sequence selected from the group consisting of SEQ ID NOs: 77-101. In some embodiments, the antibody comprises the heavy chain variable region of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15 (as shown in Table 7); and/or the antibody comprises the light chain variable region of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15 (as shown in Table 8). In some embodiments, the heavy chain variable region comprises the amino acid sequence of SEQ ID NO: 59, and/or the light chain variable region comprises the amino acid sequence of SEQ ID NO: 86; or the heavy chain variable region comprises the amino acid sequence of SEQ ID NO: 65, and/or the light chain variable region comprises the amino acid sequence of SEQ ID NO: 86.

In another aspect, the present disclosure relates to an antibody that binds to a CD33 protein, wherein the antibody comprises a heavy chain variable region comprising an amino acid sequence selected from the group consisting of SEQ ID NOs: 34, 40, 42, 52, 53, and 73-76; and/or a light chain variable region comprising an amino acid sequence selected from the group consisting of SEQ ID NOs: 77, 86, and 102. In some embodiments, he antibody comprises the heavy chain variable region of AB-H2, AB-H9, AB-H14, AB-H15, AB-H63, AB-H64, AB-H65, or AB-H66 (as shown in Table 7); and/or the antibody comprises the light chain variable region of antibody AB-H2, AB-H9, AB-H14, AB-H15, AB-H63, AB-H64, AB-H65, or AB-H66 (as shown in Table 8).

In another aspect, the present disclosure relates to an antibody that binds to a CD33 protein, wherein the antibody competes with one or more antibodies selected from the group consisting of AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, AB-64.1.15, AB-H2, AB-H9, AB-H14, AB-H15, AB-H63, AB-H64, AB-H65, AB-H66, and any combination thereof for binding to CD33.

In another aspect, the present disclosure relates to an antibody that binds to a CD33 protein, wherein the antibody binds essentially the same CD33 epitope as an antibody selected from the group consisting of AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, AB-64.1.15, AB-H2, AB-H9, AB-H14, AB-H15, AB-H63, AB-H64, AB-H65, and AB-H66.

In another aspect, the present disclosure relates to an antibody that binds to a CD33 protein, wherein the antibody comprises a heavy chain variable region and a light chain variable region, wherein the heavy chain variable region comprises: an HVR-H1 comprising a sequence according to Formula I: GX$_1$X$_2$X$_3$TDYNX$_4$H (SEQ ID NO: 186), wherein X$_1$ is Y or V, X$_2$ is T or A, X$_3$ is F, E, or H, and X$_4$ is L, F, Y, or N; an HVR-H2 comprising a sequence according to Formula II: FIYPX$_1$NX$_2$IX$_3$G (SEQ ID NO: 153), wherein X$_1$ is S or A, X$_2$ is G, Q, R, or V, and X$_3$ is T or R; and an HVR-H3 comprising a sequence according to Formula III: SX$_1$VDYFDX$_2$ (SEQ ID NO: 187), wherein X$_1$ is T, D, or F, and X$_2$ is Y, D, or L; and wherein the light chain variable region comprises: an HVR-L1 comprising a sequence according to Formula IV: X$_1$X$_2$SQX$_3$VX$_4$X$_5$STYSYMH (SEQ ID NO: 188), wherein X$_1$ is R or K, X$_2$ is A, G, or V, X$_3$ is S or D, X$_4$ is S, G, or H, and X$_5$ is T; an HVR-L2 comprising a sequence according to Formula V: YX$_1$X$_2$X$_3$X$_4$X$_5$S (SEQ ID NO: 189), wherein X$_1$ is A or E, X$_2$ is S or F, X$_3$ is N, Y, or F, X$_4$ is L or V, and X$_5$ is E or N; and an HVR-L3 comprising a sequence according to Formula VI: X$_1$HSX$_2$X$_3$X$_4$PLX$_5$ (SEQ ID NO: 157), wherein X$_1$ is Q or E, X$_2$ is W or E, X$_3$ is E or A, X$_4$ is I or L, and X$_5$ is T or E.

In another aspect, the present disclosure relates to an antibody that binds to a CD33 protein, wherein the antibody comprises a heavy chain variable region and a light chain variable region, wherein the heavy chain variable region comprises: an HVR-H1 comprising an amino acid sequence selected from the group consisting of SEQ ID NOs: 105 and 108-114; an HVR-H2 comprising an amino acid sequence selected from the group consisting of SEQ ID NOs: 115-120; and an HVR-H3 comprising an amino acid sequence selected from the group consisting of SEQ ID NOs: 121-123 and 125-126; and the light chain variable region comprises: an HVR-L1 comprising an amino acid sequence selected from the group consisting of SEQ ID NOs: 127-128 and 130-134; an HVR-L2 comprising an amino acid sequence selected from the group consisting of SEQ ID NOs: 135 and 140-145; and an HVR-L3 comprising an amino acid sequence selected from the group consisting of SEQ ID NOs: 146-151.

In some embodiments that may be combined with any of the preceding embodiments, the heavy chain variable region comprises one, two, three, or four framework regions selected from VH FR1, VH FR2, VH FR3, and VH FR4, wherein: VH FR1 comprises a sequence according to Formula VII: QVQLVQSGAEVKKPGX$_1$SVKX$_2$SCKAS (SEQ ID NO: 158), wherein X$_1$ is A or S, and X$_2$ is V or I; VH FR2 comprises the sequence of SEQ ID NO: 5; VH FR3 comprises a sequence according to Formula VIII: X$_1$AX$_2$X$_3$X$_4$X$_5$X$_6$RX$_7$TX$_8$TVDX$_9$X$_{10}$X$_{11}$STX$_{12}$YMELS SLRSEDTAVYYCAR (SEQ ID NO: 159), wherein X$_1$ is Y or S, X$_2$ is Q or E, X$_3$ is K or D, X$_4$ is F or D, X$_5$ is Q, F, E, or T, X$_6$ is G, D, or H, X$_7$ is V or A, X$_8$ is M or L, X$_9$ is T, N, or Q, X$_{10}$ is S or P, X$_{11}$ is T or A, and X$_{12}$ is V or A; and VH FR4 comprises a sequence according to Formula IX: WGQGTLX$_1$TVSS (SEQ ID NO: 160), wherein X$_1$ is V or L; and/or the light chain comprises one, two, three, or four framework regions selected from VL FR1, VL FR2, VL FR3, and VL FR4, wherein: VL FR1 comprises a sequence according to Formula X: X$_1$IX$_2$X$_3$TQSPX$_4$SLX$_5$X$_6$SX$_7$GX$_8$RX$_9$TIX$_{10}$C (SEQ ID NO: 161), wherein X$_1$ is D or G, X$_2$ is Q or V, X$_3$ is M or L, X$_4$ is S or D, X$_5$ is S, P, or A, X$_6$ is A or V, X$_7$ is V or L, X$_8$ is D or E, X$_9$ is V or A, and X$_{10}$ is T, N, or D; VL FR2 comprises a sequence according to Formula XI: WYQQKPGX$_1$X$_2$PKLLIK (SEQ ID NO: 162), wherein X$_1$ is K or Q, and X$_2$ is A or P; VL FR3 comprises a sequence according to Formula XII: GVPX$_1$RFSGSGSGTDFTLTISSLQX$_2$EDX$_3$AX$_4$YYC (SEQ ID NO: 163), wherein X$_1$ is S or D, X$_2$ is P or A, X$_3$ is F, L, or V, and X$_4$ is T or V; and VL FR4 comprises a sequence according to Formula XIII: FGQGTKLEIX$_1$ (SEQ ID NO: 164), wherein X$_1$ is K or E.

In some embodiments that may be combined with any of the preceding embodiments, the heavy chain variable region comprises one, two, three, or four framework regions selected from VH FR1, VH FR2, VH FR3, and VH FR4, wherein: VH FR1 comprises a sequence selected from the group consisting of SEQ ID NOs: 2-4; VH FR2 comprises the sequence of SEQ ID NO: 5; VH FR3 comprises a sequence selected from the group consisting of SEQ ID NOs: 6-19; and VH FR4 comprises a sequence selected from the group consisting of SEQ ID NOs: 20-21; and/or the light chain comprises one, two, three, or four framework regions selected from VL FR1, VL FR2, VL FR3, and VL FR4, wherein: VL FR1 comprises a sequence selected from the group consisting of SEQ ID NOs: 22-26; VL FR2 comprises a sequence selected from the group consisting of SEQ ID NOs: 27-28; VL FR3 comprises a sequence selected from the group consisting of SEQ ID NOs: 29-31; and VL FR4 comprises a sequence selected from the group consisting of SEQ ID NOs: 32-33. In some embodiments that may be combined with any of the preceding embodiments, the heavy chain variable region comprises a VH FR3 comprising a sequence selected from the group consisting of SEQ ID NOs: 12-15.

In another aspect, the present disclosure relates to an antibody that binds to a CD33 protein, wherein the antibody comprises a heavy chain variable region comprising an amino acid sequence selected from the group consisting of SEQ ID NOs: 38 and 40-72; and/or a light chain variable region comprising an amino acid sequence selected from the group consisting of SEQ ID NOs: 86-101.

In another aspect, the present disclosure relates to an antibody that binds to a CD33 protein, wherein the antibody comprises a heavy chain variable region comprising the amino acid sequence of SEQ ID NO: 58 and a light chain variable region comprising the amino acid sequence of SEQ ID NO: 86, a heavy chain variable region comprising the amino acid sequence of SEQ ID NO: 59 and a light chain variable region comprising the amino acid sequence of SEQ ID NO: 86, a heavy chain variable region comprising the amino acid sequence of SEQ ID NO: 65 and a light chain variable region comprising the amino acid sequence of SEQ ID NO: 86, a heavy chain variable region comprising the amino acid sequence of SEQ ID NO: 66 and a light chain variable region comprising the amino acid sequence of SEQ ID NO: 86, a heavy chain variable region comprising the amino acid sequence of SEQ ID NO: 67 and a light chain variable region comprising the amino acid sequence of SEQ ID NO: 86, a heavy chain variable region comprising the amino acid sequence of SEQ ID NO: 68 and a light chain variable region comprising the amino acid sequence of SEQ ID NO: 86, or a heavy chain variable region comprising the amino acid sequence of SEQ ID NO: 69 and a light chain variable region comprising the amino acid sequence of SEQ ID NO: 86.

In some embodiments that may be combined with any of the preceding embodiments, the antibody is of the IgG class the IgM class, or the IgA class. In some embodiments, the antibody is of the IgG class and has an IgG1, IgG2, IgG3, or IgG4 isotype. In some embodiments, the antibody has an IgG4 isotype, and wherein the antibody comprises an S228P amino acid substitution at residue position 228, an F234A amino acid substitution at residue position 234, and an L235A amino acid substitution at residue position 235, wherein the numbering of the residue position is according to EU numbering. In some embodiments, the antibody comprises one or more amino acid substitutions in the Fc region at a residue position selected from the group consisting of: C127S, L234A, L234F, L235A, L235E, S267E, K322A, L328F, A330S, P331S, E345R, E430G, S440Y, and any combination thereof, wherein the numbering of the residues is according to EU or Kabat numbering. In some embodiments, the Fc region comprises an amino acid substitution at position E430G, wherein the numbering of the residue position is according to EU numbering; the Fc region comprises an amino acid substitution at positions L243A, L235A, and P331A, wherein the numbering of the residue position is according to EU numbering; the Fc region comprises an amino acid substitution at positions L243A, L235A, P331A, and E430G, wherein the numbering of the residue position is according to EU numbering; the Fc region comprises an amino acid substitution at positions K322A and E430G, wherein the numbering of the residue position is according to EU numbering; the Fc region comprises an amino acid substitution at positions P331S and E430G, wherein the numbering of the residue position is according to EU numbering; the Fc region comprises an amino acid substitution at positions A330S, P331S, and E430G, wherein the numbering of the residue position is according to EU numbering; the Fc region comprises an amino acid substitution at positions K322A, A330S, and P331S, wherein the numbering of the residue position is according to EU numbering; the Fc region comprises an amino acid substitution at positions K322A, P331S, and E430G, wherein the numbering of the residue position is according to EU numbering; the Fc region comprises an amino acid substitution at position E430G, wherein the numbering of the residue position is according to EU numbering; the Fc region comprises an amino acid substitution at positions A330S, P331S, and E430G, wherein the numbering of the residue position is according to EU numbering; the Fc region comprises an amino acid substitution at positions S267E and L328F, wherein the numbering of the residue position is according to EU numbering; the Fc region comprises an amino acid substitution at position C127S, wherein the numbering of the residue position is according to EU numbering; or the Fc region comprises an amino acid substitution at positions E345R, E430G and S440Y, wherein the numbering of the residue position is according to EU numbering; or the Fc region comprises an amino acid substitution at positions L243A, L235A, and P331S, wherein the numbering of the residue position is according to EU numbering.

In another aspect, the present disclosure relates to an antibody that binds to a CD33 protein, wherein the antibody comprises a heavy chain comprising the amino acid sequence of SEQ ID NO: 176 and a light chain comprising the amino acid sequence of SEQ ID NO: 185. In another aspect, the present disclosure relates to an antibody that binds to a CD33 protein, wherein the antibody comprises a heavy chain comprising the amino acid sequence of SEQ ID NO: 177 and a light chain comprising the amino acid sequence of SEQ ID NO: 185. In another aspect, the present disclosure relates to an antibody that binds to a CD33 protein, wherein the antibody comprises a heavy chain comprising the amino acid sequence of SEQ ID NO: 178 and a light chain comprising the amino acid sequence of SEQ ID NO: 185. In another aspect, the present disclosure relates to an antibody that binds to a CD33 protein, wherein the antibody comprises a heavy chain comprising the amino acid sequence of SEQ ID NO: 179 and a light chain comprising the amino acid sequence of SEQ ID NO: 185. In another aspect, the present disclosure relates to an antibody that binds to a CD33 protein, wherein the antibody comprises a heavy chain comprising the amino acid sequence of SEQ ID NO: 180 and a light chain comprising the amino acid sequence of SEQ ID NO: 185. In another aspect, the present disclosure relates to an antibody that binds to a CD33 protein, wherein the antibody comprises a heavy chain comprising the amino acid sequence of SEQ ID NO: 181 and a light chain comprising the amino acid sequence of SEQ ID NO: 185. In another aspect, the present disclosure relates to an antibody that binds to a CD33 protein, wherein the antibody comprises a heavy chain comprising the amino acid sequence of SEQ ID NO: 182 and a light chain comprising the amino acid sequence of SEQ ID NO: 185. In another aspect, the present disclosure relates to an antibody that binds to a CD33 protein, wherein the antibody comprises a heavy chain comprising the amino acid sequence of SEQ ID NO: 183 and a light chain comprising the amino acid sequence of SEQ ID NO: 185. In another aspect, the present disclosure relates to an antibody that binds to a CD33 protein, wherein the antibody comprises a heavy chain comprising the amino acid sequence of SEQ ID NO: 184 and a light chain comprising the amino acid sequence of SEQ ID NO: 185. In another aspect, the present disclosure relates to an antibody that binds to a CD33 protein, wherein the antibody comprises a heavy chain comprising the amino acid sequence of SEQ ID NO: 197 and a light chain comprising the amino acid sequence of SEQ ID NO: 185. In another aspect, the present disclosure relates to an antibody that binds to a CD33 protein, wherein the antibody comprises a heavy chain comprising the amino acid sequence of SEQ ID NO: 198 and a light chain comprising the amino acid sequence of SEQ ID NO: 185. In another aspect, the present disclosure relates to an antibody that binds to a CD33 protein, wherein the antibody comprises a heavy chain comprising the amino acid sequence of SEQ ID NO: 199 and a light chain comprising the amino acid sequence of SEQ ID NO: 185. In another aspect, the present disclosure relates to an antibody that binds to a CD33 protein, wherein the antibody comprises a heavy chain comprising the amino acid sequence of SEQ ID NO: 200 and a light chain comprising the amino acid sequence of SEQ ID NO: 185. In another aspect, the present disclosure relates to an antibody that binds to a CD33 protein, wherein the antibody comprises a heavy chain comprising the amino acid sequence of SEQ ID NO: 201 and a light chain comprising the amino acid sequence of SEQ ID NO: 185. In another aspect, the present disclosure relates to an antibody that binds to a CD33 protein, wherein the antibody comprises a heavy chain comprising the amino acid sequence of SEQ ID NO: 202 and a light chain comprising the amino acid sequence of SEQ ID NO: 185. In another aspect, the present disclosure relates to an antibody that binds to a CD33 protein, wherein the antibody comprises a heavy chain comprising the amino acid sequence of SEQ ID NO: 203 and a light chain comprising the amino acid sequence of SEQ ID NO: 185. In another aspect, the present disclosure relates to an antibody that binds to a CD33 protein, wherein the antibody comprises a heavy chain comprising the amino acid sequence of SEQ ID NO: 204 and a light chain comprising the amino acid sequence of SEQ ID NO: 185. In another aspect, the present disclosure relates to an antibody that binds to a CD33 protein, wherein the antibody comprises a heavy chain comprising the amino acid sequence of SEQ ID NO: 205 and a light chain comprising the amino acid sequence of SEQ ID NO: 185.

In some embodiments that may be combined with any of the preceding embodiments, the CD33 protein is a mammalian protein or a human protein. In some embodiments, the CD33 protein is a wild-type protein. In some embodiments, the CD33 protein is a naturally occurring variant. In some embodiments that may be combined with any of the preceding embodiments, the CD33 protein is expressed on one or more cells selected from the group consisting of human dendritic cells, human macrophages, human monocytes, human osteoclasts, human neutrophils, human T cells, human T helper cell, human cytotoxic T cells, human granulocytes, and human microglia.

In some embodiments that may be combined with any of the preceding embodiments, the antibody binds specifically to a human CD33 protein. In some embodiments, the antibody binds to a human CD33 protein and does not cross-react with a CD33 ortholog or homolog from another species. In some embodiments that may be combined with any of the preceding embodiments, the antibody is an antibody fragment that binds to an epitope comprising amino acid residues on human CD33 or a mammalian CD33 protein. In some embodiments that may be combined with any of the preceding embodiments, the antibody is an antibody fragment that binds to one or more human proteins selected from the group consisting of human CD33, a naturally occurring variant of human CD33, and a disease variant of human CD33. In some embodiments, the antibody fragment is cross-linked to a second antibody fragment that binds to one or more human proteins selected from the group consisting of human CD33, a naturally occurring variant of human CD33, and a disease variant of human CD33. In some embodiments, the fragment is an Fab, Fab', Fab'-SH, F(ab')2, Fv, or scFv fragment.

In some embodiments that may be combined with any of the preceding embodiments, the antibody is a humanized antibody, a bispecific antibody, a monoclonal antibody, a multivalent antibody, a conjugated antibody, or a chimeric antibody. In some embodiments, the antibody is a monoclonal antibody. In some embodiments, the antibody is a bispecific antibody recognizing a first antigen and a second antigen. In some embodiments, the first antigen is CD33 and the second antigen is: an antigen facilitating transport across the blood-brain-barrier; an antigen facilitating transport across the blood-brain-barrier selected from the group consisting of transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, and ANG1005; a disease-causing agent selected from the group consisting of disease-causing peptides or proteins and disease-causing nucleic acids, wherein the disease-causing peptides or proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and the disease-causing nucleic acids are antisense GGCCCC (G2C4) repeat-expansion RNA; ligands and/or proteins expressed on immune cells, wherein the ligands and/or proteins selected from the group consisting of CD40, OX40, ICOS, CD28, CD137/4-1BB, CD27, GITR, PD-L1, CTLA4, PD-L2, PD-1, B7-H3, B7-H4, HVEM, LIGHT, BTLA, CD38, TIGIT, VISTA, KIR, GAL9, TIM1, TIM3, TIM4, A2AR, LAG3, DR5, CD39, CD70, CD73, TREM1, TREM2, Siglec-5, Siglec-7, Siglec-9, Siglec-11, SirpA, CD47, CSF1-receptor, and phosphatidylserine; and a protein, lipid, polysaccharide, or glycolipid expressed on one or more tumor cells.

In some embodiments that may be combined with any of the preceding embodiments, the antibody is used in combination with one or more antibodies that specifically bind a disease-causing agent selected from the group consisting of disease-causing peptides, disease-causing proteins, amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and any combination thereof; or with one or more antibodies that bind an immunomodulatory protein selected from the group consisting of: CD40, OX40, ICOS, CD28, CD137/4-1BB, CD27, GITR, PD-L1, CTLA4, PD-L2, PD-1, B7-H3, B7-H4, HVEM, LIGHT, BTLA, CD38, TIGIT, VISTA, KIR, GAL9, TIM1, TIM3, TIM4, A2AR3, DR5, CD39, CD70, CD73, LAG3, TREM1, TREM2, Siglec-5, Siglec-7, Siglec-9, Siglec-11, SirpA, CD47, CSF1-receptor, phosphatidylserine, disease-causing nucleic acids, antisense GGCCCC (G2C4) repeat-expansion RNA, and any combination thereof.

In some embodiments that may be combined with any of the preceding embodiments, the antibody has a dissociation constant ($K_D$) for human CD33 that is at least 4-fold lower than an anti-CD33 antibody comprising a heavy chain variable region comprising the amino acid sequence of SEQ ID NO: 34 and a light chain variable region comprising the amino acid sequence of SEQ ID NO: 77; at least 1-fold lower than an anti-CD33 antibody comprising a heavy chain variable region comprising the amino acid sequence of SEQ ID NO: 40 and a light chain variable region comprising the amino acid sequence of SEQ ID NO: 86; or at least 1-fold lower than an anti-CD33 antibody comprising a heavy chain variable region comprising the amino acid sequence of SEQ ID NO: 52 and a light chain variable region comprising the amino acid sequence of SEQ ID NO: 86, wherein the $K_D$ is determined by surface plasmon resonance. In some embodiments that may be combined with any of the preceding embodiments, the antibody has a dissociation constant ($K_D$) for human CD33 that ranges from about 2 nM to about 200 pM, or less than about 200 pM, and wherein the $K_D$ is determined by BioLayer Interferometry.

In some embodiments that may be combined with any of the preceding embodiments, the antibody reduces cell surface levels of CD33. In some embodiments, the CD33 is expressed on the surface of human dendritic cells. In some embodiments, the antibody reduces cell surface levels of CD33 in vitro. In some embodiments, the antibody reduces cell surface levels of CD33 in vitro with a half maximal effective concentration ($EC_{50}$) that is less than 150 pM, as measured by flow cytometry. In some embodiments, the antibody reduces cell surface levels of CD33 in vitro with an $EC_{50}$ that is at least 50% lower than an anti-CD33 antibody comprising a heavy chain variable region comprising the amino acid sequence of SEQ ID NO: 34 and a light chain variable region comprising the amino acid sequence of SEQ ID NO: 77; at least 10% lower than an anti-CD33 antibody comprising a heavy chain variable region comprising the amino acid sequence of SEQ ID NO: 40 and a light chain variable region comprising the amino acid sequence of SEQ ID NO: 86; at least 10% lower than an anti-CD33 antibody comprising a heavy chain variable region comprising the amino acid sequence of SEQ ID NO: 52 and a light chain variable region comprising the amino acid sequence of SEQ ID NO: 86; or at least 10-fold lower than an anti-CD33 antibody comprising a heavy chain variable region comprising the amino acid sequence of SEQ ID NO: 103 and a light chain variable region comprising the amino acid sequence of SEQ ID NO: 104, as measured by flow cytometry.

In another aspect, the present disclosure relates to isolated nucleic acids comprising a nucleic acid sequence encoding any of the antibodies described herein.

In another aspect, the present disclosure relates to vectors comprising any of the nucleic acids described herein. In some embodiments, the vector is an expression vector and/or a display vector.

In another aspect, the present disclosure relates to isolated host cells comprising any of the nucleic acids or vectors described herein.

In another aspect, the present disclosure relates to a method of producing an antibody that binds to CD33 comprising culturing any of the host cells described herein so that the antibody is produced. In some embodiments, the method further comprises recovering the antibody produced by the cell.

In another aspect, the present disclosure relates to an antibody produced by any of the methods described herein.

In another aspect, the present disclosure relates to pharmaceutical compositions comprising any of the antibodies described herein and a pharmaceutically acceptable carrier. In some embodiments, the present disclosure relates to the use of any of the antibodies described herein for the preparation of a medicament.

In another aspect, the present disclosure relates to a method of preventing, reducing risk, or treating a disease, disorder, or injury selected from the group consisting of dementia, frontotemporal dementia, Alzheimer's disease, vascular dementia, mixed dementia, taupathy disease, infections, and cancer, comprising administering to an individual in need thereof a therapeutically effective amount of any of the antibodies described herein. In some embodiments, the disease, disorder, or injury is cancer. In some embodiments, the cancer is selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), and multiple myeloma. In some embodiments, the present disclosure relates to the use of any of the antibodies described herein for the preparation of a medicament useful for preventing, reducing risk, or treating a disease, disorder, or injury selected from the group consisting of dementia, frontotemporal dementia, Alzheimer's disease, vascular dementia, mixed dementia, taupathy disease, infections, and cancer. In some embodiments, the disease, disorder, or injury is cancer. In some embodiments, the cancer is selected from the group consisting of bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), and multiple myeloma.

BRIEF DESCRIPTION OF THE DRAWINGS

FIG. 9A depicts human CD33 levels on the surface of microglia, FIG. 9B depicts human Siglec-7 levels on the surface of microglia, FIG. 9C depicts human CD33 levels on the surface of circulating neutrophils, FIG. 9D depicts human CD33 levels on the surface of circulating monocytes.

DETAILED DESCRIPTION

General Techniques

Figure 1:
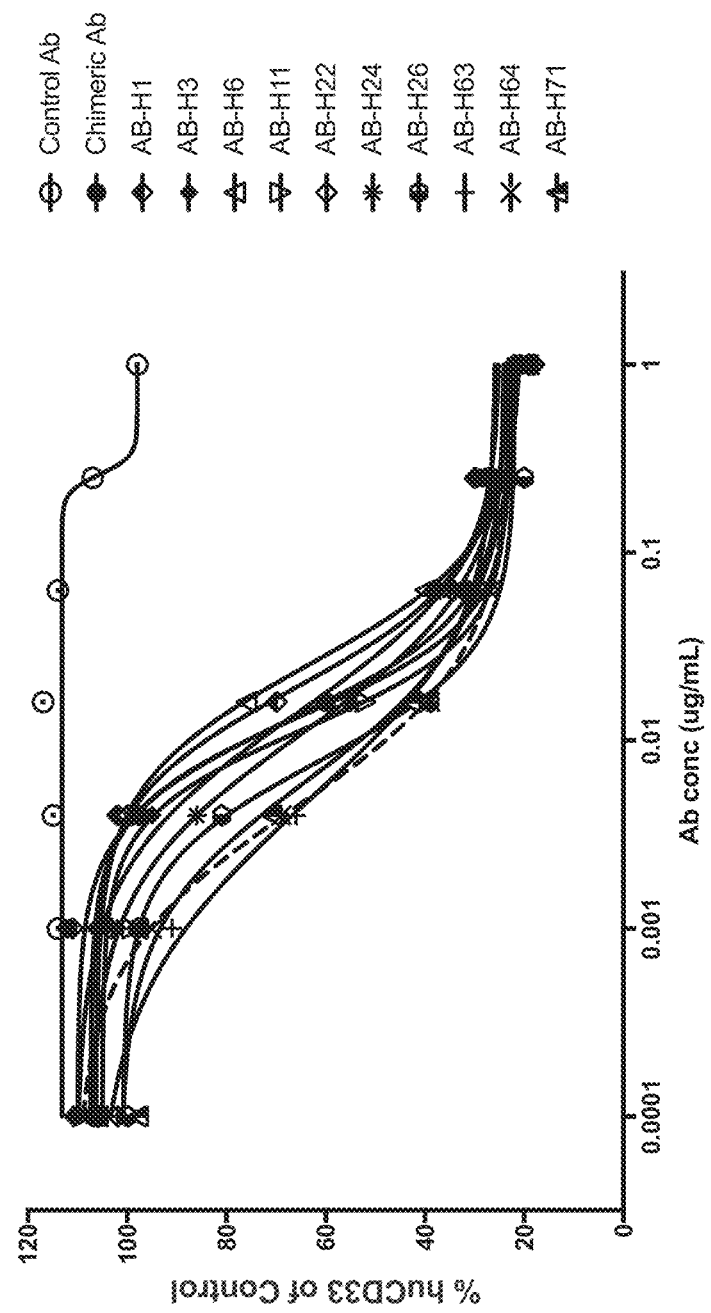
FIG. 1 depicts results from a flow cytometry assay measuring CD33 levels on the surface of primary human monocyte-derived dendritic cells after treatment with humanized CD33 antibodies.

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual, and Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty., ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J.B. Lippincott Company, 1993).

Definitions

As used herein, the term "preventing" includes providing prophylaxis with respect to occurrence or recurrence of a particular disease, disorder, or condition in an individual. An individual may be predisposed to, susceptible to a particular disease, disorder, or condition, or at risk of developing such a disease, disorder, or condition, but has not yet been diagnosed with the disease, disorder, or condition.

As used herein, an individual "at risk" of developing a particular disease, disorder, or condition may or may not have detectable disease or symptoms of disease, and may or may not have displayed detectable disease or symptoms of disease prior to the treatment methods described herein. "At risk" denotes that an individual has one or more risk factors, which are measurable parameters that correlate with development of a particular disease, disorder, or condition, as known in the art. An individual having one or more of these risk factors has a higher probability of developing a particular disease, disorder, or condition than an individual without one or more of these risk factors.

As used herein, the term "treatment" refers to clinical intervention designed to alter the natural course of the individual being treated during the course of clinical pathology. Desirable effects of treatment include decreasing the rate of progression, ameliorating or palliating the pathological state, and remission or improved prognosis of a particular disease, disorder, or condition. An individual is successfully "treated", for example, if one or more symptoms associated with a particular disease, disorder, or condition are mitigated or eliminated.

An "effective amount" refers to at least an amount effective, at dosages and for periods of time necessary, to achieve the desired therapeutic or prophylactic result. An effective amount can be provided in one or more administrations. An effective amount herein may vary according to factors such as the disease state, age, sex, and weight of the individual, and the ability of the treatment to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. An effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, administration "in conjunction" with another compound or composition includes simultaneous administration and/or administration at different times. Administration in conjunction also encompasses administration as a co-formulation or administration as separate compositions, including at different dosing frequencies or intervals, and using the same route of administration or different routes of administration.

An "individual" for purposes of treatment, prevention, or reduction of risk refers to any animal classified as a mammal, including humans, domestic and farm animals, and zoo, sport, or pet animals, such as dogs, horses, rabbits, cattle, pigs, hamsters, gerbils, mice, ferrets, rats, cats, and the like. Preferably, the individual is human.

The term "immunoglobulin" (Ig) is used interchangeably with "antibody" herein. The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity.

The basic 4-chain antibody unit is a heterotetrameric glycoprotein composed of two identical light (L) chains and two identical heavy (H) chains. The pairing of a $V_H$ and $V_L$ together forms a single antigen-binding site. For the structure and properties of the different classes of antibodies, see, e.g., *Basic and Clinical Immunology*, 8th Ed., Daniel P. Stites, Abba I. Terr and Tristram G. Parslow (eds.), Appleton & Lange, Norwalk, Conn., 1994, page 71 and Chapter 6.

The L chain from any vertebrate species can be assigned to one of two clearly distinct types, called kappa ("κ") and lambda ("λ"), based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG, and IgM, having heavy chains designated alpha ("α"), delta ("δ"), epsilon ("ε"), gamma ("γ") and mu ("μ"), respectively. The γ and α classes are further divided into subclasses (isotypes) on the basis of relatively minor differences in the CH sequence and function, e.g., humans express the following subclasses: IgG1, IgG2, IgG3, IgG4, IgA1, and IgA2. The subunit structures and three dimensional configurations of different classes of immunoglobulins are well known and described generally in, for example, Abbas et al., Cellular and Molecular Immunology, $4^{th}$ ed. (W.B. Saunders Co., 2000).

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

An "isolated" antibody, such as an anti-CD33 antibody of the present disclosure, is one that has been identified, separated and/or recovered from a component of its production environment (e.g., naturally or recombinantly). Preferably, the isolated polypeptide is free of association with all other contaminant components from its production environment. Contaminant components from its production environment, such as those resulting from recombinant transfected cells, are materials that would typically interfere with research, diagnostic or therapeutic uses for the antibody, and may include enzymes, hormones, and other proteinaceous or non-proteinaceous solutes. In preferred embodiments, the polypeptide will be purified: (1) to greater than 95% by weight of antibody as determined by, for example, the Lowry method, and in some embodiments, to greater than 99% by weight; (2) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or, preferably, silver stain. Isolated antibody includes the antibody in situ within recombinant T cells since at least one component of the antibody's natural environment will not be present. Ordinarily, however, an isolated polypeptide or antibody will be prepared by at least one purification step.

The "variable region" or "variable domain" of an antibody, such as an anti-CD33 antibody of the present disclosure, refers to the amino-terminal domains of the heavy or light chain of the antibody. The variable domains of the heavy chain and light chain may be referred to as "$V_H$" and "$V_L$", respectively. These domains are generally the most variable parts of the antibody (relative to other antibodies of the same class) and contain the antigen binding sites.

The term "variable" refers to the fact that certain segments of the variable domains differ extensively in sequence among antibodies, such as anti-CD33 antibodies of the present disclosure. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent-cellular toxicity.

The term "monoclonal antibody" as used herein refers to an antibody, such as an anti-CD33 antibody of the present disclosure, obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against one or more antigenic sites. In some embodiments, a monoclonal antibody of the present disclosure can be a bispecific antibody. In contrast to polyclonal antibody preparations which typically include different antibodies directed against different determinants (epitopes), each monoclonal antibody is directed against a single determinant on the one or more antigenic sites. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present disclosure may be made by a variety of techniques, including, for example, phage-display technologies (see, e.g., Clackson et al., *Nature*, 352:624-628 (1991); Marks et al., *J. Mol. Biol.* 222:581-597 (1992); Sidhu et al., *J. Mol. Biol.* 338(2): 299-310 (2004); Lee et al., *J. Mol. Biol.* 340(5):1073-1093 (2004); Fellouse, *Proc. Nat'l Acad. Sci. USA* 101(34):12467-472 (2004); and Lee et al., *J. Immunol. Methods* 284(1-2):119-132 (2004), the hybridoma method (e.g., Kohler and Milstein., *Nature*, 256:495-97 (1975); Hongo et al., *Hybridoma*, 14 (3):253-260 (1995), Harlow et al., *Antibodies: A Laboratory Manual*, (Cold Spring Harbor Laboratory Press, 2d ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), yeast presentation technologies (see, e.g., WO2009/036379A2; WO2010105256; WO2012009568, and Xu et al., *Protein Eng. Des. Sel.*, 26(10): 663-70 (2013), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Nat'l Acad. Sci. USA* 90:2551 (1993); Jakobovits et al., *Nature* 362:255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10:779-783 (1992); Lonberg et al., *Nature* 368:856-859 (1994); Morrison, *Nature* 368:812-813 (1994); Fishwild et al., *Nature Biotechnol.* 14:845-851 (1996); Neuberger, *Nature Biotechnol.* 14:826 (1996); and Lonberg and Huszar, *Intern. Rev. Immunol.* 13:65-93 (1995).

The terms "full-length antibody," "intact antibody" or "whole antibody" are used interchangeably to refer to an antibody, such as an anti-CD33 antibody of the present disclosure, in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10):1057-1062 (1995)); single-chain antibody molecules and multispecific antibodies formed from antibody fragments.

Papain digestion of antibodies, such as anti-CD33 antibodies of the present disclosure, produces two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

"Functional fragments" of antibodies, such as anti-CD33 antibodies of the present disclosure, comprise a portion of an intact antibody, generally including the antigen binding or variable region of the intact antibody or the F region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Nat'l Acad. Sci. USA* 90:6444-48 (1993).

As used herein, a "chimeric antibody" refers to an antibody (immunoglobulin), such as an anti-CD33 antibody of the present disclosure, in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Nat'l Acad. Sci. USA*, 81:6851-55 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies, such as anti-CD33 antibodies of the present disclosure, are chimeric antibodies that contain minimal sequence derived from non-human immunoglobulin. In one embodiment, a humanized antibody is a human immunoglobulin (recipient antibody) in which residues from an HVR of the recipient are replaced by residues from an HVR of a non-human species (donor antibody) such as mouse, rat, rabbit or non-human primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, and the like. The number of these amino acid substitutions in the FR is typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is one that possesses an amino-acid sequence corresponding to that of an antibody, such as an anti-CD33 antibody of the present disclosure, produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.,* 227: 381 (1991); Marks et al., *J. Mol. Biol.,* 222:581 (1991). Also available for the preparation of human monoclonal antibodies are methods described in Cole et al., *Monoclonal Antibodies and Cancer Therapy,* Alan R. Liss, p. 77 (1985); Boerner et al., *J. Immunol.,* 147(1):86-95 (1991). See also van Dijk and van de Winkel, *Curr. Opin. Pharmacol.* 5:368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Nat'l Acad. Sci. USA,* 103:3557-3562 (2006) regarding human antibodies generated via a human B-cell hybridoma technology. Alternatively, human antibodies can also be prepared by employing yeast libraries and methods as disclosed in, for example, WO2009/036379A2; WO2010105256; WO2012009568; and Xu et al., *Protein Eng. Des. Sel.,* 26(10): 663-70 (2013).

The term "hypervariable region," "HVR," or "HV," when used herein refers to the regions of an antibody-variable domain, such as that of an anti-CD33 antibody of the present disclosure, that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu in *Methods in Molecular Biology* 248:1-25 (Lo, ed., Human Press, Totowa, N.J., 2003)). Indeed, naturally occurring camelid antibodies consisting of a heavy chain only are functional and stable in the absence of light chain. See, e.g., Hamers-Casterman et al., *Nature* 363:446-448 (1993) and Sheriff et al., *Nature Struct. Biol.* 3:733-736 (1996).

A number of HVR delineations are in use and are encompassed herein. In some embodiments, the HVRs may be Kabat complementarity-determining regions (CDRs) based on sequence variability and are the most commonly used (Kabat et al., supra). In some embodiments, the HVRs may be Chothia CDRs. Chothia refers instead to the location of the structural loops (Chothia and Lesk *J. Mol. Biol.* 196: 901-917 (1987)). In some embodiments, the HVRs may be AbM HVRs. The AbM HVRs represent a compromise between the Kabat CDRs and Chothia structural loops, and are used by Oxford Molecular's AbM antibody-modeling software. In some embodiments, the HVRs may be "contact" HVRs. The "contact" HVRs are based on an analysis of the available complex crystal structures. The residues from each of these HVRs are noted below.

| Loop | Kabat | AbM | Chothia | Contact | |
|---|---|---|---|---|---|
| L1 | L24-L34 | L24-L34 | L26-L32 | L30-L36 | |
| L2 | L50-L56 | L50-L56 | L50-L52 | L46-L55 | |
| L3 | L89-L97 | L89-L97 | L91-L96 | L89-L96 | |
| H1 | H31-H35B | H26-H35B | H26-H32 | H30-H35B | (Kabat numbering) |

-continued

| Loop | Kabat | AbM | Chothia | Contact | |
|------|-------|-----|---------|---------|---|
| H1 | H31-H35 | H26-H35 | H26-H32 | H30-H35 | (Chothia numbering) |
| H2 | H50-H65 | H50-H58 | H53-H55 | H47-H58 | |
| H3 | H95-H102 | H95-H102 | H96-H101 | H93-H101 | |

HVRs may comprise "extended HVRs" as follows: 24-36 or 24-34 (L1), 46-56 or 50-56 (L2), and 89-97 or 89-96 (L3) in the VL, and 26-35 (H1), 50-65 or 49-65 (a preferred embodiment) (H2), and 93-102, 94-102, or 95-102 (H3) in the VH. The variable-domain residues are numbered according to EU or Kabat et al., supra, for each of these extended-HVR definitions.

"Framework" or "FR" residues are those variable-domain residues other than the HVR residues as herein defined.

The phrase "variable-domain residue-numbering as in EU or Kabat" or "amino-acid-position numbering as in EU or Kabat," and variations thereof, refers to the numbering system used for heavy-chain variable domains or light-chain variable domains of the compilation of antibodies in EU or Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g., residues 82a, 82b, and 82c, etc. according to Kabat) after heavy-chain FR residue 82. The EU or Kabat numbering of residues may be determined for a given antibody by alignment at regions of homology of the sequence of the antibody with a "standard" Kabat numbered sequence.

The EU or Kabat numbering system is generally used when referring to a residue in the variable domain (approximately residues 1-107 of the light chain and residues 1-113 of the heavy chain) (e.g., Kabat et al., Sequences of Immunological Interest. 5th Ed. Public Health Service, National Institutes of Health, Bethesda, Md. (1991)). The "EU or Kabat numbering system" or "EU index" is generally used when referring to a residue in an immunoglobulin heavy chain constant region (e.g., the EU index reported in Kabat et al., supra). The "EU index as in Kabat" refers to the residue numbering of the human IgG1 EU antibody. Unless stated otherwise herein, references to residue numbers in the variable domain of antibodies means residue numbering by the Kabat numbering system. Unless stated otherwise herein, references to residue numbers in the constant domain of antibodies means residue numbering by the EU or Kabat numbering system (e.g., see United States Patent Publication No. 2010-280227).

An "acceptor human framework" as used herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less. Where pre-existing amino acid changes are present in a VH, preferable those changes occur at only three, two, or one of positions 71H, 73H and 78H; for instance, the amino acid residues at those positions may by 71A, 73T and/or 78A. In one embodiment, the VL acceptor human framework is identical in sequence to the VL human immunoglobulin framework sequence or human consensus framework sequence.

A "human consensus framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, 5th Ed. Public Health Service, National Institutes of Health, Bethesda, Md. (1991). Examples include for the VL, the subgroup may be subgroup kappa I, kappa II, kappa III or kappa IV as in Kabat et al., supra. Additionally, for the VH, the subgroup may be subgroup I, subgroup II, or subgroup III as in Kabat et al., supra.

An "amino-acid modification" at a specified position, e.g., of an anti-CD33 antibody of the present disclosure, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody, such as an anti-CD33 antibody of the present disclosure, is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., Bio/Technology 10:779-783 (1992) describes affinity maturation by VH- and VL-domain shuffling. Random mutagenesis of HVR and/or framework residues is described by, for example: Barbas et al. Proc Nat. Acad. Sci. USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

As use herein, the term "specifically recognizes" or "specifically binds" refers to measurable and reproducible interactions such as attraction or binding between a target and an antibody, such as an anti-CD33 antibody of the present disclosure, that is determinative of the presence of the target in the presence of a heterogeneous population of molecules including biological molecules. For example, an antibody, such as an anti-CD33 antibody of the present disclosure, that specifically or preferentially binds to a target or an epitope is an antibody that binds this target or epitope with greater affinity, avidity, more readily, and/or with greater duration than it binds to other targets or other epitopes of the target. It is also understood by reading this definition that, for example, an antibody (or a moiety) that specifically or preferentially binds to a first target may or may not specifically or preferentially bind to a second target. As such, "specific binding" or "preferential binding" does not necessarily require (although it can include) exclusive binding. An antibody that specifically binds to a target may have an association constant of at least about $10^3$ $M^{-1}$ or $10^4$ $M^{-1}$, sometimes about $10^5$ $M^{-1}$ or $10^6$ $M^{-1}$, in other instances about $10^6$ $M^{-1}$ or $10^7$ $M^{-1}$, about $10^8 M^{-1}$ to $10^9$ $M^{-1}$, or about $10^{10}$ M$^{-1}$ to $10^{11}$ M$^{-1}$ or higher. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

As used herein, an "interaction" between a CD33 protein and a second protein encompasses, without limitation, protein-protein interaction, a physical interaction, a chemical interaction, binding, covalent binding, and ionic binding. As used herein, an antibody "inhibits interaction" between two proteins when the antibody disrupts, reduces, or completely eliminates an interaction between the two proteins. An antibody of the present disclosure, or fragment thereof, "inhibits interaction" between two proteins when the antibody or fragment thereof binds to one of the two proteins.

An "agonist" antibody or an "activating" antibody is an antibody, such as an agonist anti-CD33 antibody of the present disclosure, that induces (e.g., increases) one or more activities or functions of the antigen after the antibody binds the antigen.

A "blocking" antibody, an "antagonist" antibody, or an "inhibitory" antibody is an antibody, such as an anti-CD33 antibody of the present disclosure, that inhibits or reduces (e.g., decreases) antigen binding to one or more ligand after the antibody binds the antigen, and/or that inhibits or reduces (e.g., decreases) one or more activities or functions of the antigen after the antibody binds the antigen. In some embodiments, blocking antibodies, antagonist antibodies, or inhibitory antibodies substantially or completely inhibit antigen binding to one or more ligand and/or one or more activities or functions of the antigen.

Antibody "effector functions" refer to those biological activities attributable to the Fc region (a native sequence Fc region or amino acid sequence variant Fc region) of an antibody, and vary with the antibody isotype.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU or Kabat numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the present disclosure include human IgG1, IgG2, IgG3 and IgG4.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification, preferably one or more amino acid substitution(s). Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% homology with a native sequence Fc region and/or with an Fc region of a parent polypeptide, and most preferably at least about 90% homology therewith, more preferably at least about 95% homology therewith.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif ("ITAM") in its cytoplasmic domain Inhibiting receptor FcγRIIB contains an immunoreceptor tyrosine-based inhibition motif ("ITIM") in its cytoplasmic domain. (see, e.g., M. Daëron, Annu. Rev. Immunol. 15:203-234 (1997)). FcRs are reviewed in Ravetch and Kinet, Annu. Rev. Immunol. 9:457-92 (1991); Capel et al, Immunomethods 4:25-34 (1994); and de Haas et al., J. Lab. Clin. Med. 126: 330-41 (1995). Other FcRs, including those to be identified in the future, are encompassed by the term "FcR" herein. FcRs can also increase the serum half-life of antibodies.

Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants with improved or diminished binding to FcRs. See also, e.g., Shields et al., J. Biol. Chem. 9(2):6591-6604 (2001).

As used herein, "percent (%) amino acid sequence identity" and "homology" with respect to a peptide, polypeptide or antibody sequence refers to the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms known in the art needed to achieve maximal alignment over the full length of the sequences being compared.

An "isolated" nucleic acid molecule encoding an antibody, such as an anti-CD33 antibody of the present disclosure, is a nucleic acid molecule that is identified and separated from at least one contaminant nucleic acid molecule with which it is ordinarily associated in the environment in which it was produced. Preferably, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "vector," as used herein, is intended to refer to a nucleic acid molecule capable of transporting another nucleic acid to which it has been linked. One type of vector is a "plasmid," which refers to a circular double stranded DNA into which additional DNA segments may be ligated. Another type of vector is a phage vector. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) can be integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors," or simply, "expression vectors." In general, expression vectors of utility in recombinant DNA techniques are often in the form of plasmids. In the present specification, "plasmid" and "vector" may be used interchangeably as the plasmid is the most commonly used form of vector.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase or by a synthetic reaction. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may comprise modification(s) made after synthesis, such as conjugation to a label. Other types of modifications include, for example, "caps," substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotides(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid or semi-solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl-, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs, and basic nucleoside analogs such as methyl riboside. One or more phosphodiester linkages may be replaced by alternative linking groups. These alternative linking groups include, but are not limited to, embodiments wherein phosphate is replaced by P(O)S ("thioate"), P(S)S ("dithioate"), (O)NR2 ("amidate"), P(O)R, P(O)OR', CO, or CH2 ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of the present disclosure.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

The term "about" as used herein refers to the usual error range for the respective value readily known to the skilled person in this technical field. Reference to "about" a value or parameter herein includes (and describes) embodiments that are directed to that value or parameter per se.

As used herein and in the appended claims, the singular forms "a," "an," and "the" include plural reference unless the context clearly indicates otherwise. For example, reference to an "antibody" is a reference to from one to many antibodies, such as molar amounts, and includes equivalents thereof known to those skilled in the art, and so forth.

It is understood that aspect and embodiments of the present disclosure described herein include "comprising," "consisting," and "consisting essentially of" aspects and embodiments.

Overview

The present disclosure relates, in part, to anti-CD33 antibodies that exhibit one or more improved and/or enhanced functional characteristics (e.g., relative to an anti- CD33 antibody having a heavy chain variable region comprising the sequence of SEQ ID NO: 103 and a light chain variable region comprising the sequence of SEQ ID NO: 104), including, for example, antibodies capable of decreasing cell surface levels of CD33 and/or binding CD33 with improved/enhanced kinetics; methods of making and using such antibodies; pharmaceutical compositions containing such antibodies; nucleic acids encoding such antibodies; and host cells containing nucleic acids encoding such antibodies.

In some embodiments, the anti-CD33 antibodies of the present disclosure have one or more activities that are due, at least in part, to the ability of the antibodies to inhibit the interaction between CD33 and one or more natural glycan ligands. In some embodiments, the anti-CD33 antibodies of the present disclosure may have one or more activities that are due, at least in part, to the ability of the antibodies to reduce cellular expression (e.g., cell surface expression) of CD33 by inducing degradation, down regulation, cleavage, receptor desensitization, and/or lysosomal targeting of CD33. In some embodiments, the anti-CD33 antibodies exhibit one or more of the following properties: a. have a dissociation constant ($K_D$) for human CD33 that is lower than that of an anti-CD33 antibody having a heavy chain variable region comprising the sequence of SEQ ID NO:103 and a light chain variable region comprising the sequence of SEQ ID NO: 104; b. bind to human cells, such as primary human dendritic cells; c. decrease cell surface levels of CD33 (e.g., decrease cell surface levels of CD33 on primary human dendritic cells in vitro) with a half-maximal effective concentration ($EC_{50}$) that is lower than that of an anti-CD33 antibody having a heavy chain variable region comprising the sequence of SEQ ID NO:103 and a light chain variable region comprising the sequence of SEQ ID NO: 104; d. have a dissociation constant ($K_D$) for human CD33 that may range from about 8.57 nM to about 4.1 pM, for example when the $K_D$ is determined by surface plasmon resonance or BioLayer Interferometry; and/or e. decrease cell surface levels of CD33 (e.g., decreases cell surface levels of CD33 on primary human dendritic cells in vitro) with a half-maximal effective concentration ($EC_{50}$) that may range from about 151.1 pM to about 4.1 pM, for example when the $EC_{50}$ is determined in vitro by flow cytometry. As disclosed herein half-maximal effective concentration ($EC_{50}$) refers to the concentration at which an anti-CD33 antibody of the present disclosure reduces cellular levels of CD33 on a cell or in a cell to half that of untreated cells, or the concentration at which the antibody achieves half-maximal binding to CD33 on a cell.

Advantageously, anti-CD33 antibodies of the present disclosure reduce cell surface expression (e.g., up to approximately 18-fold) of CD33 more potently (e.g., with a lower $EC_{50}$) as compared to a control anti-CD33 antibody (e.g., a control anti-CD33 antibody having a heavy chain variable region comprising the sequence of SEQ ID NO: 103 and a light chain variable region comprising the sequence of SEQ ID NO: 104) (See e.g., Example 2). Moreover, advantageously, anti-CD33 antibodies of the present disclosure have a higher affinity (e.g., up to approximately 25-fold higher affinity) for CD33 (e.g., a lower $K_D$ value as measured by surface plasmon resonance) as compared to a control anti-CD33 antibody (e.g., a control anti-CD33 antibody having a heavy chain variable region comprising the sequence of SEQ ID NO:103 and a light chain variable region comprising the sequence of SEQ ID NO: 104 (See e.g., Examples 1 and 3). Surprisingly, higher affinity for CD33 does not necessarily correlate with an increase in ability or potency of reduction of cell surface expression of CD33 (See, e.g., Examples 2 and 5).

Certain aspects of the present disclosure are based, at least in part, on the identification of anti-CD33 antibodies that exhibit one or more improved and/or enhanced functional characteristics (e.g., relative to an anti-CD33 antibody having a heavy chain variable region comprising the sequence of SEQ ID NO: 103 and a light chain variable region comprising the sequence of SEQ ID NO: 104), including, an improved/enhanced ability to decrease cell surface levels of CD33 on cells, resulting in the reduction, neutralization, prevention, or curbing of one or more CD33 activities, including, without limitation, reducing cell growth of monocytes, macrophages, T cells, dendritic cells and/or microglia; reducing T cell proliferation induced by dendritic cells, bone marrow-derived dendritic cells, monocytes, microglia, M1 microglia, activated M1 microglia, M2 microglia, macrophages, M1 macrophages, activated M1 macrophages, and/or M2 macrophages; decreasing survival of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; decreasing proliferation of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; inhibiting migration of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; decreasing one or more functions of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; reducing proliferation of monocytes, macrophages, T cells, dendritic cells, neutrophils, and/or microglia; reducing the overall functionality of monocytes, macrophages, T cells, dendritic cells, neutrophils, and/or microglia; inhibition of beneficial immune response to different types of cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, acute myeloid leukemia, pancreatic cancer, prostate cancer, ovarian cancer, fibrosarcoma, and thyroid cancer; inhibition of beneficial immune response to different types of neurological disorders selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, essential tremor, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, traumatic brain injury, age related macular degeneration, glaucoma, retinitis pigmentosa, retinal degeneration, and multiple sclerosis; binding to CD33 ligand on tumor cells; binding to CD33 ligand on dendritic cells, bone marrow-derived dendritic cells, monocytes, microglia, T cells, neutrophils, and/or macrophages; inhibition of tumor cell killing by one or more of microglia, macrophages, dendritic cells, bone marrow-derived dendritic cells, neutrophils, T cells, T helper cells, or cytotoxic T cells; inhibition of anti-tumor cell proliferation activity of one or more of microglia, macrophages, dendritic cells, bone marrow-derived dendritic cells, neutrophils, T cells, T helper cells, or cytotoxic T cells; inhibition of anti-tumor cell metastasis activity of one or more of microglia, macrophages, dendritic cells, bone marrow-derived dendritic cells, neutrophils, T cells, T helper cells, or cytotoxic T cells; modulated expression of one or more inflammatory receptors, such as CD86, expressed on one or more of microglia, macrophages, dendritic cells, bone marrow-derived dendritic cells, neutrophils, T cells, T helper cells, or cytotoxic T cells; enhancing infiltration of one or more of immunosuppressor dendritic cells, immunosuppressor macrophages, myeloid derived suppressor cells, tumor-associated macrophages, immunosuppressor neutrophils, and regulatory T cells into tumors; increasing number of tumor-promoting myeloid/granulocytic immune-suppressive cells in a tumor, in peripheral blood, or other lymphoid organ; enhancing tumor-promoting activity of myeloid-derived suppressor cells; decreasing activation of tumor-specific T lymphocytes with tumor killing potential; decreasing infiltration of tumor-specific T lymphocytes with tumor killing potential; increasing tumor growth rate; increasing rate of tumor recurrence; decreasing efficacy of one or more immune-therapies that modulate anti-tumor T cell responses, optionally wherein the one or more immune-therapies are immune-therapies that target one or more proteins selected from CD40, OX40, ICOS, CD28, CD137/4-1BB, CD27, GITR, PD-L1, CTLA4, PD-L2, PD-1, B7-H3, B7-H4, HVEM, LIGHT, BTLA, VISTA, KIR, GALS, TIM1, TIM3, TIM4, A2AR, LAG3, DR-5, CD39, CD70, TREM1, TREM2, Siglec-5, Siglec-7, Siglec-9, Siglec-11, SirpA, CD447, CSF-1 receptor, and any combination thereof, or of one or chemotherapy agents and/or more cancer vaccines.

In some embodiments, treatment of cancer with anti-CD33 antibodies as described herein may: (i) increasing the number of tumor infiltrating $CD3^+$ T cells; (ii) decreasing cellular levels of CD33 in non-tumorigenic $CD14^+$ myeloid cells, optionally wherein the non-tumorigenic $CD14^+$ myeloid cells are tumor infiltrating cells or optionally wherein the non-tumorigenic $CD14^+$ myeloid cells are present in blood; (iii) reducing the number of non-tumorigenic $CD14^+$ myeloid cells, optionally wherein the non-tumorigenic $CD14^+$ myeloid cells are tumor infiltrating cells or optionally wherein the non-tumorigenic $CD14^+$ myeloid cells are present in blood; (iv) d reducing PD-L1, PD-L2, B7-H7, B7-H3, CD200R, CD163, and/or CD206 levels in one or more cells, optionally wherein the one or more cells are non-tumorigenic myeloid-derived suppressor cells (MDSC); (v) decreasing tumor growth rate of solid tumors; (vi) reducing tumor volume; (vii) increasing efficacy of one or more PD-1 inhibitors; (viii) increasing efficacy of one or more checkpoint inhibitor therapies and/or immune-modulating therapies, optionally wherein the one or more checkpoint inhibitor therapies and/or immune-modulating therapies target one or more of CTL4, the adenosine pathway, PD-L1, PD-L2, OX40, TIM3, LAG3, or any combination thereof; (ix) increasing efficacy of one or more chemotherapy agents, optionally wherein the one or more chemotherapy agents are gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), and any combination thereof; (x) i increasing proliferation of T cells in the presence of non-tumorigenic myeloid-derived suppressor cells (MDSC); (xi) inhibiting differentiation, survival, and/or one or more functions of non-tumorigenic myeloid-derived suppressor cells (MDSC); and (xii) killing CD33-expressing immunosuppressor non-tumorigenic myeloid cells and/or non-tumorigenic CD14-expressing cells in solid tumors and associated blood vessels when conjugated to a chemical or radioactive toxin.

In some embodiments, myeloid cells of the present disclosure include, without limitation, CD45+CD14+ myeloid cells, CD14+ myeloid cells, and myeloid-derived suppressor cells (MDSC). In some embodiments, myeloid cells of the present disclosure are non-tumorigenic myeloid cells. Immunosuppressor cells are sometimes also referred to as myeloid-derived suppressor cells (MDSC). In humans, MDSCs can be defined by one of the following combination of markers: (1) CD14+ HLA− DRlow/−, (2) CD14+ IL4Rα+, (3) CD14+ HLA-DR− IL4Rα+, (4) CD34+ CD14+ CD11b+ CD33+, (5) CD11b+ CD14+ CD33+, (6) CD33+ HLA-DR−, (7) Lin− HLA-DR−, (8) Lin− HLA-DR− CD33+, (9) Lin− HLA-DR− CD33+ CD11b+, (10) Lin− CD33+ CD11b+ CD15+, (11) Lin− HLA− DR− CD33+ CD11b+ CD14− CD15+, (12) CD11b+ CD14− CD33+, (13) CD11b+ CD14− HLA-DR− CD33+ CD15+, (14) CD33+ HLA-DR− CD15+, (15) CD15+ IL4Rα+, (16) CD11b+ CD15+ CD66b+, (17) CD15+ FSClow SSChigh, (18) CD15high CD33+, (19) CD11b+ CD14− CD15+, (20) CD66b+ SSChigh, and (21) CD11b+ CD15+ (see also Solito S et al. Annals of the NY Academy of Sciences, 2014). In mice, MDSCs can be defined by the expression of the surface markers CD45+, CD11b+, Gr1+, and/or Il4Ra+. Additional exemplary immunosuppressive monocytic lineages are CD45+, CD11b+, Gr1low; and CD45+, CD11c+.

CD33 Proteins

In one aspect, the present disclosure provides antibodies, such as isolated (e.g., monoclonal) antibodies, that interact with or otherwise bind to a region, such as an epitope, within a CD33 protein of the present disclosure. In some embodiments, the antibodies interact with or otherwise bind to a region, such as an epitope, within a CD33 protein of the present disclosure with improved/enhanced kinetics (e.g., relative to an anti-CD33 antibody having a heavy chain variable region comprising the sequence of SEQ ID NO: 103 and a light chain variable region comprising the sequence of SEQ ID NO: 104). In some embodiments, the antibodies interact with or otherwise bind to a region, such as an epitope, within a CD33 protein on human cells, such as dendritic cells, with a half-maximal effective concentration ($EC_{50}$) that is lower than that of a control antibody (e.g., relative to an anti-CD33 antibody having a heavy chain variable region comprising the sequence of SEQ ID NO: 103 and a light chain variable region comprising the sequence of SEQ ID NO: 104). In some embodiments, anti-CD33 antibodies of the present disclosure bind to a CD33 protein and modulate one or more CD33 activities after binding to the CD33 protein, for example, an activity associated with CD33 expression on a cell. CD33 proteins of the present disclosure include, without limitation, a mammalian CD33 protein, human CD33 protein, mouse CD33 protein, and rat CD33 protein.

CD33 is variously referred to as a CD33 molecule, Siglec3, Siglec-3, CD33 antigen (Gp67), P67, Gp67, sialic acid-binding-Ig-like lectin 3, myeloid cell surface antigen CD33, or FLJ00391.

CD33 is an immunoglobulin-like receptor primarily expressed on myeloid lineage cells, including without limitation, macrophages, dendritic cells, osteoclasts, monocytes, and microglia. In some embodiments, CD33 forms a receptor-signaling complex with CD64. In some embodiments, CD33 signaling results in the downstream inhibition of PI3K or other intracellular signals. On myeloid cells, Toll-like receptor (TLR) signals are important for the inhibition of CD33 activities, e.g., in the context of an infection response. TLRs also play a key role in the pathological inflammatory response, e.g., TLRs expressed in macrophages and dendritic cells.

The amino acid sequence of human CD33 is set forth below as SEQ ID NO: 1:

```
MPLLLLLPLL WAGALAMDPN FWLQVQESVT VQEGLCVLVP

CTFFHPIPY  YDKNSPVHGYW FREGAIISRD SPVATNKLDQ

EVQEETQGRF RLLGDPSRNN  CSLSIVDARR RDNGSYFFRM

ERGSTKYSYK SPQLSVHVTD  LTHRPKILIP GTLEPGHSKN

LTCSVSWACE QGTPPIFSWL  SAAPTSLGPR TTHSSVLIIT

PRPQDHGTNL TCQVKFAGAG  VTTERTIQLN VTYVPQNPTT

GIFPGDGSGK QETRAGVVHG  AIGGAGVTAL LALCLCLIFF

IVKTHRRKAA RTAVGRNDTH  PTTGSASPKH QKKSKLHGPT

ETSSCSGAAP TVEMDEELHY  ASLNFHGMNP SKDTSTEYSE

VRTQ
```

In some embodiments, the CD33 is a preprotein that includes a signal sequence. In some embodiments, the CD33 is a mature protein. In some embodiments, the mature CD33 protein does not include a signal sequence. In some embodiments, the mature CD33 protein is expressed on a cell. In some embodiments, the mature CD33 protein is expressed on a cell, such as the surface of a cell, including, without limitation, human dendritic cells, human macrophages, human monocytes, human osteoclasts, human neutrophils, human T cells, human T helper cell, human cytotoxic T cells, human granulocytes, and human microglia. Anti-CD33 antibodies of the present disclosure may bind any of the CD33 proteins of the present disclosure expressed on any cell disclosed herein.

CD33 proteins of the present disclosure, such as human CD33, contain several domains, including without limitation, a signal sequence located at amino acid residues 1-17 of SEQ ID NO: 1, an extracellular immunoglobulin-like variable-type (IgV) domain located at amino acid residues 19-135 of SEQ ID NO: 1, an Ig-like C2-type domain located at amino acid residues 145-228 of SEQ ID NO: 1, a transmembrane domain located at amino acid residues 260-282 of SEQ ID NO: 1, an ITIM motif 1 located at amino acid residues 338-343 of SEQ ID NO: 1, and an ITIM motif 2 located at amino acid residues 356-361 of SEQ ID NO: 1. As one of skill in the art will appreciate, the beginning and ending residues of the domains of the present disclosure may vary depending upon the computer modeling program used or the method used for determining the domain.

Certain aspects of the present disclosure provide anti-CD33 antibodies that bind to a human CD33, or a homolog thereof, including without limitation a mammalian CD33 protein and Cd33 orthologs from other species. In some embodiments, the anti-CD33 antibodies of the present disclosure bind to a human CD33, or homolog thereof, with improved/enhanced binding kinetics (e.g., relative to an anti-CD33 antibody having a heavy chain variable region comprising the sequence of SEQ ID NO: 103 and a light chain variable region comprising the sequence of SEQ ID NO: 104).

Accordingly, as used herein a "CD33" protein of the present disclosure includes, without limitation, a mammalian CD33 protein, human CD33 protein, primate CD33 protein, mouse CD33 protein, and rat CD33 protein. Additionally, anti-CD33 antibodies of the present disclosure may bind an epitope within a human CD33 protein, primate CD33. In some embodiments, anti-CD33 antibodies of the present disclosure may bind specifically to human CD33.

In some embodiments, antibodies of the present disclosure may bind CD33 in a pH dependent manner. In some embodiments, antibodies of the present disclosure can bind to CD33 at a neutral pH and be internalized without dissociating from the CD33 protein. Alternatively, at an acidic pH, antibodies of the present disclosure may dissociate from CD33 once they are internalized and are then degraded by endosome/lysosome pathway. In certain embodiments, an anti-CD33 antibody binds CD33 at a pH that ranges from 5.5 to 8.0, from 5.5 to 7.5, from 5.5 to 7.0, from 5.5 to 6.5, from 5.5 to 6.0, from 6.0 to 8.0, from 6.5 to 8.0, from 7.0 to 8.0, from 7.5 to 8.0, from 6.0 to 7.5, from 6.0 to 7.0, from 6.5 to 7.5. In certain embodiments, an anti-CD33 antibody dissociates from CD33 at a pH of less than 6.0, less than 5.5, less than 5.0, less than 4.5, less than 4.0, less than 3.5, less than 3.0, less than 2.5, or less than 2.0.

In some embodiments, antibodies of the present disclosure, bind to a wild-type CD33 protein of the present disclosure, naturally occurring variants thereof, and/or disease variants thereof.

In some embodiments, antibodies of the present disclosure bind a variant of human CD33, wherein the variant contains a single nucleotide polymorphism (SNP) rs3865444C with a (C) nucleotide. In some embodiments, antibodies of the present disclosure that decrease cellular levels of CD33 and/or that bind or interact with CD33, bind to a variant of human CD33, wherein the variant contains a SNP rs3865444 with an (A) nucleotide. In some embodiments, anti-CD33 antibodies of the present disclosure bind a variant of human CD33, wherein the variant contains a SNP rs3865444$^{AC}$ or rs3865444$^{CC}$.

In some embodiments, antibodies of the present disclosure that decrease cellular levels of CD33 and/or that bind or interact with CD33, bind a variant of human CD33, wherein the variant contains a SNP rs35112940 with GG nucleotides, AA nucleotides, or AG nucleotides. In some embodiments, antibodies of the present disclosure that decrease cellular levels of CD33 and/or that bind or interact with CD33, bind a variant of human CD33, wherein the variant contains a SNP rs12459419 with CC, CT or TT genotypes. In certain embodiments, the subject has a homozygous or heterozygous for the coding SNPs, rs1803 with GG nucleotides, CG nucleotides, or CC nucleotides.

In some embodiments, antibodies of the present disclosure that decrease cellular levels of CD33 and/or that bind or interact with CD33, bind to a CD33 protein expressed on the surface of a cell including, without limitation, human dendritic cells, human macrophages, human monocytes, human osteoclasts, human neutrophils, human T cells, human T helper cell, human cytotoxic T cells, human granulocytes, and human microglia. In some embodiments, antibodies of the present disclosure that decrease cellular levels of CD33 and/or that bind or interact with CD33, bind to a CD33 protein expressed on the surface of a cell and modulate (e.g., induce or inhibit) at least one CD33 activity of the present disclosure after binding to the surface expressed CD33 protein. In some embodiments of the present disclosure, the anti-CD33 antibody binds specifically to a CD33 protein. In some embodiments of the present disclosure, the anti-CD33 antibody further binds to at least one additional Siglec protein. In some embodiments, the anti-CD33 antibody modulates one or more activities of the at least one additional Siglec protein or of a cell expressing the at least one additional Siglec protein.

CD33 Ligands

CD33 proteins of the present disclosure can interact with (e.g., bind to) one or more CD33 ligands.

Exemplary CD33 ligands include, without limitation, sialic acid, sialic acid-containing glycolipids, sialic acid-containing glycoproteins, alpha-2,6-linked sialic acid-containing glycolipids, alpha-2,6-linked sialic acid-containing glycoproteins, alpha-2,3-linked sialic acid-containing glycolipids, alpha-2,3-linked sialic acid-containing glycoproteins, alpha-1-acid glycoprotein (AGP), CD24 protein, gangliosides (e.g., glycolipids containing a ceramide linked to a sialylated glycan), secreted mucins, CD33 ligands expressed on red blood cells, CD33 ligands expressed on bacterial cells, CD33 ligands expressed on apoptotic cells, CD33 ligands expressed on tumor cells, CD33 ligands expressed on viruses, CD33 ligands expressed on dendritic cells, CD33 ligands expressed on nerve cells, CD33 ligands expressed on glial cells, CD33 ligands expressed on microglia, CD33 ligands expressed on astrocytes, CD33 ligands on beta amyloid plaques, CD33 ligands on Tau tangles, CD33 ligands on disease-causing proteins, CD33 ligands on disease-causing peptides, CD33 ligands expressed on macrophages, CD33 ligands expressed on natural killer cells, CD33 ligands expressed on T cells, CD33 ligands expressed on T helper cells, CD33 ligands expressed on cytotoxic T cells, CD33 ligands expressed on B cells, CD33 ligands expressed on tumor-imbedded immunosuppressor dendritic cells, CD33 ligands expressed on tumor-imbedded immunosuppressor macrophages, CD33 ligands expressed on myeloid-derived suppressor cells, and CD33 ligands expressed on regulatory T cells. In some embodiments, CD33 ligands of the present disclosure are gangliosides. Gangliosides generally share a common lacto-ceramide core and one or more sialic acid residues.

Further examples of suitable ganglioside ligands are listed in Table A. Generally, a ganglioside is a molecule composed of a glycosphingolipid with one or more sialic acids (e.g., n-acetyl-neuraminic acid, NANA) linked on the sugar chain.

TABLE A

| Structures of exemplary ganglioside CD33 ligands |
|---|
| GM2-1 = aNeu5Ac(2-3)bDGalp(1-?)bDGalNAc(1-?)bDGalNAc(1-?)bDGlcp(1-1)Cer |
| GM3 = aNeu5Ac(2-3)bDGalp(1-4)bDGlcp(1-1)Cer |
| GM2,GM2a(?) = bDGalpNAc(1-4)[aNeu5Ac(2-3)]bDGalp(1-4)bDGlcp(1-1)Cer |
| GM2b(?) = aNeu5Ac(2-8)aNeu5Ac(2-3)bDGalp(1-4)bDGlcp(1-1)Cer |
| GM1,GM1a = bDGalp(1-3)bDGalNAc[aNeu5Ac(2-3)]bDGalp(1-4)bDGlcp(1-1)Cer |
| asialo-GM1,GA1 = bDGalp(1-3)bDGalpNAc(1-4)bDGalp(1-4)bDGlcp(1-1)Cer |
| asialo-GM2,GA2 = bDGalpNAc(1-4)bDGalp(1-4)bDGlcp(1-1)Cer |
| GM1b = aNeu5Ac(2-3)bDGalp(1-3)bDGalNAc(1-4)bDGalp(1-4)bDGlcp(1-1)Cer |
| GD3 = aNeu5Ac(2-8)aNeu5Ac(2-3)bDGalp(1-4)bDGlcp(1-1)Cer |
| GD2 = bDGalpNAc(1-4)[aNeu5Ac(2-8)aNeu5Ac(2-3)]bDGalp(1-4)bDGlcp(1-1)Cer |
| GD1a = aNeu5Ac(2-3)bDGalp(1-3)bDGalNAc(1-4)[aNeu5Ac(2-3)]bDGalp(1-4)bDGlcp(1-1)Cer |
| GD1alpha = aNeu5Ac(2-3)bDGalp(1-3)bDGalNAc(1-4)[aNeu5Ac(2-6)]bDGalp(1-4)bDGlcp(1-1)Cer |
| GD1b = bDGalp(1-3)bDGalNAc(1-4)[aNeu5Ac(2-8)aNeu5Ac(2-3)]bDGalp(1-4)bDGlcp(1-1)Cer |
| GT1a = aNeu5Ac(2-8)aNeu5Ac(2-3)bDGalp(1-3)bDGalNAc(1-4)[aNeu5Ac(2-3)]bDGalp(1-4)bDGlcp(1-1)Cer |
| GT1,GT1b = aNeu5Ac(2-3)bDGalp(1-3)bDGalNAc(1-4)[aNeu5Ac(2-8)aNeu5Ac(2-3)]bDGalp(1-4)bDGlcp(1-1)Cer |
| OAc-GT1b = aNeu5Ac(2-3)bDGalp(1-3)bDGalNAc(1-4)aXNeu5Ac9Ac(2-8)aNeu5Ac(2-3)]bDGalp(1-4)bDGlcp(1-1)Cer |
| GT1c = bDGalp(1-3)bDGalNAc(1-4)[aNeu5Ac(2-8)aNeu5Ac(2-8)aNeu5Ac(2-3)]bDGalp(1-4)bDGlcp(1-1)Cer |
| GT3 = aNeu5Ac(2-8)aNeu5Ac(2-8)aNeu5Ac(2-3)bDGal(1-4)bDGlc(1-1)CerGQ1b = aNeu5Ac(2-8)aNeu5Ac(2-3)bDGalp(1-3)bDGalNAc(1-4)[aNeu5Ac(2-8)aNeu5Ac(2-3)]bDGalp(1-4)bDGlcp(1-1)Cer |
| GGal = aNeu5Ac(2-3)bDGalp(1-1)Cer | where:
aNeu5Ac = 5-acetyl-alpha-neuraminic acid
aNeu5Ac9Ac = 5,9-diacetyl-alpha-neuraminic acid
bDGalp = beta-D-galactopyranose
bDGalpNAc = N-acetyl-beta-D-galactopyranose
bDGlcp = beta-D-glucopyranose
Cer = ceramide (general N-acylated sphingoid)

CD33 Antibodies

Certain aspects of the present disclosure relate to anti-CD33 antibodies comprising one or more improved and/or enhanced functional characteristics. In some embodiments, anti-CD33 antibodies of the present disclosure comprise one or more improved and/or enhanced functional characteristics relative to a control antibody (e.g., a control anti-CD33 antibody comprising a heavy chain variable region comprising the amino acid sequence of SEQ ID NO: 34 and a light chain variable region comprising the amino acid sequence of SEQ ID NO: 77; a control anti-CD33 antibody comprising a heavy chain variable region comprising the amino acid sequence of SEQ ID NO: 40 and a light chain variable region comprising the amino acid sequence of SEQ ID NO: 86; and control anti-CD33 antibody comprising a heavy chain variable region comprising the amino acid sequence of SEQ ID NO: 52 and a light chain variable region comprising the amino acid sequence of SEQ ID NO: 86; and/or a control anti-CD33 antibody comprising a heavy chain variable region comprising the amino acid sequence of SEQ ID NO: 103 and a light chain variable region comprising the amino acid sequence of SEQ ID NO: 104). In some embodiments, anti-CD33 antibodies of the present disclosure have an affinity for CD33 (e.g., human CD33) that is higher than that of a control anti-CD33 antibody (e.g., a control anti-CD33 antibody comprising a heavy chain variable region comprising the amino acid sequence of SEQ ID NO: 34 and a light chain variable region comprising the amino acid sequence of SEQ ID NO: 77; a control anti-CD33 antibody comprising a heavy chain variable region comprising the amino acid sequence of SEQ ID NO: 40 and a light chain variable region comprising the amino acid sequence of SEQ ID NO: 86; and control anti-CD33 antibody comprising a heavy chain variable region comprising the amino acid sequence of SEQ ID NO: 52 and a light chain variable region comprising the amino acid sequence of SEQ ID NO: 86; and/or a control anti-CD33 antibody comprising a heavy chain variable region comprising the amino acid sequence of SEQ ID NO: 103 and a light chain variable region comprising the amino acid sequence of SEQ ID NO: 104). In some embodiments, anti-CD33 antibodies of the present disclosure bind to human cells, such as dendritic cells, with a half-maximal effective concentration ($EC_{50}$) that is lower than that of a control antibody (e.g., a control anti-CD33 antibody comprising a heavy chain variable region comprising the amino acid sequence of SEQ ID NO: 34 and a light chain variable region comprising the amino acid sequence of SEQ ID NO: 77; a control anti-CD33 antibody comprising a heavy chain variable region comprising the amino acid sequence of SEQ ID NO: 40 and a light chain variable region comprising the amino acid sequence of SEQ ID NO: 86; and control anti-CD33 antibody comprising a heavy chain variable region comprising the amino acid sequence of SEQ ID NO: 52 and a light chain variable region comprising the amino acid sequence of SEQ ID NO: 86; and/or a control anti-CD33 antibody comprising a heavy chain variable region comprising the amino acid sequence of SEQ ID NO: 103 and a light chain variable region comprising the amino acid sequence of SEQ ID NO: 104). In some embodiments, anti-CD33 antibodies of the present disclosure decrease cellular levels (e.g., cell surface levels) of CD33 with a half-maximal effective concentration ($EC_{50}$) that is lower than that of a control antibody (e.g., a control anti-CD33 antibody comprising a heavy chain variable region comprising the sequence of SEQ ID NO: 103 and a light chain variable region comprising the sequence of SEQ ID NO: 104).

Cellular levels of CD33 may refer to, without limitation, cell surface levels of CD33, intracellular levels of CD33, and total levels of CD33. In some embodiments, a decrease in cellular levels of CD33 comprises decrease in cell surface levels of CD33. In some embodiments, anti-CD33 antibodies of the present disclosure that decrease cellular levels of CD33 (e.g., cell surface levels of CD33) have one or more of the following characteristics: (1) inhibits or reduces one or more CD33 activities; (2) the ability to inhibit or reduce binding of a CD33 to one or more of its ligands; (3) the ability to reduce CD33 expression in CD33-expressing cells; (4) the ability to interact, bind, or recognize a CD33 protein; (5) the ability to specifically interact with or bind to a CD33 protein; and (6) the ability to treat, ameliorate, or prevent any aspect of a disease or disorder described or contemplated herein.

Anti-CD33 antibodies of the present disclosure may have nanomolar or even picomolar affinities for the target antigen (e.g., human CD33). In certain embodiments, the dissociation constant ($K_D$) of the antibody is from about 0.001 to about 100 nM. In certain embodiments, the $K_D$ of the antibody is about 0.01 to about 10 nM. In certain embodiments, the $K_D$ of the antibody is about 0.202 to about 8.57 nM. In some embodiments, the $K_D$ of the antibody is less than about or equal to about 100 nM, 90 nM, 80 nM, 70 nM, 60 nM, 50 nM, 40 nM, 30 nM, 20 nM, 10 nM, 9.5 nM, 9 nM, 8.5 nM, 8 nM, 7.5 nM, 7 nM, 6.5 nM, 6 nM, 5.5 nM, 5 nM, 4.5 nM, 4 nM, 3.5 nM, 3 nM, 2.5 nM, 2 nM, 1.5 nM, 1 nM, 0.9 nM, 0.8 nM, 0.7 nM, 0.6 nM, 0.5 nM, 0.4 nM, 0.3 nM, 0.2 nM, 0.1 nM, 0.05 nM, 0.01 nM, or 0.005 nM. In some embodiments, the $K_D$ of the antibody is less than about 5.22 nM. In some embodiments, the $K_D$ of the antibody is greater than about or equal to about 0.001 nM, 0.005 nM, 0.01 nM, 0.05 nM, 0.1 nM, 0.2 nM, 0.3 nM, 0.4 nM, 0.5 nM, 0.6 nM, 0.7 nM, 0.8 nM, 0.9 nM, 1 nM, 1.5 nM, 2 nM, 2.5 nM, 3 nM 3.5 nM, 4 nM, 4.5 nM, 5 nM, 5.5 nM, 6 nM, 6.5 nM, 7 nM, 7.5 nM, 8 nM, 8.5 nM, 9 nM, 9.5 nM, 10 nM. 20 nM, 30 nM, 40 nM, 50 nM, 60 nM, 70 nM, 80 nM, or 90 nM. That is, the $K_D$ of the antibody can be any of a range of affinities having an upper limit of about 100 nM, 90 nM, 80 nM, 70 nM, 60 nM, 50 nM, 40 nM, 30 nM, 20 nM, 10 nM, 9.5 nM, 9 nM, 8.5 nM, 8 nM, 7.5 nM, 7 nM, 6.5 nM, 6 nM, 5.5 nM, 5 nM, 4.5 nM, 4 nM, 3.5 nM, 3 nM, 2.5 nM, 2 nM, 1.5 nM, 1 nM, 0.9 nM, 0.8 nM, 0.7 nM, 0.6 nM, 0.5 nM, 0.4 nM, 0.3 nM, 0.2 nM, 0.1 nM, 0.05 nM, 0.01 nM, or 0.005 nM, and an independently selected lower limit of about 0.001 nM, 0.005 nM, 0.01 nM, 0.05 nM, 0.1 nM, 0.2 nM, 0.3 nM, 0.4 nM, 0.5 nM, 0.6 nM, 0.7 nM, 0.8 nM, 0.9 nM, 1 nM, 1.5 nM, 2 nM, 2.5 nM, 3 nM 3.5 nM, 4 nM, 4.5 nM, 5 nM, 5.5 nM, 6 nM, 6.5 nM, 7 nM, 7.5 nM, 8 nM, 8.5 nM, 9 nM, 9.5 nM, 10 nM. 20 nM, 30 nM, 40 nM, 50 nM, 60 nM, 70 nM, 80 nM, or 90 nM, wherein the lower limit is less than the upper limit. In some embodiments, the $K_D$ of the antibody is any of about 10 nM, about 9 nM, about 8 nM, about 7 nM, about 6 nM, about 5 nM, about 4 nM, about 3 nM, about 2 nM, about 1 nM, about 900 pM, about 800 pM, about 700 pM, about 600 pM, about 500 pM, about 400 pM, about 300 pM, about 200 pM, or about 100 pM. Various methods of measuring antibody affinity are known in the art, including, for example, using surface plasmon resonance or BioLayer Interferometry (See e.g., Example 1 below). In some embodiments, the $K_D$ for CD33 is determined at a temperature of approximately 25° C. In some embodiments, the $K_D$ for CD33 is determined at a temperature of approximately 4° C. In some embodiments, the $K_D$ is determined using a monovalent antibody (e.g., a Fab) or a full-length antibody in a monovalent form. In some embodiments, the $K_D$ is determined using a bivalent antibody and monomeric recombinant CD33 protein.

In some embodiments, anti-CD33 antibodies of the present disclosure have a lower dissociation constant ($K_D$) for CD33 than a control anti-CD33 antibody (e.g., a control anti-CD33 antibody comprising a heavy chain variable region comprising the amino acid sequence of SEQ ID NO: 34 and a light chain variable region comprising the amino acid sequence of SEQ ID NO: 77; a control anti-CD33 antibody comprising a heavy chain variable region comprising the amino acid sequence of SEQ ID NO: 40 and a light chain variable region comprising the amino acid sequence of SEQ ID NO: 86; and control anti-CD33 antibody comprising a heavy chain variable region comprising the amino acid sequence of SEQ ID NO: 52 and a light chain variable region comprising the amino acid sequence of SEQ ID NO: 86; and/or a control anti-CD33 antibody comprising a heavy chain variable region comprising the amino acid sequence of SEQ ID NO: 103 and a light chain variable region comprising the amino acid sequence of SEQ ID NO: 104). In some embodiments, anti-CD33 antibodies of the present disclosure have a $K_D$ for a target (e.g., human CD33) that is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% lower than the $K_D$ of a control anti-CD33 antibody for the target (e.g., a control anti-CD33 antibody comprising a heavy chain variable region comprising the amino acid sequence of SEQ ID NO: 34 and a light chain variable region comprising the amino acid sequence of SEQ ID NO: 77; a control anti-CD33 antibody comprising a heavy chain variable region comprising the amino acid sequence of SEQ ID NO: 40 and a light chain variable region comprising the amino acid sequence of SEQ ID NO: 86; and control anti-CD33 antibody comprising a heavy chain variable region comprising the amino acid sequence of SEQ ID NO: 52 and a light chain variable region comprising the amino acid sequence of SEQ ID NO: 86; and/or a control anti-CD33 antibody comprising a heavy chain variable region comprising the amino acid sequence of SEQ ID NO: 103 and a light chain variable region comprising the amino acid sequence of SEQ ID NO: 104). In some embodiments, anti-CD33 antibodies of the present disclosure have a $K_D$ for a target (e.g., human CD33) that is at least about 1-fold, at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 12.5-fold, at least about 15-fold, at least about 17.5-fold, at least about 20-fold, at least about 22.5-fold, at least about 25-fold, at least about 27.5-fold, at least about 30-fold, at least about 50-fold, or at least about 100-fold lower than the $K_D$ of a control anti-CD33 antibody for the target (e.g., a control anti-CD33 antibody comprising a heavy chain variable region comprising the amino acid sequence of SEQ ID NO: 34 and a light chain variable region comprising the amino acid sequence of SEQ ID NO: 77; a control anti-CD33 antibody comprising a heavy chain variable region comprising the amino acid sequence of SEQ ID NO: 40 and a light chain variable region comprising the amino acid sequence of SEQ ID NO: 86; and control anti-CD33 antibody comprising a heavy chain variable region comprising the amino acid sequence of SEQ ID NO: 52 and a light chain variable region comprising the amino acid sequence of SEQ ID NO: 86; and/or a control anti-CD33 antibody comprising a heavy chain variable region comprising the amino acid sequence of SEQ ID NO: 103 and a light chain variable region comprising the amino acid sequence of SEQ ID NO: 104). In some embodiments, anti-CD33 antibodies of the present disclosure have a $K_D$ for human CD33 that is at least 9-fold greater than an anti-CD33 antibody having a heavy chain variable region comprising the amino acid sequence of SEQ ID NO: 34 and a light chain variable region comprising the amino acid sequence of SEQ ID NO: 77. In some embodiments, anti-CD33 antibodies of the present disclosure have a $K_D$ for human CD33 that is at least 3-fold greater than an anti-CD33 antibody having a heavy chain variable region comprising the amino acid sequence of SEQ ID NO: 40 and a light chain variable region comprising the amino acid sequence of SEQ ID NO: 86. In some embodiments, anti-CD33 antibodies of the present disclosure have a $K_D$ for human CD33 that is at least 3-fold greater than an anti-CD33 antibody having a heavy chain variable region comprising the amino acid sequence of SEQ ID NO: 52 and a light chain variable region comprising the amino acid sequence of SEQ ID NO: 86. In some embodiments, the affinity is measured by surface plasmon resonance. In some embodiments, the affinity is measured at a temperature of approximately 25° C. In some embodiments, the affinity is measured at a temperature of approximately 4° C. In some embodiments, the affinity is measured using the experimental approach as described in Example 1 below.

Anti-CD33 antibodies of the present disclosure may decrease cellular levels (e.g., cell surface levels) of CD33 with a half-maximal effective concentration ($EC_{50}$) (e.g., when measured in vitro using primary human dendritic cells) in the picomolar range. In certain embodiments, the $EC_{50}$ of the antibody is about 0.1 to about 500 pM. In certain embodiments, the $EC_{50}$ of the antibody is about 1 to about 250 pM. In certain embodiments, the $EC_{50}$ of the antibody is about 4.1 to about 151.1 pM. In some embodiments, the $EC_{50}$ of the antibody is less than about or equal to about 500 pM, 400 pM, 300 pM, 250 pM, 225 pM, 200 pM, 175 pM, 150 pM, 125 pM, 100 pM, 75 pM, 50 pM, 25 pM, 10 pM, 1 pM, or 0.5 pM. In some embodiments, the $EC_{50}$ of the antibody is less than about 74.3 pM. In some embodiments, the $EC_{50}$ of the antibody is greater than about or equal to about 0.1 pM, 0.5 pM, 1 pM, 10 pM, 25 pM, 50 pM, 75 pM, 100 pM, 125 pM, 150 pM, 175 pM, 200 pM, 225 pM, 250 pM, 300 pM, or 400 pM. That is, the $EC_{50}$ of the antibody can be any of a range having an upper limit of about 500 pM, 400 pM, 300 pM, 250 pM, 225 pM, 200 pM, 175 pM, 150 pM, 125 pM, 100 pM, 75 pM, 50 pM, 25 pM, 10 pM, 1 pM, or 0.5 pM, and an independently selected lower limit of about 0.1 pM, 0.5 pM, 1 pM, 10 pM, 25 pM, 50 pM, 75 pM, 100 pM, 125 pM, 150 pM, 175 pM, 200 pM, 225 pM, 250 pM, 300 pM, or 400 pM, wherein the lower limit is less than the upper limit. In some embodiments, the $EC_{50}$ of the antibody is any of about 1 pM, 2 pM, 3 pM, 4 pM, 5 pM, 6 pM, 7 pM, 8 pM, 9 pM, 10 pM, 15 pM, 20 pM, 25 pM, 30 pM, 35 pM, 40 pM, 45 pM, 5-pM, 55 pM, 60 pM, 65 pM, 70 pM, 75 pM, 80 pM, 85 pM, 90 pM, 95 pM, 100 pM, 105 pM, 110 pM, 115 pM, 120 pM, 125 pM, 130 pM, 135 pM, 140 pM, 145 pM, 150 pM, 155 pM, 160 pM, 165 pM, 170 pM, 175 pM, 180 pM, 185 pM, 190 pM, 195 pM, or 200 pM. Various methods of measuring antibody $EC_{50}$ values are known in the art, including, for example, by flow cytometry (See e.g., Example 2 below). In some embodiments, the $EC_{50}$ is measured in vitro using primary human dendritic cells. In some embodiments, the $EC_{50}$ is measured in vitro using primary human monocytes. In some embodiments, the $EC_{50}$ is measured in vitro using primary human macrophages. In some embodiments, the $EC_{50}$ is measured in vitro using cultured cells transfected with human CD33. In some embodiments, the $EC_{50}$ is measured at a temperature of approximately 4° C. In some embodiments, the $EC_{50}$ is measured at a temperature of approximately 25° C. In some embodiments, the $EC_{50}$ is measured at a temperature of approximately 35° C. In some embodiments, the $EC_{50}$ is measured at a temperature of approximately 37° C. In some embodiments, the $EC_{50}$ is determined using a monovalent antibody (e.g., a Fab) or a full-length antibody in a monovalent form. In some embodiments, the $EC_{50}$ is determined using antibodies containing constant regions that demonstrate enhanced Fc receptor binding. In some embodiments, the $EC_{50}$ is determined using antibodies containing constant regions that demonstrate reduced Fc receptor binding.

In some embodiments, anti-CD33 antibodies of the present disclosure decrease cellular levels (e.g., cell surface levels) of CD33 with a lower $EC_{50}$ (e.g., as measured in vitro using primary human dendritic cells) than a control anti-CD33 antibody (e.g., a control anti-CD33 antibody comprising a heavy chain variable region comprising the amino acid sequence of SEQ ID NO: 34 and a light chain variable region comprising the amino acid sequence of SEQ ID NO: 77; a control anti-CD33 antibody comprising a heavy chain variable region comprising the amino acid sequence of SEQ ID NO: 40 and a light chain variable region comprising the amino acid sequence of SEQ ID NO: 86; and control anti-CD33 antibody comprising a heavy chain variable region comprising the amino acid sequence of SEQ ID NO: 52 and a light chain variable region comprising the amino acid sequence of SEQ ID NO: 86; and/or a control anti-CD33 antibody comprising a heavy chain variable region comprising the amino acid sequence of SEQ ID NO: 103 and a light chain variable region comprising the amino acid sequence of SEQ ID NO: 104). In some embodiments, anti-CD33 antibodies of the present disclosure decrease cellular levels (e.g., cell surface levels) of CD33 with an $EC_{50}$ that is at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or at least about 99% lower than the $EC_{50}$ of a control anti-CD33 antibody (e.g., a control anti-CD33 antibody comprising a heavy chain variable region comprising the amino acid sequence of SEQ ID NO: 34 and a light chain variable region comprising the amino acid sequence of SEQ ID NO: 77; a control anti-CD33 antibody comprising a heavy chain variable region comprising the amino acid sequence of SEQ ID NO: 40 and a light chain variable region comprising the amino acid sequence of SEQ ID NO: 86; and control anti-CD33 antibody comprising a heavy chain variable region comprising the amino acid sequence of SEQ ID NO: 52 and a light chain variable region comprising the amino acid sequence of SEQ ID NO: 86; and/or a control anti-CD33 antibody comprising a heavy chain variable region comprising the amino acid sequence of SEQ ID NO: 103 and a light chain variable region comprising the amino acid sequence of SEQ ID NO: 104). In some embodiments, anti-CD33 antibodies of the present disclosure decrease cellular levels (e.g., cell surface levels) of CD33 with an $EC_{50}$ that is at least about 1-fold, at least about 1.1-fold, at least about 1.5-fold, at least about 2-fold, at least about 3-fold, at least about 4-fold, at least about 5-fold, at least about 6-fold, at least about 7-fold, at least about 8-fold, at least about 9-fold, at least about 10-fold, at least about 12.5-fold, at least about 15-fold, at least about 17.5-fold, at least about 20-fold, at least about 22.5-fold, at least about 25-fold, at least about 27.5-fold, at least about 30-fold, at least about 50-fold, or at least about 100-fold lower than the $EC_{50}$ of a control anti-CD33 antibody (e.g., a control anti-CD33 antibody comprising a heavy chain variable region comprising the amino acid sequence of SEQ ID NO: 34 and a light chain variable region comprising the amino acid sequence of SEQ ID NO: 77; a control anti-CD33 antibody comprising a heavy chain variable region comprising the amino acid sequence of SEQ ID NO: 40 and a light chain variable region comprising the amino acid sequence of SEQ ID NO: 86; and control anti-CD33 antibody comprising a heavy chain variable region compris-ing the amino acid sequence of SEQ ID NO: 52 and a light chain variable region comprising the amino acid sequence of SEQ ID NO: 86; and/or a control anti-CD33 antibody comprising a heavy chain variable region comprising the amino acid sequence of SEQ ID NO: 103 and a light chain variable region comprising the amino acid sequence of SEQ ID NO: 104). In some embodiments, anti-CD33 antibodies of the present disclosure have an $EC_{50}$ that is at least 1.6-fold lower than an anti-CD33 antibody having a heavy chain variable region comprising the amino acid sequence of SEQ ID NO: 34 and a light chain variable region comprising the amino acid sequence of SEQ ID NO: 77. In some embodiments, anti-CD33 antibodies of the present disclosure have an $EC_{50}$ that is at least 1.05-fold lower than an anti-CD33 antibody having a heavy chain variable region comprising the amino acid sequence of SEQ ID NO: 40 and a light chain variable region comprising the amino acid sequence of SEQ ID NO: 86. In some embodiments, anti-CD33 antibodies of the present disclosure have an $EC_{50}$ that is at least 1.07-fold lower than an anti-CD33 antibody having a heavy chain variable region comprising the amino acid sequence of SEQ ID NO: 52 and a light chain variable region comprising the amino acid sequence of SEQ ID NO: 86. In some embodiments, anti-CD33 antibodies of the present disclosure have an $EC_{50}$ that is at least 1.2-fold lower than an anti-CD33 antibody having a heavy chain variable region comprising the amino acid sequence of SEQ ID NO: 103 and a light chain variable region comprising the amino acid sequence of SEQ ID NO: 104. In some embodiments, the $EC_{50}$ is measured in vitro using primary human dendritic cells. In some embodiments, the $EC_{50}$ is measured in vitro using primary human monocytes. In some embodiments, the $EC_{50}$ is measured in vitro using primary human macrophages. In some embodiments, the $EC_{50}$ is measured in vitro using cultured cells transfected with human CD33. In some embodiments, the $EC_{50}$ is measured by flow cytometry. In some embodiments, the $EC_{50}$ is measured at a temperature of approximately 25° C. In some embodiments, the $EC_{50}$ is measured at a temperature of approximately 35° C. In some embodiments, the $EC_{50}$ is measured at a temperature of approximately 37° C. In some embodiments, the $EC_{50}$ is determined using antibodies containing constant regions that demonstrate enhanced Fc receptor binding. In some embodiments, the $EC_{50}$ is determined using antibodies containing constant regions that demonstrate reduced Fc receptor binding. In some embodiments, the $EC_{50}$ is measured using the experimental approach as described in Example 2 below.

Any in vitro cell-based assays or suitable in vivo model described herein or known in the art may be used to measure inhibition of interaction (e.g., binding) between CD33 and one or more CD33 ligands. In some embodiments, anti-CD33 antibodies of the present disclosure inhibit interaction (e.g., binding) between CD33 and one or more CD33 ligands by at least 21%, at least 22%, at least 23%, at least 24%, at least 25%, at least 26%, at least 27%, at least 28%, at least 29%, at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, at least 50%, at least 51%, at least 52%, at least 53%, at least 54%, at least 55%, at least 56%, at least 57%, at least 58%, at least 59%, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more at saturating antibody concentrations utilizing any in vitro assay or cell-based culture assay described herein or known in the art.

In some embodiments, anti-CD33 antibodies of the present disclosure inhibit cell surface clustering of CD33. In some embodiments, anti-CD33 antibodies of the present disclosure inhibit one or more activities of a CD33 protein, including, without limitation, counteracting one or more of phosphorylation of Tyr-340 and Tyr-358 by a Src family tyrosine kinase, such as LCK and FYN; recruitment of and binding to the tyrosine-specific protein phosphatases SHP1 and SHP2; recruitment of and binding to PLC-gamma1, which acts as a guanine nucleotide exchange factor for Dynamini-1; recruitment of and binding to SH2-domain containing protein (e.g., Crk1); recruitment of and binding to the spleen tyrosine kinase Syk; recruitment of and binding to SH3-SH2-SH3 growth factor receptor-bound protein 2 (Grb2); recruitment of and binding to multiple SH2-containing proteins; phosphorylation of Ser-307 and Ser-342 by protein kinase C; modulated expression of one or more anti-inflammatory cytokines, IL-4, IL-10, IL-13, IL-35, IL-16, TGF-beta, IL-1Ra, G-CSF, and soluble receptors for TNF, IFN-beta1a, IFN-beta1b, or IL-6 in monocytes, macrophages, T cells, dendritic cells neutrophils, and/or microglia; decreasing intracellular calcium mobilization; modulated expression of one or more pro-inflammatory cytokines IFN-a4, IFN-b, IL-1β, TNF-α, IL-6, IL-8, CRP, IL-20 family members, LIF, IFN-gamma, OSM, CNTF, GM-CSF, IL-11, IL-12, IL-17, IL-18, IL-23, CXCL10, IL-33, CRP, IL-33, MCP-1, and MIP-1-beta in monocytes, macrophages, T cells, dendritic cells, neutrophils, and/or microglia; modulated expression of one or more proteins selected from C1qa, C1qB, C1qC, C1s, C1R, C4, C2, C3, ITGB2, HMOX1, LAT2, CASP1, CSTA, VSIG4, MS4A4A, C3AR1, GPX1, TyroBP, ALOX5AP, ITGAM, SLC7A7, CD4, ITGAX, PYCARD, CD14, CD16, HLA-DR, and CCR2; inhibition of extracellular signal-regulated kinase (ERK) phosphorylation; decreasing tyrosine phosphorylation on multiple cellular proteins; modulated expression of C-C chemokine receptor 7 (CCR7); inhibition of microglial cell chemotaxis toward CCL19 and CCL21 expressing cells; activation of phosphoinositide 3-kinase; reducing cell growth of monocytes, macrophages, T cells, dendritic cells and/or microglia; reducing T cell proliferation induced by dendritic cells, bone marrow-derived dendritic cells, monocytes, microglia, M1 microglia, activated M1 microglia, M2 microglia, macrophages, M1 macrophages, activated M1 macrophages, and/or M2 macrophages; inhibition of osteoclast production, decreased rate of osteoclastogenesis, or both; decreasing survival of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; decreasing proliferation of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; inhibiting migration of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; decreasing one or more functions of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; inhibiting maturation of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; increasing cell death and apoptosis of monocytes, macrophages, T cells, dendritic cells, neutrophils, and/or microglia; reducing phagocytic activity of monocytes, macrophages, T cells, dendritic cells, neutrophils, and/or microglia; reducing proliferation of monocytes, macrophages, T cells, dendritic cells, neutrophils, and/or microglia; reducing the overall functionality of monocytes, macrophages, T cells, dendritic cells, neutrophils, and/or microglia, phosphorylation of an ITAM containing receptor; phosphorylation of a signaling molecules that mediates ITAM signaling; reducing the activation of pattern recognition receptors; reducing the activation of Toll-like receptors; reducing the activation of damage-associated of clearance of cellular and protein debris; interaction between CD33 and one or more of its ligands; interaction between CD33 and a co-receptor such as CD64; reducing one or more types of clearance selected from apoptotic neuron clearance, nerve tissue debris clearance, dysfunctional synapse clearance, non-nerve tissue debris clearance, bacteria or other foreign body clearance, disease-causing protein clearance, and tumor cell clearance; inhibition of phagocytosis of one or more of apoptotic neurons, nerve tissue debris, non-nerve tissue debris, bacteria, other foreign bodies, disease-causing proteins, disease-causing peptides, disease-causing nucleic acid, disease-causing lipids, or tumor cells; inhibition of clearance of a disease-causing nucleic acid, such as the disease-causing nucleic acid is antisense GGCCCC (G2C4) repeat-expansion RNA; activation of clearance of, a disease-causing protein selected from amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; inhibition of beneficial immune response to different types of cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, acute myeloid leukemia, pancreatic cancer, prostate cancer, ovarian cancer, fibrosarcoma, and thyroid cancer; inhibition of beneficial immune response to different types of neurological disorders selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, essential tremor, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, traumatic brain injury, age related macular degeneration, glaucoma, retinitis pigmentosa, retinal degeneration, and multiple sclerosis; inhibition of beneficial immune response-to different types of inflammatory and infectious disorders selected from lupus, acute and chronic colitis, wound healing, Crohn's disease, inflammatory bowel disease, ulcerative colitis, obesity, malaria, respiratory tract infection, sepsis, eye infection, systemic infection, lupus, arthritis, low bone density, osteoporosis, osteogenesis, osteopetrotic disease, and Paget's disease of bone; binding to CD33 ligand on tumor cells; binding to CD33 ligand on dendritic cells, bone marrow-derived dendritic cells, monocytes, microglia, T cells, neutrophils, and/or macrophages; inhibition of tumor cell killing by one or more of microglia, macrophages, dendritic cells, bone marrow-derived dendritic cells, neutrophils, T cells, T helper cells, or cytotoxic T cells; inhibition of anti-tumor cell proliferation activity of one or more of microglia, macrophages, dendritic cells, bone marrow-derived dendritic cells, neutrophils, T cells, T helper cells, or cytotoxic T cells; inhibition of anti-tumor cell metastasis activity of one or more of microglia, macrophages, dendritic cells, bone marrow-derived dendritic cells, neutrophils, T cells, T helper cells, or cytotoxic T cells; promotion of immunosuppressor dendritic cells, immunosuppressor macrophages, myeloid-derived suppressor cells, tumor-associated macrophages, or regulatory T cells; inhibition of one or more ITAM motif containing receptors, such as TREM1, TREM2, FcgR, DAP10, and DAP12; inhibition of one or more receptors containing the motif D/Ex0-2YxxL/IX6-8YxxL/I (SEQ ID NO: 165); inhibition of signaling by one or more pattern recognition receptors (PRRs), such as receptors that identify pathogen-associated molecular patterns (PAMPs), and receptors that identify damage-associated molecular patterns (DAMPs); inhibition of signaling by one or more Toll-like receptors; inhibition of the JAK-STAT signaling pathway; inhibition of nuclear factor kappa-light-chain-enhancer of activated B cells (NFκB); inhibition of PLCγ/PKC/calcium mobilization; inhibition of PI3K/Akt, Ras/MAPK signaling; reduced expression of one or more inflammatory receptors, such as CD86, expressed on one or more of microglia, macrophages, dendritic cells, bone marrow-derived dendritic cells, neutrophils, T cells, T helper cells, or cytotoxic T cells; increasing expression of one or more CD33-dependent genes; normalization of disrupted CD33-dependent gene expression; and decreasing expression of one or more ITAM-dependent genes, such as NFAT transcription factors.

In some embodiments, anti-CD33 antibodies of the present disclosure exhibit one or more activities of a CD33 protein, including, without limitation, increasing the number of tumor infiltrating CD3+ T cells; decreasing cellular levels of CD33 in CD14+ myeloid cells, such as tumor infiltrating CD14+ myeloid cells and CD14+ myeloid cells present in blood; reducing the number of CD14+ myeloid cells, such as tumor infiltrating CD14+ myeloid cells and CD14+ myeloid cells present in blood; reducing PD-L1, PD-L2, B7-H7, B7-H3, CD200R, CD163, and/or CD206 levels in one or more cells, such as myeloid-derived suppressor cells (MDSC); decreasing tumor growth rate of solid tumors; reducing tumor volume; increasing efficacy of one or more PD-1 inhibitors; increasing efficacy of one or more checkpoint inhibitor therapies and/or immune-modulating therapies, such as checkpoint inhibitor therapies and/or immune-modulating therapies that target one or more of CTL4, the adenosine pathway, PD-L1, PD-L2, OX40, TIM3, LAG3, or any combination thereof; increasing efficacy of one or more chemotherapy agents, optionally wherein the one or more of the chemotherapy agents are gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), oxaliplatin (Elotaxin®), leucovorin, temazolamide (Temodar®), and any combination thereof; increasing proliferation of T cells in the presence of myeloid-derived suppressor cells (MDSC); inhibiting differentiation, survival, and/or one or more functions of myeloid-derived suppressor cells (MDSC); and killing CD33-expressing immunosuppressor non-tumorigenic myeloid cells and/or non-tumorigenic CD14-expressing cells in solid tumors and associated blood vessels when conjugated to a chemical or radioactive toxin.

In some embodiments, the anti-CD33 antibodies inhibit interaction (e.g., binding) between a CD33 protein of the present disclosure and one or more CD33 ligands including, without limitation, CD33 ligands expressed on red blood cells, CD33 ligands expressed on bacterial cells, CD33 ligands expressed on apoptotic cells, CD33 ligands expressed on tumor cells, CD33 ligands expressed on viruses, CD33 ligands expressed on dendritic cells, CD33 ligands expressed on nerve cells, CD33 ligands expressed on glial cells, CD33 ligands expressed on microglia, CD33 ligands expressed on astrocytes, CD33 ligands on beta amyloid plaques, CD33 ligands on Tau tangles, CD33 ligands on disease-causing proteins, CD33 ligands on disease-causing peptides, CD33 ligands expressed on macrophages, CD33 ligands expressed on natural killer cells, CD33 ligands expressed on T cells, CD33 ligands expressed on T helper cells, CD33 ligands expressed on cytotoxic T cells, CD33 ligands expressed on B cells, CD33 ligands expressed on tumor-imbedded immunosuppressor dendritic cells, CD33 ligands expressed on tumor-imbedded immunosuppressor macrophages, CD33 ligands expressed on myeloid-derived suppressor cells, CD33 ligands expressed on regulatory T cells, secreted mucins, sialic acid, sialic acid-containing glycolipids, sialic acid-containing glycoproteins, alpha-2,6-linked sialic acid-containing glycolipids, alpha-2,6-linked sialic acid-containing glycoproteins, alpha-2,3-linked sialic acid-containing glycolipids, alpha-2,3-linked sialic acid-containing glycoproteins, alpha-1-acid glycoprotein (AGP), CD24 protein, and gangliosides.

In some embodiments, anti-CD33 antibodies of the present disclosure bind to a CD33 protein of the present disclosure expressed on the surface of cell and the naked antibodies inhibit interaction (e.g., binding) between the CD33 protein and one or more CD33 ligands. In some embodiments, anti-CD33 antibodies of the present disclosure that bind to a CD33 protein of the present inhibit interaction (e.g., binding) between the CD33 protein and one or more CD33 ligands by reducing the effective levels of CD33 that is available to interact with these proteins either on the cell surface or inside the cell. In some embodiments, anti-CD33 antibodies of the present disclosure that bind to a CD33 protein of the present inhibit interaction (e.g., binding) between the CD33 protein and one or more CD33 ligands by inducing degradation of CD33.

As used herein, levels of CD33 may refer to expression levels of the gene encoding CD33; to expression levels of one or more transcripts encoding CD33; to expression levels of CD33 protein; and/or to the amount of CD33 protein present within cells and/or on the cell surface. Any methods known in the art for measuring levels of gene expression, transcription, translation, and/or protein abundance or localization may be used to determine the levels of CD33.

Additionally, anti-CD33 antibodies of the present disclosure can be used to prevent, reduce risk of, or treat dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and/or *Haemophilus* influenza. In some embodiments, anti-CD33 antibodies of the present disclosure can be used for inducing or promoting the survival, maturation, functionality, migration, or proliferation of one or more immune cells in an individual in need thereof; or for decreasing the activity, functionality, or survival of regulatory T cells, tumor-imbedded immunosuppressor dendritic cells, tumor-imbedded immunosuppressor macrophages, myeloid-derived suppressor cells, tumor-associated macrophages, acute myeloid leukemia (AML) cells, chronic lymphocytic leukemia (CLL) cell, and/or chronic myeloid leukemia (CML) cell in an individual in need thereof. In some embodiments, anti-CD33 antibodies of the present disclosure are monoclonal antibodies.

In some embodiments, an isolated anti-CD33 antibody of the present disclosure decreases cellular levels of CD33 (e.g., cell surface levels, intracellular levels, and/or total levels). In some embodiments, an isolated anti-CD33 antibody of the present disclosure induces downregulation of CD33. In some embodiments, an isolated anti-CD33 antibody of the present disclosure induces cleavage of CD33. In some embodiments, an isolated anti-CD33 antibody of the present disclosure induces internalization of CD33. In some embodiments, an isolated anti-CD33 antibody of the present disclosure induces shedding of CD33. In some embodiments, an isolated anti-CD33 antibody of the present disclosure induces degradation of CD33. In some embodiments, an isolated anti-CD33 antibody of the present disclosure induces desensitization of CD33. In some embodiments, an isolated anti-CD33 antibody of the present disclosure acts as a ligand mimetic to transiently activate CD33. In some embodiments, an isolated anti-CD33 antibody of the present disclosure acts as a ligand mimetic and transiently activates CD33 before inducing a decrease in cellular levels of CD33 and/or inhibition of interaction (e.g., binding) between CD33 and one or more CD33 ligands. In some embodiments, an isolated anti-CD33 antibody of the present disclosure acts as a ligand mimetic and transiently activates CD33 before inducing degradation of CD33. In some embodiments, an isolated anti-CD33 antibody of the present disclosure acts as a ligand mimetic and transiently activates CD33 before inducing cleavage of CD33. In some embodiments, an isolated anti-CD33 antibody of the present disclosure acts as a ligand mimetic and transiently activates CD33 before inducing internalization of CD33. In some embodiments, an isolated anti-CD33 antibody of the present disclosure acts as a ligand mimetic and transiently activates CD33 before inducing shedding of CD33. In some embodiments, an isolated anti-CD33 antibody of the present disclosure acts as a ligand mimetic and transiently activates CD33 before inducing downregulation of CD33 expression. In some embodiments, an isolated anti-CD33 antibody of the present disclosure acts as a ligand mimetic and transiently activates CD33 before inducing desensitization of CD33.

In some embodiments, an isolated anti-CD33 antibody of the present disclosure is a human antibody, a humanized antibody, a bispecific antibody, a monoclonal antibody, a multivalent antibody, or a chimeric antibody. Exemplary descriptions of such antibodies are found throughout the present disclosure.

In some embodiments, anti-CD33 antibodies of the present disclosure bind to a human CD33, or a homolog thereof, including without limitation, a mammalian CD33 protein. In some embodiments, anti-CD33 antibodies of the present disclosure specifically bind to human CD33. In some embodiments, anti-CD33 antibodies of the present disclosure bind to human CD33 and are not cross-reactive with CD33 orthologs or homologs from other species.

In some embodiments, anti-CD33 antibodies of the present disclosure bind to a CD33 protein of the present disclosure expressed on the surface of a cell and modulate (e.g., induce or inhibit) one or more CD33 activities of the present disclosure after binding to the surface-expressed CD33 protein. In some embodiments, anti-CD33 antibodies of the present disclosure are inert antibodies.

Anti-CD33 Antibody-Binding Regions

In some embodiments, anti-CD33 antibodies of the present disclosure may bind a conformational epitope. In some embodiments, anti-CD33 antibodies of the present disclosure may bind a discontinuous CD33 epitope. In some embodiments, the discontinuous CD33 epitope comprises two or more peptides, three or more peptides, four or more peptides, five or more peptides, six or more peptides, seven or more peptides, eight or more peptides, nine or more peptides, or 10 or more peptides. In some embodiments, anti-CD33 antibodies of the present disclosure may bind a CD33 epitope comprising one or more peptides. As disclosed herein, CD33 epitopes may comprise one or more peptides comprising five or more, six or more, seven or more, eight or more, nine or more, 10 or more, 11 or more, 12 or more, 13 or more 14 or more, 15 or more, 16 or more, 17 or more, 18 or more, 19 or more, or 20 or more amino acid residues of the amino acid sequence of SEQ ID NO: 1, or five or more, six or more, seven or more, eight or more, nine or more, 10 or more, 11 or more, 12 or more, 13 or more 14 or more, 15 or more, 16 or more, 17 or more, 18 or more, 19 or more, or 20 or more amino acid residues on a mammalian CD33 protein corresponding to the amino acid sequence of SEQ ID NO: 1.

In some embodiments, anti-CD33 antibodies of the present disclosure bind to an epitope of human CD33 that is the same as or overlaps with the CD33 epitope bound by an anti-CD33 antibody comprising a heavy chain variable region comprising the amino acid sequence of SEQ ID NO: 103 and a light chain variable region comprising the amino acid sequence of SEQ ID NO: 104. In some embodiments, anti-CD33 antibodies of the present disclosure bind essentially the same CD33 epitope bound by an anti-CD33 antibody comprising a heavy chain variable region comprising the amino acid sequence of SEQ ID NO: 103 and a light chain variable region comprising the amino acid sequence of SEQ ID NO: 104.

In some embodiments, anti-CD33 antibodies of the present disclosure competitively inhibit binding of an anti-CD33 antibody comprising a heavy chain variable region comprising the amino acid sequence of SEQ ID NO: 103 and a light chain variable region comprising the amino acid sequence of SEQ ID NO: 104. In some embodiments, anti-CD33 antibodies of the present disclosure compete with an anti-CD33 antibody comprising a heavy chain variable region comprising the amino acid sequence of SEQ ID NO: 103 and a light chain variable region comprising the amino acid sequence of SEQ ID NO: 104 for binding to CD33.

In some embodiments, anti-CD33 antibodies of the present disclosure competitively inhibit binding of at least one antibody selected from any of the antibodies listed in Tables 3A-3C, 4A-4C, 5A-5D, 6A-6D, 7 and 8. In some embodiments, anti-CD33 antibodies of the present disclosure competitively inhibit binding of at least one antibody selected from AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, AB-64.1.15, AB-H2, AB-H9, AB-H14, AB-H15, AB-H63, AB-H64, AB-H65, AB-H66, and any combination thereof. In some embodiments, an anti-CD33 antibody of the present disclosure competes with one or more antibodies selected from AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, AB-64.1.15, AB-H2, AB-H9, AB-H14, AB-H15, AB-H63, AB-H64, AB-H65, AB-H66, and any combination thereof, for binding to CD33 when the anti-CD33 antibody reduces the binding of one or more antibodies selected from AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, AB-64.1.15, AB-H2, AB-H9, AB-H14, AB-H15, AB-H63, AB-H64, AB-H65, AB-H66, and any combination thereof to CD33 by an amount the ranges from about 50% to 100%, as compared to binding to CD33 in the absence of the anti-CD33 antibody. In some embodiments, an anti-CD33 antibody of the present disclosure competes with one or more antibodies selected from AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, AB-64.1.15, AB-H2, AB-H9, AB-H14, AB-H15, AB-H63, AB-H64, AB-H65, AB-H66, and any combination thereof for binding to CD33 when the anti-CD33 antibody reduces the binding of one or more antibodies selected from AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, AB-64.1.15, AB-H2, AB-H9, AB-H14, AB-H15, AB-H63, AB-H64, AB-H65, AB-H66, and any combination thereof to CD33 by at least 50%, at least 55%, by at least 60%, at least 65%, at least 70%, at least 75%, at least 80%, at least 85%, at least 90%, at least 95%, or 100%, as compared to binding to CD33 in the absence of the anti-CD33 antibody. In some embodiments, an anti-CD33 antibody of the present disclosure that reduces the binding of one or more antibodies selected from AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, AB-64.1.15, AB-H2, AB-H9, AB-H14, AB-H15, AB-H63, AB-H64, AB-H65, AB-H66, and any combination thereof to CD33 by 100% indicates that the anti-CD33 antibody essential completely blocks the binding of one or more antibodies selected from AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, AB-64.1.15, AB-H2, AB-H9, AB-H14, AB-H15, AB-H63, AB-H64, AB-H65, AB-H66, and any combination thereof to CD33. In some embodiments, the anti-CD33 antibody and the one or more antibodies selected from AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, AB-64.1.15, AB-H2, AB-H9, AB-H14, AB-H15, AB-H63, AB-H64, AB-H65, AB-H66, and any combination thereof are present in an amount that corresponds to a 10:1 ratio, 9:1 ratio, 8:1 ratio, 7:1 ratio, 6:1 ratio, 5:1 ratio, 4:1 ratio, 3:1 ratio, 2:1 ratio, 1:1 ratio, 0.75:1 ratio, 0.5:1 ratio, 0.25:1 ratio, 0.1:1 ratio, 0.075:1 ratio, 0.050:1 ratio, 0.025:1 ratio, 0.01:1 ratio, 0.0075: ratio, 0.0050:1 ratio, 0.0025:1 ratio, 0.001: ratio, 0.00075:1 ratio, 0.00050:1 ratio, 0.00025:1 ratio, 0.0001: ratio, 1:10 ratio, 1:9 ratio, 1:8 ratio, 1:7 ratio, 1:6 ratio, 1:5 ratio, 1:4 ratio, 1:3 ratio, 1:2 ratio, 1:0.75 ratio, 1:0.5 ratio, 1:0.25 ratio, 1:0.1 ratio, 1:0.075 ratio, 1:0.050 ratio, 1:0.025 ratio, 1:0.01 ratio, 1:0.0075 ratio, 1:0.0050 ratio, 1:0.0025 ratio, 1:0.001 ratio, 1:0.00075 ratio, 1:0.00050 ratio, 1:0.00025 ratio, or 1:0.0001ratio of anti-CD33 antibody to one or more antibodies selected from AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, AB-64.1.15, AB-H2, AB-H9, AB-H14, AB-H15, AB-H63, AB-H64, AB-H65, AB-H66, and any combination thereof. In some embodiments, the anti-CD33 antibody is present in excess by an amount that ranges from about 1.5-fold to 100-fold, or greater than 100-fold compared to the amount of the one or more antibodies selected from AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, AB-64.1.15, AB-H2, AB-H9, AB-H14, AB-H15, AB-H63, AB-H64, AB-H65, AB-H66, and any combination thereof. In some embodiments, the anti-CD33 antibody is present in an amount that is about a 2-fold, 3-fold, 4-fold, 5-fold, 6-fold, 7-fold, 8-fold, 9-fold, 10-fold, 15-fold, 20-fold, 25-fold, 30-fold, 35-fold, 40-fold, 45-fold, 50-fold, 55-fold, 60-fold, 65-fold, 70-fold, 75-fold, 80-fold, 85-fold, 90-fold, 95-fold, or 100-fold excess compared to the amount of the one or more antibodies selected from AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, AB-64.1.15, AB-H2, AB-H9, AB-H14, AB-H15, AB-H63, AB-H64, AB-H65, AB-H66, and any combination thereof.

In some embodiments, anti-CD33 antibodies of the present disclosure bind to an epitope of human CD33 that is the same as or overlaps with the CD33 epitope bound by at least one antibody selected from any of the antibodies listed in Tables 3A-3C, 4A-4C, 5A-5D, 6A-6D, 7 and 8. In some embodiments, anti-CD33 antibodies of the present disclosure bind to an epitope of human CD33 that is the same as or overlaps with the CD33 epitope bound by at least one antibody selected from AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, AB-64.1.15, AB-H2, AB-H9, AB-H14, AB-H15, AB-H63, AB-H64, AB-H65, AB-H66.

In some embodiments, anti-CD33 antibodies of the present disclosure bind essentially the same CD33 epitope bound by at least one antibody selected from any of the antibodies listed in Tables 3A-3C, 4A-4C, 5A-5D, 6A-6D, 7 and 8. In some embodiments, anti-CD33 antibodies of the present disclosure bind essentially the same CD33 epitope bound by at least one antibody selected from AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, AB-64.1.15, AB-H2, AB-H9, AB-H14, AB-H15, AB-H63, AB-H64, AB-H65, AB-H66. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In some embodiments, anti-CD33 antibodies of the present disclosure compete with one or more antibodies selected from AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, AB-64.1.15, AB-H2, AB-H9, AB-H14, AB-H15, AB-H63, AB-H64, AB-H65, AB-H66, and any combination thereof for binding to CD33.

Any suitable competition assay or CD33 binding assay known in the art, such as BIAcore analysis, ELISA assays, or flow cytometry, may be utilized to determine whether an anti-CD33 antibody competes with one or more antibodies selected from AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, AB-64.1.15, AB-H2, AB-H9, AB-H14, AB-H15, AB-H63, AB-H64, AB-H65, AB-H66, and any combination thereof for binding to CD33. In an exemplary competition assay, immobilized CD33 or cells expressing CD33 on the cell surface are incubated in a solution comprising a first labeled antibody that binds to CD33 (e.g., human or non-human primate) and a second unlabeled antibody that is being tested for its ability to compete with the first antibody for binding to CD33. The second antibody may be present in a hybridoma supernatant. As a control, immobilized CD33 or cells expressing CD33 is incubated in a solution comprising the first labeled antibody but not the second unlabeled antibody. After incubation under conditions permissive for binding of the first antibody to CD33, excess unbound antibody is removed, and the amount of label associated with immobilized CD33 or cells expressing CD33 is measured. If the amount of label associated with immobilized CD33 or cells expressing CD33 is substantially reduced in the test sample relative to the control sample, then that indicates that the second antibody is competing with the first antibody for binding to CD33. See, Harlow and Lane (1988) *Antibodies: A Laboratory Manual* ch. 14 (Cold Spring Harbor Laboratory, Cold Spring Harbor, N.Y.).

Anti-CD33 Antibody Light Chain and Heavy Chain Variable Regions

In some embodiments, anti-CD33 antibodies of the present disclosure comprise a heavy chain variable region comprising one or more (e.g., one or more, two or more, or all three) HVRs selected from HVR-H1, HVR-H2, and HVR-H3 (as shown in Tables 3A-3C). In some embodiments, the heavy chain variable region comprises an HVR-H1, an HVR-H2, and an HVR-H3 (as shown in Tables 3A-3C). In some embodiments, the antibody is not an antibody comprising a heavy chain variable region comprising an HVR-H1 comprising the sequence of GYTFTDYNLH (SEQ ID NO: 105), an HVR-H2 comprising the sequence of FIYPSNGITG (SEQ ID NO: 115), and an HVR-H3 comprising the sequence of STVDYFDY (SEQ ID NO: 121).

In some embodiments, the HVR-H1 comprises a sequence according to Formula I: GX$_1$X$_2$X$_3$TDYNX$_4$H (SEQ ID NO: 152), wherein X$_1$ is Y, A, or V, X$_2$ is T or A, X$_3$ is F, E, or H, and X$_4$ is L, F, Y, or N. In some embodiments, the HVR-H1 comprises a sequence selected from SEQ ID NOs: 105-114. In some embodiments, the HVR-H2 comprises a sequence according to Formula II: FIYPX$_1$NX$_2$IX$_3$G (SEQ ID NO: 153), wherein X$_1$ is S or A, X$_2$ is G, Q, R, or V, and X$_3$ is T or R. In some embodiments, the HVR-H2 comprises a sequence selected from SEQ ID NOs: 115-120. In some embodiments, the HVR-H3 comprises a sequence according to Formula III: SX$_1$VDYFDX$_2$ (SEQ ID NO: 154), wherein X$_1$ is T, D, F, or S, and X$_2$ is Y, D, or L. In some embodiments, the HVR-H3 comprises a sequence selected from SEQ ID NOs: 121-126.

In some embodiments, the heavy chain variable region comprises an HVR-H1 according to Formula I, an HVR-H2 according to Formula II, and an HVR-H3 according to Formula III, and the antibody is not an antibody comprising a heavy chain variable region comprising an HVR-H1 comprising the sequence of GYTFTDYNLH (SEQ ID NO: 105), an HVR-H2 comprising the sequence of FIYPSNGITG (SEQ ID NO: 115), and an HVR-H3 comprising the sequence of STVDYFDY (SEQ ID NO: 121). In some embodiments, the heavy chain variable region comprises an HVR-H1 comprising a sequence selected from SEQ ID NOs: 105-114, and HVR-H2 comprising a sequence selected from SEQ ID NOs: 115-120, and an HVR-H3 comprising a sequence selected from SEQ ID NOs: 121-126, and the antibody is not an antibody comprising a heavy chain variable region comprising an HVR-H1 comprising the sequence of GYTFTDYNLH (SEQ ID NO: 105), an HVR-H2 comprising the sequence of FIYPSNGITG (SEQ ID NO: 115), and an HVR-H3 comprising the sequence of STVDYFDY (SEQ ID NO: 121).

In some embodiments, the heavy chain variable region comprises the HVR-H1, HVR-H2, and HVR-H3 of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15, and any combination thereof (as shown in Tables 3A to 3C).

In some embodiments, anti-CD33 antibodies of the present disclosure comprise a heavy chain variable region, wherein the heavy chain variable region comprises one or more of: (a) an HVR-H1 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-H1 amino acid sequence of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15; (b) an HVR-H2 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-H2 amino acid sequence of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15; and (c) an HVR-H3 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-H3 amino acid sequence of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15, and the antibody is not an antibody comprising a heavy chain variable region comprising an HVR-H1 comprising the sequence of GYTFTDYNLH (SEQ ID NO: 105), an HVR-H2 comprising the sequence of FIYPSNGITG (SEQ ID NO: 115), and an HVR-H3 comprising the sequence of STVDYFDY (SEQ ID NO: 121).

In some embodiments, anti-CD33 antibodies of the present disclosure comprise an HVR-H1 comprising the amino acid sequence GYTFTDYNLH (SEQ ID NO: 105), an HVR-H2 comprising the amino acid sequence FIYPSNRITG (SEQ ID NO: 119), and an HVR-H3 comprising the amino acid sequence SDVDYFDY (SEQ ID NO: 122). In some embodiments, anti-CD33 antibodies of the present disclosure comprise an HVR-H1 comprising the amino acid sequence GYTFTDYNLH (SEQ ID NO: 105), an HVR-H2 comprising the amino acid sequence FIYPSNQITG (SEQ ID NO: 118), and an HVR-H3 comprising the amino acid sequence SDVDYFDY (SEQ ID NO: 122).

In some embodiments, anti-CD33 antibodies of the present disclosure comprise a light chain variable region comprising one or more (e.g., one or more, two or more, or all three) HVRs selected from HVR-L1, HVR-L2, and HVR-L3 (as shown in Tables 4A-4C). In some embodiments, the light chain variable region comprises an HVR-L1, an HVR-L2, and an HVR-L3 (as shown in Tables 4A-4C). In some embodiments, the antibody is not an antibody comprising a light chain variable region comprising an HVR-L1 comprising the sequence of RASQSVSTSTYSYMH (SEQ ID NO: 127), an HVR-L2 comprising the sequence of YASNLES (SEQ ID NO: 135), and an HVR-L3 comprising the sequence of QHSWEIPLT (SEQ ID NO: 146).

In some embodiments, the HVR-L1 comprises a sequence according to Formula IV: $X_1X_2SQX_3VX_4X_5STYSYMH$ (SEQ ID NO: 155), wherein $X_1$ is R or K, $X_2$ is A, G, or V, $X_3$ is S or D, $X_4$ is S, G, or H, and $X_5$ is T or A. In some embodiments, the HVR-L1 comprises a sequence selected from SEQ ID NOs: 127-134. In some embodiments, the HVR-L2 comprises a sequence according to Formula V: $YX_1X_2X_3X_4X_5S$ (SEQ ID NO: 156), wherein $X_1$ is A, V, or E, $X_2$ is 5, V, or F, $X_3$ is N, A, Y, or F, $X_4$ is L or V, and $X_5$ is E, G, or N. In some embodiments, the HVR-L2 comprises a sequence selected from SEQ ID NOs: 135-145. In some embodiments, the HVR-L3 comprises a sequence according to Formula VI: $X_1HSX_2X_3X_4PLX_5$ (SEQ ID NO: 157), wherein $X_1$ is Q or E, $X_2$ is W or E, $X_3$ is E or A, $X_4$ is I or L, and $X_5$ is T or E. In some embodiments, the HVR-13 comprises a sequence selected from SEQ ID NOs: 146-151.

In some embodiments, the light chain variable region comprises an HVR-L1 according to Formula IV, an HVR-L2 according to Formula V, and an HVR-L3 according to Formula VI, and the antibody is not an antibody comprising a light chain variable region comprising an HVR-L1 comprising the sequence of RASQSVSTSTYSYMH (SEQ ID NO: 127), an HVR-L2 comprising the sequence of YASNLES (SEQ ID NO: 135), and an HVR-L3 comprising the sequence of QHSWEIPLT (SEQ ID NO: 146). In some embodiments, the light chain variable region comprises an HVR-L1 comprising a sequence selected from SEQ ID NOs: 127-134, and HVR-L2 comprising a sequence selected from SEQ ID NOs: 135-145, and an HVR-L3 comprising a sequence selected from SEQ ID NOs: 146-151, and the antibody is not an antibody comprising a light chain variable region comprising an HVR-L1 comprising the sequence of RASQSVSTSTYSYMH (SEQ ID NO: 127), an HVR-L2 comprising the sequence of YASNLES (SEQ ID NO: 135), and an HVR-L3 comprising the sequence of QHSWEIPLT (SEQ ID NO: 146).

In some embodiments, the light chain variable region comprises the HVR-L1, HVR-L2, and HVR-L3 of antibody AB-14.3, AB-14.4, AB-14.6, AB-14.7, AB-14.8, AB-14.9, AB-14.10, AB-14.11, AB-63.6, AB-63.7, AB-63.8, AB-63.9, AB-63.10, AB-63.11, AB-63.12, AB-63.14, AB-63.15, AB-63.16, AB-63.17, AB-63.18, AB-64.2, AB-64.3, AB-64.4, AB-64.5, AB-64.6, AB-64.7, or AB-64.8, and any combination thereof (as shown in Tables 4A to 4C).

In some embodiments, anti-CD33 antibodies of the present disclosure comprise a light chain variable region, wherein the light chain variable region comprises one or more of: (a) an HVR-L1 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-L1 amino acid sequence of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15; (b) an HVR-L2 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-L2 amino acid sequence of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15; and (c) an HVR-L3 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-L3 amino acid sequence of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15, and the antibody is not an antibody comprising a light chain variable region comprising an HVR-L1 comprising the sequence of RASQSVSTSTYSYMH (SEQ ID NO: 127), an HVR-L2 comprising the sequence of YASNLES (SEQ ID NO: 135), and an HVR-L3 comprising the sequence of QHSWEIPLT (SEQ ID NO: 146).

In some embodiments, anti-CD33 antibodies of the present disclosure comprise an HVR-L1 comprising the amino acid sequence RASQSVSTSTYSYMH (SEQ ID NO: 127), an HVR-L2 comprising the amino acid sequence YASNLES (SEQ ID NO: 135), and an HVR-L3 comprising the amino acid sequence QHSWEIPLT (SEQ ID NO: 146). In some embodiments, anti-CD33 antibodies of the present disclosure comprise an HVR-L1 comprising the amino acid sequence RASQSVSTSTYSYMH (SEQ ID NO: 127), an HVR-L2 comprising the amino acid sequence YASNLES (SEQ ID NO: 135), and an HVR-L3 comprising the amino acid sequence QHSWEIPLT (SEQ ID NO: 146).

In some embodiments, anti-CD33 antibodies of the present disclosure comprise a heavy chain variable region comprising one or more (e.g., one or more, two or more, or all three) HVRs selected from HVR-H1, HVR-H2, and HVR-H3 (as shown in Tables 3A-3C), and a light chain variable region comprising one or more (e.g., one or more, two or more, or all three) HVRs selected from HVR-L1, HVR-L2, and HVR-L3 (as shown in Tables 4A-4C). In some embodiments, the heavy chain variable region comprises an HVR-H1, an HVR-H2, and an HVR-H3 (as shown in Tables 3A-3C), and the light chain variable region comprises an HVR-L1, an HVR-L2, and an HVR-L3 (as shown in tables 4A-4C). In some embodiments, the antibody is not an antibody comprising a heavy chain variable region comprising an HVR-H1 comprising the sequence of GYTFTDYNLH (SEQ ID NO: 105), an HVR-H2 comprising the sequence of FIYPSNGITG (SEQ ID NO: 115), and an HVR-H3 comprising the sequence of STVDYFDY (SEQ ID NO: 121), and a light chain variable region comprising an HVR-L1 comprising the sequence of RASQSVSTSTYSYMH (SEQ ID NO: 127), an HVR-L2 comprising the sequence of YASNLES (SEQ ID NO: 135), and an HVR-L3 comprising the sequence of QHSWEIPLT (SEQ ID NO: 146).

In some embodiments, the heavy chain variable region comprises an HVR-H1 according to Formula I, an HVR-H2 according to Formula II, and an HVR-H3 according to Formula III, and the light chain variable region comprises an HVR-L1 according to Formula IV, an HVR-L2 according to Formula V, and an HVR-L3 according to Formula VI, and the antibody is not an antibody comprising a heavy chain variable region comprising an HVR-H1 comprising the sequence of GYTFTDYNLH (SEQ ID NO: 105), an HVR-H2 comprising the sequence of FIYPSNGITG (SEQ ID NO: 115), and an HVR-H3 comprising the sequence of STVDYFDY (SEQ ID NO: 121), and a light chain variable region comprising an HVR-L1 comprising the sequence of RASQSVSTSTYSYMH (SEQ ID NO: 127), an HVR-L2 comprising the sequence of YASNLES (SEQ ID NO: 135), and an HVR-L3 comprising the sequence of QHSWEIPLT (SEQ ID NO: 146). In some embodiments, the heavy chain variable region comprises an HVR-H1 comprising a sequence selected from SEQ ID NOs: 105-114, and HVR-H2 comprising a sequence selected from SEQ ID NOs: 115-120, and an HVR-H3 comprising a sequence selected from SEQ ID NOs: 121-126, and the light chain variable region comprises an HVR-L1 comprising a sequence selected from SEQ ID NOs: 127-134, and HVR-L2 comprising a sequence selected from SEQ ID NOs: 135-145, and an HVR-L3 comprising a sequence selected from SEQ ID NOs: 146-151, and the antibody is not an antibody comprising a heavy chain variable region comprising an HVR-H1 comprising the sequence of GYTFTDYNLH (SEQ ID NO: 105), an HVR-H2 comprising the sequence of FIYPSNGITG (SEQ ID NO: 115), and an HVR-H3 comprising the sequence of STVDYFDY (SEQ ID NO: 121), and a light chain variable region comprising an HVR-L1 comprising the sequence of RASQSVSTSTYSYMH (SEQ ID NO: 127), an HVR-L2 comprising the sequence of YASNLES (SEQ ID NO: 135), and an HVR-L3 comprising the sequence of QHSWEIPLT (SEQ ID NO: 146).

In some embodiments, anti-CD33 antibodies of the present disclosure comprise a heavy chain variable region comprising the HVR-H1, HVR-H2, and HVR-H3 of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15, and any combination thereof (as shown in Tables 3A to 3C); and a light chain variable region comprising the HVR-L1, HVR-L2, and HVR-L3 of antibody AB-14.3, AB-14.4, AB-14.6, AB-14.7, AB-14.8, AB-14.9, AB-14.10, AB-14.11, AB-63.6, AB-63.7, AB-63.8, AB-63.9, AB-63.10, AB-63.11, AB-63.12, AB-63.14, AB-63.15, AB-63.16, AB-63.17, AB-63.18, AB-64.2, AB-64.3, AB-64.4, AB-64.5, AB-64.6, AB-64.7, or AB-64.8, and any combination thereof (as shown in Tables 4A to 4C). In some embodiments, anti-CD33 antibodies of the present disclosure comprise a heavy chain variable region comprising an HVR-H1, HVR-H2, and HVR-H3 and a light chain variable region comprising an HVR-L1, HVR-L2, and HVR-L3, wherein the antibody comprises the HVR-H1, HVR-H2, HVR-H3, HVR-L1, HVR-L2, and HVR-L3 of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15 (as shown in Tables 3A to 3C and 4A to 4C).

In some embodiments, anti-CD33 antibodies of the present disclosure comprise a heavy chain variable region and a light chain variable region, wherein the heavy chain variable region comprises one or more of: (a) an HVR-H1 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-H1 amino acid sequence of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15; (b) an HVR-H2 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-H2 amino acid sequence of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15; and (c) an HVR-H3 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-H3 amino acid sequence of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15, and the antibody is not an antibody comprising a heavy chain variable region comprising an HVR-H1 comprising the sequence of GYTFTDYNLH (SEQ ID NO: 105), an HVR-H2 comprising the sequence of FIYPSNGITG (SEQ ID NO: 115), and an HVR-H3 comprising the sequence of STVDYFDY (SEQ ID NO: 121); and wherein the light chain variable region comprises one or more of: (a) an HVR-L1 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-L1 amino acid sequence of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15; (b) an HVR-L2 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-L2 amino acid sequence of antibody B-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15; and (c) an HVR-L3 comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to an HVR-L3 amino acid sequence of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15, and the antibody is not an antibody comprising a light chain variable region comprising an HVR-L1 comprising the sequence of RASQSVSTSTYSYMH (SEQ ID NO: 127), an HVR-L2 comprising the sequence of YASNLES (SEQ ID NO: 135), and an HVR-L3 comprising the sequence of QHSWEIPLT (SEQ ID NO: 146).

In some embodiments, anti-CD33 antibodies of the present disclosure comprise an HVR-H1 comprising the amino acid sequence GYTFTDYNLH (SEQ ID NO: 105), an HVR-H2 comprising the amino acid sequence FIYPSNRITG (SEQ ID NO: 119), an HVR-H3 comprising the amino acid sequence SDVDYFDY (SEQ ID NO: 122), an HVR-L1 comprising the amino acid sequence RASQSVSTSTY-SYMH (SEQ ID NO: 127), an HVR-L2 comprising the amino acid sequence YASNLES (SEQ ID NO: 135), and an HVR-L3 comprising the amino acid sequence QHSWEIPLT (SEQ ID NO: 146). In some embodiments, anti-CD33 antibodies of the present disclosure comprise an HVR-H1 comprising the amino acid sequence GYTFTDYNLH (SEQ ID NO: 105), an HVR-H2 comprising the amino acid sequence FIYPSNQITG (SEQ ID NO: 118), an HVR-H3 comprising the amino acid sequence SDVDYFDY (SEQ ID NO: 122), an HVR-L1 comprising the amino acid sequence RASQSVSTSTYSYMH (SEQ ID NO: 127), an HVR-L2 comprising the amino acid sequence YASNLES (SEQ ID NO: 135), and an HVR-L3 comprising the amino acid sequence QHSWEIPLT (SEQ ID NO: 146).

In some embodiments, anti-CD33 antibodies of the present disclosure comprise a heavy chain variable region comprising an amino acid sequence selected from SEQ ID NOs: 34-72. In some embodiments, the heavy chain variable region comprises the amino acid sequence of SEQ ID NO: 59. In some embodiments, the heavy chain variable region comprises the amino acid sequence of SEQ ID NO: 65. In some embodiments, anti-CD33 antibodies of the present disclosure comprise a heavy chain variable region of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15 (as shown in Table 7). In some embodiments, anti-CD33 antibodies of the present disclosure comprise a heavy chain variable region comprising an HVR-H1 comprising the amino acid sequence GYTFTDYNLH (SEQ ID NO: 105), an HVR-H2 comprising the amino acid sequence FIYPSNRITG (SEQ ID NO: 119), and an HVR-H3 comprising the amino acid sequence SDVDYFDY (SEQ ID NO: 122). In some embodiments, anti-CD33 antibodies of the present disclosure comprise a heavy chain variable region comprising an HVR-H1 comprising the amino acid sequence GYTFTDYNLH (SEQ ID NO: 105), an HVR-H2 comprising the amino acid sequence FIYPSNQITG (SEQ ID NO: 118), and an HVR-H3 comprising the amino acid sequence SDVDYFDY (SEQ ID NO: 122).

In some embodiments, anti-CD33 antibodies of the present disclosure comprise a light chain variable region comprising an amino acid sequence selected from SEQ ID NOs: 77-101. In some embodiments, the light chain variable region comprises the amino acid sequence of SEQ ID NO: 86. In some embodiments, anti-CD33 antibodies of the present disclosure comprise a light chain variable region of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15 (as shown in Table 8). In some embodiments, anti-CD33 antibodies of the present disclosure comprise a light chain variable region comprising an HVR-L1 comprising the amino acid sequence RASQSVSTSTYSYMH (SEQ ID NO: 127), an HVR-L2 comprising the amino acid sequence YASNLES (SEQ ID NO: 135), and an HVR-L3 comprising the amino acid sequence QHSWEIPLT (SEQ ID NO: 146). In some embodiments, anti-CD33 antibodies of the present disclosure comprise a light chain variable region comprising an HVR-L1 comprising the amino acid sequence RASQSVSTSTYSYMH (SEQ ID NO: 127), an HVR-L2 comprising the amino acid sequence YASNLES (SEQ ID NO: 135), and an HVR-L3 comprising the amino acid sequence QHSWEIPLT (SEQ ID NO: 146).

In some embodiments, anti-CD33 antibodies of the present disclosure comprise a heavy chain variable region comprising an amino acid sequence selected from SEQ ID NOs: 34-72 and a light chain variable region comprising an amino acid sequence selected from SEQ ID NOs: 77-101. In some embodiments, the heavy chain variable region comprises the amino acid sequence of SEQ ID NO: 59, and the light chain variable region comprises the amino acid sequence of SEQ ID NO: 86. In some embodiments, the heavy chain variable region comprises the amino acid sequence of SEQ ID NO: 65, and the light chain variable region comprises the amino acid sequence of SEQ ID NO: 86. In some embodiments, anti-CD33 antibodies of the present disclosure comprise a heavy chain variable region of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15 (as shown in Table 7) and a light chain variable region of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15 (as shown in Table 8). In some embodiments, anti-CD33 antibodies of the present disclosure comprise a heavy chain variable region comprising an HVR-H1 comprising the amino acid sequence GYTFTDYNLH (SEQ ID NO: 105), an HVR-H2 comprising the amino acid sequence FIYPSNRITG (SEQ ID NO: 119), an HVR-H3 comprising the amino acid sequence SDVDYFDY (SEQ ID NO: 122), and a light chain variable region comprising an HVR-L1 comprising the amino acid sequence RASQSVSTSTYSYMH (SEQ ID NO: 127), an HVR-L2 comprising the amino acid sequence YASNLES (SEQ ID NO: 135), and an HVR-L3 comprising the amino acid sequence QHSWEIPLT (SEQ ID NO: 146). In some embodiments, anti-CD33 antibodies of the present disclosure comprise a heavy chain variable region comprising an HVR-H1 comprising the amino acid sequence GYTFTDYNLH (SEQ ID NO: 105), an HVR-H2 comprising the amino acid sequence FIYPSNQITG (SEQ ID NO: 118), an HVR-H3 comprising the amino acid sequence SDVDYFDY (SEQ ID NO: 122), and a light chain variable region comprising an HVR-L1 comprising the amino acid sequence RASQSVSTSTYSYMH (SEQ ID NO: 127), an HVR-L2 comprising the amino acid sequence YASNLES (SEQ ID NO: 135), and an HVR-L3 comprising the amino acid sequence QHSWEIPLT (SEQ ID NO: 146).

In some embodiments, anti-CD33 antibodies of the present disclosure comprise a heavy chain variable region comprising an amino acid sequence selected from SEQ ID NOs: 34, 40, 42, 52, 53, and 73-76. In some embodiments, the antibody comprises a heavy chain variable region of AB-H2, AB-H9, AB-H14, AB-H15, AB-H63, AB-H64, AB-H65, or AB-H66 (as shown in Table 7). In some embodiments, anti-CD33 antibodies of the present disclosure comprise a light chain variable region comprising an amino acid sequence selected from SEQ ID NOs: 77, 86, and 102. In some embodiments, the antibody comprises a light chain variable region of antibody AB-H2, AB-H9, AB-H14, AB-H15, AB-H63, AB-H64, AB-H65, or AB-H66 (as shown in Table 8). In some embodiments, anti-CD33 antibodies of the present disclosure comprise a heavy chain variable region comprising an amino acid sequence selected from SEQ ID NOs: 34, 40, 42, 52, 53, and 73-76, and a light chain variable region comprising an amino acid sequence selected from SEQ ID NOs: 77, 86, and 102. In some embodiments, the antibody comprises a heavy chain variable region of AB-H2, AB-H9, AB-H14, AB-H15, AB-H63, AB-H64, AB-H65, or AB-H66 (as shown in Table 7), and a light chain variable region of antibody AB-H2, AB-H9, AB-H14, AB-H15, AB-H63, AB-H64, AB-H65, or AB-H66 (as shown in Table 8).

Any of the antibodies of the present disclosure may be produced by a cell line. In some embodiments, the cell line may be a mammalian cell line. In certain embodiments, the cell line may be a hybridoma cell line. In other embodiments, the cell line may be a yeast cell line. Any cell line known in the art suitable for antibody production may be used to produce an antibody of the present disclosure. Exemplary cell lines for antibody production are described throughout the present disclosure.

In some embodiments, the anti-CD33 antibody is an anti-CD33 monoclonal antibody selected from AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, AB-64.1.15, AB-H2, AB-H9, AB-H14, AB-H15, AB-H63, AB-H64, AB-H65, or AB-H66.

In some embodiments, anti-CD33 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1 or to the amino acid sequence of SEQ ID NO: 52; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1 or to the amino acid sequence of SEQ ID NO: 86. In some embodiments, anti-CD33 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1 or to the amino acid sequence of SEQ ID NO: 52, wherein the heavy chain variable domain comprises the HVR-H1, HVR-H2, and HVR-H3 amino acid sequences of antibody AB-64.1. In some embodiments, anti-CD33 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1 or to the amino acid sequence of SEQ ID NO: 86, wherein the light chain variable domain comprises the HVR-L1, HVR-L2, and HVR-L3 amino acid sequences of antibody AB-64.1. In some embodiments, the anti-CD33 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1 or to the amino acid sequence of SEQ ID NO: 52 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the heavy chain variable domain amino acid sequence of antibody AB-64.1 or the amino acid sequence of SEQ ID NO: 52. In certain embodiments, a total of 1 to 5 amino acids have been substituted, inserted and/or deleted in the heavy chain variable domain amino acid sequence of antibody AB-64.1 or the amino acid sequence of SEQ ID NO: 52. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VH sequence of antibody CD33 or of SEQ ID NO: 52, including post-translational modifications of that sequence. In a particular embodiment, the VH comprises one, two or three HVRs selected from: (a) the HVR-H1 amino acid sequence of antibody AB-64.1, (b) the HVR-H2 amino acid sequence of antibody AB-64.1, and (c) the HVR-H3 amino acid sequence of antibody AB-64.1. In some embodiments, anti-CD33 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1 or to the amino acid sequence of SEQ ID NO: 86 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the light chain variable domain amino acid sequence of antibody AB-64.1 or the amino acid sequence of SEQ ID NO: 86. In certain embodiments, a total of 1 to 5 amino acids have been substituted, inserted and/or deleted in the light chain variable domain amino acid sequence of antibody AB-64.1 or the amino acid sequence of SEQ ID NO: 86. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VL sequence of antibody AB-64.1 or of SEQ ID NO: 86, including post-translational modifications of that sequence. In a particular embodiment, the VL comprises one, two or three HVRs selected from: (a) the HVR-L1 amino acid sequence of antibody AB-64.1, (b) the HVR-L2 amino acid sequence of antibody AB-64.1, and (c) the HVR-L3 amino acid sequence of antibody AB-64.1.

In some embodiments, anti-CD33 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.1 or to the amino acid sequence of SEQ ID NO: 58; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.1 or to the amino acid sequence of SEQ ID NO: 86. In some embodiments, anti-CD33 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.1 or to the amino acid sequence of SEQ ID NO: 58, wherein the heavy chain variable domain comprises the HVR-H1, HVR-H2, and HVR-H3 amino acid sequences of antibody AB-64.1.1. In some embodiments, anti-CD33 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.1 or to the amino acid sequence of SEQ ID NO: 86, wherein the light chain variable domain comprises the HVR-L1, HVR-L2, and HVR-L3 amino acid sequences of antibody AB-64.1.1. In some embodiments, the anti-CD33 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.1 or to the amino acid sequence of SEQ ID NO: 58 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the heavy chain variable domain amino acid sequence of antibody AB-64.1.1 or the amino acid sequence of SEQ ID NO: 58. In certain embodiments, a total of 1 to 5 amino acids have been substituted, inserted and/or deleted in the heavy chain variable domain amino acid sequence of antibody AB-64.1.1 or the amino acid sequence of SEQ ID NO: 58. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VH sequence of antibody CD33 or of SEQ ID NO: 58, including post-translational modifications of that sequence. In a particular embodiment, the VH comprises one, two or three HVRs selected from: (a) the HVR-H1 amino acid sequence of antibody AB-64.1.1, (b) the HVR-H2 amino acid sequence of antibody AB-64.1.1, and (c) the HVR-H3 amino acid sequence of antibody AB-64.1.1. In some embodiments, anti-CD33 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.1 or to the amino acid sequence of SEQ ID NO: 86 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the light chain variable domain amino acid sequence of antibody AB-64.1.1 or the amino acid sequence of SEQ ID NO: 86. In certain embodiments, a total of 1 to 5 amino acids have been substituted, inserted and/or deleted in the light chain variable domain amino acid sequence of antibody AB-64.1.1 or the amino acid sequence of SEQ ID NO: 86. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VL sequence of antibody AB-64.1.1 or of SEQ ID NO: 86, including post-translational modifications of that sequence. In a particular embodiment, the VL comprises one, two or three HVRs selected from: (a) the HVR-L1 amino acid sequence of antibody AB-64.1.1, (b) the HVR-L2 amino acid sequence of antibody AB-64.1.1, and (c) the HVR-L3 amino acid sequence of antibody AB-64.1.1.

In some embodiments, anti-CD33 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.2 or to the amino acid sequence of SEQ ID NO: 59; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.2 or to the amino acid sequence of SEQ ID NO: 86. In some embodiments, anti-CD33 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.2 or to the amino acid sequence of SEQ ID NO: 59, wherein the heavy chain variable domain comprises the HVR-H1, HVR-H2, and HVR-H3 amino acid sequences of antibody AB-64.1.2. In some embodiments, anti-CD33 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.2 or to the amino acid sequence of SEQ ID NO: 86, wherein the light chain variable domain comprises the HVR-L1, HVR-L2, and HVR-L3 amino acid sequences of antibody AB-64.1.2. In some embodiments, the anti-CD33 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.2 or to the amino acid sequence of SEQ ID NO: 59 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the heavy chain variable domain amino acid sequence of antibody AB-64.1.2 or the amino acid sequence of SEQ ID NO: 59. In certain embodiments, a total of 1 to 5 amino acids have been substituted, inserted and/or deleted in the heavy chain variable domain amino acid sequence of antibody AB-64.1.2 or the amino acid sequence of SEQ ID NO: 59. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VH sequence of antibody CD33 or of SEQ ID NO: 59, including post-translational modifications of that sequence. In a particular embodiment, the VH comprises one, two or three HVRs selected from: (a) the HVR-H1 amino acid sequence of antibody AB-64.1.2, (b) the HVR-H2 amino acid sequence of antibody AB-64.1.2, and (c) the HVR-H3 amino acid sequence of antibody AB-64.1.2. In some embodiments, anti-CD33 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.2 or to the amino acid sequence of SEQ ID NO: 86 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the light chain variable domain amino acid sequence of antibody AB-64.1.2 or the amino acid sequence of SEQ ID NO: 86. In certain embodiments, a total of 1 to 5 amino acids have been substituted, inserted and/or deleted in the light chain variable domain amino acid sequence of antibody AB-64.1.2 or the amino acid sequence of SEQ ID NO: 86. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VL sequence of antibody AB-64.1.2 or of SEQ ID NO: 86, including post-translational modifications of that sequence. In a particular embodiment, the VL comprises one, two or three HVRs selected from: (a) the HVR-L1 amino acid sequence of antibody AB-64.1.2, (b) the HVR-L2 amino acid sequence of antibody AB-64.1.2, and (c) the HVR-L3 amino acid sequence of antibody AB-64.1.2.

In some embodiments, anti-CD33 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.3 or to the amino acid sequence of SEQ ID NO: 60; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.3 or to the amino acid sequence of SEQ ID NO: 86. In some embodiments, anti-CD33 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.3 or to the amino acid sequence of SEQ ID NO: 60, wherein the heavy chain variable domain comprises the HVR-H1, HVR-H2, and HVR-H3 amino acid sequences of antibody AB-64.1.3. In some embodiments, anti-CD33 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.3 or to the amino acid sequence of SEQ ID NO: 86, wherein the light chain variable domain comprises the HVR-L1, HVR-L2, and HVR-L3 amino acid sequences of antibody AB-64.1.3. In some embodiments, the anti-CD33 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.3 or to the amino acid sequence of SEQ ID NO: 60 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the heavy chain variable domain amino acid sequence of antibody AB-64.1.3 or the amino acid sequence of SEQ ID NO: 60. In certain embodiments, a total of 1 to 5 amino acids have been substituted, inserted and/or deleted in the heavy chain variable domain amino acid sequence of antibody AB-64.1.3 or the amino acid sequence of SEQ ID NO: 60. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VH sequence of antibody CD33 or of SEQ ID NO: 60, including post-translational modifications of that sequence. In a particular embodiment, the VH comprises one, two or three HVRs selected from: (a) the HVR-H1 amino acid sequence of antibody AB-64.1.3, (b) the HVR-H2 amino acid sequence of antibody AB-64.1.3, and (c) the HVR-H3 amino acid sequence of antibody AB-64.1.3. In some embodiments, anti-CD33 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.3 or to the amino acid sequence of SEQ ID NO: 86 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the light chain variable domain amino acid sequence of antibody AB-64.1.3 or the amino acid sequence of SEQ ID NO: 86. In certain embodiments, a total of 1 to 5 amino acids have been substituted, inserted and/or deleted in the light chain variable domain amino acid sequence of antibody AB-64.1.3 or the amino acid sequence of SEQ ID NO: 86. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VL sequence of antibody AB-64.1.3 or of SEQ ID NO: 86, including post-translational modifications of that sequence. In a particular embodiment, the VL comprises one, two or three HVRs selected from: (a) the HVR-L1 amino acid sequence of antibody AB-64.1.3, (b) the HVR-L2 amino acid sequence of antibody AB-64.1.3, and (c) the HVR-L3 amino acid sequence of antibody AB-64.1.3.

In some embodiments, anti-CD33 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.4 or to the amino acid sequence of SEQ ID NO: 61; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.4 or to the amino acid sequence of SEQ ID NO: 86. In some embodiments, anti-CD33 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.4 or to the amino acid sequence of SEQ ID NO: 61, wherein the heavy chain variable domain comprises the HVR-H1, HVR-H2, and HVR-H3 amino acid sequences of antibody AB-64.1.4. In some embodiments, anti-CD33 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.4 or to the amino acid sequence of SEQ ID NO: 86, wherein the light chain variable domain comprises the HVR-L1, HVR-L2, and HVR-L3 amino acid sequences of antibody AB-64.1.4. In some embodiments, the anti-CD33 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.4 or to the amino acid sequence of SEQ ID NO: 61 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the heavy chain variable domain amino acid sequence of antibody AB-64.1.4 or the amino acid sequence of SEQ ID NO: 61. In certain embodiments, a total of 1 to 5 amino acids have been substituted, inserted and/or deleted in the heavy chain variable domain amino acid sequence of antibody AB-64.1.4 or the amino acid sequence of SEQ ID NO: 61. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VH sequence of antibody CD33 or of SEQ ID NO: 61, including post-translational modifications of that sequence. In a particular embodiment, the VH comprises one, two or three HVRs selected from: (a) the HVR-H1 amino acid sequence of antibody AB-64.1.4, (b) the HVR-H2 amino acid sequence of antibody AB-64.1.4, and (c) the HVR-H3 amino acid sequence of antibody AB-64.1.4. In some embodiments, anti-CD33 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.4 or to the amino acid sequence of SEQ ID NO: 86 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the light chain variable domain amino acid sequence of antibody AB-64.1.4 or the amino acid sequence of SEQ ID NO: 86. In certain embodiments, a total of 1 to 5 amino acids have been substituted, inserted and/or deleted in the light chain variable domain amino acid sequence of antibody AB-64.1.4 or the amino acid sequence of SEQ ID NO: 86. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VL sequence of antibody AB-64.1.4 or of SEQ ID NO: 86, including post-translational modifications of that sequence. In a particular embodiment, the VL comprises one, two or three HVRs selected from: (a) the HVR-L1 amino acid sequence of antibody AB-64.1.4, (b) the HVR-L2 amino acid sequence of antibody AB-64.1.4, and (c) the HVR-L3 amino acid sequence of antibody AB-64.1.4.

In some embodiments, anti-CD33 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.5 or to the amino acid sequence of SEQ ID NO: 62; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.5 or to the amino acid sequence of SEQ ID NO: 86. In some embodiments, anti-CD33 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.5 or to the amino acid sequence of SEQ ID NO: 62, wherein the heavy chain variable domain comprises the HVR-H1, HVR-H2, and HVR-H3 amino acid sequences of antibody AB-64.1.5. In some embodiments, anti-CD33 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.5 or to the amino acid sequence of SEQ ID NO: 86, wherein the light chain variable domain comprises the HVR-L1, HVR-L2, and HVR-L3 amino acid sequences of antibody AB-64.1.5. In some embodiments, the anti-CD33 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.5 or to the amino acid sequence of SEQ ID NO: 62 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the heavy chain variable domain amino acid sequence of antibody AB-64.1.5 or the amino acid sequence of SEQ ID NO: 62. In certain embodiments, a total of 1 to 5 amino acids have been substituted, inserted and/or deleted in the heavy chain variable domain amino acid sequence of antibody AB-64.1.5 or the amino acid sequence of SEQ ID NO: 62. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VH sequence of antibody CD33 or of SEQ ID NO: 62, including post-translational modifications of that sequence. In a particular embodiment, the VH comprises one, two or three HVRs selected from: (a) the HVR-H1 amino acid sequence of antibody AB-64.1.5, (b) the HVR-H2 amino acid sequence of antibody AB-64.1.5, and (c) the HVR-H3 amino acid sequence of antibody AB-64.1.5. In some embodiments, anti-CD33 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.5 or to the amino acid sequence of SEQ ID NO: 86 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the light chain variable domain amino acid sequence of antibody AB-64.1.5 or the amino acid sequence of SEQ ID NO: 86. In certain embodiments, a total of 1 to 5 amino acids have been substituted, inserted and/or deleted in the light chain variable domain amino acid sequence of antibody AB-64.1.5 or the amino acid sequence of SEQ ID NO: 86. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VL sequence of antibody AB-64.1.5 or of SEQ ID NO: 86, including post-translational modifications of that sequence. In a particular embodiment, the VL comprises one, two or three HVRs selected from: (a) the HVR-L1 amino acid sequence of antibody AB-64.1.5, (b) the HVR-L2 amino acid sequence of antibody AB-64.1.5, and (c) the HVR-L3 amino acid sequence of antibody AB-64.1.5.

In some embodiments, anti-CD33 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.6 or to the amino acid sequence of SEQ ID NO: 63; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.6 or to the amino acid sequence of SEQ ID NO: 86. In some embodiments, anti-CD33 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.6 or to the amino acid sequence of SEQ ID NO: 63, wherein the heavy chain variable domain comprises the HVR-H1, HVR-H2, and HVR-H3 amino acid sequences of antibody AB-64.1.6. In some embodiments, anti-CD33 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.6 or to the amino acid sequence of SEQ ID NO: 86, wherein the light chain variable domain comprises the HVR-L1, HVR-L2, and HVR-L3 amino acid sequences of antibody AB-64.1.6. In some embodiments, the anti-CD33 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.6 or to the amino acid sequence of SEQ ID NO: 63 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the heavy chain variable domain amino acid sequence of antibody AB-64.1.6 or the amino acid sequence of SEQ ID NO: 63. In certain embodiments, a total of 1 to 5 amino acids have been substituted, inserted and/or deleted in the heavy chain variable domain amino acid sequence of antibody AB-64.1.6 or the amino acid sequence of SEQ ID NO: 63. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VH sequence of antibody CD33 or of SEQ ID NO: 63, including post-translational modifications of that sequence. In a particular embodiment, the VH comprises one, two or three HVRs selected from: (a) the HVR-H1 amino acid sequence of antibody AB-64.1.6, (b) the HVR-H2 amino acid sequence of antibody AB-64.1.6, and (c) the HVR-H3 amino acid sequence of antibody AB-64.1.6. In some embodiments, anti-CD33 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.6 or to the amino acid sequence of SEQ ID NO: 86 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the light chain variable domain amino acid sequence of antibody AB-64.1.6 or the amino acid sequence of SEQ ID NO: 86. In certain embodiments, a total of 1 to 5 amino acids have been substituted, inserted and/or deleted in the light chain variable domain amino acid sequence of antibody AB-64.1.6 or the amino acid sequence of SEQ ID NO: 86. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VL sequence of antibody AB-64.1.6 or of SEQ ID NO: 86, including post-translational modifications of that sequence. In a particular embodiment, the VL comprises one, two or three HVRs selected from: (a) the HVR-L1 amino acid sequence of antibody AB-64.1.6, (b) the HVR-L2 amino acid sequence of antibody AB-64.1.6, and (c) the HVR-L3 amino acid sequence of antibody AB-64.1.6.

In some embodiments, anti-CD33 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.7 or to the amino acid sequence of SEQ ID NO: 64; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.7 or to the amino acid sequence of SEQ ID NO: 86. In some embodiments, anti-CD33 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.7 or to the amino acid sequence of SEQ ID NO: 64, wherein the heavy chain variable domain comprises the HVR-H1, HVR-H2, and HVR-H3 amino acid sequences of antibody AB-64.1.7. In some embodiments, anti-CD33 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.7 or to the amino acid sequence of SEQ ID NO: 86, wherein the light chain variable domain comprises the HVR-L1, HVR-L2, and HVR-L3 amino acid sequences of antibody AB-64.1.7. In some embodiments, the anti-CD33 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.7 or to the amino acid sequence of SEQ ID NO: 64 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the heavy chain variable domain amino acid sequence of antibody AB-64.1.7 or the amino acid sequence of SEQ ID NO: 64. In certain embodiments, a total of 1 to 5 amino acids have been substituted, inserted and/or deleted in the heavy chain variable domain amino acid sequence of antibody AB-64.1.7 or the amino acid sequence of SEQ ID NO: 64. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VH sequence of antibody CD33 or of SEQ ID NO: 64, including post-translational modifications of that sequence. In a particular embodiment, the VH comprises one, two or three HVRs selected from: (a) the HVR-H1 amino acid sequence of antibody AB-64.1.7, (b) the HVR-H2 amino acid sequence of antibody AB-64.1.7, and (c) the HVR-H3 amino acid sequence of antibody AB-64.1.7. In some embodiments, anti-CD33 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.7 or to the amino acid sequence of SEQ ID NO: 86 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the light chain variable domain amino acid sequence of antibody AB-64.1.7 or the amino acid sequence of SEQ ID NO: 86. In certain embodiments, a total of 1 to 5 amino acids have been substituted, inserted and/or deleted in the light chain variable domain amino acid sequence of antibody AB-64.1.7 or the amino acid sequence of SEQ ID NO: 86. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VL sequence of antibody AB-64.1.7 or of SEQ ID NO: 86, including post-translational modifications of that sequence. In a particular embodiment, the VL comprises one, two or three HVRs selected from: (a) the HVR-L1 amino acid sequence of antibody AB-64.1.7, (b) the HVR-L2 amino acid sequence of antibody AB-64.1.7, and (c) the HVR-L3 amino acid sequence of antibody AB-64.1.7.

In some embodiments, anti-CD33 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.8 or to the amino acid sequence of SEQ ID NO: 65; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.8 or to the amino acid sequence of SEQ ID NO: 86. In some embodiments, anti-CD33 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.8 or to the amino acid sequence of SEQ ID NO: 65, wherein the heavy chain variable domain comprises the HVR-H1, HVR-H2, and HVR-H3 amino acid sequences of antibody AB-64.1.8. In some embodiments, anti-CD33 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.8 or to the amino acid sequence of SEQ ID NO: 86, wherein the light chain variable domain comprises the HVR-L1, HVR-L2, and HVR-L3 amino acid sequences of antibody AB-64.1.8. In some embodiments, the anti-CD33 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.8 or to the amino acid sequence of SEQ ID NO: 65 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the heavy chain variable domain amino acid sequence of antibody AB-64.1.8 or the amino acid sequence of SEQ ID NO: 65. In certain embodiments, a total of 1 to 5 amino acids have been substituted, inserted and/or deleted in the heavy chain variable domain amino acid sequence of antibody AB-64.1.8 or the amino acid sequence of SEQ ID NO: 65. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VH sequence of antibody CD33 or of SEQ ID NO: 65, including post-translational modifications of that sequence. In a particular embodiment, the VH comprises one, two or three HVRs selected from: (a) the HVR-H1 amino acid sequence of antibody AB-64.1.8, (b) the HVR-H2 amino acid sequence of antibody AB-64.1.8, and (c) the HVR-H3 amino acid sequence of antibody AB-64.1.8. In some embodiments, anti-CD33 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.8 or to the amino acid sequence of SEQ ID NO: 86 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the light chain variable domain amino acid sequence of antibody AB-64.1.8 or the amino acid sequence of SEQ ID NO: 86. In certain embodiments, a total of 1 to 5 amino acids have been substituted, inserted and/or deleted in the light chain variable domain amino acid sequence of antibody AB-64.1.8 or the amino acid sequence of SEQ ID NO: 86. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VL sequence of antibody AB-64.1.8 or of SEQ ID NO: 86, including post-translational modifications of that sequence. In a particular embodiment, the VL comprises one, two or three HVRs selected from: (a) the HVR-L1 amino acid sequence of antibody AB-64.1.8, (b) the HVR-L2 amino acid sequence of antibody AB-64.1.8, and (c) the HVR-L3 amino acid sequence of antibody AB-64.1.8.

In some embodiments, anti-CD33 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.9 or to the amino acid sequence of SEQ ID NO: 66; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.9 or to the amino acid sequence of SEQ ID NO: 86. In some embodiments, anti-CD33 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.9 or to the amino acid sequence of SEQ ID NO: 66, wherein the heavy chain variable domain comprises the HVR-H1, HVR-H2, and HVR-H3 amino acid sequences of antibody AB-64.1.9. In some embodiments, anti-CD33 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.9 or to the amino acid sequence of SEQ ID NO: 86, wherein the light chain variable domain comprises the HVR-L1, HVR-L2, and HVR-L3 amino acid sequences of antibody AB-64.1.9. In some embodiments, the anti-CD33 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.9 or to the amino acid sequence of SEQ ID NO: 66 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the heavy chain variable domain amino acid sequence of antibody AB-64.1.9 or the amino acid sequence of SEQ ID NO: 66. In certain embodiments, a total of 1 to 5 amino acids have been substituted, inserted and/or deleted in the heavy chain variable domain amino acid sequence of antibody AB-64.1.9 or the amino acid sequence of SEQ ID NO: 66. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VH sequence of antibody CD33 or of SEQ ID NO: 66, including post-translational modifications of that sequence. In a particular embodiment, the VH comprises one, two or three HVRs selected from: (a) the HVR-H1 amino acid sequence of antibody AB-64.1.9, (b) the HVR-H2 amino acid sequence of antibody AB-64.1.9, and (c) the HVR-H3 amino acid sequence of antibody AB-64.1.9. In some embodiments, anti-CD33 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.9 or to the amino acid sequence of SEQ ID NO: 86 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the light chain variable domain amino acid sequence of antibody AB-64.1.9 or the amino acid sequence of SEQ ID NO: 86. In certain embodiments, a total of 1 to 5 amino acids have been substituted, inserted and/or deleted in the light chain variable domain amino acid sequence of antibody AB-64.1.9 or the amino acid sequence of SEQ ID NO: 86. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VL sequence of antibody AB-64.1.9 or of SEQ ID NO: 86, including post-translational modifications of that sequence. In a particular embodiment, the VL comprises one, two or three HVRs selected from: (a) the HVR-L1 amino acid sequence of antibody AB-64.1.9, (b) the HVR-L2 amino acid sequence of antibody AB-64.1.9, and (c) the HVR-L3 amino acid sequence of antibody AB-64.1.9.

In some embodiments, anti-CD33 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.10 or to the amino acid sequence of SEQ ID NO: 67; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.10 or to the amino acid sequence of SEQ ID NO: 86. In some embodiments, anti-CD33 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.10 or to the amino acid sequence of SEQ ID NO: 67, wherein the heavy chain variable domain comprises the HVR-H1, HVR-H2, and HVR-H3 amino acid sequences of antibody AB-64.1.10. In some embodiments, anti-CD33 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.10 or to the amino acid sequence of SEQ ID NO: 86, wherein the light chain variable domain comprises the HVR-L1, HVR-L2, and HVR-L3 amino acid sequences of antibody AB-64.1.10. In some embodiments, the anti-CD33 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.10 or to the amino acid sequence of SEQ ID NO: 67 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the heavy chain variable domain amino acid sequence of antibody AB-64.1.10 or the amino acid sequence of SEQ ID NO: 67. In certain embodiments, a total of 1 to 5 amino acids have been substituted, inserted and/or deleted in the heavy chain variable domain amino acid sequence of antibody AB-64.1.10 or the amino acid sequence of SEQ ID NO: 67. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VH sequence of antibody CD33 or of SEQ ID NO: 67, including post-translational modifications of that sequence. In a particular embodiment, the VH comprises one, two or three HVRs selected from: (a) the HVR-H1 amino acid sequence of antibody AB-64.1.10, (b) the HVR-H2 amino acid sequence of antibody AB-64.1.10, and (c) the HVR-H3 amino acid sequence of antibody AB-64.1.10. In some embodiments, anti-CD33 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.10 or to the amino acid sequence of SEQ ID NO: 86 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the light chain variable domain amino acid sequence of antibody AB-64.1.10 or the amino acid sequence of SEQ ID NO: 86. In certain embodiments, a total of 1 to 5 amino acids have been substituted, inserted and/or deleted in the light chain variable domain amino acid sequence of antibody AB-64.1.10 or the amino acid sequence of SEQ ID NO: 86. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VL sequence of antibody AB-64.1.10 or of SEQ ID NO: 86, including post-translational modifications of that sequence. In a particular embodiment, the VL comprises one, two or three HVRs selected from: (a) the HVR-L1 amino acid sequence of antibody AB-64.1.10, (b) the HVR-L2 amino acid sequence of antibody AB-64.1.10, and (c) the HVR-L3 amino acid sequence of antibody AB-64.1.10.

In some embodiments, anti-CD33 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.11 or to the amino acid sequence of SEQ ID NO: 68; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.11 or to the amino acid sequence of SEQ ID NO: 86. In some embodiments, anti-CD33 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.11 or to the amino acid sequence of SEQ ID NO: 68, wherein the heavy chain variable domain comprises the HVR-H1, HVR-H2, and HVR-H3 amino acid sequences of antibody AB-64.1.11. In some embodiments, anti-CD33 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.11 or to the amino acid sequence of SEQ ID NO: 86, wherein the light chain variable domain comprises the HVR-L1, HVR-L2, and HVR-L3 amino acid sequences of antibody AB-64.1.11. In some embodiments, the anti-CD33 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.11 or to the amino acid sequence of SEQ ID NO: 68 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the heavy chain variable domain amino acid sequence of antibody AB-64.1.11 or the amino acid sequence of SEQ ID NO: 68. In certain embodiments, a total of 1 to 5 amino acids have been substituted, inserted and/or deleted in the heavy chain variable domain amino acid sequence of antibody AB-64.1.11 or the amino acid sequence of SEQ ID NO: 68. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VH sequence of antibody CD33 or of SEQ ID NO: 68, including post-translational modifications of that sequence. In a particular embodiment, the VH comprises one, two or three HVRs selected from: (a) the HVR-H1 amino acid sequence of antibody AB-64.1.11, (b) the HVR-H2 amino acid sequence of antibody AB-64.1.11, and (c) the HVR-H3 amino acid sequence of antibody AB-64.1.11. In some embodiments, anti-CD33 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.11 or to the amino acid sequence of SEQ ID NO: 86 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the light chain variable domain amino acid sequence of antibody AB-64.1.11 or the amino acid sequence of SEQ ID NO: 86. In certain embodiments, a total of 1 to 5 amino acids have been substituted, inserted and/or deleted in the light chain variable domain amino acid sequence of antibody AB-64.1.11 or the amino acid sequence of SEQ ID NO: 86. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VL sequence of antibody AB-64.1.11 or of SEQ ID NO: 86, including post-translational modifications of that sequence. In a particular embodiment, the VL comprises one, two or three HVRs selected from: (a) the HVR-L1 amino acid sequence of antibody AB-64.1.11, (b) the HVR-L2 amino acid sequence of antibody AB-64.1.11, and (c) the HVR-L3 amino acid sequence of antibody AB-64.1.11.

In some embodiments, anti-CD33 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.12 or to the amino acid sequence of SEQ ID NO: 69; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.12 or to the amino acid sequence of SEQ ID NO: 86. In some embodiments, anti-CD33 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.12 or to the amino acid sequence of SEQ ID NO: 69, wherein the heavy chain variable domain comprises the HVR-H1, HVR-H2, and HVR-H3 amino acid sequences of antibody AB-64.1.12. In some embodiments, anti-CD33 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.12 or to the amino acid sequence of SEQ ID NO: 86, wherein the light chain variable domain comprises the HVR-L1, HVR-L2, and HVR-L3 amino acid sequences of antibody AB-64.1.12. In some embodiments, the anti-CD33 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.12 or to the amino acid sequence of SEQ ID NO: 69 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the heavy chain variable domain amino acid sequence of antibody AB-64.1.12 or the amino acid sequence of SEQ ID NO: 69. In certain embodiments, a total of 1 to 5 amino acids have been substituted, inserted and/or deleted in the heavy chain variable domain amino acid sequence of antibody AB-64.1.12 or the amino acid sequence of SEQ ID NO: 69. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VH sequence of antibody CD33 or of SEQ ID NO: 69, including post-translational modifications of that sequence. In a particular embodiment, the VH comprises one, two or three HVRs selected from: (a) the HVR-H1 amino acid sequence of antibody AB-64.1.12, (b) the HVR-H2 amino acid sequence of antibody AB-64.1.12, and (c) the HVR-H3 amino acid sequence of antibody AB-64.1.12. In some embodiments, anti-CD33 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.12 or to the amino acid sequence of SEQ ID NO: 86 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the light chain variable domain amino acid sequence of antibody AB-64.1.12 or the amino acid sequence of SEQ ID NO: 86. In certain embodiments, a total of 1 to 5 amino acids have been substituted, inserted and/or deleted in the light chain variable domain amino acid sequence of antibody AB-64.1.12 or the amino acid sequence of SEQ ID NO: 86. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VL sequence of antibody AB-64.1.12 or of SEQ ID NO: 86, including post-translational modifications of that sequence. In a particular embodiment, the VL comprises one, two or three HVRs selected from: (a) the HVR-L1 amino acid sequence of antibody AB-64.1.12, (b) the HVR-L2 amino acid sequence of antibody AB-64.1.12, and (c) the HVR-L3 amino acid sequence of antibody AB-64.1.12.

In some embodiments, anti-CD33 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.13 or to the amino acid sequence of SEQ ID NO: 52; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.13 or to the amino acid sequence of SEQ ID NO: 86. In some embodiments, anti-CD33 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.13 or to the amino acid sequence of SEQ ID NO: 52, wherein the heavy chain variable domain comprises the HVR-H1, HVR-H2, and HVR-H3 amino acid sequences of antibody AB-64.1.13. In some embodiments, anti-CD33 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.13 or to the amino acid sequence of SEQ ID NO: 86, wherein the light chain variable domain comprises the HVR-L1, HVR-L2, and HVR-L3 amino acid sequences of antibody AB-64.1.13. In some embodiments, the anti-CD33 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.13 or to the amino acid sequence of SEQ ID NO: 52 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the heavy chain variable domain amino acid sequence of antibody AB-64.1.13 or the amino acid sequence of SEQ ID NO: 52. In certain embodiments, a total of 1 to 5 amino acids have been substituted, inserted and/or deleted in the heavy chain variable domain amino acid sequence of antibody AB-64.1.13 or the amino acid sequence of SEQ ID NO: 52. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VH sequence of antibody CD33 or of SEQ ID NO: 52, including post-translational modifications of that sequence. In a particular embodiment, the VH comprises one, two or three HVRs selected from: (a) the HVR-H1 amino acid sequence of antibody AB-64.1.13, (b) the HVR-H2 amino acid sequence of antibody AB-64.1.13, and (c) the HVR-H3 amino acid sequence of antibody AB-64.1.13. In some embodiments, anti-CD33 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.13 or to the amino acid sequence of SEQ ID NO: 86 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the light chain variable domain amino acid sequence of antibody AB-64.1.13 or the amino acid sequence of SEQ ID NO: 86. In certain embodiments, a total of 1 to 5 amino acids have been substituted, inserted and/or deleted in the light chain variable domain amino acid sequence of antibody AB-64.1.13 or the amino acid sequence of SEQ ID NO: 86. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VL sequence of antibody AB-64.1.13 or of SEQ ID NO: 86, including post-translational modifications of that sequence. In a particular embodiment, the VL comprises one, two or three HVRs selected from: (a) the HVR-L1 amino acid sequence of antibody AB-64.1.13, (b) the HVR-L2 amino acid sequence of antibody AB-64.1.13, and (c) the HVR-L3 amino acid sequence of antibody AB-64.1.13.

In some embodiments, anti-CD33 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.14 or to the amino acid sequence of SEQ ID NO: 71; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.14 or to the amino acid sequence of SEQ ID NO: 86. In some embodiments, anti-CD33 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.14 or to the amino acid sequence of SEQ ID NO: 71, wherein the heavy chain variable domain comprises the HVR-H1, HVR-H2, and HVR-H3 amino acid sequences of antibody AB-64.1.14. In some embodiments, anti-CD33 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.14 or to the amino acid sequence of SEQ ID NO: 86, wherein the light chain variable domain comprises the HVR-L1, HVR-L2, and HVR-L3 amino acid sequences of antibody AB-64.1.14. In some embodiments, the anti-CD33 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.14 or to the amino acid sequence of SEQ ID NO:

71 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the heavy chain variable domain amino acid sequence of antibody AB-64.1.14 or the amino acid sequence of SEQ ID NO: 71. In certain embodiments, a total of 1 to 5 amino acids have been substituted, inserted and/or deleted in the heavy chain variable domain amino acid sequence of antibody AB-64.1.14 or the amino acid sequence of SEQ ID NO: 71. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VH sequence of antibody CD33 or of SEQ ID NO: 71, including post-translational modifications of that sequence. In a particular embodiment, the VH comprises one, two or three HVRs selected from: (a) the HVR-H1 amino acid sequence of antibody AB-64.1.14, (b) the HVR-H2 amino acid sequence of antibody AB-64.1.14, and (c) the HVR-H3 amino acid sequence of antibody AB-64.1.14. In some embodiments, anti-CD33 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.14 or to the amino acid sequence of SEQ ID NO: 86 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the light chain variable domain amino acid sequence of antibody AB-64.1.14 or the amino acid sequence of SEQ ID NO: 86. In certain embodiments, a total of 1 to 5 amino acids have been substituted, inserted and/or deleted in the light chain variable domain amino acid sequence of antibody AB-64.1.14 or the amino acid sequence of SEQ ID NO: 86. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VL sequence of antibody AB-64.1.14 or of SEQ ID NO: 86, including post-translational modifications of that sequence. In a particular embodiment, the VL comprises one, two or three HVRs selected from: (a) the HVR-L1 amino acid sequence of antibody AB-64.1.14, (b) the HVR-L2 amino acid sequence of antibody AB-64.1.14, and (c) the HVR-L3 amino acid sequence of antibody AB-64.1.14.

In some embodiments, anti-CD33 antibodies of the present disclosure comprise a light chain variable domain and a heavy chain variable domain, wherein the heavy chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.15 or to the amino acid sequence of SEQ ID NO: 72; and/or the light chain variable domain comprises an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.15 or to the amino acid sequence of SEQ ID NO: 86. In some embodiments, anti-CD33 antibodies of the present disclosure comprise a heavy chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.15 or to the amino acid sequence of SEQ ID NO: 72, wherein the heavy chain variable domain comprises the HVR-H1, HVR-H2, and HVR-H3 amino acid sequences of antibody AB-64.1.15. In some embodiments, anti-CD33 antibodies of the present disclosure comprise a light chain variable domain comprising an amino acid sequence with at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.15 or to the amino acid sequence of SEQ ID NO: 86, wherein the light chain variable domain comprises the HVR-L1, HVR-L2, and HVR-L3 amino acid sequences of antibody AB-64.1.15. In some embodiments, the anti-CD33 antibody comprises a heavy chain variable domain (VH) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a heavy chain variable domain amino acid sequence of antibody AB-64.1.15 or to the amino acid sequence of SEQ ID NO: 72 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the heavy chain variable domain amino acid sequence of antibody AB-64.1.15 or the amino acid sequence of SEQ ID NO: 72. In certain embodiments, a total of 1 to 5 amino acids have been substituted, inserted and/or deleted in the heavy chain variable domain amino acid sequence of antibody AB-64.1.15 or the amino acid sequence of SEQ ID NO: 72. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VH sequence of antibody CD33 or of SEQ ID NO: 72, including post-translational modifications of that sequence. In a particular embodiment, the VH comprises one, two or three HVRs selected from: (a) the HVR-H1 amino acid sequence of antibody AB-64.1.15, (b) the HVR-H2 amino acid sequence of antibody AB-64.1.15, and (c) the HVR-H3 amino acid sequence of antibody AB-64.1.15. In some embodiments, anti-CD33 antibodies of the present disclosure comprise a light chain variable domain (VL) sequence having at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% identity to a light chain variable domain amino acid sequence of antibody AB-64.1.15 or to the amino acid sequence of SEQ ID NO: 86 and contains substitutions (e.g., conservative substitutions, insertions, or deletions relative to the reference sequence), but the anti-CD33 antibody comprising that sequence retains the ability to bind to CD33. In certain embodiments, a total of 1 to 10 amino acids have been substituted, inserted, and/or deleted in the light chain variable domain amino acid sequence of antibody AB-64.1.15 or the amino acid sequence of SEQ ID NO: 86. In certain embodiments, a total of 1 to 5 amino acids have been substituted, inserted and/or deleted in the light chain variable domain amino acid sequence of antibody AB-64.1.15 or the amino acid sequence of SEQ ID NO: 86. In certain embodiments, substitutions, insertions, or deletions occur in regions outside the HVRs (i.e., in the FR regions). In some embodiments, the substitutions, insertions, or deletions occur in in the FR regions. Optionally, the anti-CD33 antibody comprises the VL sequence of antibody AB-64.1.15 or of SEQ ID NO: 86, including post-translational modifications of that sequence. In a particular embodiment, the VL comprises one, two or three HVRs selected from: (a) the HVR-L1 amino acid sequence of antibody AB-64.1.15, (b) the HVR-L2 amino acid sequence of antibody AB-64.1.15, and (c) the HVR-L3 amino acid sequence of antibody AB-64.1.15.

In some embodiments, the anti-CD33 antibody is anti-CD33 monoclonal antibody AB-64.1.2. In some embodiments, the anti-CD33 antibody is an isolated antibody which binds essentially the same CD33 epitope as AB-64.1.2. In some embodiments, the anti-CD33 antibody is an isolated antibody comprising the HVR-H1, HVR-H2, and HVR-H3 of the heavy chain variable domain of monoclonal antibody AB-64.1.2. In some embodiments, the anti-CD33 antibody is an isolated antibody comprising the HVR-L1, HVR-L2, and HVR-L3 of the light chain variable domain of monoclonal antibody AB-64.1.2. In some embodiments, the anti-CD33 antibody is an isolated antibody comprising the HVR-H1, HVR-H2, and HVR-H3 of the heavy chain variable domain and the HVR-L1, HVR-L2, and HVR-L3 of the light chain variable domain of monoclonal antibody AB-64.1.2.

In some embodiments, the anti-CD33 antibody is anti-CD33 monoclonal antibody AB-64.1.8. In some embodiments, the anti-CD33 antibody is an isolated antibody which binds essentially the same CD33 epitope as AB-64.1.8. In some embodiments, the anti-CD33 antibody is an isolated antibody comprising the HVR-H1, HVR-H2, and HVR-H3 of the heavy chain variable domain of monoclonal antibody AB-64.1.8. In some embodiments, the anti-CD33 antibody is an isolated antibody comprising the HVR-L1, HVR-L2, and HVR-L3 of the light chain variable domain of monoclonal antibody AB-64.1.8. In some embodiments, the anti-CD33 antibody is an isolated antibody comprising the HVR-H1, HVR-H2, and HVR-H3 of the heavy chain variable domain and the HVR-L1, HVR-L2, and HVR-L3 of the light chain variable domain of monoclonal antibody AB-64.1.8.

In certain embodiments, the anti-CD33 antibody is an antagonist antibody. In certain embodiments, the anti-CD33 antibody is an agonist antibody or an inert antibody. In some embodiments, anti-CD33 antibodies of the present disclosure are of the IgG class the IgM class, or the IgA class. In some embodiments, anti-CD33 antibodies of the present disclosure are of the IgG class and have an IgG1, IgG2, IgG3, or IgG4 isotype.

Additional anti-CD33 antibodies, e.g., antibodies that specifically bind to a CD33 protein of the present disclosure, may be identified, screened, and/or characterized for their physical/chemical properties and/or biological activities by various assays known in the art.

Anti-CD33 Antibodies Capable of Binding Fc Gamma Receptors

In some embodiments, anti-CD33 antibodies of the present disclosure retain the ability to bind Fc gamma receptors. In some embodiments, such antibodies when they have the correct epitope specificity that is compatible with receptor activation may have features that enable them to cluster and transiently stimulate, for example, the CD33 receptor. In some embodiments, such antibodies may subsequently act as longer-term inhibitors of CD33 expression and/or one or more activities of a CD33 protein by inducing CD33 degradation, CD33 desensitization, CD33 cleavage, CD33 internalization, CD33 shedding, downregulation of CD33 expression, and/or lysosomal degradation of CD33.

In vivo, anti-CD33 antibodies of the present disclosure may cluster receptors and transiently activate CD33 by any one or more of multiple potential mechanisms. Some isotypes of human antibodies such as IgG2 have, due to their unique structure, an intrinsic ability to cluster receptors, or retain receptors in a clustered configuration, thereby transiently activating receptors such as CD33 without binding to an Fc receptor (e.g., White et al., (2015) Cancer Cell 27, 138-148).

In some embodiments, other antibodies may cluster receptors (e.g., CD33) by binding to Fcg receptors on adjacent cells. In some embodiments, binding of the constant IgG Fc region of the antibody to Fcg receptors may lead to aggregation of the antibodies, and the antibodies in turn may aggregate the receptors to which they bind through their variable region (Chu et al (2008) Mol Immunol, 45:3926-3933; and Wilson et al., (2011) Cancer Cell 19, 101-113). In some embodiments, binding to the inhibitory Fcg receptor FcgR (FcgRIIB) that does not elicit cytokine secretion, oxidative burst, increased phagocytosis, and enhanced antibody-dependent, cell-mediated cytotoxicity (ADCC) is a preferred way to cluster antibodies in vivo, since binding to FcgRIIB is not associated with adverse immune response effects.

There are other mechanisms by which anti-CD33 antibodies of the present disclosure can cluster receptors. For example, antibody fragments (e.g., Fab fragments) that are cross-linked together may be used to cluster receptors (e.g., CD33) in a manner similar to antibodies with Fc regions that bind Fcg receptors, as described above. In some embodiments, cross-linked antibody fragments (e.g., Fab fragments) may transiently function as agonist antibodies if they induce receptor clustering on the cell surface and bind an appropriate epitope on the target (e.g., CD33).

Therefore, in some embodiments, antibodies of the present disclosure that bind a CD33 protein may include antibodies that due to their epitope specificity bind CD33 and transiently activate one or more CD33 activities before they, for example, decrease cellular levels of CD33, inhibit one or more CD33 activities, and/or inhibit interaction (e.g., binding) between CD33 and one or more CD33 ligands. In some embodiments, such antibodies may bind to the ligand-binding site on CD33 and transiently mimic the action of a natural ligand, or stimulate the target antigen to transduce signal by binding to one or more domains that are not the ligand-binding sites. In some embodiments, such antibodies would not interfere with ligand binding. In some embodiments, regardless of whether antibodies bind or do not bind to the ligand-binding site on CD33, the antibodies may subsequently act as longer term inhibitors of CD33 expression and/or one or more activities of a CD33 protein by inducing CD33 degradation, CD33 desensitization, CD33 cleavage, CD33 internalization, CD33 shedding, downregulation of CD33 expression, and/or lysosomal degradation of CD33.

In some embodiments, an anti-CD33 antibody of the present disclosure is an antibody that transiently induces one or more activities of a CD33 protein. In some embodiments, the antibody transiently induces the one or more activities after binding to a CD33 protein that is expressed in a cell. In some embodiments, the CD33 protein is expressed on a cell surface. In some embodiments, the one or more activities of a CD33 protein that are transiently induced by anti-CD33 antibodies of the present disclosure may include, without limitation, phosphorylation of Tyr-340 and Tyr-358 by a Src family tyrosine kinase, such as LCK and FYN; recruitment of and binding to the tyrosine-specific protein phosphatases SHP1 and SHP2; recruitment of and binding to PLC-gamma1, which acts as a guanine nucleotide exchange factor for Dynamini-1; recruitment of and binding to SH2-domain containing protein (e.g., Crk1); recruitment of and binding to the spleen tyrosine kinase Syk; recruitment of and binding to SH3-SH2-SH3 growth factor receptor-bound protein 2 (Grb2); recruitment of and binding to multiple SH2-containing proteins; phosphorylation of Ser-307 and Ser-342 by protein kinase C; modulated expression of one or more anti-inflammatory cytokines, IL-4, IL-10, IL-13, IL-35, IL-16, TGF-beta, IL-1Rα, G-CSF, and soluble receptors for TNF, IFN-beta1a, IFN-beta1b, or IL-6 in monocytes, macrophages, T cells, dendritic cells neutrophils, and/or microglia; decreasing intracellular calcium mobilization; modulated expression of one or more pro-inflammatory cytokines IFN-a4, IFN-b, IL-1β, TNF-α, IL-6, IL-8, CRP, IL-20 family members, LIF, IFN-gamma, OSM, CNTF, GM-CSF, IL-11, IL-12, IL-17, IL-18, IL-23, CXCL10, IL-33, CRP, IL-33, MCP-1, and MIP-1-beta in monocytes, macrophages, T cells, dendritic cells, neutrophils, and/or microglia; modulated expression of one or more proteins selected from C1qa, C1qB, C1qC, C1s, C1R, C4, C2, C3, ITGB2, HMOX1, LAT2, CASP1, CSTA, VSIG4, MS4A4A, C3AR1, GPX1, TyroBP, ALOX5AP, ITGAM, SLC7A7, CD4, ITGAX, PYCARD, CD14, CD16, HLA-DR, and CCR2; inhibition of extracellular signal-regulated kinase (ERK) phosphorylation; decreasing tyrosine phosphorylation on multiple cellular proteins; modulated expression of C-C chemokine receptor 7 (CCR7); inhibition of microglial cell chemotaxis toward CCL19 and CCL21 expressing cells; activation of phosphoinositide 3-kinase; reducing cell growth of monocytes, macrophages, T cells, dendritic cells and/or microglia; reducing T cell proliferation induced by dendritic cells, bone marrow-derived dendritic cells, monocytes, microglia, M1 microglia, activated M1 microglia, M2 microglia, macrophages, M1 macrophages, activated M1 macrophages, and/or M2 macrophages; inhibition of osteoclast production, decreased rate of osteoclastogenesis, or both; decreasing survival of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; decreasing proliferation of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; inhibiting migration of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; decreasing one or more functions of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; inhibiting maturation of neutrophils, dendritic cells, bone marrow-derived dendritic cells, macrophages, M1 macrophages, activated M1 macrophages, M2 macrophages, monocytes, osteoclasts, T cells, T helper cells, cytotoxic T cells, granulocytes, microglia, M1 microglia, activated M1 microglia, and/or M2 microglia; increasing cell death and apoptosis of monocytes, macrophages, T cells, dendritic cells, neutrophils, and/or microglia; reducing phagocytic activity of monocytes, macrophages, T cells, dendritic cells, neutrophils, and/or microglia; reducing proliferation of monocytes, macrophages, T cells, dendritic cells, neutrophils, and/or microglia; reducing the overall functionality of monocytes, macrophages, T cells, dendritic cells, neutrophils, and/or microglia, phosphorylation of an ITAM containing receptor; phosphorylation of a signaling molecules that mediates ITAM signaling; reducing the activation of pattern recognition receptors; reducing the activation of Toll-like receptors; reducing the activation of damage-associated of clearance of cellular and protein debris; interaction between CD33 and one or more of its ligands; interaction between CD33 and a co-receptor such as CD64; reducing one or more types of clearance selected from apoptotic neuron clearance, dysfunctional synapse clearance, nerve tissue debris clearance, non-nerve tissue debris clearance, bacteria or other foreign body clearance, disease-causing protein clearance, and tumor cell clearance; inhibition of phagocytosis of one or more of apoptotic neurons, nerve tissue debris, non-nerve tissue debris, bacteria, other foreign bodies, disease-causing proteins, disease-causing peptides, disease-causing nucleic acid, disease-causing lipids, or tumor cells; inhibition of clearance of a disease-causing nucleic acid, such as the disease-causing nucleic acid is antisense GGCCCC (G2C4) repeat-expansion RNA; activation of clearance of, a disease-causing protein selected from amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides; inhibition of beneficial immune response to different types of cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, acute myeloid leukemia, pancreatic cancer, prostate cancer, ovarian cancer, fibrosarcoma, and thyroid cancer; inhibition of beneficial immune response to different types of neurological disorders selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, essential tremor, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, Sarcoidosis, diseases of aging, seizures, spinal cord injury, traumatic brain injury, age related macular degeneration, glaucoma, retinitis pigmentosa, retinal degeneration, and multiple sclerosis; inhibition of beneficial immune response-to different types of inflammatory and infectious disorders selected from lupus, acute and chronic colitis, wound healing, Crohn's disease, inflammatory bowel disease, ulcerative colitis, obesity, malaria, respiratory tract infection, sepsis, eye infection, systemic infection, lupus, arthritis, low bone density, osteoporosis, osteogenesis, osteopetrotic disease, and Paget's disease of bone; inhibition of phagocytosis of one or more of apoptotic neurons, nerve tissue debris, dysfunctional synapses, non-nerve tissue debris, bacteria, other foreign bodies, disease-causing proteins, disease-causing peptides, disease-causing nucleic acids, or tumor cells, where the disease-causing nucleic acids may be an antisense GGCCCC (G2C4) repeat-expansion RNA, the disease-causing proteins may include amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and the tumor cells may be from a cancer selected from bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, or thyroid cancer; binding to CD33 ligand on tumor cells; binding to CD33 ligand on dendritic cells, bone marrow-derived dendritic cells, monocytes, microglia, T cells, neutrophils, and/or macrophages; inhibition of tumor cell killing by one or more of microglia, macrophages, dendritic cells, bone marrow-derived dendritic cells, neutrophils, T cells, T helper cells, or cytotoxic T cells; inhibition of anti-tumor cell proliferation activity of one or more of microglia, macrophages, dendritic cells, bone marrow-derived dendritic cells, neutrophils, T cells, T helper cells, or cytotoxic T cells; inhibition of anti-tumor cell metastasis activity of one or more of microglia, macrophages, dendritic cells, bone marrow-derived dendritic cells, neutrophils, T cells, T helper cells, or cytotoxic T cells; promotion of immunosuppressor dendritic cells, immunosuppressor macrophages, myeloid-derived suppressor cells, tumor-associated macrophages, or regulatory T cells; inhibition of one or more ITAM motif containing receptors, such as TREM1, TREM2, FcgR, DAP10, and DAP12; inhibition of one or more receptors containing the motif D/Ex0-2YxxL/IX6-8YxxL/I (SEQ ID NO:165); inhibition of signaling by one or more pattern recognition receptors (PRRs), such as receptors that identify pathogen-associated molecular patterns (PAMPs), and receptors that identify damage-associated molecular patterns (DAMPs); inhibition of signaling by one or more Toll-like receptors; inhibition of the JAK-STAT signaling pathway; inhibition of nuclear factor kappa-light-chain-enhancer of activated B cells (NFκB); inhibition of PLCγ/PKC/calcium mobilization; inhibition of PI3K/Akt, Ras/MAPK signaling; modulated expression of one or more inflammatory receptors, such as CD86, expressed on one or more of microglia, macrophages, dendritic cells, bone marrow-derived dendritic cells, neutrophils, T cells, T helper cells, or cytotoxic T cells; increasing expression of one or more CD33-dependent genes; normalization of disrupted CD33-dependent gene expression; and decreasing expression of one or more ITAM-dependent genes, such as NFAT transcription factors. Anti-CD33 antibodies of the present disclosure may be tested for their ability to transiently induce one or more activities of a CD33 protein utilizing any suitable technique or assay known in the art and disclosed herein. Regardless of the activities that such antibodies transiently induce, such antibodies may subsequently act as longer-term inhibitors of CD33 expression and/or one or more activities of a CD33 protein by inducing CD33 degradation, CD33 desensitization, CD33 cleavage, CD33 internalization, CD33 shedding, downregulation of CD33 expression, and/or lysosomal degradation of CD33. In some embodiments, the CD33 antibody transiently induces one or more activities of a CD33 protein independently of binding to an Fc receptor.

Exemplary antibody Fc isotypes and modifications are provided in Table B below. In some embodiments, an anti-CD33 antibody of the present disclosure that is capable of binding an Fc gamma receptor has an Fc isotype listed in Table B below.

TABLE B

Exemplary anti-CD33 antibody Fc isotypes that are capable of binding Fc gamma receptor

| Fc Isotype | Mutation (EU numbering scheme) |
|---|---|
| IgG1 | N297A |
| IgG1 | D265A and N297A |
| IgG1 | D270A |
| IgG1 | L234A and L235A<br>L234A and G237A<br>L234A and L235A and G237A |

TABLE B-continued

Exemplary anti-CD33 antibody Fc isotypes that are capable of binding Fc gamma receptor

| Fc Isotype | Mutation (EU numbering scheme) |
|---|---|
| IgG1 | D270A, and/or P238D, and/or L328E, and/or E233D, and/or G237D and/or H268D, and/or P271G, and/or A330R |
| IgG1 | P238D and L328E and E233D and G237D and H268D and P271G and A330R |
| IgG1 | P238D and L328E and G237D and H268D and P271G and A330R |
| IgG1 | P238D and S267E and L328F and E233D and G237D and H268D and P271G and A330R |
| IgG1 | P238D and S267E and L328F and G237D and H268D and P271G and A330R |
| IgG2 | V234A and G237A |
| IgG4 | L235A and G237A and E318A |
| IgG4 | S228P and L236E |
| IgG2/4 hybrid | IgG2 aa 118 to 260 and IgG4 aa 261 to 447<br>H268Q and V309L; and A330S and P331S |
| IgG1 | C226S and C229S and E233P and L234V and L235A |
| IgG1 | L234F and L235E and P331S |
| IgG2 | C232S or C233S |
| IgG2 | A330S and P331S |
| IgG1 | S267E and L328F<br>S267E alone |
| IgG2 | S267E and L328F |
| IgG4 | S267E and L328F |
| IgG2 | WT HC with Kappa (light chain) LC<br>HC C127S with Kappa LC<br>Kappa LC C214S<br>Kappa LC C214S and HC C233S<br>Kappa LC C214S and HC C232S<br>Any of the above listed mutations together with P330S and P331S mutations<br>F(ab')2 fragment of WT IgG1 and any of the above listed mutations |
| IgG1 | Substitute the Constant Heavy 1 (CH1) and hinge region of IgG1 With CH1 and hinge region of IGg2<br>ASTKGPSVFP LAPCSRSTSE STAALGCLVK<br>DYFPEPVTVS WNSGALTSGV HTFPAVLQSS<br>GLYSLSSVVT VPSSNFGTQT YTCNVDHKPS<br>NTKVDKTVER KCCVECPPCP (SEQ ID NO: 166)<br>With a Kappa LC |
| IgG1 | Any of the above listed mutations together with A330L/A330S and/or L234F and/or L235E and/or P331S |
| IgG1, IgG2, or IgG4 | Any of the above listed mutations together with M252Y and/or S254T and/or T256E |
| Mouse IgG1, mouse IgG2a, mouse IgG2b | For mouse disease models |
| IgG4 | WT |
| IgG1 | Any of the above listed mutation together with E430G, E430S, E430F, E430T, E345K, E345Q, E345R, E345Y, S440Y, S440W and/or any combination thereof. |

TABLE B-continued

Exemplary anti-CD33 antibody Fc isotypes that are capable of binding Fc gamma receptor

| Fc Isotype | Mutation (EU numbering scheme) |
|---|---|
| IgG2 | Any of the above listed mutation together with E430G, E430S, E430F, E430T, E345K, E345Q, E345R, E345Y, S440Y, S440W and/or any combination thereof. |

In addition to the isotypes described in Table C, and without wishing to be bound to theory, it is thought that antibodies with human IgG1 or IgG3 isotypes and mutants thereof (e.g. Strohl (2009) Current Opinion in Biotechnology 2009, 20:685-691) that bind the Fcg Receptors I, IIA, IIC, IIIA, IIIB in human and/or Fcg Receptors I, III and IV in mouse, may also act as transient agonist antibodies.

In some embodiments, the Fc gamma receptor-binding antibody is of the IgG class, the IgM class, or the IgA class. In some embodiments, the Fc gamma receptor-binding antibody has an IgG1, IgG2, IgG3, or IgG4 isotype. In some embodiments, the antibody comprises one or more (e.g., one or more, two or more, three or more, four or more, five or more, six or more, seven or more, eight or more, nine or more, 10 or more, 11 or more, 12 or more, or all thirteen) amino acid substitutions in the Fc region at a residue position selected from the group consisting of: C127S, L234A, L234F, L235A, L235E, S267E, K322A, L328F, A330S, P331S, E345R, E430G, S440Y in any combination (residue position according to EU or Kabat numbering). In some embodiments, the Fc region comprises an amino acid substitution at position E430G. In some embodiments, the Fc region comprises an amino acid substitution at positions L243A, L235A, and P331A. In some embodiments, the Fc region comprises an amino acid substitution at positions L243A, L235A, P331A. In some embodiments, the Fc region comprises an amino acid substitution at positions K322A and E430G. In some embodiments, the Fc region comprises an amino acid substitution at positions P331S and E430G. In some embodiments, the Fc region comprises an amino acid substitution at positions A330S, P331S, and E430G. In some embodiments, the Fc region comprises an amino acid substitution at positions K322A, A330S, and P331S. In some embodiments, the Fc region comprises an amino acid substitution at positions K322A, P331S, and E430G. In some embodiments, the Fc region comprises an amino acid substitution at positions A330S, P331S, and E430G. In some embodiments, the Fc region comprises an amino acid substitution at positions S267E and L328F. In some embodiments, the Fc region comprises an amino acid substitution at position C127S. In some embodiments, the Fc region comprises an amino acid substitution at positions E345R, E430G and S440Y. In some embodiments, the Fc region comprises an amino acid substitution at positions L243A, L235A, and P331S.

In certain embodiments, the Fc gamma receptor-binding antibody has an IgG2 isotype. In some embodiments, the Fc gamma receptor-binding antibody contains a human IgG2 constant region. In some embodiments, the human IgG2 constant region includes an Fc region. In some embodiments, the Fc gamma receptor-binding antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from V234A (Alegre et al., (1994) Transplantation 57:1537-1543. 31; Xu et al., (2000) Cell Immunol, 200:16-26), G237A (Cole et al. (1999) Transplantation, 68:563-571), H268Q, V309L, A330S, P331S (US 2007/0148167; Armour et al. (1999) Eur J Immunol 29: 2613-2624; Armour et al. (2000) The Haematology Journal 1(Suppl.1):27; Armour et al. (2000) The Haematology Journal 1(Suppl.1):27), C232S, and/or C233S (White et al. (2015) Cancer Cell 27, 138-148), S267E, L328F (Chu et al., (2008) Mol Immunol, 45:3926-3933), M252Y, S254T, and/or T256E, where the amino acid position is according to the EU or Kabat numbering convention.

In some embodiments, the Fc gamma receptor-binding antibody has an IgG2 isotype with a heavy chain constant domain that contains a C127S amino acid substitution, where the amino acid position is according to the EU or Kabat numbering convention (White et al., (2015) Cancer Cell 27, 138-148; Lightle et al., (2010) PROTEIN SCIENCE 19:753-762; and WO2008079246).

In some embodiments, the Fc gamma receptor-binding antibody has an IgG2 isotype with a Kappa light chain constant domain that contains a C214S amino acid substitution, where the amino acid position is according to the EU or Kabat numbering convention (White et al., (2015) Cancer Cell 27, 138-148; Lightle et al., (2010) PROTEIN SCIENCE 19:753-762; and WO2008079246).

In certain embodiments, the Fc gamma receptor-binding antibody has an IgG1 isotype. In some embodiments, the Fc gamma receptor-binding antibody contains a mouse IgG1 constant region. In some embodiments, the Fc gamma receptor-binding antibody contains a human IgG1 constant region. In some embodiments, the human IgG1 constant region includes an Fc region. In some embodiments, the Fc gamma receptor-binding antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from N297A (Bolt S et al. (1993) Eur J Immunol 23:403-411), D265A (Shields et al. (2001) R. J. Biol. Chem. 276, 6591-6604), D270A, L234A, L235A (Hutchins et al. (1995) Proc Natl Acad Sci USA, 92:11980-11984; Alegre et al., (1994) Transplantation 57:1537-1543. 31; Xu et al., (2000) Cell Immunol, 200:16-26), G237A (Alegre et al. (1994) Transplantation 57:1537-1543. 31; Xu et al. (2000) Cell Immunol, 200:16-26), P238D, L328E, E233D, G237D, H268D, P271G, A330R, C226S, C229S, E233P, L234V, L234F, L235E (McEarchern et al., (2007) Blood, 109:1185-1192), P331S (Sazinsky et al., (2008) Proc Natl Acad Sci USA 2008, 105:20167-20172), S267E, L328F, A330L, M252Y, S254T, T256E, N297Q, P238S, P238A, A327Q, A327G, P329A, K322A, and/or T394D, where the amino acid position is according to the EU or Kabat numbering convention.

In some embodiments, the antibody includes an IgG2 isotype heavy chain constant domain 1(CH1) and hinge region (White et al., (2015) Cancer Cell 27, 138-148). In certain embodiments, the IgG2 isotype CH1 and hinge region contain the amino acid sequence of ASTKGPSVF-PLAPCSRSTSESTAALGCLVKDYFPEPVTVSWNS-GALTSGVHTFPAVLQSSGLYSLS SVVTVPSSNFGTQ-TYTCNVDHKPSNTKVDKTVERKCCVECPPCP (SEQ ID NO: 166). In some embodiments, the antibody Fc region contains a S267E amino acid substitution, a L328F amino acid substitution, or both, and/or a N297A or N297Q amino acid substitution, where the amino acid position is according to the EU or Kabat numbering convention.

In certain embodiments, the Fc gamma receptor-binding antibody has an IgG4 isotype. In some embodiments, the Fc gamma receptor-binding antibody contains a human IgG4 constant region. In some embodiments, the human IgG4 constant region includes an Fc region. In some embodiments, the Fc gamma receptor-binding antibody binds an inhibitory Fc receptor. In certain embodiments, the inhibitory Fc receptor is inhibitory Fc-gamma receptor IIB (FcγIIB). In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from L235A, G237A, S228P, L236E (Reddy et al., (2000) J Immunol, 164:1925-1933), S267E, E318A, L328F, M252Y, S254T, and/or T256E, where the amino acid position is according to the EU or Kabat numbering convention.

In certain embodiments, the Fc gamma receptor-binding antibody has a hybrid IgG2/4 isotype. In some embodiments, the Fc gamma receptor-binding antibody includes an amino acid sequence containing amino acids 118 to 260 according to EU or, Kabat numbering of human IgG2 and amino acids 261-447 according to EU or, Kabat numbering of human IgG4 (WO 1997/11971; WO 2007/106585).

In certain embodiments, the antibody contains a mouse IgG4 constant region (Bartholomaeus, et al. (2014). J. Immunol. 192, 2091-2098).

In some embodiments, the Fc region further contains one or more additional amino acid substitutions selected from the group consisting of A330L, L234F; L235E, or P331S according to EU or, Kabat numbering; and any combination thereof.

In certain embodiments, the antibody contains one or more amino acid substitutions in the Fc region at a residue position selected from C127S, L234A, L234F, L235A, L235E, S267E, K322A, L328F, A330S, P331S, E345R, E430G, S440Y, and any combination thereof, where the numbering of the residues is according to EU or Kabat numbering. In some embodiments, the Fc region contains an amino acid substitution at positions E430G, L243A, L235A, and P331S, where the numbering of the residue position is according to EU numbering. In some embodiments, the Fc region contains an amino acid substitution at positions E430G and P331S, where the numbering of the residue position is according to EU numbering. In some embodiments, the Fc region contains an amino acid substitution at positions E430G and K322A, where the numbering of the residue position is according to EU numbering. In some embodiments, the Fc region contains an amino acid substitution at positions E430G, A330S, and P331S, where the numbering of the residue position is according to EU numbering. In some embodiments, the Fc region contains an amino acid substitution at positions E430G, K322A, A330S, and P331S, where the numbering of the residue position is according to EU numbering. In some embodiments, the Fc region contains an amino acid substitution at positions E430G, K322A, and A330S, where the numbering of the residue position is according to EU numbering. In some embodiments, the Fc region contains an amino acid substitution at positions E430G, K322A, and P331S, where the numbering of the residue position is according to EU numbering. In some embodiments, the Fc region contains an amino acid substitution at positions S267E and L328F, where the numbering of the residue position is according to EU numbering. In some embodiments, the Fc region contains an amino acid substitution at position C127S, where the numbering of the residue position is according to EU numbering. In some embodiments, the Fc region contains an amino acid substitution at positions E345R, E430G and S440Y, where the numbering of the residue position is according to EU numbering. In some embodiments, the Fc region comprises an amino acid substitution at positions L243A, L235A, and P331S, wherein the numbering of the residue position is according to EU numbering.

Inert Antibodies

Another class of anti-CD33 antibodies of the present disclosure includes inert antibodies. As used herein, "inert" antibodies refer to antibodies that specifically bind their target antigen (e.g., CD33) but do not modulate (e.g., decrease/inhibit or activate/induce) antigen function. For example, in the case of CD33, inert antibodies do not modulate cellular levels of CD33, do not modulate interaction (e.g., binding) between CD33 and one or more CD33 ligands, or do not modulate one or more activities of a CD33 protein. In some embodiments, antibodies that do not have the ability to cluster CD33 on the cell surface may be inert antibodies even if they have an epitope specificity that is compatible with receptor activation.

In some embodiments, antibodies that bind a CD33 protein may include antibodies that bind CD33 but, due to their epitope specificity, or characteristics, do not decrease cellular levels of CD33 and/or inhibit interaction (e.g., binding) between CD33 and one or more CD33 ligands. In some embodiments, such antibodies can be used as cargo to, for example, transport toxins (e.g., chemotherapeutics) into tumor cells. Therefore, in some embodiments, antibodies of the present disclosure are inert antibodies that bind CD33 but are incapable of decreasing cellular levels of CD33, inhibiting interaction (e.g., binding) between CD33 and one or more CD33 ligands, or inducing one or more activities of a CD33 protein.

Antibodies that either decrease or do not decrease cellular levels of CD33 on cells can be combined with an inert Fc region that displays reduced binding to one or more Fcg Receptor. Examples of such Fc regions and modifications are provided in Table D below. In some embodiments, the antibody with an inert Fc region has an Fc isotype listed in Table D below.

Inhibitory Anti-CD33 Antibodies

A third class of anti-CD33 antibodies of the present disclosure includes antibodies that block or otherwise inhibit one or more CD33 activities. In some embodiments, antibodies that bind a CD33 protein may include antibodies that reduce cellular levels of CD33 (e.g., cell surface levels of CD33), inhibit interaction (e.g., binding) between CD33 and/or one or more CD33 ligands, and inhibit one or more activities of a CD33 protein. Such antibodies inhibit one or more activities of a CD33 protein either by preventing interaction (e.g., binding) between CD33 and one or more CD33 ligands or by preventing signal transduction from the extracellular domain of CD33 into the cell cytoplasm in the presence of one or more CD33 ligands. Antibodies also can inhibit one or more activities of a CD33 protein by decreasing cell surface levels of CD33 by inducing CD33 degradation, CD33 desensitization, CD33 cleavage, CD33 internalization, CD33 shedding, downregulation of CD33 expression, and/or lysosomal degradation of CD33. In some embodiments, such anti-CD33 antibodies may not transiently activate CD33.

In some embodiments, anti-CD33 antibodies of the present disclosure may have the epitope specificity of a transient agonist anti-CD33 antibody of the present disclosure, but have an Fc domain that is not capable of binding Fcg receptors and thus is unable to, for example, transiently clustering and activating CD33.

In some embodiments, anti-CD33 antibodies of the present disclosure have, without limitation, one or more of the following activities: the ability to decrease binding of a CD33 protein to one or more CD33 ligands, such as sialic acid-containing glycolipid s or sialic acid-containing glycoproteins, the ability to decrease the binding of a suppressor of cytokine signaling (SOCS) protein (e.g., SOCS3 protein) to a CD33 protein, the ability to increase the proteasomal degradation of a CD33 protein, the ability to reduce functional expression of CD33 on the surface of circulating dendritic cells, macrophages, monocytes, T cells, and/or microglia, the ability to decrease phosphorylation of Tyr-340 and Tyr-358 by a Src family tyrosine kinase such as LCK and FYN, the ability to decrease recruitment of and binding to the tyrosine-specific protein phosphatases SHP1 and SHP2, the ability to decrease recruitment of and binding to PLC-g1, which acts as a guanine nucleotide, exchange factor for Dynamin-1, the ability to decrease recruitment of and binding to Crk1, the ability to decrease recruitment of and binding to the Spleen tyrosine kinase Syk, the ability to decrease recruitment of and binding to SH3-SH2-SH3 growth factor receptor-bound protein 2 (Grb2), the ability to decrease recruitment of and binding to multiple SH2 containing proteins, the ability to increase intracellular calcium mobilization, the ability to modulate production of pro-inflammatory cytokines IL-1β, IL-8, and TNF-α, the ability to decrease activation of phosphoinositide 3-kinase, the ability to increase the growth of monocytes, macrophages, dendritic cells, T cells, and/or microglia, the ability to increase the survival of monocytes, macrophages, dendritic cells, T cells, and/or microglia, the ability to increase tyrosine phosphorylation on multiple cellular proteins, the ability to increase phagocytic activity of monocytes, macrophages, dendritic cells and/or microglia, the ability to increase cell proliferation of monocytes, macrophages, dendritic cells, T cells, and/or microglia, the ability to increase phosphorylation of signaling molecules that mediates ITAM signaling, the ability to increase the function of pattern recognition receptors, the ability to increase the function of Toll-like receptors, the ability to increases the function of damage-associated molecular pattern (DAMP) receptors, the ability to modulate expression of C-C chemokine receptor 7 (CCR7), and the ability to increase of clearance of cellular and protein debris.

In some embodiments, anti-CD33 antibodies of the present disclosure have an Fc region that displays reduced binding to one or more Fcg Receptor. Examples of such Fc regions and modifications are provided in Table D below. In some embodiments, the antibody has an Fc isotype listed in Table D below.

Antibody Fc Isotypes with Reduced Binding to Fc Gamma Receptors

In some embodiments, anti-CD33 antibodies with reduced binding to Fc gamma receptors have an Fc isotype listed in Table C below.

TABLE C

Exemplary anti-CD33 antibody Fc isotypes with reduced binding to Fc gamma receptor

| Fc Isotype | Mutation (EU numbering scheme) |
|---|---|
| IgG1 | N297A or N297Q and/or D270A |
| IgG1 | D265A, D270A, and/or N297A |
| IgG1 | L234A and L235A |
| IgG2 | V234A and G237A |
| IgG4 | F235A and G237A and E318A |
|  | E233P and/or F234V |
|  | N297A or N297Q |
| IgG4 | S228P and L236E |
|  | S241P |
|  | S241P and L248E |
|  | S228P and F234A and L235A |
| IgG2 | H268Q and V309L and A330S and P331S |
| IgG1 | C220S and C226S and C229S and P238S |
| IgG1 | C226S and C229S and E233P and L234V, and L235A |
| IgG1 | E233P and L234V and L235A and G236-deleted |
|  | P238A |
|  | D265A |
|  | N297A |
|  | A327Q or A327G |
|  | P329A |
| IgG1 | K322A and L234A and L235A |
| IgG1 | L234F and L235E and P331S |
| IgG1 or IgG4 | T394D |
| IgG2 | C232S or C233S |
|  | N297A or N297Q |
| IgG2 | V234A and G237A and P238S and H268A and V309L and A330S and P331S |
| IgG1, IgG2, or IgG4 | delta a, b, c, ab, ac, g modifications |
| IgG1 | Any of the above listed mutations together with A330L or L234F and/or L235E and/or P331S |
| IgG1, IgG2, or IgG4 | Any of the above listed mutations together with M252Y and/or S254T and/or T256E |

In certain embodiments, the anti-CD33antibody has an IgG1 isotype. In some embodiments, the antibody contains a mouse IgG1 constant region. In some embodiments, the antibody contains a human IgG1 constant region. In some embodiments, the human IgG1 constant region includes an Fc region. In some embodiments, the Fc region contains one or more modifications. For example, in some embodiments, the Fc region contains one or more amino acid substitutions (e.g., relative to a wild-type Fc region of the same isotype).

In some embodiments, the one or more amino acid substitutions are selected from N297A, N297Q (Bolt S et al. (1993) *Eur J Immunol* 23:403-411), D265A, D270A, L234A, L235A (McEarchern et al., (2007) *Blood,* 109:1185-1192), C226S, C229S (McEarchern et al., (2007) *Blood,* 109:1185-1192), P238S (Davis et al., (2007) *J Rheumatol,* 34:2204-2210), E233P, L234V (McEarchern et al., (2007) *Blood,* 109:1185-1192), P238A, A327Q, A327G, P329A (Shields R L, et al., (2001) *J Biol Chem.* 276(9):6591-604), K322A, L234F, L235E (Hezareh, et al., (2001) *J Virol* 75, 12161-12168; Oganesyan et al., (2008). *Acta Crystallographica* 64, 700-704), P331S (Oganesyan et al., (2008) *Acta Crystallographica* 64, 700-704), T394D (Wilkinson et al. (2013) *MAbs* 5(3): 406-417), A330L, M252Y, S254T, and/or T256E, where the amino acid position is according to the EU or Kabat numbering convention. In certain embodiments, the Fc region further includes an amino acid deletion at a position corresponding to glycine 236 according to the EU or Kabat numbering convention.

In some embodiments, the anti-CD33 antibody has an IgG1 isotype with a heavy chain constant region that contains a C220S amino acid substitution according to the EU or Kabat numbering convention. In some embodiments, the Fc region further contains one or more additional amino acid substitutions selected from A330L, L234F; L235E, and/or P331S according to EU or Kabat numbering convention. In certain embodiments, the anti-CD33 antibody has an IgG2 isotype. In some embodiments, the anti-CD33 antibody contains a human IgG2 constant region. In some embodiments, the human IgG2 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from P238S, V234A, G237A, H268A, H268Q, H268E, V309L, N297A, N297Q, V309L, A330S, P331S, C232S, C233S, M252Y, S254T, and/or T256E, where the amino acid position is according to the EU or Kabat numbering convention (Vafa O. et al., (2014) Methods 65:114-126).

In certain embodiments, the anti-CD33 antibody has an IgG4 isotype. In some embodiments, the anti-CD33 antibody contains a human IgG4 constant region. In some embodiments, the human IgG4 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from E233P, F234V, L235A, G237A, E318A (Hutchins et al. (1995) *Proc Natl Acad Sci USA*, 92:11980-11984), S228P, L234A/F234A, L236E, S241P, L248E (Reddy et al., (2000) *J Immunol*, 164:1925-1933; Angal et al., (1993) *Mol Immunol*. 30(1):105-8; U.S. Pat. No. 8,614,299 B2; Vafa O. et al., (2014) Methods 65:114-126), T394D, M252Y, S254T, T256E, N297A, and/or N297Q, where the amino acid position is according to the EU or Kabat numbering convention. In some embodiments the antibody has an IgG4 isotype, and comprises an S228P amino acid substitution at residue position 228, an F234A amino acid substitution at residue position 234, and an L235A amino acid substitution at residue position 235 (residue position according to EU numbering).

In some embodiments, the Fc region further contains one or more additional amino acid substitutions selected from a M252Y, S254T, and/or T256E, where the amino acid position is according to the EU or Kabat numbering convention.

Further IgG Mutations

In some embodiments, one or more of the IgG1 variants described herein may be combined with an A330L mutation (Lazar et al., (2006) Proc Natl Acad Sci USA, 103:4005-4010), or one or more of L234F, L235E, and/or P331S mutations (Sazinsky et al., (2008) Proc Natl Acad Sci USA, 105:20167-20172), where the amino acid position is according to the EU or Kabat numbering convention, to eliminate complement activation. In some embodiments, the IgG variants described herein may be combined with one or more mutations to enhance the anti-CD33 antibody half-life in human serum (e.g. M252Y, S254T, T256E mutations according to the EU or Kabat numbering convention)

(Dall'Acqua et al., (2006) J Biol Chem, 281:23514-23524; and Strohl e al., (2009) Current Opinion in Biotechnology, 20:685-691).

In some embodiments, an IgG4 variant of the present disclosure may be combined with an S228P mutation according to the EU or Kabat numbering convention (Angal et al., (1993) Mol Immunol, 30:105-108) and/or with one or more mutations described in Peters et al., (2012) J Biol Chem. 13; 287(29):24525-33) to enhance antibody stabilization.

Bispecific Antibodies

Certain aspects of the present disclosure relate to bispecific antibodies that bind to one or more domains on a CD33 protein of the present disclosure and a second antigen. Methods of generating bispecific antibodies are well known in the art and described herein. In some embodiments, bispecific antibodies of the present disclosure bind to one or more amino acid residues of a CD33 protein of the present disclosure, such as one or more amino acid residues of human CD33 (SEQ ID NO: 1), or amino acid residues on a CD33 protein corresponding to amino acid residues of SEQ ID NO: 1. In some embodiments, bispecific antibodies of the present disclosure recognize a first antigen and a second antigen. In some embodiments, the first antigen is a CD33 protein or a naturally occurring variant thereof. In some embodiments, the second antigen is also a CD33 protein, or a naturally occurring variant thereof. In some embodiments, the second antigen is an antigen facilitating transport across the blood-brain-barrier (see, e.g., Gabathuler R., *Neurobiol. Dis.* 37 (2010) 48-57). Such second antigens include, without limitation, transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, Angiopep peptides such as ANG1005 (see, e.g., Gabathuler, 2010), and other cell surface proteins that are enriched on blood-brain barrier endothelial cells (see, e.g., Daneman et al., PLoS One. 2010 Oct. 29; 5(10):e13741). In some embodiments, the second antigen is a disease-causing protein including, without limitation, amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides. In some embodiments, the second antigen is one or more ligands and/or proteins expressed on immune cells, including without limitation, CD40, OX40, ICOS, CD28, CD137/4-1BB, CD27, GITR, PD-L1, CTLA4, PD-L2, PD-1, B7-H3, B7-H4, HVEM, LIGHT, BTLA, CD38, TIGIT, VISTA, KIR, GALS, TIM1, TIM3, TIM4, A2AR, LAG3, DR5, CD39, CD70, CD73, TREM1, TREM2, Siglec-5, Siglec-7, Siglec-9, Siglec-11, SirpA, CD47, CSF1-receptor, CD3, and phosphatidylserine. In some embodiments, the second antigen is a protein, lipid, polysaccharide, or glycolipid expressed on one or more tumor cells.

Antibody Fragments

Certain aspects of the present disclosure relate to antibody fragments that bind to one or more of a CD33 protein of the present disclosure, a naturally occurring variant of a CD33 protein, and a disease variant of a CD33 protein. In some embodiments, the antibody fragment is an Fab, Fab', Fab'-SH, F(ab')2, Fv or scFv fragment.

In some embodiments, the antibody fragment is used in combination with a second CD33 antibody and/or with one or more antibodies that specifically bind a disease-causing protein selected from: amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and any combination thereof; or with one or more antibodies that bind an immunomodulatory protein selected from the group consisting of: CD40, OX40, ICOS, CD28, CD137/4-1BB, CD27, GITR, PD-L1, CTLA4, PD-L2, PD-1, B7-H3, B7-H4, HVEM, LIGHT, BTLA, CD38, TIGIT, VISTA, KIR, GALS, TIM1, TIM3, TIM4, A2AR, LAG3, DR5, CD39, CD70, CD73, TREM1, TREM2, CD47, CSF-1 receptor, Siglec-5, Siglec-7, Siglec-9, Siglec-11, phosphatidylserine, and any combination thereof.

In some embodiments, antibody fragments of the present disclosure may be functional fragments that bind the same epitope as any of the anti-CD33 antibodies of the present disclosure. In some embodiments, the antibody fragments are miniaturized versions of the anti-CD33 antibodies or antibody fragments of the present disclosure that have the same epitope of the corresponding full-length antibody, but have much smaller molecule weight. Such miniaturized anti-CD33 antibody fragments may have better brain penetration ability and a shorter half-life, which is advantageous for imaging and diagnostic utilities (see e.g., Lütje S et al., *Bioconjug Chem.* 2014 Feb. 19; 25(2):335-41; Tavaré R et al., *Proc Natl Acad Sci USA.* 2014 Jan. 21; 111(3):1108-13; and Wiehr S et al., *Prostate.* 2014 May; 74(7):743-55). Accordingly, in some embodiments, anti-CD33 antibody fragments of the present disclosure have better brain penetration as compared to their corresponding full-length antibodies and/or have a shorter half-life as compared to their corresponding full-length antibodies.

Antibody Frameworks

Any of the antibodies described herein further include a framework. In some embodiments, the framework is a human immunoglobulin framework. For example, in some embodiments, an antibody (e.g., an anti-CD33 antibody) comprises HVRs as in any of the above embodiments and further comprises an acceptor human framework, e.g., a human immunoglobulin framework or a human consensus framework. Human immunoglobulin frameworks may be part of the human antibody, or a non-human antibody may be humanized by replacing one or more endogenous frameworks with human framework region(s). Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

In some embodiments, anti-CD33 antibodies of the present disclosure comprise a heavy chain variable region comprising one or more (e.g., one or more, two or more, three or more, or all four) framework regions selected from VH FR1, VH FR2, VH FR3, and VH FR4 (as shown in Tables 5A-5D). In some embodiments, the VH FR1 comprises a sequence according to Formula VII: QVQLVQSGAEVKKPGX$_1$SVKX$_2$SCKAS (SEQ ID NO: 158), wherein X$_1$ is A or S, and X$_2$ is V or I. In some embodiments, VH FR1 comprises a sequence selected from the group consisting of SEQ ID NOs: 2-4. In some embodiments, the VH Fr2 comprises the sequence of SEQ ID NO: 5. In some embodiments, the VH FR3 comprises a sequence according to Formula VIII: X$_1$AX$_2$X$_3$X$_4$X$_5$X$_6$RX$_7$TX$_8$TVDX$_9$X$_{10}$X$_{11}$STX$_{12}$YMELSSLRSEDTAVYYCAR (SEQ ID NO: 159), wherein X$_1$ is Y or S, X$_2$ is Q or E, X$_3$ is K or D, X$_4$ is F or D, X$_5$ is Q, F, E, or T, X$_6$ is G, D, or H, X$_7$ is V or A, X$_8$ is M or L, X$_9$ is T, N, or Q, X$_{10}$ is S or P, X$_{11}$ is T or A, and X$_{12}$ is V or A. In some embodiments, VH FR3 comprises a sequence selected from the group consisting of SEQ ID NOs: 6-19. In some embodiments, VH FR4 comprises a sequence according to Formula IX: WGQGTLX$_1$TVSS (SEQ ID NO: 160), wherein X$_1$ is V or L. In some embodiments, VH FR4 comprises a sequence selected from the group consisting of SEQ ID NOs: 20-21. In some embodiments, an antibody comprises a heavy chain variable region comprising a VH FR1 according to Formula VII, a VH FR2 comprising the sequence of SEQ ID NO: 5, a VH FR3 according to Formula VIII, and VH FR4 according to Formula IX. In some embodiments, anti-CD33 antibodies of the present disclosure comprise a heavy chain variable region comprising a VH FR1 comprising a sequence selected from SEQ ID NOs: 2-4, a VH FR2 comprising the sequence of SEQ ID NO: 5, a VH FR3 comprising a sequence selected from SEQ ID NOs: 6-19, and VH FR4 comprising a sequence selected from SEQ ID NOs: 20-21. In some embodiments, anti-CD33 antibodies of the present disclosure comprise a heavy chain variable region comprising a VH FR1, a VH FR2, a VH FR3, and VH FR4 of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15 (as shown in Table 7).

In some embodiments, anti-CD33 antibodies of the present disclosure comprise a light chain variable region comprising one or more (e.g., one or more, two or more, three or more, or all four) framework regions selected from VL FR1, VL FR2, VL FR3, and VL FR4 (as shown in Tables 6A-6D). In some embodiments, the VL FR1 comprises a sequence according to Formula X: $X_1IX_2X_3TQSPX_4SLX_5X_6SX_7GX_8RX_9TIX_{10}C$ (SEQ ID NO: 161), wherein $X_1$ is D or G, $X_2$ is Q or V, $X_3$ is M or L, $X_4$ is S or D, $X_5$ is S, P, or A, $X_6$ is A or V, $X_7$ is V or L, $X_8$ is D or E, $X_9$ is V or A, and $X_{10}$ is T, N, or D. In some embodiments, VL FR1 comprises a sequence selected from the group consisting of SEQ ID NOs: 22-26. In some embodiments, the VL FR2 comprises a sequence according to Formula XI: $WYQQKPGX_1X_2PKLLIK$ (SEQ ID NO: 162), wherein $X_1$ is K or Q, and $X_2$ is A or P. In some embodiments, the VL FR2 comprises a sequence selected from the group consisting of SEQ ID NOs: 27-28. In some embodiments, the VL FR3 comprises a sequence according to Formula XII: $GVPX_1RFSGSGSGTDFTLTISSLQ-X_2EDX_3AX_4YYC$ (SEQ ID NO: 163), wherein $X_1$ is S or D, $X_2$ is P or A, $X_3$ is F, L, or V, and $X_4$ is T or V. In some embodiments, VL FR3 comprises a sequence selected from the group consisting of SEQ ID NOs: 29-31. In some embodiments, VL FR4 comprises a sequence according to Formula XIII: $FGQGTKLEIX_1$ (SEQ ID NO: 164), wherein $X_1$ is K or E. In some embodiments, VL FR4 comprises a sequence selected from the group consisting of SEQ ID NOs: 32-33. In some embodiments, anti-CD33 antibodies of the present disclosure comprise a light chain variable region comprising a VL FR1 according to Formula X, a VL FR2 according to Formula XI, a VL FR3 according to Formula XII, and VL FR4 according to Formula XIII. In some embodiments, anti-CD33 antibodies of the present disclosure comprise a light chain variable region comprising a VL FR1 comprising a sequence selected from SEQ ID NOs: 22-26, a VL FR2 comprising a sequence selected from SEQ ID NOs: 27-28, a VL FR3 comprising a sequence selected from SEQ ID NOs: 29-31, and VL FR4 comprising a sequence selected from SEQ ID NOs: 32-33. In some embodiments, anti-CD33 antibodies of the present disclosure comprise a light chain variable region comprising a VL FR1, a VL FR2, a VL FR3, and VL FR4 of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15 (as shown in Table 8).

In some embodiments, anti-CD33 antibodies of the present disclosure comprise a heavy chain variable region comprising one or more (e.g., one or more, two or more, three or more, or all four) framework regions selected from VH FR1, VH FR2, VH FR3, and VH FR4 (as shown in Tables 5A-5D), and a light chain variable region comprising one or more (e.g., one or more, two or more, three or more, or all four) framework regions selected from VL FR1, VL FR2, VL FR3, and VL FR4 (as shown in Tables 6A-6D). In some embodiments, anti-CD33 antibodies of the present disclosure comprise a heavy chain variable region comprising a VH FR1 according to Formula VII, a VH FR2 comprising the sequence of SEQ ID NO: 5, a VH FR3 according to Formula VIII, and VH FR4 according to Formula IX, and a light chain variable region comprising a VL FR1 according to Formula X, a VL FR2 according to Formula XI, a VL FR3 according to Formula XII, and VL FR4 according to Formula XIII. In some embodiments, anti-CD33 antibodies of the present disclosure comprise a heavy chain variable region comprising a VH FR1 comprising a sequence selected from SEQ ID NOs: 2-4, a VH FR2 comprising the sequence of SEQ ID NO: 5, a VH FR3 comprising a sequence selected from SEQ ID NOs: 6-19, and VH FR4 comprising a sequence selected from SEQ ID NOs: 20-21, a light chain variable region comprising a VL FR1 comprising a sequence selected from SEQ ID NOs: 22-26, a VL FR2 comprising a sequence selected from SEQ ID NOs: 27-28, a VL FR3 comprising a sequence selected from SEQ ID NOs: 29-31, and VL FR4 comprising a sequence selected from SEQ ID NOs: 32-33. In some embodiments, anti-CD33 antibodies of the present disclosure comprise a heavy chain variable region comprising a VH FR1, a VH FR2, a VH FR3, and VH FR4 of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15 (as shown in Table 7), and a light chain variable region comprising a VL FR1, a VL FR2, a VL FR3, and VL FR4 of antibody AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, or AB-64.1.15 (as shown in Table 8).

CD33 Activities

Modulated Expression of Immune-Related Proteins

In some embodiments, anti-CD33 antibodies of the present disclosure may modulate expression of PD-L1, PD-L2, B7-H2, B7-H3, CD200R, CD163 and/or CD206 after binding to a CD33 protein expressed in a cell. Modulated (e.g., increased or decreased) expression may include, without limitation, modulation in gene expression, modulation in transcriptional expression, or modulation in protein expression. Any method known in the art for determining gene, transcript (e.g., mRNA), and/or protein expression may be used. For example, Northern blot analysis may be used to determine anti-inflammatory mediator gene expression levels, RT-PCR may be used to determine the level of anti-inflammatory mediator transcription, and Western blot analysis may be used to determine anti-inflammatory mediator protein levels.

As used herein, PD-L1, PD-L2, B7-H2, B7-H3, CD200R, CD163 and/or CD206 may have modulated expression if its expression in one or more cells of a subject treated with anti-CD33 antibodies of the present disclosure is modulated (e.g., increased or decreased) as compared to the expression of PD-L1, PD-L2, B7-H2, B7-H3, CD200R, CD163 and/or CD206 expressed in one or more cells of a corresponding subject that is not treated with the antibody. In some embodiments, an anti-CD33 antibody of the present disclosure may modulate PD-L1, PD-L2, B7-H2, B7-H3, CD200R, CD163 and/or CD206 expression in one or more cells of a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to PD-L1, PD-L2, B7-H3, CD200R, CD163 and/or CD206 expression in one or more cells of a corresponding subject that is not treated with the antibody. In other embodiments, an anti-CD33 antibody of the present disclosure modulates PD-L1, PD-L2, B7-H2, B7-H3, CD200R, CD163 and/or CD206 expression in one or more cells of a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to PD-L1, PD-L2, B7-H2, B7-H3, CD200R, CD163 and/or CD206 expression in one or more cells of a corresponding subject that is not treated with the antibody.

In some embodiments, anti-CD33 antibodies of the present disclosure are useful for preventing, lowering the risk of, or treating conditions and/or diseases associated with abnormal levels of PD-L1, PD-L2, B7-H2, B7-H3, CD200R, CD163 and/or CD206, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

Enhancement or Normalization of the Ability of Bone Marrow-Derived Dendritic Cells to Induce Antigen-Specific T Cell Proliferation In some embodiments, anti-CD33 antibodies of the present disclosure may enhance and/or normalize the ability of bone marrow-derived dendritic cells to induce antigen-specific T cell proliferation after binding to a CD33 protein expressed in a cell.

In some embodiments, antagonist anti-CD33 antibodies of the present disclosure may enhance and/or normalize the ability of bone marrow-derived dendritic cells to induce antigen-specific T cell proliferation in one or more bone marrow-derived dendritic cells of a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the ability of bone marrow-derived dendritic cells to induce antigen-specific T cell proliferation in one or more bone marrow-derived dendritic cells of a corresponding subject that is not treated with the antibody. In other embodiments, an antagonist anti-CD33 antibody may enhance and/or normalize the ability of bone marrow-derived dendritic cells to induce antigen-specific T cell proliferation in one or more bone marrow-derived dendritic cells of a subject by at least at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the ability of bone marrow-derived dendritic cells to induce antigen-specific T cell proliferation in one or more bone marrow-derived dendritic cells of a corresponding subject that is not treated with the antibody.

In some embodiments, anti-CD33 antibodies of the present disclosure are beneficial for preventing, lowering the risk of, or treating conditions and/or diseases associated with decreased or dysregulated ability of bone marrow-derived dendritic cells to induce antigen-specific T cell proliferation, including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

Proliferation and Survival of CD33-Expressing Cells

In some embodiments, anti-CD33 antibodies of the present disclosure may increase the proliferation, survival, and/or function of dendritic cells, macrophages, monocytes, neutrophils, osteoclasts, Langerhans cells of skin, Kupffer cells, T cells, T helper cells, cytotoxic T cells, and microglial cells after binding to CD33 protein expressed on a cell.

Microglial cells are a type of glial cell that are the resident macrophages of the brain and spinal cord, and thus act as the first and main form of active immune defense in the central nervous system (CNS). Microglial cells constitute 20% of the total glial cell population within the brain. Microglial cells are constantly scavenging the CNS for plaques, damaged neurons and infectious agents. The brain and spinal cord are considered "immune privileged" organs in that they are separated from the rest of the body by a series of endothelial cells known as the blood-brain barrier, which prevents most pathogens from reaching the vulnerable nervous tissue. In the case where infectious agents are directly introduced to the brain or cross the blood-brain barrier, microglial cells must react quickly to limit inflammation and destroy the infectious agents before they damage the sensitive neural tissue. Due to the unavailability of antibodies from the rest of the body (few antibodies are small enough to cross the blood brain barrier), microglia must be able to recognize foreign bodies, swallow them, and act as antigen-presenting cells activating T cells. Since this process must be done quickly to prevent potentially fatal damage, microglial cells are extremely sensitive to even small pathological changes in the CNS. They achieve this sensitivity in part by having unique potassium channels that respond to even small changes in extracellular potassium.

As used herein, macrophages of the present disclosure include, without limitation, M1 macrophages, activated M1 macrophages, and M2 macrophages. As used herein, microglial cells of the present disclosure include, without limitation, M1 microglial cells, activated M1 microglial cells, and M2 microglial cells.

In some embodiments, anti-CD33 antibodies of the present disclosure may increase the expression of CD80, CD83 and/or CD86 on dendritic cells, monocytes, and/or macrophages.

As used herein, the rate of proliferation, survival, and/or function of macrophages, dendritic cells, monocytes, T cells, neutrophils, and/or microglia may include increased expression if the rate of proliferation, survival, and/or function of dendritic cells, macrophages, monocytes, neutrophils, osteoclasts, Langerhans cells of skin, Kupffer cells, and/or microglia in a subject treated with an anti-CD33 antibody of the present disclosure is greater than the rate of proliferation, survival, and/or function of dendritic cells, macrophages, monocytes, osteoclasts, Langerhans cells of skin, Kupffer cells, T cells, neutrophils, and/or microglia in a corresponding subject that is not treated with the antibody. In some embodiments, an anti-CD33 antibody of the present disclosure may increase the rate of proliferation, survival, and/or function of dendritic cells, macrophages, monocytes, osteoclasts, Langerhans cells of skin, Kupffer cells, T cells, and/or microglia in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the rate of proliferation, survival, and/or function of dendritic cells, macrophages, monocytes, osteoclasts, Langerhans cells of skin, Kupffer cells, T cells, and/or microglia in a corresponding subject that is not treated with the antibody. In other embodiments, an anti-CD33 antibody of the present disclosure may increase the rate of proliferation, survival, and/or function of dendritic cells, macrophages, monocytes, osteoclasts, Langerhans cells of skin, Kupffer cells, T cells, and/or microglia in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the rate of proliferation, survival, and/or function of dendritic cells, macrophages, monocytes, osteoclasts, Langerhans cells of skin, Kupffer cells, T cells, and/or microglia in a corresponding subject that is not treated with the antibody.

In some embodiments, anti-CD33 antibodies of the present disclosure are beneficial for preventing, lowering the risk of, or treating conditions and/or diseases associated with a reduction in proliferation, survival, increased apoptosis and/or function of dendritic cells, neutrophils, macrophages, monocytes, osteoclasts, Langerhans cells of skin, Kupffer cells, T cells, and/or microglia including without limitation, dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza.

CD33-Dependent Activation of Immune Cells

In some embodiments, antagonist anti-CD33 antibodies of the present disclosure may increase the activity of cytotoxic T cells helper T cells or both. In some embodiments, antagonist anti-CD33 antibodies of the present disclosure are beneficial for preventing, lowering the risk of, or treating conditions and/or diseases associated with decreased activity of cytotoxic T cells helper T cells or both, including without limitation, tumors, including solid tumors such as bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer.

In some embodiments, antagonist anti-CD33 antibodies of the present disclosure may induce an increase in proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells. In some embodiments, antagonist anti-CD33 antibodies of the present disclosure induce an increase in proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells in the presence of myeloid-derived suppressor cells (MDSC).

As used herein, the rate of proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells may include an increased rate if the rate of proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells in a subject treated with an anti-CD33 antibody of the present disclosure is greater than the rate of proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells in a corresponding subject that is not treated with the antibody. In some embodiments, an anti-CD33 antibody of the present disclosure may increase proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the level of proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells in a corresponding subject that is not treated with the antibody. In other embodiments, an anti-CD33 antibody of the present disclosure may increase proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the level of proliferation, survival, activity, and/or number of T cells, cytotoxic T cells, CD3$^+$ T cells, helper T cells, dendritic cells, macrophages, monocytes, neutrophils, osteoclasts, Langerhans cells of skin, Kupffer cells, and/or microglial cells in a corresponding subject that is not treated with the antibody.

CD33-Dependent Inhibition of Tumor-Associated Immune Cells

In some embodiments, agonist anti-CD33 antibodies of the present disclosure may decrease the activity, decrease the proliferation, decrease the survival, decrease the functionality, decrease infiltration to tumors or lymphoid organs (e.g., the spleen and lymph nodes), the number of CD14$^+$ myeloid cells, decrease tumor growth rate, reduce tumor volume, reduce or inhibit differentiation, survival, and/or one or more functions of myeloid-derived suppressor cells (MDSC), and/or promote apoptosis of T-regulatory cells or inhibitory tumor-imbedded immunosuppressor dendritic cells or, tumor-associated macrophages or, myeloid-derived suppressor cells. In some embodiments, agonist anti-CD33 antibodies of the present disclosure are beneficial for preventing, lowering the risk of, or treating conditions and/or diseases associated with the activity of one or more type of immune suppressor cells, including without limitation, tumors, including solid tumors that do not express CD33 such as bladder cancer, brain cancer, breast cancer, colon cancer, rectal cancer, endometrial cancer, kidney cancer, renal cell cancer, renal pelvis cancer, lung cancer, melanoma, non-Hodgkin's lymphoma, pancreatic cancer, prostate cancer, ovarian cancer, fibrosarcoma, thyroid cancer, and blood tumors that express CD33, such as leukemia cells.

In some embodiments, antagonist anti-CD33 antibodies of the present disclosure may decrease the number of CD14$^+$ myeloid cells, decrease tumor growth rate, reduce tumor volume, or reduce or inhibit differentiation, survival, and/or one or more functions of myeloid-derived suppressor cells (MDSC).

In some embodiments, an anti-CD33 antibody of the present disclosure may decrease the number of CD14$^+$ myeloid cells, decrease tumor growth rate, reduce tumor volume, or reduce or inhibit differentiation, survival, and/or one or more functions of myeloid-derived suppressor cells (MDSC) in a subject by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the number of CD14$^+$ myeloid cells, tumor growth rate, tumor volume, or level of differentiation, survival, and/or one or more functions of myeloid-derived suppressor cells (MDSC) in a corresponding subject that is not treated with the antibody. In other embodiments, an anti-CD33 antibody of the present disclosure, may decrease the number of CD14$^+$ myeloid cells, decrease tumor growth rate, reduce tumor volume, or reduce or inhibit differentiation, survival, and/or one or more functions of myeloid-derived suppressor cells (MDSC) in a subject by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the number of CD14$^+$ myeloid cells, tumor growth rate, tumor volume, or level of differentiation, survival, and/or one or more functions of myeloid-derived suppressor cells (MDSC) in a corresponding subject that is not treated with the antibody.

Increased Efficacy of Checkpoint Inhibitor Therapies

In some embodiments, antagonist anti-CD33 antibodies of the present disclosure may increase the efficacy of one or more checkpoint inhibitor therapies and/or immune-modulating therapies, such as PD-1 inhibitors or therapies that target one or more of CTL4, the adenosine pathway, PD-L1, PD-L2, OX40, TIM3, and/or LAG3.

In some embodiments, an anti-CD33 antibody of the present disclosure may increase the efficacy of one or more checkpoint inhibitor therapies and/or immune-modulating therapies, such as PD-1 inhibitors or therapies that target one or more of CTL4, the adenosine pathway, PD-L1, PD-L2, OX40, TIM3, and/or LAG3 in a subject receiving such one or more therapies by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the level of effectiveness of one or more checkpoint inhibitor therapies and/or immune-modulating therapies, such as PD-1 inhibitors or therapies that target one or more of CTL4, the adenosine pathway, PD-L1, PD-L2, OX40, TIM3, and/or LAG3 in a corresponding subject receiving such one or more therapies that is not treated with the antibody. In other embodiments, an anti-CD33 antibody of the present disclosure may increase the efficacy of one or more checkpoint inhibitor therapies and/or immune-modulating therapies, such as PD-1 inhibitors or therapies that target one or more of CTL4, the adenosine pathway, PD-L1, PD-L2, OX40, TIM3, and/or LAG3 in a subject receiving such one or more therapies by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the level of effectiveness of one or more checkpoint inhibitor therapies and/or immune-modulating therapies, such as PD-1 inhibitors or therapies that target one or more of CTL4, the adenosine pathway, PD-L1, PD-L2, OX40, TIM3, and/or LAG3 in a corresponding subject receiving such one or more therapies that is not treated with the antibody.

Increased Efficacy of Chemotherapeutic Agents

In some embodiments, antagonist anti-CD33 antibodies of the present disclosure may increase the efficacy of one or more chemotherapy agents, such as gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), oxaliplatin (Elotaxin®), leucovorin, and/or temozolomide (Temodar®).

In some embodiments, an anti-CD33 antibody of the present disclosure may increase the efficacy of one or more chemotherapy agents in a subject receiving such one or more therapies by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 100%, at least 110%, at least 115%, at least 120%, at least 125%, at least 130%, at least 135%, at least 140%, at least 145%, at least 150%, at least 160%, at least 170%, at least 180%, at least 190%, or at least 200% for example, as compared to the level of effectiveness of one or more chemotherapy agents in a corresponding subject receiving such one or more therapies that is not treated with the antibody. In other embodiments, an anti-CD33 antibody of the present disclosure may increase the efficacy of one or more chemotherapy agents in a subject receiving such one or more therapies by at least 1.5 fold, at least 1.6 fold, at least 1.7 fold, at least 1.8 fold, at least 1.9 fold, at least 2.0 fold, at least 2.1 fold, at least 2.15 fold, at least 2.2 fold, at least 2.25 fold, at least 2.3 fold, at least 2.35 fold, at least 2.4 fold, at least 2.45 fold, at least 2.5 fold, at least 2.55 fold, at least 3.0 fold, at least 3.5 fold, at least 4.0 fold, at least 4.5 fold, at least 5.0 fold, at least 5.5 fold, at least 6.0 fold, at least 6.5 fold, at least 7.0 fold, at least 7.5 fold, at least 8.0 fold, at least 8.5 fold, at least 9.0 fold, at least 9.5 fold, or at least 10 fold, for example, as compared to the level of effectiveness of one or more chemotherapy agents in a corresponding subject receiving such one or more therapies that is not treated with the antibody.

Antibody Preparation

Anti-CD33 antibodies of the present disclosure can encompass polyclonal antibodies, monoclonal antibodies, humanized and chimeric antibodies, human antibodies, antibody fragments (e.g., Fab, Fab'-SH, Fv, scFv, and F(ab')$_2$), bispecific and polyspecific antibodies, multivalent antibodies, heteroconjugate antibodies, conjugated antibodies, library derived antibodies, antibodies having modified effector functions, fusion proteins containing an antibody portion, and any other modified configuration of the immunoglobulin molecule that includes an antigen recognition site, such as an epitope having amino acid residues of a CD33 protein of the present disclosure, including glycosylation variants of antibodies, amino acid sequence variants of antibodies, and covalently modified antibodies. The anti-CD33 antibodies may be human, murine, rat, or of any other origin (including chimeric or humanized antibodies).

(1) Polyclonal Antibodies

Polyclonal antibodies, such as polyclonal anti-CD33 antibodies, are generally raised in animals by multiple subcutaneous (sc) or intraperitoneal (ip) injections of the relevant antigen and an adjuvant. It may be useful to conjugate the relevant antigen (e.g., a purified or recombinant CD33 protein of the present disclosure) to a protein that is immunogenic in the species to be immunized, e.g., keyhole limpet hemocyanin (KLH), serum albumin, bovine thyroglobulin, or soybean trypsin inhibitor, using a bifunctional or derivatizing agent, e.g., maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are independently lower alkyl groups. Examples of adjuvants which may be employed include Freund's complete adjuvant and MPL-TDM adjuvant (monophosphoryl Lipid A, synthetic trehalose dicorynomycolate). The immunization protocol may be selected by one skilled in the art without undue experimentation.

The animals are immunized against the desired antigen, immunogenic conjugates, or derivatives by combining, e.g., 100 μg (for rabbits) or 5 (for mice) of the protein or conjugate with 3 volumes of Freund's complete adjuvant and injecting the solution intradermally at multiple sites. One month later, the animals are boosted with ⅕ to 1/10 the original amount of peptide or conjugate in Freund's complete adjuvant by subcutaneous injection at multiple sites. Seven to fourteen days later, the animals are bled and the serum is assayed for antibody titer. Animals are boosted until the titer plateaus. Conjugates also can be made in recombinant cell culture as protein fusions. Also, aggregating agents such as alum are suitable to enhance the immune response.

(2) Monoclonal Antibodies

Monoclonal antibodies, such as monoclonal anti-CD33 antibodies, are obtained from a population of substantially homogeneous antibodies, i.e., the individual antibodies comprising the population are identical except for possible naturally occurring mutations and/or post-translational modifications (e.g., isomerizations, amidations) that may be present in minor amounts. Thus, the modifier "monoclonal" indicates the character of the antibody as not being a mixture of discrete antibodies.

For example, the monoclonal anti-CD33 antibodies may be made using the hybridoma method first described by Kohler et al., Nature, 256:495 (1975), or may be made by recombinant DNA methods (U.S. Pat. No. 4,816,567).

In the hybridoma method, a mouse or other appropriate host animal, such as a hamster, is immunized as hereinabove described to elicit lymphocytes that produce or are capable of producing antibodies that will specifically bind to the protein used for immunization (e.g., a purified or recombinant CD33 protein of the present disclosure). Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The immunizing agent will typically include the antigenic protein (e.g., a purified or recombinant CD33 protein of the present disclosure) or a fusion variant thereof. Generally peripheral blood lymphocytes ("PBLs") are used if cells of human origin are desired, while spleen or lymph node cells are used if non-human mammalian sources are desired. The lymphoctyes are then fused with an immortalized cell line using a suitable fusing agent, such as polyethylene glycol, to form a hybridoma cell. Goding, Monoclonal Antibodies: Principles and Practice, Academic Press (1986), pp. 59-103.

Immortalized cell lines are usually transformed mammalian cells, particularly myeloma cells of rodent, bovine or human origin. Usually, rat or mouse myeloma cell lines are employed. The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which are substances that prevent the growth of HGPRT-deficient cells.

Preferred immortalized myeloma cells are those that fuse efficiently, support stable high-level production of antibody by the selected antibody-producing cells, and are sensitive to a medium such as HAT medium. Among these, preferred are murine myeloma lines, such as those derived from MOPC-21 and MPC-11 mouse tumors (available from the Salk Institute Cell Distribution Center, San Diego, Calif. USA), as well as SP-2 cells and derivatives thereof (e.g., X63-Ag8-653) (available from the American Type Culture Collection, Manassas, Va. USA). Human myeloma and mouse-human heteromyeloma cell lines have also been described for the production of human monoclonal antibodies (Kozbor, J. Immunol., 133:3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen (e.g., a CD33 protein of the present disclosure). Preferably, the binding specificity of monoclonal antibodies produced by hybridoma cells is determined by immunoprecipitation or by an in vitro binding assay, such as radioimmunoassay (RIA) or enzyme-linked immunosorbent assay (ELISA).

The culture medium in which the hybridoma cells are cultured can be assayed for the presence of monoclonal antibodies directed against the desired antigen (e.g., a CD33 protein of the present disclosure). Preferably, the binding affinity and specificity of the monoclonal antibody can be determined by immunoprecipitation or by an in vitro binding assay, such as radioimmunoassay (RIA) or enzyme-linked assay (ELISA). Such techniques and assays are known in the in art. For example, binding affinity may be determined by the Scatchard analysis of Munson et al., Anal. Biochem., 107:220 (1980).

After hybridoma cells are identified that produce antibodies of the desired specificity, affinity, and/or activity, the clones may be subcloned by limiting dilution procedures and grown by standard methods (Goding, supra). Suitable culture media for this purpose include, for example, D-MEM or RPMI-1640 medium. In addition, the hybridoma cells may be grown in vivo as tumors in a mammal.

The monoclonal antibodies secreted by the subclones are suitably separated from the culture medium, ascites fluid, or serum by conventional immunoglobulin purification procedures such as, for example, protein A-Sepharose chromatography, hydroxylapatite chromatography, gel electrophoresis, dialysis, affinity chromatography, and other methods as described above.

Anti-CD33 monoclonal antibodies may also be made by recombinant DNA methods, such as those disclosed in U.S.

Pat. No. 4,816,567, and as described above. DNA encoding the monoclonal antibodies is readily isolated and sequenced using conventional procedures (e.g., by using oligonucleotide probes that specifically bind to genes encoding the heavy and light chains of murine antibodies). The hybridoma cells serve as a preferred source of such DNA. Once isolated, the DNA may be placed into expression vectors, which are then transfected into host cells such as *E. coli* cells, simian COS cells, Chinese hamster ovary (CHO) cells, or myeloma cells that do not otherwise produce immunoglobulin protein, in order to synthesize monoclonal antibodies in such recombinant host cells. Review articles on recombinant expression in bacteria of DNA encoding the antibody include Skerra et al., *Curr. Opin. Immunol.*, 5:256-262 (1993) and Plückthun, *Immunol. Rev.* 130:151-188 (1992).

In certain embodiments, anti-CD33 antibodies can be isolated from antibody phage libraries generated using the techniques described in McCafferty et al., *Nature*, 348:552-554 (1990). Clackson et al., *Nature*, 352:624-628 (1991) and Marks et al., *J. Mol. Biol.*, 222:581-597 (1991) described the isolation of murine and human antibodies, respectively, from phage libraries. Subsequent publications describe the production of high affinity (nanomolar ("nM") range) human antibodies by chain shuffling (Marks et al., *Bio/Technology*, 10:779-783 (1992)), as well as combinatorial infection and in vivo recombination as a strategy for constructing very large phage libraries (Waterhouse et al., *Nucl. Acids Res.*, 21:2265-2266 (1993)). Thus, these techniques are viable alternatives to traditional monoclonal antibody hybridoma techniques for isolation of monoclonal antibodies of desired specificity (e.g., those that bind a CD33 protein of the present disclosure).

The DNA encoding antibodies or fragments thereof may also be modified, for example, by substituting the coding sequence for human heavy- and light-chain constant domains in place of the homologous murine sequences (U.S. Pat. No. 4,816,567; Morrison, et al., *Proc. Natl Acad. Sci. USA*, 81:6851 (1984)), or by covalently joining to the immunoglobulin coding sequence all or part of the coding sequence for a non-immunoglobulin polypeptide. Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

The monoclonal antibodies described herein (e.g., anti-CD33 antibodies of the present disclosure or fragments thereof) may by monovalent, the preparation of which is well known in the art. For example, one method involves recombinant expression of immunoglobulin light chain and a modified heavy chain. The heavy chain is truncated generally at any point in the Fc region so as to prevent heavy chain crosslinking. Alternatively, the relevant cysteine residues may be substituted with another amino acid residue or are deleted so as to prevent crosslinking. In vitro methods are also suitable for preparing monovalent antibodies. Digestion of antibodies to produce fragments thereof, particularly Fab fragments, can be accomplished using routine techniques known in the art.

Chimeric or hybrid anti-CD33 antibodies also may be prepared in vitro using known methods in synthetic protein chemistry, including those involving crosslinking agents. For example, immunotoxins may be constructed using a disulfide-exchange reaction or by forming a thioether bond. Examples of suitable reagents for this purpose include iminothiolate and methyl-4-mercaptobutyrimidate.

(3) Humanized Antibodies

Anti-CD33 antibodies of the present disclosure or antibody fragments thereof may further include humanized or human antibodies. Humanized forms of non-human (e.g., murine) antibodies are chimeric immunoglobulins, immunoglobulin chains or fragments thereof (such as Fab, Fab'-SH, Fv, scFv, F(ab')$_2$ or other antigen-binding subsequences of antibodies) which contain minimal sequence derived from non-human immunoglobulin. Humanized antibodies include human immunoglobulins (recipient antibody) in which residues from a complementarity determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally will also comprise at least a portion of an immunoglobulin constant region (Fc), typically that of a human immunoglobulin. Jones et al., *Nature* 321: 522-525 (1986); Riechmann et al., *Nature* 332: 323-329 (1988) and Presta, *Curr. Opin. Struct. Biol.* 2: 593-596 (1992).

Methods for humanizing non-human antibodies are well known in the art. Generally, a humanized antibody has one or more amino acid residues introduced into it from a source which is non-human. These non-human amino acid residues are often referred to as "import" residues, which are typically taken from an "import" variable domain Humanization can be essentially performed following the method of Winter and co-workers, Jones et al., *Nature* 321:522-525 (1986); Riechmann et al., *Nature* 332:323-327 (1988); Verhoeyen et al., *Science* 239:1534-1536 (1988), or through substituting rodent CDRs or CDR sequences for the corresponding sequences of a human antibody. Accordingly, such "humanized" antibodies are chimeric antibodies (U.S. Pat. No. 4,816,567), wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody. Sims et al., *J. Immunol.*, 151:2296 (1993); Chothia et al., *J. Mol. Biol.*, 196:901 (1987). Another method uses a particular framework derived from the consensus sequence of all human antibodies of a particular subgroup of light or heavy chains. The same framework may be used for several different humanized antibodies. Carter et al., *Proc. Nat'l Acad. Sci. USA* 89:4285 (1992); Presta et al., *J. Immunol.* 151:2623 (1993).

Furthermore, it is important that antibodies be humanized with retention of high affinity for the antigen and other favorable biological properties. To achieve this goal, according to a preferred method, humanized antibodies are prepared by a process of analyzing the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen or antigens (e.g., CD33 proteins of the present disclosure), is achieved. In general, the CDR residues are directly and most substantially involved in influencing antigen binding.

Various forms of the humanized anti-CD33 antibody are contemplated. For example, the humanized anti-CD33 antibody may be an antibody fragment, such as an Fab, which is optionally conjugated with one or more cytotoxic agent(s) in order to generate an immunoconjugate. Alternatively, the humanized anti-CD33 antibody may be an intact antibody, such as an intact IgG1 antibody.

(4) Antibody Fragments

In certain embodiments there are advantages to using anti-CD33 antibody fragments, rather than whole anti-CD33 antibodies. Smaller fragment sizes allow for rapid clearance and better brain penetration.

Various techniques have been developed for the production of antibody fragments. Traditionally, these fragments were derived via proteolytic digestion of intact antibodies (see, e.g., Morimoto et al., *J. Biochem. Biophys. Method.* 24:107-117 (1992); and Brennan et al., *Science* 229:81 (1985)). However, these fragments can now be produced directly by recombinant host cells, for example, using nucleic acids encoding anti-CD33 antibodies of the present disclosure. Fab, Fv and scFv antibody fragments can all be expressed in and secreted from *E. coli*, thus allowing the straightforward production of large amounts of these fragments. A anti-CD33 antibody fragments can also be isolated from the antibody phage libraries as discussed above. Alternatively, Fab'-SH fragments can be directly recovered from *E. coli* and chemically coupled to form F(ab')$_2$ fragments (Carter et al., *Bio/Technology* 10:163-167 (1992)). According to another approach, F(ab')$_2$ fragments can be isolated directly from recombinant host cell culture. Production of Fab and F(ab')$_2$ antibody fragments with increased in vivo half-lives are described in U.S. Pat. No. 5,869,046. In other embodiments, the antibody of choice is a single chain Fv fragment (scFv). See WO 93/16185; U.S. Pat. Nos. 5,571,894 and 5,587,458. The anti-CD33 antibody fragment may also be a "linear antibody," e.g., as described in U.S. Pat. No. 5,641,870. Such linear antibody fragments may be monospecific or bispecific.

(5) Bispecific and Polyspecific Antibodies

Bispecific antibodies (BsAbs) are antibodies that have binding specificities for at least two different epitopes, including those on the same or another protein (e.g., one or more CD33 proteins of the present disclosure). Alternatively, one part of a BsAb can be armed to bind to the target CD33 antigen, and another can be combined with an arm that binds to a second protein. Such antibodies can be derived from full length antibodies or antibody fragments (e.g., F(ab')$_2$ bispecific antibodies).

Methods for making bispecific antibodies are known in the art. Traditional production of full length bispecific antibodies is based on the coexpression of two immunoglobulin heavy-chain/light chain pairs, where the two chains have different specificities. Millstein et al., *Nature*, 305:537-539 (1983). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829 and in Traunecker et al., *EMBO J.,* 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, $C_H2$, and $C_H3$ regions. It is preferred to have the first heavy-chain constant region ($C_H1$) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only half of the bispecific molecules provides for an easy way of separation. This approach is disclosed in WO 94/04690. For further details of generating bispecific antibodies, see, for example, Suresh et al., *Methods in Enzymology* 121: 210 (1986).

According to another approach described in WO 96/27011 or U.S. Pat. No. 5,731,168, the interface between a pair of antibody molecules can be engineered to maximize the percentage of heterodimers which are recovered from recombinant cell culture. The preferred interface comprises at least a part of the $C_H3$ region of an antibody constant domain. In this method, one or more small amino acid side chains from the interface of the first antibody molecule are replaced with larger side chains (e.g., tyrosine or tryptophan). Compensatory "cavities" of identical or similar size to the large side chains(s) are created on the interface of the second antibody molecule by replacing large amino acid side chains with smaller ones (e.g., alanine or threonine).

This provides a mechanism for increasing the yield of the heterodimer over other unwanted end-products such as homodimers.

Techniques for generating bispecific antibodies from antibody fragments have been described in the literature. For example, bispecific antibodies can be prepared using chemical linkage. Brennan et al., *Science* 229:81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-TNB derivative to form the bispecific antibody. The bispecific antibodies produced can be used as agents for the selective immobilization of enzymes.

Fab' fragments may be directly recovered from *E. coli* and chemically coupled to form bispecific antibodies. Shalaby et al., *J. Exp. Med.* 175: 217-225 (1992) describes the production of fully humanized bispecific antibody F(ab')$_2$ molecules. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bivalent antibody fragments directly from recombinant cell culture have also been described. For example, bivalent heterodimers have been produced using leucine zippers. Kostelny et al., *J. Immunol.*, 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. The "diabody" technology described by Hollinger et al., *Proc. Nat'l Acad. Sci. USA*, 90: 6444-6448 (1993) has provided an alternative mechanism for making bispecific/bivalent antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific/bivalent antibody fragments by the use of single-chain Fv (sFv) dimers has also been reported. See Gruber et al., *J. Immunol.*, 152:5368 (1994).

Antibodies with more than two valencies are also contemplated. For example, trispecific antibodies can be prepared. Tutt et al., *J. Immunol.* 147:60 (1991).

Exemplary bispecific antibodies may bind to two different epitopes on a given molecule (e.g., a CD33 protein of the present disclosure). Alternatively, an arm targeting a CD33 signaling component may be combined with an arm which binds to a triggering molecule on a leukocyte such as a T cell receptor molecule (e.g., CD2, CD3, CD28 or B7), or Fc receptors for IgG (FcγR), such as FcγRI (CD64), FcγRII (CD32) and FcγRIII (CD16) so as to focus cellular defense mechanisms to the cell expressing the particular protein. Bispecific antibodies may also be used to localize cytotoxic agents to cells which express a particular protein. Such antibodies possess a protein-binding arm and an arm which binds a cytotoxic agent or a radionuclide chelator, such as EOTUBE, DPTA, DOTA or TETA. Another bispecific antibody of interest binds the protein of interest and further binds tissue factor (TF).

(6) Multivalent Antibodies

A multivalent antibody may be internalized (and/or catabolized) faster than a bivalent antibody by a cell expressing an antigen to which the antibodies bind. The anti-CD33 antibodies of the present disclosure or antibody fragments thereof can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises an Fc region or a hinge region. In this scenario, the antibody will comprise an Fc region and three or more antigen binding sites amino-terminal to the Fc region. The preferred multivalent antibody herein contains three to about eight, but preferably four, antigen binding sites. The multivalent antibody contains at least one polypeptide chain (and preferably two polypeptide chains), wherein the polypeptide chain or chains comprise two or more variable domains. For instance, the polypeptide chain or chains may comprise VD1-(X1)n-VD2-(X2)n-Fc, wherein VD1 is a first variable domain, VD2 is a second variable domain, Fc is one polypeptide chain of an Fc region, X1 and X2 represent an amino acid or polypeptide, and n is 0 or 1. Similarly, the polypeptide chain or chains may comprise $V_H$-$C_H$1-flexible linker-$V_H$-$C_H$1-Fc region chain; or $V_H$-$C_H$1-$V_H$-$C_H$1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain. The multivalent antibodies may recognize the CD33 antigen as well as, without limitation, additional antigens A beta peptide, antigen or an alpha synuclain protein antigen or, Tau protein antigen or, TDP-43 protein antigen or, prion protein antigen or, huntingtin protein antigen, or RAN, translation Products antigen, including the DiPeptide Repeats, (DPRs peptides) composed of glycine-alanine (GA), glycine-proline (GP), glycine-arginine (GR), proline-alanine (PA), or proline-arginine (PR), insulin receptor, insulin like growth factor receptor, transferrin receptor, or any other antigen that facilitates antibody transfer across the blood brain barrier.

(7) Heteroconjugate Antibodies

Heteroconjugate antibodies are also within the scope of the present disclosure. Heteroconjugate antibodies are composed of two covalently joined antibodies (e.g., anti-CD33 antibodies of the present disclosure or antibody fragments thereof). For example, one of the antibodies in the heteroconjugate can be coupled to avidin, the other to biotin. Such antibodies have, for example, been proposed to target immune system cells to unwanted cells, U.S. Pat. No. 4,676,980, and have been used to treat HIV infection. International Publication Nos. WO 91/00360, WO 92/200373 and EP 0308936. It is contemplated that the antibodies may be prepared in vitro using known methods in synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980. Heteroconjugate antibodies may be made using any convenient cross-linking methods. Suitable cross-linking agents are well known in the art, and are disclosed in U.S. Pat. No. 4,676,980, along with a number of cross-linking techniques.

(8) Effector Function Engineering

It may also be desirable to modify an anti-CD33 antibody of the present disclosure to modify effector function and/or to increase serum half-life of the antibody. For example, the Fc receptor binding site on the constant region may be modified or mutated to remove or reduce binding affinity to certain Fc receptors, such as FcγRI, FcγRII, and/or FcγRIII. In some embodiments, the effector function is impaired by removing N-glycosylation of the Fc region (e.g., in the CH 2 domain of IgG) of the antibody. In some embodiments, the effector function is impaired by modifying regions such as 233-236, 297, and/or 327-331 of human IgG as described in PCT WO 99/58572 and Armour et al., *Molecular Immunology* 40: 585-593 (2003); Reddy et al., *J. Immunology* 164:1925-1933 (2000).

To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule.

(9) Other Amino Acid Sequence Modifications

Amino acid sequence modifications of anti-CD33 antibodies of the present disclosure, or antibody fragments thereof, are also contemplated. For example, it may be desirable to improve the binding affinity and/or other biological properties of the antibodies or antibody fragments Amino acid sequence variants of the antibodies or antibody fragments are prepared by introducing appropriate nucleotide changes into the nucleic acid encoding the antibodies or antibody fragments, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics (i.e., the ability to bind or physically interact with a CD33 protein of the present disclosure). The amino acid changes also may alter post-translational processes of the antibody, such as changing the number or position of glycosylation sites.

A useful method for identification of certain residues or regions of the anti-CD33 antibody that are preferred locations for mutagenesis is called "alanine scanning mutagenesis" as described by Cunningham and Wells in *Science*, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with the target antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, alanine scanning or random mutagenesis is conducted at the target codon or region and the expressed antibody variants are screened for the desired activity.

Amino acid sequence insertions include amino- ("N") and/or carboxy- ("C") terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in the Table D below under the heading of "preferred substitutions". If such substitutions result in a change in biological activity, then more substantial changes, denominated "exemplary substitutions" in Table D, or as further described below in reference to amino acid classes, may be introduced and the products screened.

TABLE D

Amino acid substitutions

| Original Residue | Exemplary Substitutions | Preferred Substitutions |
|---|---|---|
| Ala (A) | val; leu; ile | val |
| Arg (R) | lys; gln; asn | lys |
| Asn (N) | gln; his; asp, lys; arg | gln |
| Asp (D) | glu; asn | glu |
| Cys (C) | ser; ala | ser |
| Gln (Q) | asn; glu | asn |
| Glu (E) | asp; gln | asp |
| Gly (G) | ala | ala |
| His (H) | asn; gln; lys; arg | arg |
| Ile (I) | leu; val; met; ala; phe; norleucine | leu |
| Leu (L) | norleucine; ile; val; met; ala; phe | ile |
| Lys (K) | arg; gln; asn | arg |
| Met (M) | leu; phe; ile | leu |
| Phe (F) | leu; val; ile; ala; tyr | tyr |
| Pro (P) | ala | ala |
| Ser (S) | thr | thr |
| Thr (T) | Ser | ser |
| Trp (W) | tyr; phe | tyr |
| Tyr (Y) | trp; phe; thr; ser | phe |
| Val (V) | ile; leu; met; phe; ala; norleucine | leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) hydrophobic: norleucine, met, ala, val, leu, ile;
(2) neutral hydrophilic: cys, ser, thr;
(3) acidic: asp, glu;
(4) basic: asn, gln, his, lys, arg;
(5) residues that influence chain orientation: gly, pro; and
(6) aromatic: trp, tyr, phe.

Non-conservative substitutions entail exchanging a member of one of these classes for another class.

Any cysteine residue not involved in maintaining the proper conformation of the antibody also may be substituted, generally with serine, to improve the oxidative stability of the molecule and prevent aberrant crosslinking Conversely, cysteine bond(s) may be added to the antibody to improve its stability (particularly where the antibody is an antibody fragment, such as an Fv fragment).

A particularly preferred type of substitutional variant involves substituting one or more hypervariable region residues of a parent antibody (e.g. a humanized or human anti-CD33 antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and the antigen (e.g., a CD33 protein of the present disclosure). Such contact residues and neighboring residues are candidates for substitution according to the techniques elaborated herein. Once such variants are generated, the panel of variants is subjected to screening as described herein and antibodies with superior properties in one or more relevant assays may be selected for further development. Affinity maturation may also be performed by employing a yeast presentation technology such as that disclosed in, for example, WO2009/036379A2; WO2010105256; WO2012009568; and Xu et al., Protein Eng. Des. Sel., 26(10): 663-70 (2013).

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Nucleic acid molecules encoding amino acid sequence variants of the anti-IgE antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibodies (e.g., anti-CD33 antibodies of the present disclosure) or antibody fragments.

(10) Antibody Conjugates

Anti-CD33 antibodies of the present disclosure, or antibody fragments thereof, can be conjugated to a detectable marker, a toxin, or a therapeutic agent. Any suitable method known in the art for conjugating molecules, such as a detectable marker, a toxin, or a therapeutic agent to antibodies may be used.

For example, drug conjugation involves coupling of a biological active cytotoxic (anticancer) payload or drug to an antibody that specifically targets a certain tumor marker (e.g. a protein that, ideally, is only to be found in or on tumor cells). Antibodies track these proteins down in the body and attach themselves to the surface of cancer cells. The biochemical reaction between the antibody and the target protein (antigen) triggers a signal in the tumor cell, which then absorbs or internalizes the antibody together with the cytotoxin. After the ADC is internalized, the cytotoxic drug is released and kills the cancer. Due to this targeting, ideally the drug has lower side effects and gives a wider therapeutic window than other chemotherapeutic agents. Technics to conjugate antibodies are disclosed are known in the art (see, e.g., Jane de Lartigue, OncLive Jul. 5, 2012; ADC Review on antibody-drug conjugates; and Ducry et al., (2010). *Bioconjugate Chemistry* 21 (1): 5-13).

In some embodiments, an anti-CD33 antibody of the present disclosure may be conjugated to a toxin selected from ricin, ricin A-chain, doxorubicin, daunorubicin, a maytansinoid, taxol, ethidium bromide, mitomycin, etoposide, tenoposide, vincristine, vinblastine, colchicine, dihydroxy anthracin dione, actinomycin, diphtheria toxin, *Pseudomonas* exotoxin (PE) A, PE40, abrin, abrin A chain, modeccin A chain, alpha-sarcin, gelonin, mitogellin, retstrictocin, phenomycin, enomycin, curicin, crotin, calicheamicin, *Saponaria officinalis* inhibitor, glucocorticoid, auristatin, auromycin, yttrium, bismuth, combrestatin, duocarmycins, dolastatin, cc1065, and a cisplatin.

(11) Other Antibody Modifications

Anti-CD33 antibodies of the present disclosure, or antibody fragments thereof, can be further modified to contain additional non-proteinaceous moieties that are known in the art and readily available. Preferably, the moieties suitable for derivatization of the antibody are water-soluble polymers. Non-limiting examples of water-soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone)polyethylene glycol, polypropylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc. Such techniques and other suitable formulations are disclosed in *Remington: The Science and Practice of Pharmacy,* 20th Ed., Alfonso Gennaro, Ed., Philadelphia College of Pharmacy and Science (2000).

Binding Assays and Other Assays

Anti-CD33 antibodies of the present disclosure may be tested for antigen binding activity, e.g., by known methods such as ELISA, surface plasmon resonance (SPR), Western blot, etc.

In some embodiments, competition assays may be used to identify an antibody that competes with any of the antibodies described herein. In some embodiments, competition assays may be used to identify an antibody that competes with any of the antibodies listed in Tables 3A-3C, 4A-34, 5A-5D, 6A-6D, 7, and 8, or selected from AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, AB-64.1.15, AB-H2, AB-H9, AB-H14, AB-H15, AB-H63, AB-H64, AB-H65, or AB-H66 for binding to CD33. In certain embodiments, such a competing antibody binds to the same epitope (e.g., a linear or a conformational epitope) that is bound by any of the antibodies listed in Tables 3A-3C, 4A-4C, 5A-5D, 6A-6D, 7, and 8, or selected from AB-14.1, AB-14.2, AB-14.3, AB-14.4, AB-14.5, AB-14.6, AB-14.7, AB-14.8, AB-14.9, AB-14.10, AB-14.11, AB-63.4, AB-63.5, AB-63.6, AB-63.7, AB-63.8, AB-63.9, AB-63.10, AB-63.11, AB-63.12, AB-63.13, AB-63.14, AB-63.15, AB-63.16, AB-63.17, AB-63.18, AB-64.1, AB-64.2, AB-64.3, AB-64.4, AB-64.5, AB-64.6, AB-64.7, AB-64.8, AB-64.1.1, AB-64.1.2, AB-64.1.3, AB-64.1.4, AB-64.1.5, AB-64.1.6, AB-64.1.7, AB-64.1.8, AB-64.1.9, AB-64.1.10, AB-64.1.11, AB-64.1.12, AB-64.1.13, AB-64.1.14, AB-64.1.15, AB-H2, AB-H9, AB-H14, AB-H15, AB-H63, AB-H64, AB-H65, or AB-H66. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

In an exemplary competition assay, immobilized CD33 or cells expressing CD33 on a cell surface are incubated in a solution comprising a first labeled antibody that binds to CD33 (e.g., human or non-human primate) and a second unlabeled antibody that is being tested for its ability to compete with the first antibody for binding to CD33. The second antibody may be present in a hybridoma supernatant. As a control, immobilized CD33 or cells expressing CD33 is incubated in a solution comprising the first labeled antibody but not the second unlabeled antibody. After incubation under conditions permissive for binding of the first antibody to CD33, excess unbound antibody is removed, and the amount of label associated with immobilized CD33 or cells expressing CD33 is measured. If the amount of label associated with immobilized CD33 or cells expressing CD33 is substantially reduced in the test sample relative to the control sample, then that indicates that the second antibody is competing with the first antibody for binding to CD33. See, Harlow and Lane (1988) *Antibodies: A Laboratory Manual* ch. 14 (Cold Spring Harbor Laboratory, Cold Spring Harbor, N.Y.).

Nucleic Acids, Vectors, and Host Cells

Anti-CD33 antibodies of the present disclosure may be produced using recombinant methods and compositions, e.g., as described in U.S. Pat. No. 4,816,567. In some embodiments, isolated nucleic acids having a nucleotide sequence encoding any of the anti-CD33 antibodies of the present disclosure are provided. Such nucleic acids may encode an amino acid sequence containing the VL and/or an amino acid sequence containing the VH of the anti-CD33 antibody (e.g., the light and/or heavy chains of the antibody). In some embodiments, one or more vectors (e.g., expression vectors) containing such nucleic acids are provided. In some embodiments, a host cell containing such nucleic acid is also provided. In some embodiments, the host cell contains (e.g., has been transduced with): (1) a vector containing a nucleic acid that encodes an amino acid sequence containing the VL of the antibody and an amino acid sequence containing the VH of the antibody, or (2) a first vector containing a nucleic acid that encodes an amino acid sequence containing the VL of the antibody and a second vector containing a nucleic acid that encodes an amino acid sequence containing the VH of the antibody. In some embodiments, the host cell is eukaryotic, e.g., a Chinese Hamster Ovary (CHO) cell or lymphoid cell (e.g., Y0, NS0, Sp20 cell).

Methods of making an anti-CD33 antibody of the present disclosure are provided. In some embodiments, the method includes culturing a host cell of the present disclosure containing a nucleic acid encoding the anti-CD33 antibody, under conditions suitable for expression of the antibody. In some embodiments, the antibody is subsequently recovered from the host cell (or host cell culture medium).

For recombinant production of an anti-CD33 antibody of the present disclosure, a nucleic acid encoding the anti-CD33 antibody is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable vectors containing a nucleic acid sequence encoding any of the anti-CD33 antibodies of the present disclosure, or fragments thereof polypeptides (including antibodies) described herein include, without limitation, cloning vectors and expression vectors. Suitable cloning vectors can be constructed according to standard techniques, or may be selected from a large number of cloning vectors available in the art. While the cloning vector selected may vary according to the host cell intended to be used, useful cloning vectors generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mpl8, mpl9, pBR322, pMB9, ColE1, pCR1, RP4, phage DNAs, and shuttle vectors such as pSA3 and pAT28. These and many other cloning vectors are available from commercial vendors such as BioRad, Strategene, and Invitrogen.

Expression vectors generally are replicable polynucleotide constructs that contain a nucleic acid of the present disclosure. The expression vector may replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the nucleic acids of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell. In some embodiments, the vector contains a nucleic acid containing one or more amino acid sequences encoding an anti-CD33 antibody of the present disclosure.

Suitable host cells for cloning or expression of antibody-encoding vectors include prokaryotic or eukaryotic cells. For example, anti-CD33 antibodies of the present disclosure may be produced in bacteria, in particular when glycosylation and Fc effector function are not needed. For expression of antibody fragments and polypeptides in bacteria (e.g., U.S. Pat. Nos. 5,648,237, 5,789,199, and 5,840,523; and Charlton, *Methods in Molecular Biology*, Vol. 248 (B. K. C. Lo, ed., Humana Press, Totowa, N.J., 2003), pp. 245-254, describing expression of antibody fragments in *E. coli*). After expression, the antibody may be isolated from the bacterial cell paste in a soluble fraction and can be further purified.

In addition to prokaryotes, eukaryotic microorganisms, such as filamentous fungi or yeast, are also suitable cloning or expression hosts for antibody-encoding vectors, including fungi and yeast strains whose glycosylation pathways have been "humanized," resulting in the production of an antibody with a partially or fully human glycosylation pattern (e.g., Gerngross, *Nat. Biotech.* 22:1409-1414 (2004); and Li et al., *Nat. Biotech.* 24:210-215 (2006)).

Suitable host cells for the expression of glycosylated antibody can also be derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells. Plant cell cultures can also be utilized as hosts (e.g., U.S. Pat. Nos. 5,959,177, 6,040,498, 6,420,548, 7,125,978, and 6,417,429, describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in *Mather, Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR– CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

Pharmaceutical Compositions

Anti-CD33 antibodies of the present disclosure can be incorporated into a variety of formulations for therapeutic administration by combining the anti-CD33 antibodies with appropriate pharmaceutically acceptable carriers or diluents, and may be formulated into preparations in solid, semi-solid, liquid or gaseous forms. Examples of such formulations include, without limitation, tablets, capsules, powders, granules, ointments, solutions, suppositories, injections, inhalants, gels, microspheres, and aerosols. Pharmaceutical compositions can include, depending on the formulation desired, pharmaceutically-acceptable, non-toxic carriers of diluents, which are vehicles commonly used to formulate pharmaceutical compositions for animal or human administration. The diluent is selected so as not to affect the biological activity of the combination. Examples of such diluents include, without limitation, distilled water, buffered water, physiological saline, PBS, Ringer's solution, dextrose solution, and Hank's solution. A pharmaceutical composition or formulation of the present disclosure can further include other carriers, adjuvants, or non-toxic, nontherapeutic, non-immunogenic stabilizers, excipients and the like. The compositions can also include additional substances to approximate physiological conditions, such as pH adjusting and buffering agents, toxicity adjusting agents, wetting agents and detergents.

A pharmaceutical composition of the present disclosure can also include any of a variety of stabilizing agents, such as an antioxidant for example. When the pharmaceutical composition includes a polypeptide, the polypeptide can be complexed with various well-known compounds that enhance the in vivo stability of the polypeptide, or otherwise enhance its pharmacological properties (e.g., increase the half-life of the polypeptide, reduce its toxicity, and enhance solubility or uptake). Examples of such modifications or complexing agents include, without limitation, sulfate, gluconate, citrate and phosphate. The polypeptides of a composition can also be complexed with molecules that enhance their in vivo attributes. Such molecules include, without limitation, carbohydrates, polyamines, amino acids, other peptides, ions (e.g., sodium, potassium, calcium, magnesium, manganese), and lipids.

Further examples of formulations that are suitable for various types of administration can be found in Remington's *Pharmaceutical Sciences*, Mace Publishing Company, Philadelphia, Pa., 17th ed. (1985). For a brief review of methods for drug delivery, see, Langer, *Science* 249:1527-1533 (1990).

For oral administration, the active ingredient can be administered in solid dosage forms, such as capsules, tablets, and powders, or in liquid dosage forms, such as elixirs, syrups, and suspensions. The active component(s) can be encapsulated in gelatin capsules together with inactive ingredients and powdered carriers, such as glucose, lactose, sucrose, mannitol, starch, cellulose or cellulose derivatives, magnesium stearate, stearic acid, sodium saccharin, talcum, magnesium carbonate. Examples of additional inactive ingredients that may be added to provide desirable color, taste, stability, buffering capacity, dispersion or other known desirable features are red iron oxide, silica gel, sodium lauryl sulfate, titanium dioxide, and edible white ink. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric-coated for selective disintegration in the gastrointestinal tract. Liquid dosage forms for oral administration can contain coloring and flavoring to increase patient acceptance.

Formulations suitable for parenteral administration include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives.

The components used to formulate the pharmaceutical compositions are preferably of high purity and are substantially free of potentially harmful contaminants (e.g., at least National Food (NF) grade, generally at least analytical grade, and more typically at least pharmaceutical grade). Moreover, compositions intended for in vivo use are usually sterile. To the extent that a given compound must be synthesized prior to use, the resulting product is typically substantially free of any potentially toxic agents, particularly any endotoxins, which may be present during the synthesis or purification process. Compositions for parental administration are also sterile, substantially isotonic and made under GMP conditions.

Formulations may be optimized for retention and stabilization in the brain or central nervous system. When the agent is administered into the cranial compartment, it is desirable for the agent to be retained in the compartment, and not to diffuse or otherwise cross the blood brain barrier. Stabilization techniques include cross-linking, multimerizing, or linking to groups such as polyethylene glycol, polyacrylamide, neutral protein carriers, etc. in order to achieve an increase in molecular weight.

Other strategies for increasing retention include the entrapment of an anti-CD33 antibody of the present disclosure in a biodegradable or bioerodible implant. The rate of release of the therapeutically active agent is controlled by the rate of transport through the polymeric matrix, and the biodegradation of the implant. The transport of drug through the polymer barrier will also be affected by compound solubility, polymer hydrophilicity, extent of polymer cross-linking, expansion of the polymer upon water absorption so as to make the polymer barrier more permeable to the drug, geometry of the implant, and the like. The implants are of dimensions commensurate with the size and shape of the region selected as the site of implantation. Implants may be particles, sheets, patches, plaques, fibers, microcapsules and the like and may be of any size or shape compatible with the selected site of insertion.

The implants may be monolithic, i.e. having the active agent homogenously distributed through the polymeric matrix, or encapsulated, where a reservoir of active agent is encapsulated by the polymeric matrix. The selection of the polymeric composition to be employed will vary with the site of administration, the desired period of treatment, patient tolerance, the nature of the disease to be treated and the like. Characteristics of the polymers will include biodegradability at the site of implantation, compatibility with the agent of interest, ease of encapsulation, a half-life in the physiological environment.

Biodegradable polymeric compositions which may be employed may be organic esters or ethers, which when degraded result in physiologically acceptable degradation products, including the monomers. Anhydrides, amides, orthoesters or the like, by themselves or in combination with other monomers, may find use. The polymers will be condensation polymers. The polymers may be cross-linked or non-cross-linked. Of particular interest are polymers of hydroxyaliphatic carboxylic acids, either homo- or copolymers, and polysaccharides. Included among the polyesters of interest are polymers of D-lactic acid, L-lactic acid, racemic lactic acid, glycolic acid, polycaprolactone, and combinations thereof. By employing the L-lactate or D-lactate, a slowly biodegrading polymer is achieved, while degradation is substantially enhanced with the racemate. Copolymers of glycolic and lactic acid are of particular interest, where the rate of biodegradation is controlled by the ratio of glycolic to lactic acid. The most rapidly degraded copolymer has roughly equal amounts of glycolic and lactic acid, where either homopolymer is more resistant to degradation. The ratio of glycolic acid to lactic acid will also affect the brittleness of in the implant, where a more flexible implant is desirable for larger geometries. Among the polysaccharides of interest are calcium alginate, and functionalized celluloses, particularly carboxymethylcellulose esters characterized by being water insoluble, a molecular weight of about 5 kD to 500 kD, etc. Biodegradable hydrogels may also be employed in the implants of the present disclosure. Hydrogels are typically a copolymer material, characterized by the ability to imbibe a liquid. Exemplary biodegradable hydrogels which may be employed are described in Heller in: Hydrogels in Medicine and Pharmacy, N. A. Peppes ed., Vol. III, CRC Press, Boca Raton, Fla., 1987, pp 137-149.

Pharmaceutical Dosages

Pharmaceutical compositions of the present disclosure containing an anti-CD33 antibody of the present disclosure may be administered to an individual in need of treatment with the antibody, preferably a human, in accord with known methods, such as intravenous administration as a bolus or by continuous infusion over a period of time, by intramuscular, intraperitoneal, intracerobrospinal, intracranial, intraspinal, subcutaneous, intra-articular, intrasynovial, intrathecal, oral, topical, or inhalation routes.

Dosages and desired drug concentration of pharmaceutical compositions of the present disclosure may vary depending on the particular use envisioned. The determination of the appropriate dosage or route of administration is well within the skill of an ordinary artisan Animal experiments provide reliable guidance for the determination of effective doses for human therapy. Interspecies scaling of effective doses can be performed following the principles described in Mordenti, J. and Chappell, W. "The Use of Interspecies Scaling in Toxicokinetics," In *Toxicokinetics and New Drug Development*, Yacobi et al., Eds, Pergamon Press, New York 1989, pp. 42-46.

For in vivo administration of any of the anti-CD33 antibodies of the present disclosure, normal dosage amounts may vary from about 10 ng/kg up to about 100 mg/kg of an individual's body weight or more per day, preferably about 1 mg/kg/day to 10 mg/kg/day, depending upon the route of administration. For repeated administrations over several days or longer, depending on the severity of the disease, disorder, or condition to be treated, the treatment is sustained until a desired suppression of symptoms is achieved.

An exemplary dosing regimen may include administering an initial dose of an anti-CD33 antibody of about 2 mg/kg, followed by a weekly maintenance dose of about 1 mg/kg every other week. Other dosage regimens may be useful, depending on the pattern of pharmacokinetic decay that the physician wishes to achieve. For example, dosing an individual from one to twenty-one times a week is contemplated herein. In certain embodiments, dosing ranging from about 3 µg/kg to about 2 mg/kg (such as about 3 µg/kg, about 10 µg/kg, about 30 µg/kg, about 100 µg/kg, about 300 µg/kg, about 1 mg/kg, and about 2/mg/kg) may be used. In certain embodiments, dosing frequency is three times per day, twice per day, once per day, once every other day, once weekly, once every two weeks, once every four weeks, once every five weeks, once every six weeks, once every seven weeks, once every eight weeks, once every nine weeks, once every ten weeks, or once monthly, once every two months, once every three months, or longer. Progress of the therapy is easily monitored by conventional techniques and assays. The dosing regimen, including the anti-CD33 antibody administered, can vary over time independently of the dose used.

Dosages for a particular anti-CD33 antibody may be determined empirically in individuals who have been given one or more administrations of the anti-CD33 antibody. Individuals are given incremental doses of an anti-CD33 antibody. To assess efficacy of an anti-CD33 antibody, a clinical symptom of any of the diseases, disorders, or conditions of the present disclosure (e.g., frontotemporal dementia, Alzheimer's disease, vascular dementia, seizures, retinal dystrophy, a traumatic brain injury, a spinal cord injury, long-term depression, atherosclerotic vascular diseases, and undesirable symptoms of normal aging) can be monitored.

Administration of an anti-CD33 antibody of the present disclosure can be continuous or intermittent, depending, for example, on the recipient's physiological condition, whether the purpose of the administration is therapeutic or prophylactic, and other factors known to skilled practitioners. The administration of an anti-CD33 antibody, may be essentially continuous over a preselected period of time or may be in a series of spaced doses.

Guidance regarding particular dosages and methods of delivery is provided in the literature; see, for example, U.S. Pat. Nos. 4,657,760; 5,206,344; or 5,225,212. It is within the scope of the present disclosure that different formulations will be effective for different treatments and different disorders, and that administration intended to treat a specific organ or tissue may necessitate delivery in a manner different from that to another organ or tissue. Moreover, dosages may be administered by one or more separate administrations, or by continuous infusion. For repeated administrations over several days or longer, depending on the condition, the treatment is sustained until a desired suppression of disease symptoms occurs. However, other dosage regimens may be useful. The progress of this therapy is easily monitored by conventional techniques and assays.

Therapeutic Uses

As disclosed herein, anti-CD33 antibodies of the present disclosure may be used for preventing, reducing risk, or treating dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and/or *Haemophilus* influenza. In some embodiments, the CD33 antibodies are agonist antibodies. In some embodiments, the antibodies are inert antibodies. In some embodiments, the antibodies are antagonist antibodies.

In some embodiments, the present disclosure provides methods of preventing, reducing risk, or treating dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, cancer, bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and/or *Haemophilus* influenza, by administering to an individual in need thereof a therapeutically effective amount of an antibody of the present disclosure that decreases cellular levels of CD33, inhibits interaction between CD33 and one or more CD33 ligands, or both.

In some embodiments, the present disclosure provides methods of preventing, reducing risk, or treating cancer, by administering to an individual in need thereof, a therapeutically effective amount of an antibody of the present disclosure that decreases cellular levels of CD33, inhibits interaction between CD33 and one or more CD33 ligands, or both. In some embodiments, the antibody inhibits one or more CD33 activities selected from: (a) promoting proliferation, maturation, migration, differentiation, and/or functionality of one or more of immunosuppressor dendritic cells, immunosuppressor macrophages, immunosuppressor neutrophils, non-tumorigenic myeloid derived suppressor cells, tumor-associated macrophages, non-tumorigenic $CD14^+$ myeloid cells, and regulatory T cells; (b) enhancing infiltration of one or more of immunosuppressor dendritic cells, immunosuppressor macrophages, immunosuppressor neutrophils, non-tumorigenic myeloid derived suppressor cells, tumor-associated macrophages, and regulatory T cells into tumors; (c) increasing number of tumor-promoting myeloid/granulocytic immune-suppressive cells and/or non-tumorigenic $CD14^+$ myeloid cells in a tumor, in peripheral blood, or other lymphoid organ; (d) decreasing activation of tumor-specific T lymphocytes with tumor killing potential; (e) decreasing infiltration of tumor-specific T lymphocytes with tumor killing potential; (f) increasing tumor volume; (g) increasing tumor growth rate; (h) increasing metastasis; (i) increasing rate of tumor recurrence; (j) increasing expression of one or more PD-1 ligands; (k) decreasing efficacy of one or more immune-therapies that modulate anti-tumor T cell responses, optionally wherein the one or more immune-therapies are immune-therapies that target one or more proteins selected from the group consisting of CD40, OX40, ICOS, CD28, CD137/4-1BB, CD27, GITR, PD-L1, CTLA4, PD-L2, PD-1, B7-H3, B7-H4, HVEM, LIGHT, BTLA, CD38, TIGIT, VISTA, KIR, GALS, TIM1, TIM3, TIM4, A2AR, LAG3, DR5, CD39, CD70, CD73, TREM1, TREM2, Siglec-5, Siglec-7, Siglec-9, Siglec-11, SirpA, CD47, CSF-1 receptor, and any combination thereof, or of one or more cancer vaccines; and (l) decreasing efficacy of one or more chemotherapy agents, optionally wherein the one or more of the chemotherapy agents are gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), oxaliplatin (Elotaxin®), leucovorin, temozolmide (Temodar®), and any combination thereof. In some embodiments, the antibody exhibits one or more activities selected from: (a) increasing the number of tumor infiltrating $CD3^+$ T cells; (b) decreasing cellular levels of CD33 in non-tumorigenic $CD14^+$ myeloid cells, optionally wherein the non-tumorigenic $CD14^+$ myeloid cells are tumor infiltrating cells or optionally wherein the non-tumorigenic $CD14^+$ myeloid cells are present in blood; (c) reducing the number of non-tumorigenic $CD14^+$ myeloid cells, optionally wherein the non-tumorigenic $CD14^+$ myeloid cells are tumor infiltrating cells or optionally wherein the non-tumorigenic $CD14^+$ myeloid cells are present in blood; (d) reducing PD-L1 levels in one or more cells, optionally wherein the one or more cells are non-tumorigenic myeloid-derived suppressor cells (MDSC); (e) decreasing tumor growth rate of solid tumors; (f) reducing tumor volume; (g) increasing efficacy of one or more PD-1 inhibitors; (h) increasing efficacy of one or more checkpoint inhibitor therapies and/or immune-modulating therapies, optionally wherein the one or more checkpoint inhibitor therapies and/or immune-modulating therapies target one or more of CTL4, the adenosine pathway, PD-L1, PD-L2, OX40, TIM3, LAG3, or any combination thereof; (i) increasing efficacy of one or more chemotherapy agents, optionally wherein the one or more of the chemotherapy agents are gemcitabine, capecitabine, anthracyclines, doxorubicin (Adriamycin®), epirubicin (Ellence®), taxanes, paclitaxel (Taxol®), docetaxel (Taxotere®), 5-fluorouracil (5-FU), cyclophosphamide (Cytoxan®), carboplatin (Paraplatin®), oxaliplatin (Elotaxin®), leucovorin, temozolmide (Temodar®), and any combination thereof; and (j) killing CD33-expressing immunosuppressor myeloid cells and/or CD14-expressing cells in solid tumors and associated blood vessels when conjugated to a chemical or radioactive toxin.

As disclosed herein, anti-CD33 antibodies of the present disclosure may also be used for inducing and/or promoting the survival maturation, functionality, migration, or proliferation of one or more immune cells (e.g., innate immune cells or adaptive immune cells). In some embodiments, the present disclosure provides methods of inducing or promoting the survival, maturation, functionality, migration, or proliferation of one or more immune cells in an individual in need thereof, by administering to the individual a therapeutically effective amount of an antibody of the present disclosure that decreases cellular levels of CD33, inhibits interaction between CD33 and one or more CD33 ligands, or both. In some embodiments, the one or more immune cells are selected from dendritic cells, macrophages, microglia, neutrophils, T cells, T helper cells, cytotoxic T cells, and any combination thereof.

In some embodiments, the antibody is an agonist anti-CD33 antibody. In some embodiments, the antibody is a transient agonist anti-CD33 antibody of the present disclosure that initially acts as an agonist and then acts as a long-term antagonist antibody. In some embodiments, the antibody is an inert anti-CD33 antibody. In some embodiments, the antibody is an antagonist anti-CD33 antibody. In some embodiments, the anti-CD33 antibody reduces cellular (e.g., cell surface, intracellular, or total) levels of CD33. In some embodiments, the anti-CD33 antibody induces degradation of CD33. In some embodiments, the anti-CD33 antibody induces cleavage of CD33. In some embodiments, the anti-CD33 antibody induces internalization of CD33. In some embodiments, the anti-CD33 antibody induces shedding of CD33. In some embodiments, the anti-CD33 antibody induces downregulation of CD33 expression. In some embodiments, the anti-CD33 antibody inhibits interaction (e.g., binding) between CD33 and one or more CD33 ligands. In some embodiments, the anti-CD33 antibody transiently activates and then induces degradation of CD33. In some embodiments, the anti-CD33 antibody transiently activates and then induces cleavage of CD33. In some embodiments, the anti-CD33 antibody transiently activates and then induces internalization of CD33. In some embodiments, the anti-CD33 antibody transiently activates and then induces shedding of CD33. In some embodiments, the anti-CD33 antibody transiently activates and then induces downregulation of CD33 expression. In some embodiments, the anti-CD33 antibody transiently activates and then induces decreased expression of CD33. In certain embodiments, the individual has a CD33 variant allele having single nucleotide polymorphisms (SNPs) rs3865444 CC or AC. In certain embodiments, the individual has a CD33 variant allele having single nucleotide polymorphisms (SNPs) 2459419 CC or CT.

As disclosed herein, anti-CD33 antibodies of the present disclosure may further be used for decreasing the activity, functionality, or survival of regulatory T cells, tumor-imbedded immunosuppressor dendritic cells, tumor-imbedded immunosuppressor macrophages, myeloid-derived suppressor cells, tumor-associated macrophages, acute myeloid leukemia (AML) cells, chronic lymphocytic leukemia (CLL) cell, and/or chronic myeloid leukemia (CML) cells. In some embodiments, the present disclosure provides methods of decreasing the activity, functionality, or survival of regulatory T cells, tumor-imbedded immunosuppressor dendritic cells, tumor-imbedded immunosuppressor macrophages, myeloid-derived suppressor cells, tumor-associated macrophages, acute myeloid leukemia (AML) cells, chronic lymphocytic leukemia (CLL) cell, or chronic myeloid leukemia (CML) cells in an individual in need thereof, by administering to the individual a therapeutically effective amount of an antibody that binds or interacts with CD33. In some embodiments, the antibody is selected from an antagonist antibody, an inert antibody, or an agonist antibody. In some embodiments, the antibody is an isolated anti-CD33 antibody or anti-CD33 antibody conjugate of the present disclosure. In some embodiments, the anti-CD33 antibody conjugate comprises an anti-CD33 antibody conjugated to a detectable marker, a toxin, or a therapeutic agent.

As disclosed herein, anti-CD33 antibodies of the present disclosure may be used for decreasing cellular levels of CD33, inhibiting interaction between CD33 and one or more CD33 ligands, or both on one or more cells in vitro or in vivo. In some embodiments, the present disclosure provides methods of decreasing cellular levels of CD33, inhibiting interaction between CD33 and one or more CD33 ligands, or both on one or more cells in an individual in need thereof, by administering to the individual a therapeutically effective amount of an isolated anti-CD33 antibody of the present disclosure. In some embodiments, the anti-CD33 antibody decreases cellular levels of CD33 in vivo.

As disclosed herein, anti-CD33 antibodies of the present disclosure may be used for decreasing cellular levels of CD33 on one or more cells, including without limitation, dendritic cells, bone marrow-derived dendritic cells, monocytes, microglia, T cells, and macrophages, and/or cell lines. In some embodiments, the present disclosure provides methods of decreasing cellular levels of CD33 on one or more cells in an individual in need thereof, by administering to the individual a therapeutically effective amount of an anti-CD33 antibody of the present disclosure. In some embodiments, the one or more cells are selected from dendritic cells, bone marrow-derived dendritic cells, monocytes, microglia, T cells, and macrophages, and any combination thereof. In some embodiments, the anti-CD33 antibody decreases cellular levels of CD33 in vivo. Cellular levels of CD33 may refer to, without limitation, cell surface levels of CD33, intracellular levels of CD33, and total levels of CD33. In some embodiments, a decrease in cellular levels of CD33 comprises decrease in cell surface levels of CD33. As used herein, cell surface levels of CD33 may be measured by any in vitro cell-based assays or suitable in vivo model described herein or known in the art. In some embodiments, a decrease in cellular levels of CD33 comprises a decrease in intracellular levels of CD33. As used herein, intracellular levels of CD33 may be measured by any in vitro cell-based assays or suitable in vivo model described herein or known in the art. In some embodiments, a decrease in cellular levels of CD33 comprises a decrease in total levels of CD33. As used herein, total levels of CD33 may be measured by any in vitro cell-based assays or suitable in vivo model described herein or known in the art. In some embodiments, the anti-CD33 antibodies induce CD33 degradation, CD33 cleavage, CD33 internalization, CD33 shedding, and/or downregulation of CD33 expression. In some embodiments, cellular levels of CD33 are measured on primary cells (e.g., dendritic cells, bone marrow-derived dendritic cells, monocytes, microglia, T cells, and macrophages) or on cell lines utilizing an in vitro cell assay.

Other aspects of the present disclosure relate to a method of selecting a subject in need thereof for treatment with an anti-CD33 antibody, the method comprising: a. obtaining a sample (e.g., blood sample) from the subject; b. detecting the CD33 alleles present in the subject; and c. selecting the subject for treatment with the antibody that binds or interacts with CD33 is the subject has one or more CD33 alleles, wherein the one or more CD33 alleles are selected from the group consisting of rs3865444$^{AC}$, and rs3865444$^{CC}$. Other aspects of the present disclosure relate to a method of assessing responsiveness of a subject in need thereof to an antibody that binds or interacts with CD33, the method comprising: a. measuring the expression levels of CD45$^+$ and CD14$^+$ on non-tumorigenic myeloid cells in a blood sample obtained from the subject prior to administering to the subject an anti-CD33 antibody; b. administering to the subject a therapeutically effective amount of the antibody; and c. measuring the expression levels of CD45$^+$ and CD14$^+$ on non-tumorigenic myeloid cells in a blood sample obtained from the subject after administration of the anti-CD33 antibody, wherein a reduction in the levels of CD45$^+$ CD14$^+$ on non-tumorigenic myeloid cells after administration of the anti-CD33 antibody indicates the subject is responsive to the agent. Any suitable methods for obtaining a sample, such as a blood sample, may be used. Further, it will be appreciated that any known method of detecting CD33 variants and/or alleles, such as SNP analysis, may be used. In some embodiments, the method of assessing responsiveness further comprises administering one or more additional therapeutically effective amounts of the antibody. In some embodiments, the subject is human.

In some embodiments the individual has a variant of CD33. In some embodiments, the variant includes, without limitation, one or more polymorphisms selected from: (a) SNP rs3865444$^{AC}$; (b) SNP rs3865444$^{CC}$; (c) SNP rs35112940$^{GG,\ AA,\ AG}$; and (d) SNP rs12459419$^{CC,\ CT\ or\ TT}$; and any combinations thereof.

In some embodiments, the methods of the present disclosure may further involve the coadministration of anti-CD33 antibodies or bispecific anti-CD33 antibodies, with antibodies that bind to pattern recognition receptors, antibodies that bind to Toll-like receptors, antibodies that bind to damage-associated molecular pattern (DAMP) receptors, and/or antibodies that bind to cytokine or antibodies to interleukins).

In some embodiments, the methods of the present disclosure may further include administering to the individual at least one antibody that specifically binds to an inhibitory checkpoint molecule, and/or one or more standard or investigational anti-cancer therapies. In some embodiments, the at least one antibody that specifically binds to an inhibitory checkpoint molecule is administered in combination with the anti-CD33 antibody. In some embodiments, the at least one antibody that specifically binds to an inhibitory checkpoint molecule is selected from an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti- B- and T-lymphocyte attenuator (BTLA) antibody, an anti-Killer inhibitory receptor (KIR) antibody, an anti-GALS antibody, an anti-TIM3 antibody, an anti-AZAR antibody, an anti-LAG-3 antibody, an anti-phosphatidylserine antibody, an anti-CD27 antibody, an anti-TNFa antibody, an anti-Siglec-5 antibody, an anti-Siglec-7 antibody, an anti-Siglec-9 antibody, an anti-Siglec-11 antibody, an antagonistic anti-TREM1 antibody, an antagonistic anti-TREM2 antibody, and any combination thereof. In some embodiments, the one or more standard or investigational anti-cancer therapies are selected from radiotherapy, cytotoxic chemotherapy, targeted therapy, imatinib therapy, trastuzumab therapy, etanercept therapy, adoptive cell transfer (ACT) therapy, chimeric antigen receptor T cell transfer (CAR-T) therapy, vaccine therapy, and cytokine therapy.

In some embodiments, the methods of the present disclosure may further include administering to the individual at least one antibody that specifically binds to an inhibitory cytokine. In some embodiments, the at least one antibody that specifically binds to an inhibitory cytokine is administered in combination with the anti-CD33 antibody. In some embodiments, the at least one antibody that specifically binds to an inhibitory cytokine is selected from an anti-CCL2 antibody, an anti-CSF-1 antibody, an anti-IL-2 antibody, and any combination thereof.

In some embodiments, the methods of the present disclosure may further include administering to the individual at least one agonistic antibody that specifically binds to a stimulatory checkpoint protein. In some embodiments, the at least one agonistic antibody that specifically binds to a stimulatory checkpoint protein is administered in combination with the anti-CD33 antibody. In some embodiments, the at least one agonistic antibody that specifically binds to a stimulatory checkpoint protein is selected from an agonist anti-CD40 antibody, an agonist anti-OX40 antibody, an agonist anti-ICOS antibody, an agonist anti-CD28 antibody, an agonistic anti-TREM1 antibody, an agonistic anti-TREM2 antibody, an agonist anti-CD137/4-1BB antibody, an agonist anti-CD27 antibody, an agonist anti-glucocorticoid-induced TNFR-related protein GITR antibody, and any combination thereof.

In some embodiments, the methods of the present disclosure may further include administering to the individual at least one stimulatory cytokine. In some embodiments, the at least one stimulatory cytokine is administered in combination with the anti-CD33 antibody. In some embodiments, the at least one stimulatory cytokine is selected from IFN-a4, IFN-b, IL-1β, TNF-α, IL-6, IL-8, CRP, IL-20 family members, LIF, IFN-gamma, OSM, CNTF, GM-CSF, IL-11, IL-12, IL-17, IL-18, IL-23, CXCL10, IL-33, CRP, IL-33, MCP-1, MIP-1-beta, and any combination thereof.

In some embodiments, a subject or individual is a mammal Mammals include, without limitation, domesticated animals (e.g., cows, sheep, cats, dogs, and horses), primates (e.g., humans and non-human primates such as monkeys), rabbits, and rodents (e.g., mice and rats). In some embodiments, the subject or individual is a human.

Dementia

Dementia is a non-specific syndrome (i.e., a set of signs and symptoms) that presents as a serious loss of global cognitive ability in a previously unimpaired person, beyond what might be expected from normal ageing. Dementia may be static as the result of a unique global brain injury. Alternatively, dementia may be progressive, resulting in long-term decline due to damage or disease in the body. While dementia is much more common in the geriatric population, it can also occur before the age of 65. Cognitive areas affected by dementia include, without limitation, memory, attention span, language, and problem solving. Generally, symptoms must be present for at least six months to before an individual is diagnosed with dementia.

Exemplary forms of dementia include, without limitation, frontotemporal dementia, Alzheimer's disease, vascular dementia, semantic dementia, and dementia with Lewy bodies.

In some embodiments, administering an anti-CD33 antibody of the present disclosure can prevent, reduce the risk, and/or treat dementia. In some embodiments, an anti-CD33 antibody may modulate one or more CD33 activities in an individual having dementia.

Frontotemporal Dementia

Frontotemporal dementia (FTD) is a condition resulting from the progressive deterioration of the frontal lobe of the brain. Over time, the degeneration may advance to the temporal lobe. Second only to Alzheimer's disease (AD) in prevalence, FTD accounts for 20% of pre-senile dementia cases. The clinical features of FTD include memory deficits, behavioral abnormalities, personality changes, and language impairments (Cruts, M. & Van Broeckhoven, C., Trends Genet. 24:186-194 (2008); Neary, D., et al., Neurology 51:1546-1554 (1998); Ratnavalli, E., Brayne, C., Dawson, K. & Hodges, J. R., Neurology 58:1615-1621 (2002)).

A substantial portion of FTD cases are inherited in an autosomal dominant fashion, but even in one family, symptoms can span a spectrum from FTD with behavioral disturbances, to Primary Progressive Aphasia, to Cortico-Basal Ganglionic Degeneration. FTD, like most neurodegenerative diseases, can be characterized by the pathological presence of specific protein aggregates in the diseased brain. Historically, the first descriptions of FTD recognized the presence of intraneuronal accumulations of hyperphosphorylated Tau protein in neurofibrillary tangles or Pick bodies. A causal role for the microtubule associated protein Tau was supported by the identification of mutations in the gene encoding the Tau protein in several families (Hutton, M., et al., Nature 393:702-705 (1998). However, the majority of FTD brains show no accumulation of hyperphosphorylated Tau but do exhibit immunoreactivity to ubiquitin (Ub) and TAR DNA binding protein (TDP43) (Neumann, M., et al., Arch. Neurol. 64:1388-1394 (2007)). A majority of those FTD cases with Ub inclusions (FTD-U) were shown to carry mutations in the Progranulin gene.

In some embodiments, administering an anti-CD33 antibody of the present disclosure, can prevent, reduce the risk, and/or treat FTD. In some embodiments, administering an anti-CD33 antibody, may modulate one or more CD33 activities in an individual having FTD.

Alzheimer's Disease

Alzheimer's disease (AD) is the most common form of dementia. There is no cure for the disease, which worsens as it progresses, and eventually leads to death. Most often, AD is diagnosed in people over 65 years of age. However, the less-prevalent early-onset Alzheimer's can occur much earlier.

Common symptoms of Alzheimer's disease include, behavioral symptoms, such as difficulty in remembering recent events; cognitive symptoms, confusion, irritability and aggression, mood swings, trouble with language, and long-term memory loss. As the disease progresses bodily functions are lost, ultimately leading to death. Alzheimer's disease develops for an unknown and variable amount of time before becoming fully apparent, and it can progress undiagnosed for years.

In some embodiments, administering an anti-CD33 antibody of the present disclosure can prevent, reduce the risk, and/or treat Alzheimer's disease. In some embodiments, administering an anti-CD33 antibody, may modulate one or more CD33 activities in an individual having Alzheimer's disease.

Parkinson's Disease

Parkinson's disease, which may be referred to as idiopathic or primary parkinsonism, hypokinetic rigid syndrome (HRS), or paralysis agitans, is a neurodegenerative brain disorder that affects motor system control. The progressive death of dopamine-producing cells in the brain leads to the major symptoms of Parkinson's. Most often, Parkinson's disease is diagnosed in people over 50 years of age. Parkinson's disease is idiopathic (having no known cause) in most people. However, genetic factors also play a role in the disease.

Symptoms of Parkinson's disease include, without limitation, tremors of the hands, arms, legs, jaw, and face, muscle rigidity in the limbs and trunk, slowness of movement (bradykinesia), postural instability, difficulty walking, neuropsychiatric problems, changes in speech or behavior, depression, anxiety, pain, psychosis, dementia, hallucinations, and sleep problems.

In some embodiments, administering an anti-CD33 antibody of the present disclosure can prevent, reduce the risk, and/or treat Parkinson's disease. In some embodiments, administering an anti-CD33 antibody, may modulate one or more CD33 activities in an individual having Parkinson's disease.

Amyotrophic Lateral Sclerosis (ALS)

As used herein, amyotrophic lateral sclerosis (ALS) or, motor neuron disease or, Lou Gehrig's disease are used interchangeably and refer to a debilitating disease with varied etiology characterized by rapidly progressive weakness, muscle atrophy and fasciculations, muscle spasticity, difficulty speaking (dysarthria), difficulty swallowing (dysphagia), and difficulty breathing (dyspnea).

It has been shown that Progranulin plays a role in ALS (Schymick, J C et al., (2007) J Neurol Neurosurg Psychiatry; 78:754-6) and protects again the damage caused by ALS causing proteins such as TDP-43 (Laird, A S et al., (2010). PLoS ONE 5: e13368). It was also demonstrated that pro-NGF induces p75 mediated death of oligodendrocytes and corticospinal neurons following spinal cord injury (Beatty et al., Neuron (2002), 36, pp. 375-386; Giehl et al, Proc. Natl. Acad. Sci USA (2004), 101, pp 6226-30).

In some embodiments, administering an anti-CD33 antibody of the present disclosure can prevent, reduce the risk, and/or treat ALS. In some embodiments, administering an anti-CD33 antibody, may modulate one or more CD33 activities in an individual having amyotrophic lateral sclerosis.

Huntington's Disease

Huntington's disease (HD) is an inherited neurodegenerative disease caused by an autosomal dominant mutation in the Huntingtin gene (HTT). Expansion of a cytokine-adenine-guanine (CAG) triplet repeat within the Huntingtin gene results in production of a mutant form of the Huntingtin protein (Htt) encoded by the gene. This mutant Huntingtin protein (mHtt) is toxic and contributes to neuronal death. Symptoms of Huntington's disease most commonly appear between the ages of 35 and 44, although they can appear at any age.

Symptoms of Huntington's disease, include, without limitation, motor control problems, jerky, random movements (chorea), abnormal eye movements, impaired balance, seizures, difficulty chewing, difficulty swallowing, cognitive problems, altered speech, memory deficits, thinking difficulties, insomnia, fatigue, dementia, changes in personality, depression, anxiety, and compulsive behavior.

In some embodiments, administering as an anti-CD33 antibody of the present disclosure can prevent, reduce the risk, and/or treat Huntington's disease (HD). In some embodiments, administering an anti-CD33 antibody, may modulate one or more CD33 activities in an individual having Huntington's disease.

Taupathy Disease

Taupathy diseases, or Tauopathies, are a class of neurodegenerative disease caused by aggregation of the microtubule-associated protein tau within the brain. Alzheimer's disease (AD) is the most well-known taupathy disease, and involves an accumulation of tau protein within neurons in the form of insoluble neurofibrillary tangles (NFTs). Other taupathy diseases and disorders include progressive supranuclear palsy, dementia pugilistica (chromic traumatic encephalopathy), frontotemporal dementia and parkinsonism linked to chromosome 17, Lytico-Bodig disease (Parkinson-dementia complex of Guam), Tangle-predominant dementia, Ganglioglioma and gangliocytoma, Meningioangiomatosis, Subacute sclerosing panencephalitis, lead encephalopathy, tuberous sclerosis, Hallervorden-Spatz disease, lipofuscinosis, Pick's disease, corticobasal degeneration, Argyrophilic grain disease (AGD), Huntington's disease, and frontotemporal lobar degeneration.

In some embodiments, administering an anti-CD33 antibody of the present disclosure, can prevent, reduce the risk, and/or treat taupathy disease. In some embodiments, administering an anti-CD33 antibody, may modulate one or more CD33 activities in an individual having a taupathy disease.

Multiple Sclerosis

Multiple sclerosis (MS) can also be referred to as disseminated sclerosis or encephalomyelitis disseminata. MS is an inflammatory disease in which the fatty myelin sheaths around the axons of the brain and spinal cord are damaged, leading to demyelination and scarring as well as a broad spectrum of signs and symptoms. MS affects the ability of nerve cells in the brain and spinal cord to communicate with each other effectively. Nerve cells communicate by sending electrical signals called action potentials down long fibers called axons, which are contained within an insulating substance called myelin. In MS, the body's own immune system attacks and damages the myelin. When myelin is lost, the axons can no longer effectively conduct signals. MS onset usually occurs in young adults, and is more common in women. http://en.wikipedia.org/wiki/Multiple_sclerosis-cite_note-pmid8970977-1

Symptoms of MS include, without limitation, changes in sensation, such as loss of sensitivity or tingling; pricking or numbness, such as hypoesthesia and paresthesia; muscle weakness; clonus; muscle spasms; difficulty in moving; difficulties with coordination and balance, such as ataxia; problems in speech, such as dysarthria, or in swallowing, such as dysphagia; visual problems, such as nystagmus, optic neuritis including phosphenes, and diplopia; fatigue; acute or chronic pain; and bladder and bowel difficulties; cognitive impairment of varying degrees; emotional symptoms of depression or unstable mood; Uhthoffs phenomenon, which is an exacerbation of extant symptoms due to an exposure to higher than usual ambient temperatures; and Lhermitte's sign, which is an electrical sensation that runs down the back when bending the neck.

In some embodiments, administering an anti-CD33 antibody of the present disclosure can prevent, reduce the risk, and/or treat multiple sclerosis. In some embodiments, administering an anti-CD33 antibody may modulate one or more CD33 activities in an individual having multiple sclerosis.

Cancer

Further aspects of the present disclosure provide methods for preventing, reducing risk, or treating cancer, by administering to an individual in need thereof a therapeutically effective amount of an isolated anti-CD33 antibody of the present disclosure. Any of the isolated antibodies of the present disclosure may be used in these methods. In some embodiments, the isolated antibody is an agonist antibody of the present disclosure. In other embodiments, the isolated antibody is an antagonist antibody of the present disclosure. In other embodiments, the isolated antibody is an inert antibody of the present disclosure. In other embodiments, the isolated antibody is an antibody conjugate of the present disclosure.

As disclosed herein, the tumor microenvironment is known to contain a heterogeneous immune infiltrate, which includes T lymphocytes, macrophages and cells of myeloid/granulocytic lineage. The presence and activity of T-regulatory cells, tumor-imbedded immunosuppressor myeloid cells, and/or M2-macrophages in tumors is associated with poor prognosis. In contrast, the presence and activity of cytotoxic T cells is beneficial for cancer therapy. Therapies that directly or indirectly enhance the activity of cytotoxic T cells and reduce the number and activity of the various immunosuppressor cells, are expected to provide significant therapeutic benefit. A seminal preclinical study has shown synergies between drugs that target immunosuppressor cells (e.g., CSF1/CSF1R blocking antibodies) and immune checkpoint blocking antibodies that activate cytotoxic T cells, indicating that manipulating both cell types shows efficacy in tumor models where individual therapies are poorly effective (Zhu Y; Cancer Res. 2014 Sep. 15; 74(18): 5057-69). Therefore, in some embodiments, blocking CD33, which is expressed on myeloid cells, subset of T cells, and tumor-associated immune cells, may stimulate beneficial anti-tumor immune response, resulting in a therapeutic anti-tumor immune response.

In some embodiments, the methods for preventing, reducing risk, or treating an individual having cancer further include administering to the individual at least one antibody that specifically binds to an inhibitory checkpoint molecule. Examples of antibodies that specifically bind to an inhibitory checkpoint molecule include, without limitation, an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti-BTLA antibody, an anti-GALS antibody, an anti-TIM3 antibody, an anti-AZAR antibody, an anti-LAG-3 antibody, an anti-phosphatidylserine antibody, and any combination thereof. In some embodiments, the at least one antibody that specifically binds to an inhibitory checkpoint molecule is administered in combination with an antagonist anti-CD33 antibody of the present disclosure.

In some embodiments, a cancer to be prevented or treated by the methods of the present disclosure includes, without limitation, squamous cell cancer (e.g., epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer and gastrointestinal stromal cancer, pancreatic cancer, glioblastoma, cervical cancer, ovarian cancer, liver cancer, bladder cancer, cancer of the urinary tract, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, melanoma, superficial spreading melanoma, lentigo maligna melanoma, acral lentiginous melanomas, nodular melanomas, multiple myeloma and B cell lymphoma; chronic lymphocytic leukemia (CLL); acute lymphoblastic leukemia (ALL); hairy cell leukemia; chronic myeloblastic leukemia; and post-transplant lymphoproliferative disorder (PTLD), as well as abnormal vascular proliferation associated with phakomatoses, edema (such as that associated with brain tumors), Meigs' syndrome, brain, as well as head and neck cancer, and associated metastases. In some embodiments, the cancer is colorectal cancer. In some embodiments, the cancer is selected from non-small cell lung cancer, glioblastoma, neuroblastoma, renal cell carcinoma, bladder cancer, ovarian cancer, melanoma, breast carcinoma, gastric cancer, and hepatocellular carcinoma. In some embodiments, the cancer is triple-negative breast carcinoma. In some embodiments, the cancer may be an early stage cancer or a late stage cancer. In some embodiments, the cancer may be a primary tumor. In some embodiments, the cancer may be a metastatic tumor at a second site derived from any of the above types of cancer.

In some embodiments, anti-CD33 antibodies of the present disclosure may be used for preventing, reducing risk, or treating cancer, including, without limitation, bladder cancer breast cancer, colon and rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, and thyroid cancer.

In some embodiments, the present disclosure provides methods of preventing, reducing risk, or treating an individual having cancer, by administering to the individual a therapeutically effective amount of an anti-CD33 antibody of the present disclosure.

In some embodiments, the method further includes administering to the individual at least one antibody that specifically binds to an inhibitory immune checkpoint molecule, and/or another standard or investigational anti-cancer therapy. In some embodiments, the at least one antibody that specifically binds to an inhibitory checkpoint molecule is administered in combination with the anti-CD33 antibody of the present disclosure. In some embodiments, the at least one antibody that specifically binds to an inhibitory checkpoint molecule is selected from an anti-PD-L1 antibody, an anti-CTLA4 antibody, an anti-PD-L2 antibody, an anti-PD-1 antibody, an anti-B7-H3 antibody, an anti-B7-H4 antibody, and anti-HVEM antibody, an anti- B- and T-lymphocyte attenuator (BTLA) antibody, an anti-Killer inhibitory receptor (KIR) antibody, an anti-GALS antibody, an anti-TIM3 antibody, an anti-AZAR antibody, an anti-LAG-3 antibody, an anti-phosphatidylserine antibody, an anti-CD27 antibody, and any combination thereof. In some embodiments, the standard or investigational anti-cancer therapy is one or more therapies selected from radiotherapy, cytotoxic chemotherapy, targeted therapy, imatinib (Gleevec®), trastuzumab (Herceptin®), adoptive cell transfer (ACT), chimeric antigen receptor T cell transfer (CAR-T), vaccine therapy, and cytokine therapy.

In some embodiments, the method further includes administering to the individual at least one antibody that specifically binds to an inhibitory cytokine. In some embodiments, the at least one antibody that specifically binds to an inhibitory cytokine is administered in combination with the anti-CD33 antibody of the present disclosure. In some embodiments, the at least one antibody that specifically binds to an inhibitory cytokine is selected from an anti-CCL2 antibody, an anti-CSF-1 antibody, an anti-IL-2 antibody, and any combination thereof.

In some embodiments, the method further includes administering to the individual at least one agonistic antibody that specifically binds to a stimulatory immune checkpoint protein. In some embodiments, the at least one agonistic antibody that specifically binds to a stimulatory checkpoint protein is administered in combination with the anti-CD33 antibody of the present disclosure. In some embodiments, the at least one agonistic antibody that specifically binds to a stimulatory checkpoint protein is selected from an agonist anti-CD40 antibody, an agonist anti-OX40 antibody, an agonist anti-ICOS antibody, an agonist anti-CD28 antibody, an agonist anti-CD137/4-1BB antibody, an agonist anti-CD27 antibody, an agonist anti-glucocorticoid-induced TNFR-related protein GITR antibody, and any combination thereof.

In some embodiments, the method further includes administering to the individual at least one stimulatory cytokine. In some embodiments, the at least one stimulatory cytokine is administered in combination with the anti-CD33 antibody of the present disclosure. In some embodiments, the at least one stimulatory cytokine is selected from TNF-α, IL-6, IL-8, CRP, IL-20 family member, LIF, OSM, CNTF, IL-11, IL-12, IL-17, IL-8, CRP, IFN-α, IFN-β, IL-2, IL-18, GM-CSF, G-CSF, and any combination thereof.

Kits/Articles of Manufacture

The present disclosure also provides kits and/or articles of manufacture containing an anti-CD33 antibody described herein, or a functional fragment thereof. Kits and/or articles of manufacture of the present disclosure may include one or more containers comprising a purified antibody of the present disclosure. In some embodiments, the kits and/or articles of manufacture further include instructions for use in accordance with the methods of this disclosure.

In some embodiments, these instructions comprise a description of administration of the anti-CD33 antibody described herein to prevent, reduce risk, or treat an individual having a disease, disorder, or injury selected from dementia, frontotemporal dementia, Alzheimer's disease, vascular dementia, mixed dementia, Creutzfeldt-Jakob disease, normal pressure hydrocephalus, amyotrophic lateral sclerosis, Huntington's disease, taupathy disease, Nasu-Hakola disease, stroke, acute trauma, chronic trauma, lupus, acute and chronic colitis, rheumatoid arthritis, wound healing, Crohn's disease, inflammatory bowel disease, ulcerative colitis, obesity, malaria, essential tremor, central nervous system lupus, Behcet's disease, Parkinson's disease, dementia with Lewy bodies, multiple system atrophy, Shy-Drager syndrome, progressive supranuclear palsy, cortical basal ganglionic degeneration, acute disseminated encephalomyelitis, granulomartous disorders, sarcoidosis, diseases of aging, seizures, spinal cord injury, traumatic brain injury, age related macular degeneration, glaucoma, retinitis pigmentosa, retinal degeneration, respiratory tract infection, sepsis, eye infection, systemic infection, lupus, arthritis, multiple sclerosis, low bone density, osteoporosis, osteogenesis, osteopetrotic disease, Paget's disease of bone, and cancer including bladder cancer, brain cancer, breast cancer, colon cancer, rectal cancer, endometrial cancer, kidney cancer, renal cell cancer, renal pelvis cancer, leukemia, lung cancer, melanoma, non-Hodgkin's lymphoma, pancreatic cancer, prostate cancer, ovarian cancer, fibrosarcoma, acute lymphoblastic leukemia (ALL), acute myeloid leukemia (AML), chronic lymphocytic leukemia (CLL), chronic myeloid leukemia (CML), multiple myeloma, polycythemia vera, essential thrombocytosis, primary or idiopathic myelofibrosis, primary or idiopathic myelosclerosis, myeloid-derived tumors, tumors that express CD33, thyroid cancer, infections, CNS herpes, parasitic infections, Trypanosome infection, *Cruzi* infection, *Pseudomonas aeruginosa* infection, *Leishmania donovani* infection, group B *Streptococcus* infection, *Campylobacter jejuni* infection, *Neisseria meningiditis* infection, type I HIV, and *Haemophilus* influenza, according to any methods of this disclosure.

In some embodiments, the instructions comprise a description of how to detect a CD33 protein, for example in an individual, in a tissue sample, or in a cell. The kit and/or article of manufacture may further comprise a description of selecting an individual suitable for treatment based on identifying whether that individual has the disease and the stage of the disease.

In some embodiments, the kits and/or articles of manufacture may further include another antibody of the present disclosure (e.g., at least one antibody that specifically binds to an inhibitory checkpoint molecule, at least one antibody that specifically binds to an inhibitory cytokine, and/or at least one agonistic antibody that specifically binds to a stimulatory checkpoint protein) and/or at least one stimulatory cytokine. In some embodiments, the kits and/or articles of manufacture may further include instructions for using the antibody and/or stimulatory cytokine in combination with an anti-CD33 antibody described herein, instructions for using an anti-CD33 antibody described herein in combination with an antibody and/or stimulatory cytokine, or instructions for using an anti-CD33 antibody described herein and an antibody and/or stimulatory cytokine, according to any methods of this disclosure.

The instructions generally include information as to dosage, dosing schedule, and route of administration for the intended treatment. The containers may be unit doses, bulk packages (e.g., multi-dose packages) or sub-unit doses. Instructions supplied in the kits and/or articles of manufacture of the present disclosure are typically written instructions on a label or package insert (e.g., a paper sheet included in the kit), but machine-readable instructions (e.g., instructions carried on a magnetic or optical storage disk) are also acceptable.

The label or package insert indicates that the composition is used for treating, e.g., a disease of the present disclosure. Instructions may be provided for practicing any of the methods described herein.

The kits and/or articles of manufacture of this disclosure are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit and/or article of manufacture may have a sterile access port (for example the container may be an intravenous solution bag or a vial having a stopper pierceable by a hypodermic injection needle). The container may also have a sterile access port (e.g., the container may be an intravenous solution bag or a vial having a stopper pierceable by a hypodermic injection needle). At least one active agent in the composition is an anti-CD33 antibody described herein. The container may further comprise a second pharmaceutically active agent.

Kits and/or articles of manufacture may optionally provide additional components such as buffers and interpretive information. Normally, the kit comprises a container and a label or package insert(s) on or associated with the container.

Diagnostic Uses

The isolated antibodies of the present disclosure (e.g., an anti-CD33 antibody described herein) also have diagnostic utility. This disclosure therefore provides for methods of using the antibodies of this disclosure, or functional fragments thereof, for diagnostic purposes, such as the detection of a CD33 protein in an individual or in tissue samples derived from an individual.

In some embodiments, the individual is a human. In some embodiments, the individual is a human patient suffering from, or at risk for developing a disease, disorder, or injury of the present disclosure. In some embodiments, the diagnostic methods involve detecting a CD33 protein in a biological sample, such as a biopsy specimen, a tissue, or a cell. An anti-CD33 antibody described herein is contacted with the biological sample and antigen-bound antibody is detected. For example, a biopsy specimen may be stained with an anti-CD33 antibody described herein in order to detect and/or quantify disease-associated cells. The detection method may involve quantification of the antigen-bound antibody. Antibody detection in biological samples may occur with any method known in the art, including immunofluorescence microscopy, immunocytochemistry, immunohistochemistry, ELISA, FACS analysis, immunoprecipitation, or micro-positron emission tomography. In certain embodiments, the antibody is radiolabeled, for example with $^{18}F$ and subsequently detected utilizing micro-positron emission tomography analysis. Antibody-binding may also be quantified in a patient by non-invasive techniques such as positron emission tomography (PET), X-ray computed tomography, single-photon emission computed tomography (SPECT), computed tomography (CT), and computed axial tomography (CAT).

In other embodiments, an isolated antibody of the present disclosure (e.g., an anti-CD33 antibody described herein) may be used to detect and/or quantify, for example, microglia in a brain specimen taken from a preclinical disease model (e.g., a non-human disease model). As such, an isolated antibody of the present disclosure (e.g., an anti-CD33 antibody described herein) may be useful in evaluating therapeutic response after treatment in a model for a nervous system disease or injury such as frontotemporal dementia, Alzheimer's disease, vascular dementia, seizures, retinal dystrophy, atherosclerotic vascular diseases, Nasu-Hakola disease, or multiple sclerosis, as compared to a control.

The present disclosure will be more fully understood by reference to the following Examples. They should not, however, be construed as limiting the scope of the present disclosure. All citations throughout the disclosure are hereby expressly incorporated by reference.

EXAMPLES

Example 1: Humanization of a Murine Anti-CD33 Antibody, and Affinity Measurements of Such Humanized Variants The purpose of the following example was to generate humanized variants of a parental mouse CD33 antibody, and to determine the affinities of the humanized antibodies for CD33. The parental mouse anti-CD33 antibody contained a heavy chain variable region comprising the sequence of EVQLQQSGPELVKPGASVKISCKASGYTFTDYNLH-WVKLSHGKSLEWIGFIYPSNGITGYNQKFK NKATLT-VDNSSSTAYMELRSLTSEDSAVYYCARSTVDYFDY-WGQGTTLTVSS (SEQ ID NO: 103), and a light chain variable region comprising the sequence of DIVLTQS-PASLAVSLGQRATMSCRASQSVSTSTYSYMHWY-QQKPGQPPKLLIKYASNLESGVPA RFSGSGSGTDFTL-NIHPVEEEDTATYYCQHSWEIPLTFGAGTKLELK (SEQ ID NO: 104). The mouse CD33 antibody above which contains a heavy chain variable region comprising the sequence of SEQ ID NO:103 and light chain variable region comprising the sequence of SEQ ID NO:104 is the murine anti-CD33 antibody 2F5.1, which is disclosed in WO 2016/201388.

The parental mouse CD33 antibody (murine anti-CD33 antibody 2F5.1) was humanized by grafting the CDRs of the parental mouse antibody onto human germline frameworks closest in sequence to the mouse antibody. Antibodies with one or more framework back-mutations were also generated. In total, 88 humanized antibodies were produced. A chimeric antibody, which contained the heavy chain variable region (SEQ ID NO: 103) and the light chain variable region (SEQ ID NO: 104) of the parental mouse anti-CD33 antibody, was also made and used as a comparator (Chimeric Ab). A variant of the Chimeric Ab, Chimeric Ab #2, was also made, in which a mutation was introduced into VH-FR3 to remove a predicted N-linked glycosylation site. Chimeric Ab #2 contained the heavy chain variable region EVQLQQS-GPELVKPGASVKISCKASGYTFTDYNLHWVKLSH-GKSLEWIGFIYPSNGITGYNQKFK NKATLT-VDTSSSTAYMELRSLTSEDSAVYYCARSTVDYFDY-WGQGTTLTVSS (SEQ ID NO: 167), and the light chain variable region of SEQ ID NO: 104.

The affinities ($K_D$) of the humanized antibodies for human CD33 were measured for each antibody by BioLayer Interferometry in a ForteBio assay according to standard techniques (Estep et al. (2013) MAbs 5(2): 270-8). Briefly, Fab's were generated for each antibody by papain digestion, and monomeric affinities of the antibodies for CD33 were measured as follows: human CD33 was immobilized on the sensor tip, and was incubated in assay buffer containing each Fab at 100 nM for 180 seconds to measure association rate, after which the tips were transferred to assay buffer for 180 seconds to measure dissociation rate. The assay was carried out at room temperature.

The majority of the 88 humanized antibodies exhibited affinities that were within 3-fold of the parental mouse antibody (data not shown and in Table 1). The data for 8 of these humanized antibodies (AB-H2, AB-H9, AB-H14, AB-H15, AB-H63, AB-H64, AB-H65, and AB-H66) are shown in Table 1 below.

TABLE 1 monovalent affinity for CD33 of humanized antibodies

| Antibody | Monovalent affinity, $K_D$ (M): |
|---|---|
| Chimeric Ab | 5.22E−09 |
| AB-H2 | 3.24E−09 |
| AB-H9 | 3.50E−09 |
| AB-H14 | 3.42E−09 |
| AB-H15 | 5.45E−09 |
| AB-H63 | 4.07E−09 |

TABLE 1-continued monovalent affinity for CD33 of humanized antibodies

| Antibody | Monovalent affinity, $K_D$ (M): |
|---|---|
| AB-H64 | 4.08E−09 |
| AB-H65 | 8.57E−09 |
| AB-H66 | 5.54E−09 |

The affinity parameters for 10 of the 88 humanized antibodies (AB-H1, AB-H3, AB-H6, AB-H11, AB-H22, AB-H24, AB-H26, AB-H63, AB-H64, and AB-H71) were measured in a separate experiment by a more sensitive technique, surface plasmon resonance (BIAcore), and compared to Chimeric Ab and Chimeric Ab #2. BIAcore measurements were performed as follows: human CD33 was immobilized on the surface of a C1 chip, and Fabs were injected for 300 s to monitor association, followed by a 900 s flow in running buffer to monitor dissociation. The Fabs were measured at 5 concentrations: a high concentration of 27 nM and 3-fold serial dilutions. The results are shown in Table 2 below. The 10 humanized antibodies had affinities ranging from 1.13 nM to 6.02 nM and were within 4-fold of the Chimeric Ab.

TABLE 2 monovalent affinity for CD33 of humanized antibodies

| Antibody | Fab $K_D$ (M) monovalent | $k_{on}$ (1/Ms) | $k_{off}$ (1/s) | Fold Change to Chimeric Ab |
|---|---|---|---|---|
| Chimeric Ab | 1.63E−09 | 9.95E+05 | 1.62E−03 | — |
| Chimeric Ab #2 | 2.89E−09 | 9.91E+05 | 2.86E−03 | 0.56 |
| AB-H1 | 1.58E−09 | 1.18E+06 | 1.86E−03 | 1.03 |
| AB-H3 | 1.13E−09 | 1.23E+06 | 1.40E−03 | 1.43 |
| AB-H6 | 1.37E−09 | 1.10E+06 | 1.51E−03 | 1.18 |
| AB-H11 | 1.33E−09 | 1.22E+06 | 1.62E−03 | 1.22 |
| AB-H22 | 2.63E−09 | 6.90E+05 | 1.82E−03 | 0.62 |
| AB-H24 | 6.02E−09 | 3.79E+05 | 2.28E−03 | 0.27 |
| AB-H26 | 5.86E−09 | 4.00E+05 | 2.34E−03 | 0.28 |
| AB-H63 | 3.53E−09 | 7.44E+05 | 2.63E−03 | 0.46 |
| AB-H64 | 2.15E−09 | 1.03E+06 | 2.21E−03 | 0.76 |
| AB-H71 | 1.88E−09 | 1.87E+06 | 3.51E−03 | 0.87 |

Example 2: CD33 Cell Surface Downregulation Using the Humanized Antibodies

The purpose of the following example was to test whether the humanized anti-CD33 antibodies (as described in Example 1) were able to reduce the cell surface level of CD33 on primary human dendritic cells.

Monocytes were isolated from blood from healthy human donors using the RosetteSep™ monocyte isolation antibody cocktail (StemCell Technologies). The isolated monocytes were differentiated into dendritic cells with 100 ng/mL GM-CSF and 100 ng/mL IL-4 (Peprotech). Dendritic cells were plated in 24-well plates at 200,000 cells per mL, or in 6-well dishes at 500,000 cells in 2 mLs of RPMI supplemented with 10% Hyclone FBS, 2 mM glutamine, pen/strep, and non-essential amino acids. Anti-CD33 antibodies, or isotype control antibodies, were added to the wells and were incubated for 24 hours at 37° C. with 5% $CO_2$. Cell surface receptor expression was detected by FACS analysis according to standard techniques. Briefly, cells were incubated with anti-CD33-FITC clone HIM3-4 for 30 minutes on ice in the dark. Cells were washed twice in FACS buffer (PBS+2% FBS, 2 mM EDTA), and flow cytometry was performed on a BD FACS Canto. Data were analyzed using FlowJo software (Ashland, Oreg.), and CD33 surface expression was calculated as a percent of receptor expression relative to the expression in the absence of antibody.

All 88 humanized antibodies were able to reduce the level of cell-surface CD33; however, they exhibited a range of potencies, with many antibodies being much less effective than the parental antibody in decreasing cell-surface CD33. This was surprising, as the affinities of the antibodies were within 3 to 4-fold of the parental antibody. Of all of the antibodies tested, AB-H64 was the most potent. A comparison of ten of the humanized antibodies (AB-H1, AB-H3, AB-H6, AB-H11, AB-H22, AB-H24, AB-H26, AB-H63, AB-H64, and AB-H71) is shown in FIG. 1.

The half-maximal concentration ($EC_{50}$) and maximal downregulation by each of these antibodies are summarized in Table 3 below. Despite all of the antibodies having similar binding affinities, they displayed a range in their ability to decrease the level of cell-surface CD33, and AB-H64 was the most potent antibody. Thus, characteristics besides affinity contribute to the ability of an antibody to internalize its cell-surface receptor.

TABLE 3

CD33 cell surface downregulation with humanized antibodies

| Antibody | Receptor downregulation, ($EC_{50}$) (pM): | Maximal downregulation (% CD33 remaining) |
|---|---|---|
| Chimeric Ab | 86.9 | 24.1 |
| Chimeric Ab 2 | 118.7 | 23.2 |
| AB-H1 | 127.3 | 25.0 |
| AB-H3 | 93.3 | 21.2 |
| AB-H6 | 168.9 | 20.6 |
| AB-H11 | 77.2 | 23.3 |
| AB-H22 | 90.1 | 22.6 |
| AB-H24 | 72.5 | 22.2 |
| AB-H26 | 51.9 | 21.9 |
| AB-H63 | 32.0 | 20.3 |
| AB-H64 | 29.0 | 22.4 |
| AB-H71 | 41.2 | 25.8 |

While the humanized antibodies exhibited a range of potencies compared to the parental mouse antibody for decreasing the levels of cell-surface CD33, eight of the humanized antibodies showed unexpectedly increased potency over the comparator antibody. The data for these 8 antibodies are shown in Table 4 below. Of these antibodies, AB-H63 and AB-H64 were the most potent in downregulating cell surface CD33.

TABLE 4

CD33 cell surface downregulation with humanized antibodies

| Antibody | Receptor downregulation, ($EC_{50}$) (pM): |
|---|---|
| Chimeric Ab | 74.3 |
| AB-H2 | 51.7 |
| AB-H9 | 23.4 |
| AB-H14 | 42.0 |
| AB-H15 | 58.6 |
| AB-H63 | 4.1 |
| AB-H64 | 13.7 |
| AB-H65 | 48.1 |
| AB-H66 | 39.3 |

Chimeric Ab #2 was also evaluated for its ability to reduce cell-surface CD33. The data are summarized in Table 3 above. Compared to the parental antibody, Chimeric Ab, Chimeric Ab #2 was unexpectedly less potent in downregulating CD33. The only difference between these antibodies is the presence of an N-linked glycosylation site in VH-FR3 in Chimeric Ab. In AB-H64, the N-linked glycosylation site is also retained in VH-FR3, which suggests that the Fab glycosylation in this antibody may contribute to its potency in internalizing CD33.

Example 3: Affinity Maturation of Humanized Antibodies, and Characterization of Such Affinity Matured Antibodies The purpose of this example was to generate and characterize affinity matured anti-CD33 antibodies.

Affinity maturation was performed on three of the humanized antibodies, AB-H14, AB-H63, and AB-H64, by yeast display. Briefly, residues in the polynucleotides encoding the heavy or light chains of the three humanized antibodies were mutagenized and expressed in yeast. Yeast cells expressing the mutants that showed improved binding to soluble recombinant human CD33 protein were selected through several rounds of FACS sorting.

It total, 11 affinity matured clones were selected from the AB-H14 lineage, 15 affinity matured clones were selected from the AB-H63 lineage, and 8 clones from the AB-H64 lineage. The heavy chain variable region HVR sequences of the antibodies are depicted in Tables 9A to 9C below. The light chain variable region HVR sequences of the antibodies are depicted in Tables 10A to 10C below. The heavy chain framework regions of the antibodies are depicted in Tables 11A to 11D below. The light chain framework regions of the antibodies are depicted in Tables 12A to 12D below. The heavy chain variable region sequences of the antibodies are depicted in Table 13 below. The light chain variable region sequences of the antibodies are depicted in Table 14 below.

The affinities of AB-H64 and its variants (Table 5) for human CD33 were measured by Fortebio assay according to the method described in Example 1 above.

TABLE 5A

Fortebio assay affinity measurements of humanized antibody AB-H64, and its variants, for human CD33

| Antibody | Monovalent affinity, $K_D$ (M): | Fold affinity improvement over parental Ab (AB-H64): |
|---|---|---|
| AB-H64 | 2.86E−09 | — |
| AB-64.1 | 8.85E−10 | 3.23 |
| AB-64.2 | 7.86E−10 | 3.64 |
| AB-64.3 | 4.38E−10 | 6.53 |
| AB-64.4 | 3.60E−10 | 7.95 |
| AB-64.5 | 3.69E−10 | 7.76 |
| AB-64.6 | 3.36E−10 | 8.52 |
| AB-64.7 | 2.40E−10 | 11.94 |
| AB-64.8 | 2.77E−10 | 10.32 |

Affinity matured antibodies derived from the humanized antibody AB-H64 (AB-64.1 through AB-64.8) showed 3- to 12-fold improvements in affinity, as measured by ForteBio as shown in Table 5A.

In a separate experiment, as determined by the more sensitive BIAcore technique, affinity parameters of affinity matured antibodies derived from the humanized antibody AB-H64 were measured and were directly compared to that of the Chimeric Ab, according to the method described in Example 1 above. Compared to the Chimeric Ab, the affinity matured antibodies exhibited 15- to 443-fold improvements in affinity, and compared to AB-H64, showed 20- to 586-fold improvements in affinity, shown in Table 5B.

TABLE 5B

BIAcore affinity measurements of humanized antibody AB-H64, and its variants, for human CD33

| Antibody | Fab $K_D$ (M) monovalent | $k_{on}$ (1/Ms) | $k_{off}$ (1/s) | Fold Change to Chimeric Ab | Fold Change to AB-H64 |
|---|---|---|---|---|---|
| Chimeric Ab | 1.63E−09 | 9.95E+05 | 1.62E−03 | — | |
| AB-H64 | 2.15E−09 | 1.03E+06 | 2.21E−03 | 0.76 | — |
| AB-64.1 | 1.05E−10 | 4.61E+06 | 4.85E−04 | 15.45 | 20.43 |
| AB-64.2 | 4.58E−11 | 3.00E+06 | 1.37E−04 | 35.50 | 46.93 |
| AB-64.3 | 5.37E−12 | 4.98E+06 | 2.67E−05 | 302.96 | 400.57 |
| AB-64.4 | 3.67E−12 | 5.40E+06 | 1.98E−05 | 443.10 | 585.87 |
| AB-64.5 | 1.01E−11 | 6.30E+06 | 6.33E−05 | 161.70 | 213.79 |
| AB-64.6 | 6.30E−12 | 6.26E+06 | 3.95E−05 | 258.09 | 341.24 |
| AB-64.7 | 9.97E−12 | 8.78E+06 | 8.75E−05 | 163.17 | 215.74 |
| AB-64.8 | 6.71E−12 | 7.15E+06 | 4.80E−05 | 242.46 | 320.58 |
| AB-64.1.2 | 1.85E−10 | 2.74E+06 | 5.07E−04 | 8.80 | 11.63 |
| AB-64.1.8 | 1.75E−10 | 3.62E+06 | 6.34E−04 | 9.29 | 12.28 |

The affinity matured antibodies were characterized for their ability to decrease cell-surface levels of CD33. The half-maximal effective concentration ($EC_{50}$) of AB-H64 and its variants (Table 6A) for decreasing CD33 on primary human dendritic cells was measured according to the method described in Example 2 above.

TABLE 6A

CD33 cell surface downregulation with AB-H64 and its affinity matured variants

| Antibody | Receptor downregulation, ($EC_{50}$) (pM): |
|---|---|
| AB-H64 | 36.6 |
| AB-64.1 | 18.5 |
| AB-64.2 | 31.1 |
| AB-64.3 | 25.7 |
| AB-64.4 | 23.6 |
| AB-64.5 | 26.3 |
| AB-64.6 | 34.0 |
| AB-64.7 | 30.6 |
| AB-64.8 | 27.2 |

The majority of the affinity matured antibodies exhibited substantial improvement in potency over the parental antibodies. Unexpectedly, AB-64.1, which was not the highest affinity antibody, was the most effective in reducing CD33 levels.

Figure 2:
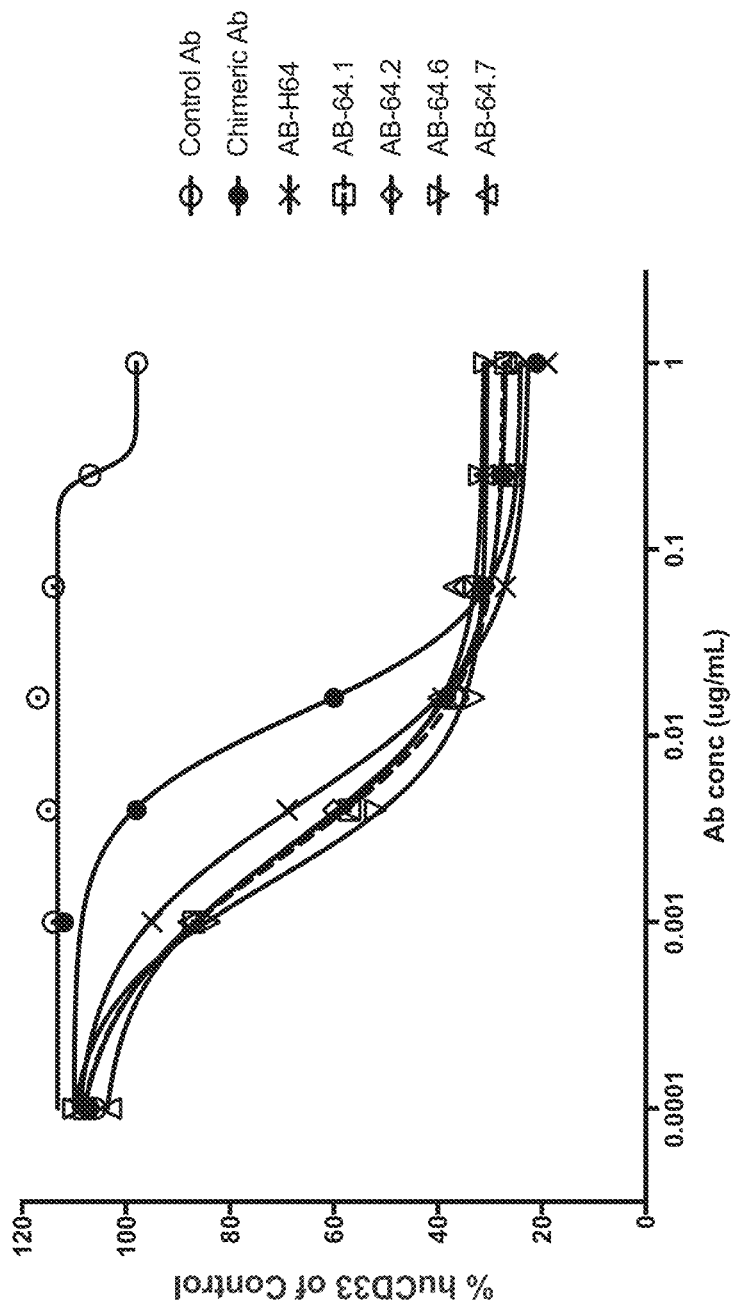
FIG. 2 depicts flow cytometry results measuring CD33 levels on the surface of primary human monocyte-derived dendritic cells after incubation with different concentrations of affinity matured CD33 antibodies.

In a separate experiment, two variants that showed modest 20- to 50-fold improvements in affinity, AB-64.1 and AB-64.2, and two variants that had greater affinity improvements, 215- to 340-fold, AB-64.6 and AB-64.7, were directly compared to the parental humanized antibody, AB-H64, and to the Chimeric Ab for their ability to reduce cell surface levels of CD33, according to the method described in Example 2 above. The data are shown in FIG. 2 and the half-maximal effective concentration ($EC_{50}$) and maximal CD33 reduction are summarized in Table 6B.

TABLE 6B

CD33 cell surface downregulation with humanized antibodies

| Antibody | Receptor downregulation, (EC$_{50}$) (pM): | Maximal downregulation (% CD33 remaining) |
|---|---|---|
| Chimeric Ab | 86.9 | 24.1 |
| Chimeric Ab 2 | 118.7 | 23.2 |
| AB-H64 | 29.0 | 22.4 |
| AB-64.1 | 15.4 | 27.3 |
| AB-64.2 | 16.6 | 26.8 |
| AB-64.6 | 11.3 | 30.6 |
| AB-64.7 | 17.0 | 31.2 |
| AB-64.1.2 | 18.9 | 24.8 |
| AB-64.1.8 | 28.2 | 30.1 |

Unexpectedly, for the H64 lineage antibodies, the CD33 antibodies with the highest affinity were not the most effective in maximally reducing the levels of cell-surface CD33. Of the affinity matured antibodies, AB-64.1 and AB-64.2, which had moderate affinity improvements, showed the best maximal CD33 decreases. All of the affinity matured antibodies exhibited increased potency in reducing cell surface CD33 compared to the Chimeric Ab or the humanized antibody, AB-H64. Of all of the affinity matured antibodies, AB-64.1 (as well as its variant AB-64.1.2) consistently exhibited the best enhancement in potency over the Chimeric Ab and the humanized antibody, AB-H64.

Example 4: Assessing Affinity and EC$_{50}$ Values for Antibodies with Additional Amino Acid Modifications The purpose of this example was to determine if additional amino acid modifications designed to remove potential manufacturing liability sequences impacted either the affinity of the antibodies for CD33, or their ability to reduce cell-surface levels of CD33.

Additional amino acid modifications were generated in AB-64.1, and the affinities of the resultant antibodies (AB-64.1.1 through AB-64.1.15) were measures by ForteBio assay (See the methods of Example 1) (Table 7 below). The affinity parameters of two of the antibodies, 64.1.2 and 64.1.8, were measured in a separate experiment by BIAcore, where they were directly compared to the parental antibody, AB-64.1, the parental humanized antibody, AB-H64, and the Chimeric Ab. The data are shown in Table 5B above.

TABLE 7 affinity measurements for modified variants of AB-64.1

| Antibody | Monovalent affinity, K$_D$ (M): |
|---|---|
| AB-64.1 | 4.99E−10 |
| AB-64.1.1 | 4.29E−10 |
| AB-64.1.2 | 9.02E−10 |
| AB-64.1.3 | 6.47E−10 |
| AB-64.1.4 | 6.39E−10 |
| AB-64.1.5 | 6.97E−10 |
| AB-64.1.6 | 8.36E−10 |
| AB-64.1.7 | 3.91E−10 |
| AB-64.1.8 | 8.02E−10 |
| AB-64.1.9 | 1.06E−09 |
| AB-64.1.10 | 1.45E−09 |
| AB-64.1.11 | 1.15E−09 |
| AB-64.1.12 | 9.22E−10 |
| AB-64.1.13 | 1.45E−09 |

TABLE 7-continued affinity measurements for modified variants of AB-64.1

| Antibody | Monovalent affinity, K$_D$ (M): |
|---|---|
| AB-64.1.14 | 7.43E−10 |
| AB-64.1.15 | 4.12E−10 |

Modification of the HVR-H2 sequence from FIYPSNGITG (SEQ ID NO: 115) to FIYPSNRITG (SEQ ID NO: 119), FIYPSNQITG (SEQ ID NO: 118), or FIYPSNVITG (SEQ ID NO: 120) did not have a substantial impact on affinity, as the measured K$_D$ values of antibodies that contained these changes were within 3-fold of the parental antibody AB-64.1.

Modification of the VH FR3 sequence from YAQKFQGRATLTVDNSTSTAYMELSSLRSEDTAVYYCAR (SEQ ID NO: 12) to YAQKFQGRATLTVDNSASTAYMELSSLRSEDTAVYYCAR (SEQ ID NO: 18), YAQKFQGRATLTVDQSTSTAYMELSSLRSEDTA VYYCAR (SEQ ID NO: 17), YAQKFQGRATLTVDTSTSTAYMELSSLRSEDTAVYYCAR (SEQ ID NO: 16), or YAQKFQGRATLTVDNPTSTAYMELSSLRSEDTAVYYCAR (SEQ ID NO: 19) also did not have a substantial impact on affinity, as the measured K$_D$ values of antibodies that contained these changes were also within 3-fold of the parental antibody AB-64.1.

The antibodies with the additional amino acid modifications were also tested for their ability to reduce cell-surface levels of CD33. Table 8 shows the percentage of CD33 remaining on the surface of primary human dendritic cells after treatment with AB-64.1 and its variants at 0.16 µg/mL for 24 hours.

TABLE 8

CD33 cell surface downregulation with AB-64.1 and its variants

| Antibody | Receptor downregulation, (% remaining at 0.16 µg/mL antibody) |
|---|---|
| AB-64.1 | 37.2 |
| AB-64.1.1 | 37.0 |
| AB-64.1.2 | 32.4 |
| AB-64.1.3 | 38.5 |
| AB-64.1.4 | 38.0 |
| AB-64.1.5 | 37.3 |
| AB-64.1.6 | 37.0 |
| AB-64.1.7 | 35.9 |
| AB-64.1.8 | 32.7 |
| AB-64.1.9 | 37.4 |
| AB-64.1.10 | 39.8 |
| AB-64.1.11 | 38.6 |
| AB-64.1.12 | 38.5 |
| AB-64.1.13 | 35.9 |
| AB-64.1.14 | 38.4 |
| AB-64.1.15 | 38.9 |

Modification of the HVR-H2 sequence from FIYPSNGITG (SEQ ID NO: 115) to FIYPSNRITG (SEQ ID NO: 119), FIYPSNQITG (SEQ ID NO: 118), or FIYPSNVITG (SEQ ID NO: 120) did not have a substantial impact on the ability of the antibodies to decrease cell-surface CD33, as the percent of CD33 remaining on the cell surface after incubation with the antibodies containing these modifications was within 5% of the parental antibody AB-64.1.

Modification of the VH FR3 sequence from YAQKFQGRATLTVDNSTSTAYMELSSLRSEDTAVYYCAR (SEQ ID NO: 12) to YAQKFQGRATLTVDNS ASTAYMELSSLRSEDTAVYYCAR (SEQ ID NO: 18), YAQKFQGRATLTVDQSTSTAYMELSSLRSEDTA VYYCAR (SEQ ID NO: 17), YAQKFQGRATLTVD TSTSTAYMELSSLRSEDTAVYYCAR (SEQ ID NO: 16), or YAQKFQGRATLTVDNPTSTAYMELSSLRSEDTA VYYCAR (SEQ ID NO: 19) also did not have a substantial impact on the ability of the antibodies to decrease cell-surface CD33, as the percent of CD33 remaining on the cell surface after incubation with the antibodies containing these modifications was within 5% of the parental antibody AB-64.1.

In a separate experiment, the ability of two of the variants, AB-64.1.2 and AB-64.1.8, to reduce CD33 was evaluated and compared to the parental antibody, AB-64.1, the humanized parental antibody AB-H64, and the Chimeric Ab. Table 6B above shows the half-maximal effective concentration ($EC_{50}$) and maximal CD33 reduction on the surface of primary human dendritic cells after 24 hours exposure to the antibodies.

Modification of the HVR-H2 sequence from FIYPSNGITG (SEQ ID NO: 115) to FIYPSNRITG (SEQ ID NO: 119) or FIYPSNQITG (SEQ ID NO: 118) did not have a substantial impact on the ability of the antibodies to decrease cell-surface CD33, as the $EC_{50}$ of antibodies containing these modifications was within 2-fold of the parental antibody AB-64.1 and the maximal decrease of CD33 on the cell surface after incubation with antibodies containing these modifications was within 5% of the parental antibody AB-64.1.

Modification of the VH FR3 sequence from YAQKFQGRATLTVDNSTSTAYMELSSLRSEDTAVYYCAR (SEQ ID NO: 12) to YAQKFQGRATLTVDNSASTAYMELSSLRSEDTAVYYCAR (SEQ ID NO: 18) also did not have a substantial impact on the ability of the antibodies to decrease cell-surface CD33, as the $EC_{50}$ of antibodies containing these modifications was within 2-fold of the parental antibody AB-64.1 and the maximal decrease of CD33 on the cell surface after incubation with antibodies containing these modifications was within 5% of the parental antibody AB-64.1.

AB-64.1.2 displayed both increased potency and increased maximal reduction in cell surface CD33 compared to AB-64.1.8. In AB-64.1.2, the potential N-linked glycosylation site in VH-FR3 retained, while in AB-64.1.8, it has been removed, suggesting that the Fab glycosylation may contribute to the ability of this antibody to decrease cell surface CD33. In a comparison with its parental lineage antibodies, AB-64.1.2 had similar potency in decreasing cell surface CD33 compared to its parental antibody AB-64.1, showed a 1.5-fold increase in potency, compared to the parental humanized antibody, AB-H64, and exhibited a 4.6-fold increase in potency compared to the Chimeric Ab.

TABLE 9A

| EU or Kabat heavy chain HVR H1 sequences of anti-CD33 antibodies | | |
|---|---|---|
| Ab(s) | HVR H1 | SEQ ID NO: |
| AB-H14; AB-H63; AB-63.6; AB-63.7; AB-63.13; AB-63.14; AB-H64; AB-64.1; AB-64.2; AB-64.3; AB-64.4; AB-64.1.1; AB-64.1.2; AB-64.1.3; AB-64.1.4; AB-64.1.5; AB-64.1.6; AB-64.1.7; AB-64.1.8; AB-64.1.9; AB-64.1.10; AB-64.1.11; AB-64.1.12; AB-64.1.13; AB-64.1.14; and AB-64.1.15 | GYTFTDYNLH | 105 |
| AB-14.1 | GATFTDYNFH | 106 |
| AB-14.2 | GATFTDYNYH | 107 |
| AB-14.3; AB-14.4; AB-14.5; AB-14.6; AB-14.7; AB-14.8; AB-14.9; AB-14.10; AB-14.11; AB-63.4; AB-63.15; AB-63.16; AB-63.17; AB-64.5; AB-64.6; AB-64.7; and AB-64.8 | GYTFTDYNYH | 108 |
| AB-63.5 | GYTFTDYNNH | 109 |
| AB-63.8 | GVTFTDYNYH | 110 |
| AB-63.9 | GYAFTDYNLH | 111 |
| AB-63.10 | GYTETDYNLH | 112 |
| AB-63.11 and AB-63.12 | GYTFTDYNFH | 113 |
| AB-63.18 | GYTHTDYNLH | 114 |
| Formula I | $GX_1X_2X_3TDYNX_4H$<br>$X_1$ is Y, A, or V<br>$X_2$ is T or A<br>$X_3$ is F, E, or H<br>$X_4$ is L, F, Y, or N | 152 |

TABLE 9B

EU or Kabat heavy chain HVR H2 sequences of anti-CD33 antibodies

| Ab(s) | HVR H2 | SEQ ID NO: |
|---|---|---|
| AB-H14; AB-14.1; AB-14.2; AB-14.3; AB-14.4; AB-14.5; AB-14.6; AB-14.7; AB-14.8; AB-14.9; AB-14.10; AB-14.11; AB-H63; AB-63.4; AB-63.5; AB-63.6; AB-63.7; AB-63.8; AB-63.9; AB-63.10; AB-63.12; AB-63.14; AB-63.15; AB-63.16; AB-63.17; AB-63.18; AB-H64; AB-64.1; AB-64.2; AB-64.3; AB-64.4; AB-64.5; AB-64.6; AB-64.7; AB-64.8; AB-64.1.4; AB-64.1.5; AB-64.1.6; and AB-64.1.7 | FIYPSNGITG | 115 |
| AB-63.11 | FIYPANGITG | 116 |
| AB-63.13 | FIYPSNGIRG | 117 |
| AB-64.1.1; AB-64.1.8; and AB-64.1.9 | FIYPSNQITG | 118 |
| AB-64.1.2; AB-64.1.10; AB-64.1.11; and AB-64.1.12 | FIYPSNRITG | 119 |
| AB-64.1.3; AB-64.1.13; AB-64.1.14; and AB-64.1.15 | FIYPSNVITG | 120 |
| Formula II | FIYPX$_1$NX$_2$IX$_3$G<br>X$_1$ is S or A<br>X$_2$ is G, Q, R, or V<br>X$_3$ is T or R | 153 |

TABLE 9C

EU or Kabat heavy chain HVR H3 sequences of anti-CD33 antibodies

| Ab(s) | HVR H3 | SEQ ID NO: |
|---|---|---|
| AB-H14; AB-14.4; AB-H63; AB-63.4; AB-63.6; AB-63.7; AB-63.8; AB-H64; and AB-64.2 | STVDYFDY | 121 |
| AB-14.1; AB-14.3; AB-14.5; AB-14.6; AB-14.7; AB-14.8; AB-14.9; AB-14.10; AB-63.5; AB-63.9; AB-63.10; AB-63.11; AB-63.13; AB-63.14; AB-63.16; AB-63.17; AB-63.18; AB-64.1; AB-64.4; AB-64.5; AB-64.6; AB-64.7; AB-64.8; AB-64.1.1; AB-64.1.2; AB-64.1.3; AB-64.1.4; AB-64.1.5; AB-64.1.6; AB-64.1.7; AB-64.1.8; AB-64.1.9; AB-64.1.10; AB-64.1.11; AB-64.1.12; AB-64.1.13; AB-64.1.14; and AB-64.1.15 | SDVDYFDY | 122 |
| AB-14.2 and AB-64.3 | SFVDYFDY | 123 |
| AB-14.11 | SSVDYFDY | 124 |
| AB-63.12 | STVDYFDD | 125 |
| AB-63.15 | SDVDYFDL | 126 |
| Formula III | SX$_1$VDYFDX$_2$<br>X$_1$ is T, D, F, or S<br>X$_2$ is Y, D, or L | 154 |

TABLE 10A

EU or Kabat light chain HVR L1 sequences of anti-CD33 antibodies

| Ab(s) | HVR L1 | SEQ ID NO: |
|---|---|---|
| AB-H14; AB-14.1; AB-H63; AB-63.4; AB-63.5; AB-63.13; AB-63.18; AB-H64; AB-64.1; AB-64.1.1; AB-64.1.2; AB-64.1.3; AB-64.1.4; AB-64.1.5; AB-64.1.6; AB-64.1.7; AB-64.1.8; AB-64.1.9; AB-64.1.10; AB-64.1.11; AB-64.1.12; AB-64.1.13; AB-64.1.14; and AB-64.1.15 | RASQSVSTSTYSYMH | 127 |
| AB-14.6; AB-14.7; AB-14.8; AB-14.9; AB-64.5; and AB-64.7 | RASQSVGTSTYSYMH | 128 |
| AB-14.10 | RASQSVSASTYSYMH | 129 |
| AB-14.2, AB-14.3; AB-14.4; AB-14.5; AB-14.11; AB-63.6; AB-63.7; AB-63.8; AB-63.9; AB-63.10; AB-63.11; AB-63.12; AB-63.15; AB-64.3; AB-64.4; AB-64.6; and AB-64.8 | RASQDVSTSTYSYMH | 130 |
| AB-63.14 | KASQDVSTSTYSYMH | 131 |
| AB-63.16 | RASQSVHTSTYSYMH | 132 |
| AB-63.17 | RGSQSVSTSTYSYMH | 133 |
| AB-64.2 | RVSQDVSTSTYSYMH | 134 |
| Formula IV | $X_1X_2SQX_3VX_4X_5STYSYMH$<br>$X_1$ is R or K<br>$X_2$ is A, G, or V<br>$X_3$ is S or D<br>$X_4$ is S, G, or H<br>$X_5$ is T or A | 155 |

TABLE 10B

EU or Kabat light chain HVR L2 sequences of anti-CD33 antibodies

| Ab(s) | HVR L2 | SEQ ID NO: |
|---|---|---|
| AB-H14; AB-14.1; AB-14.2; AB-14.5; AB-14.7; AB-14.10; AB-H63; AB-63.4; AB-63.5; AB-63.6; AB-63.8; AB-63.10; AB-63.11; AB-63.13; AB-63.14; AB-63.16; AB-H64; AB-64.1; AB-64.2; AB-64.5; AB-64.8; AB-64.1.1; AB-64.1.2; AB-64.1.3; AB-64.1.4; AB-64.1.5; AB-64.1.6; AB-64.1.7; AB-64.1.8; AB-64.1.9; AB-64.1.10; AB-64.1.11; AB-64.1.12; AB-64.1.13; AB-64.1.14; and AB-64.1.15 | YASNLES | 135 |
| AB-14.3; AB-14.4; and AB-14.11 | YVSNLES | 136 |
| AB-14.6 | YASALES | 137 |
| AB-14.8 | YASNLGS | 138 |
| AB-14.9 | YAVNLES | 139 |
| AB-63.7 | YAFNLES | 140 |
| AB-63.9; AB-64.3; and AB-64.4 | YASYLES | 141 |
| AB-63.12 and AB-63.15 | YASNVES | 142 |
| AB-63.17 and AB-63.18 | YESNLES | 143 |
| AB-64.6 | YASFLES | 144 |
| AB-64.7 | YASNLNS | 145 |
| Formula V | $YX_1X_2X_3X_4X_5S$<br>$X_1$ is A, V, or E<br>$X_2$ is S, V, or F | 156 |

TABLE 10B-continued

EU or Kabat light chain HVR L2 sequences of anti-CD33 antibodies

| Ab(s) | HVR L2 | SEQ ID NO: |
|---|---|---|
|  | $X_3$ is N, A, Y, or F<br>$X_4$ is L or V<br>$X_5$ is E, G, or N |  |

TABLE 10C

EU or Kabat light chain HVR L3 sequences of anti-CD33 antibodies

| Ab(s) | HVR L3 | SEQ ID NO: |
|---|---|---|
| AB-H14; AB-14.1; AB-14.2; AB-14.3; AB-14.4; AB-14.5; AB-14.6; AB-14.7; AB-14.8; AB-14.9; AB-14.10; AB-14.11; AB-H63; AB-63.4; AB-63.5; AB-63.6, AB-63.8; AB-63.11; AB-63.14; AB-63.15; AB-63.16; AB-63.17; AB-63.18; AB-H64; AB-64.1; AB-64.2; AB-64.5; AB-64.6; AB-64.8; AB-64.1.1; AB-64.1.2; AB-64.1.3; AB-64.1.4; AB-64.1.5; AB-64.1.6; AB-64.1.7; AB-64.1.8; AB-64.1.9; AB-64.1.10; AB-64.1.11; AB-64.1.12; AB-64.1.13; AB-64.1.14; and AB-64.1.15 | QHSWEIPLT | 146 |
| AB-63.7 | QHSWEIPLE | 147 |
| AB-63.9; AB-64.3; and AB-64.4 | EHSWEIPLT | 148 |
| AB-63.10 | QHSWELPLT | 149 |
| AB-63.12 | QHSWAIPLT | 150 |
| AB-63.13 and AB-64.7 | QHSEEIPLT | 151 |
| Formula VI | $X_1HSX_2X_3X_4PLX_5$<br>$X_1$ is Q or E<br>$X_2$ is W or E<br>$X_3$ is E or A<br>$X_4$ is I or L<br>$X_5$ is T or E | 157 |

TABLE 11A

EU or Kabat heavy chain framework 1 sequences of anti-CD33 antibodies

| Ab(s) | VH FR1 | SEQ ID NO: |
|---|---|---|
| AB-H14; AB-14.1; AB-14.2; AB-14.3; AB-14.4; AB-14.5; AB-14.6; AB-14.7; AB-14.8; AB-14.9; AB-14.10; AB-14.11; AB-H63; AB-63.4; AB-63.5; AB-63.6; AB-63.7; AB-63.9; AB-63.10; AB-63.11; AB-63.12; AB-63.13; AB-63.15; AB-63.16; and AB-63.17 | QVQLVQSGAEVKKPGASVKVSCKAS | 2 |
| AB-63.8; AB-63.14; and AB-63.18 | QVQLVQSGAEVKKPGSSVKVSCKAS | 3 |
| AB-H64; AB-64.1; AB-64.2; AB-64.3; AB-64.4; AB-64.5; AB-64.6; AB-64.7; AB-64.8; AB-64.1.1; AB-64.1.2; AB-64.1.3; AB-64.1.4; AB-64.1.5; AB-64.1.6; AB-64.1.7; AB-64.1.8; AB-64.1.9; AB-64.1.10; AB-64.1.11; AB-64.1.12; AB-64.1.13; AB-64.1.14; and AB-64.1.15 | QVQLVQSGAEVKKPGASVKISCKAS | 4 |
| Formula VII | QVQLVQSGAEVKKPGX$_1$SVKX$_2$SCKAS<br>$X_1$ is A or S<br>$X_2$ is V or I | 158 |

TABLE 11B

EU or Kabat heavy chain framework 2 sequences of anti-CD33 antibodies

| Ab(s) | VH FR2 | SEQ ID NO: |
|---|---|---|
| AB-H14; AB-14.1; AB-14.2; AB-14.3; AB-14.4; AB-14.5; AB-14.6; AB-14.7; AB-14.8; AB-14.9; AB-14.10; AB-14.11; AB-H63; AB-63.4; AB-63.5; AB-63.6; AB-63.7; AB-63.8; AB-63.9; AB-63.10; AB-63.11; AB-63.12; AB-63.13; AB-63.14; AB-63.15; AB-63.16; AB-63.17; AB-63.18; AB-H64; AB-64.1; AB-64.2; AB-64.3; AB-64.4; AB-64.5; AB-64.6; AB-64.7; AB-64.8; AB-64.1.1; AB-64.1.2; AB-64.1.3; AB-64.1.4; AB-64.1.5; AB-64.1.6; AB-64.1.7; AB-64.1.8; AB-64.1.9; AB-64.1.10; AB-64.1.11; AB-64.1.12; AB-64.1.13; AB-64.1.14; and AB-64.1.15 | WVRQAPGQGLEWIG | 5 |

TABLE 11C

EU or Kabat heavy chain framework 3 sequences of anti-CD33 antibodies

| Ab(s) | VH FR3 | SEQ ID NO: |
|---|---|---|
| AB-H14; AB-14.4; AB-14.5; AB-14.6; AB-14.7; AB-14.8; AB-14.9; AB-14.10; AB-14.11; AB-H63; AB-63.4; AB-63.5; AB-63.6; AB-63.7; AB-63.9; AB-63.10; AB-63.13; AB-63.14; AB-63.15; AB-63.16; AB-63.17; and AB-63.18 | YAQKFQGRVTMTVDTSTSTVYMELSSLRSEDTAVYYCAR | 6 |
| AB-14.1 | YAQDFQGRVTMTVDTSTSTVYMELSSLRSEDTAVYYCAR | 7 |
| AB-14.2 and AB-63.8 | YAQKFQDRVTMTVDTSTSTVYMELSSLRSEDTAVYYCAR | 8 |
| AB-14.3 | SAQKFQGRVTMTVDTSTSTVYMELSSLRSEDTAVYYCAR | 9 |
| AB-63.11 | YAQKDQGRVTMTVDTSTSTVYMELSSLRSEDTAVYYCAR | 10 |
| AB-63.12 | YAQKFTGRVTMTVDTSTSTVYMELSSLRSEDTAVYYCAR | 11 |
| AB-H64; AB-64.1; AB-64.2; AB-64.4; AB-64.6; AB-64.7; AB-64.1.1; AB-64.1.2; and AB-64.1.3 | YAQKFQGRATLTVDNSTSTAYMELSSLRSEDTAVYYCAR | 12 |
| AB-64.3 | YAEKFEGRATLTVDNSTSTAYMELSSLRSEDTAVYYCAR | 13 |
| AB-64.5 | YAQKFFGRATLTVDNSTSTAYMELSSLRSEDTAVYYCAR | 14 |
| AB-64.8 | YAQKFQHRATLTVDNSTSTAYMELSSLRSEDTAVYYCAR | 15 |
| AB-64.1.4; AB-64.1.10; and AB-64.1.13 | YAQKFQGRATLTVDTSTSTAYMELSSLRSEDTAVYYCAR | 16 |
| AB-64.1.5; AB-64.1.11; and AB-64.1.14 | YAQKFQGRATLTVDQSTSTAYMELSSLRSEDTAVYYCAR | 17 |
| AB-64.1.6; AB-64.1.8; AB-64.1.12; and AB-64.1.15 | YAQKFQGRATLTVDNSASTAYMELSSLRSEDTAVYYCAR | 18 |
| AB-64.1.7 and AB-64.1.9 | YAQKFQGRATLTVDNPTSTAYMELSSLRSEDTAVYYCAR | 19 |
| Formula VIII | $X_1AX_2X_3X_4X_5X_6RX_7TX_8TVDX_9X_{10}X_{11}STX_{12}$YMELSSLRSEDTAVYYCAR<br>$X_1$ is Y or S<br>$X_2$ is Q or E<br>$X_3$ is K or D<br>$X_4$ is F or D<br>$X_5$ is Q, F, E, or T<br>$X_6$ is G, D, or H<br>$X_7$ is V or A<br>$X_8$ is M or L<br>$X_9$ is T, N, or Q<br>$X_{10}$ is S or P<br>$X_{11}$ is T or A<br>$X_{12}$ is V or A | 159 |

TABLE 11D

EU or Kabat heavy chain framework 4 sequences of anti-CD33 antibodies

| Ab(s) | VH FR4 | SEQ ID NO: |
|---|---|---|
| AB-H14; AB-14.1; AB-14.2; AB-14.3; AB-14.4; AB-14.5; AB-14.6; AB-14.7; AB-14.8; AB-14.9; AB-14.10; AB-14.11; AB-H63; AB-63.4; AB-63.5; AB-63.6; AB-63.7; AB-63.8; AB-63.9; AB-63.10; AB-63.11; AB-63.12; AB-63.13; AB-63.14; AB-63.15; AB-63.16; AB-63.17; and AB-63.18 | WGQGTLVTVSS | 20 |
| AB-H64; AB-64.1; AB-64.2; AB-64.3; AB-64.4; AB-64.5; AB-64.6; AB-64.7; AB-64.8; AB-64.1.1; AB-64.1.2; AB-64.1.3; AB-64.1.4; AB-64.1.5; AB-64.1.6; AB-64.1.7; AB-64.1.8; AB-64.1.9; AB-64.1.10; AB-64.1.11; AB-64.1.12; AB-64.1.13; AB-64.1.14; and AB-64.1.15 | WGQGTLLTVSS | 21 |
| Formula IX | WGQGTLX$_1$TVSS<br>X$_1$ is V or L | 160 |

TABLE 12A

EU or Kabat light chain framework 1 sequences of anti-CD33 antibodies

| Ab(s) | VL FR1 | SEQ ID NO: |
|---|---|---|
| AB-H14; AB-14.1; AB-14.2; AB-14.3; AB-14.4; AB-14.5; AB-14.6; AB-14.7; AB-14.10; and AB-14.11 | DIQMTQSPSSLSASVGDRVTITC | 22 |
| AB-14.8 | DIQMTQSPSSLPASVGDRVTITC | 23 |
| AB-14.9 | GIQMTQSPSSLSASVGDRVTITC | 24 |
| AB-H63; AB-63.4; AB-63.5; AB-63.6; AB-63.7; AB-63.8; AB-63.9; AB-63.10; AB-63.11; AB-63.12; AB-63.13; AB-63.14; AB-63.15; AB-63.16; AB-63.17; AB-63.18; AB-H64; AB-64.1; AB-64.2; AB-64.3; AB-64.4; AB-64.5; AB-64.6; AB-64.7; AB-64.8; AB-64.1.1; AB-64.1.2; AB-64.1.3; AB-64.1.4; AB-64.1.5; AB-64.1.6; AB-64.1.7; AB-64.1.8; AB-64.1.9; AB-64.1.10; AB-64.1.11; AB-64.1.12; AB-64.1.13; AB-64.1.14; and AB-64.1.15 | DIVLTQSPDSLAVSLGERATINC | 25 |
| AB-63.14 | DIVLTQSPDSLAVSLGERATIDC | 26 |
| Formula X | X$_1$IX$_2$X$_3$TQSPX$_4$SLX$_5$X$_6$SX$_7$GX$_8$RX$_9$TIX$_{10}$C<br>X$_1$ is D or G<br>X$_2$ is Q or V<br>X$_3$ is M or L<br>X$_4$ is S or D<br>X$_5$ is S, P, or A<br>X$_6$ is A or V<br>X$_7$ is V or L<br>X$_8$ is D or E<br>X$_9$ is V or A<br>X$_{10}$ is T, N, or D | 161 |

TABLE 12B

EU or Kabat light chain framework 2 sequences of anti-CD33 antibodies

| Ab(s) | VL FR2 | SEQ ID NO: |
|---|---|---|
| AB-H14; AB-14.1; AB-14.2; AB-14.3; AB-14.4; AB-14.6; AB-14.7; AB-14.8; AB-14.9; AB-14.10; and AB-14.11 | WYQQKPGKAPKLLIK | 27 |
| AB-H63; AB-63.4; AB-63.5; AB-63.6; AB-63.7; AB-63.8; AB-63.9; AB-63.10; AB-63.11; AB-63.12; AB-63.13; AB-63.14; AB-63.15; AB-63.16; AB-63.17; AB-63.18; AB-H64; AB-64.1; AB-64.2; AB-64.3; AB-64.4; AB-64.5; AB- | WYQQKPGQPPKLLIK | 28 |

TABLE 12B-continued

EU or Kabat light chain framework 2 sequences of anti-CD33 antibodies

| Ab(s) | VL FR2 | SEQ ID NO: |
|---|---|---|
| 64.6; AB-64.7; AB-64.8; AB-64.1.1; AB-64.1.2; AB-64.1.3; AB-64.1.4; AB-64.1.5; AB-64.1.6; AB-64.1.7; AB-64.1.8; AB-64.1.9; AB-64.1.10; AB-64.1.11; AB-64.1.12; AB-64.1.13; AB-64.1.14; and AB-64.1.15 | | |
| AB-14.5 | WYQRKPGKAPKLLIK | 168 |
| Formula XI | WYQQKPGX$_1$X$_2$PKLLIK<br>X$_1$ is K or Q<br>X$_2$ is A or P | 162 |
| Formula XIV | WYQX$_1$KPGX$_2$X$_3$PKLLIK<br>X$_1$ is Q or R<br>X$_2$ is K or Q<br>X$_3$ is A or P | 169 |

TABLE 12C

EU or Kabat light chain framework 3 sequences of anti-CD33 antibodies

| Ab(s) | VL FR3 | SEQ ID NO: |
|---|---|---|
| AB-H14; AB-14.1; AB-14.2; AB-14.3; AB-14.4; AB-14.5; AB-14.6; AB-14.7; AB-14.8; AB-14.9; and AB-14.11 | GVPSRFSGSGSGTDFTLTISSLQPEDFATYYC | 29 |
| AB-14.10 | GVPSRFSGSGSGTDFTLTISSLQPEDLATYYC | 30 |
| AB-H63; AB-63.4; AB-63.5; AB-63.6; AB-63.7; AB-63.8; AB-63.9; AB-63.10; AB-63.11; AB-63.12; AB-63.13; AB-63.14; AB-63.15; AB-63.16; AB-63.17; AB-63.18; AB-H64; AB-64.1; AB-64.2; AB-64.3; AB-64.4; AB-64.5; AB-64.6; AB-64.7; AB-64.8; AB-64.1.1; AB-64.1.2; AB-64.1.3; AB-64.1.4; AB-64.1.5; AB-64.1.6; AB-64.1.7; AB-64.1.8; AB-64.1.9; AB-64.1.10; AB-64.1.11; AB-64.1.12; AB-64.1.13; AB-64.1.14; and AB-64.1.15 | GVPDRFSGSGSGTDFTLTISSLQAEDVAVYYC | 31 |
| Formula XII | GVPX$_1$RFSGSGSGTDFTLTISSLQX$_2$EDX$_3$AX$_4$YYC<br>X$_1$ is S or D<br>X$_2$ is P or A<br>X$_3$ is F, L, or V<br>X$_4$ is T or V | 163 |

TABLE 12D

EU or Kabat light chain framework 4 sequences of anti-CD33 antibodies

| Ab(s) | VL FR4 | SEQ ID NO: |
|---|---|---|
| AB-H14; AB-14.1; AB-14.2; AB-14.3; AB-14.4; AB-14.5; AB-14.6; AB-14.7; AB-14.8; AB-14.9; AB-14.10; AB-14.11; AB-H63; AB-63.4; AB-63.5; AB-63.6; AB-63.7; AB-63.8; AB-63.9; AB-63.10; AB-63.11; AB-63.12; AB-63.13; AB-63.14; AB-63.16; AB-63.17; AB-63.18; AB-H64; AB-64.1; AB-64.2; AB-64.3; AB-64.4; AB-64.5; AB-64.6; AB-64.7; AB-64.8; AB-64.1.1; AB-64.1.2; AB-64.1.3; AB-64.1.4; AB-64.1.5; AB-64.1.6; AB-64.1.7; AB-64.1.8; AB-64.1.9; AB-64.1.10; AB-64.1.11; AB-64.1.12; AB-64.1.13; AB-64.1.14; and AB-64.1.15 | FGQGTKLEIK | 32 |

TABLE 12D-continued

EU or Kabat light chain framework 4 sequences of anti-CD33 antibodies

| Ab(s) | VL FR4 | SEQ ID NO: |
|---|---|---|
| AB-63.15 | FGQGTKLEIE | 33 |
| Formula XIII | FGQGTKLEIX$_1$<br>X$_1$ is K or E | 164 |

TABLE 13

EU or Kabat heavy chain variable region sequences of anti-CD33 antibodies

| Ab(s) | HCVR | SEQ ID NO: |
|---|---|---|
| AB-14.1 | QVQLVQSGAEVKKPGASVKVSCKASGATFTDYNFHWVRQAPGQG<br>LEWIGFIYPSNGITGYAQDFQGRVTMTVDTSTSTVYMELSSLRS<br>EDTAVYYCARSDVDYFDYWGQGTLVTVSS | 34 |
| AB-14.2 | QVQLVQSGAEVKKPGASVKVSCKASGATFTDYNYHWVRQAPGQG<br>LEWIGFIYPSNGITGYAQKFQDRVTMTVDTSTSTVYMELSSLRS<br>EDTAVYYCARSFVDYFDYWGQGTLVTVSS | 35 |
| AB-14.3 | QVQLVQSGAEVKKPGASVKVSCKASGYTFTDYNYHWVRQAPGQG<br>LEWIGFIYPSNGITGSAQKFQGRVTMTVDTSTSTVYMELSSLRS<br>EDTAVYYCARSDVDYFDYWGQGTLVTVSS | 36 |
| AB-14.4 | QVQLVQSGAEVKKPGASVKVSCKASGYTFTDYNYHWVRQAPGQG<br>LEWIGFIYPSNGITGYAQKFQGRVTMTVDTSTSTVYMELSSLRS<br>EDTAVYYCADSTVDYFDYWGQGTLVTVSS | 37 |
| AB-14.5; AB-14.6;<br>AB-14.7;<br>AB-14.8; AB-14.9;<br>AB-14.10, AB-63.16;<br>and AB-63.17 | QVQLVQSGAEVKKPGASVKVSCKASGYTFTDYNYHWVRQAPGQG<br>LEWIGFIYPSNGITGYAQKFQGRVTMTVDTSTSTVYMELSSLRS<br>EDTAVYYCARSDVDYFDYWGQGTLVTVSS | 38 |
| AB-14.11 | QVQLVQSGAEVKKPGASVKVSCKASGYTFTDYNYHWVRQAPGQG<br>LEWIGFIYPSNGITGYAQKFQGRVTMTVDTSTSTVYMELSSLRS<br>EDTAVYYCARSSVDYFDYWGQGTLVTVSS | 39 |
| AB-63.4 | QVQLVQSGAEVKKPGASVKVSCKASGYTFTDYNYHWVRQAPGQG<br>LEWIGFIYPSNGITGYAQKFQGRVTMTVDTSTSTVYMELSSLRS<br>EDTAVYYCARSTVDYFDYWGQGTLVTVSS | 40 |
| AB-63.5 | QVQLVQSGAEVKKPGASVKVSCKASGYTFTDYNNHWVRQAPGQG<br>LEWIGFIYPSNGITGYAQKFQGRVTMTVDTSTSTVYMELSSLRS<br>EDTAVYYCARSDVDYFDYWGQGTLVTVSS | 41 |
| AB-H14; AB-H63;<br>AB-63.6; AB-63.7;<br>and AB-H2 | QVQLVQSGAEVKKPGASVKVSCKASGYTFTDYNLHWVRQAPGQG<br>LEWIGFIYPSNGITGYAQKFQGRVTMTVDTSTSTVYMELSSLRS<br>EDTAVYYCARSTVDYFDYWGQGTLVTVSS | 42 |
| AB-63.8 | QVQLVQSGAEVKKPGSSVKVSCKASGVTFTDYNYHWVRQAPGQG<br>LEWIGFIYPSNGITGYAQKFQDRVTMTVDTSTSTVYMELSSLRS<br>EDTAVYYCARSTVDYFDYWGQGTLVTVSS | 43 |
| AB-63.9 | QVQLVQSGAEVKKPGASVKVSCKASGYAFTDYNLHWVRQAPGQG<br>LEWIGFIYPSNGITGYAQKFQGRVTMTVDTSTSTVYMELSSLRS<br>EDTAVYYCARSDVDYFDYWGQGTLVTVSS | 44 |
| AB-63.10 | QVQLVQSGAEVKKPGASVKVSCKASGYTETDYNLHWVRQAPGQG<br>LEWIGFIYPSNGITGYAQKFQGRVTMTVDTSTSTVYMELSSLRS<br>EDTAVYYCARSDVDYFDYWGQGTLVTVSS | 45 |
| AB-63.11 | QVQLVQSGAEVKKPGASVKVSCKASGYTFTDYNFHWVRQAPGQG<br>LEWIGFIYPANGITGYAQKDQGRVTMTVDTSTSTVYMELSSLRS<br>EDTAVYYCARSDVDYFDYWGQGTLVTVSS | 46 |
| AB-63.12 | QVQLVQSGAEVKKPGASVKVSCKASGYTFTDYNFHWVRQAPGQG<br>LEWIGFIYPSNGITGYAQKFTGRVTMTVDTSTSTVYMELSSLRS<br>EDTAVYYCARSTVDYFDDWGQGTLVTVSS | 47 |

TABLE 13-continued

EU or Kabat heavy chain variable region sequences of anti-CD33 antibodies

| Ab(s) | HCVR | SEQ ID NO: |
|---|---|---|
| AB-63.13 | QVQLVQSGAEVKKPGASVKVSCKASGYTFTDYNLHWVRQAPGQG<br>LEWIGFIYPSNGIRGYAQKFQGRVTMTVDTSTSTVYMELSSLRS<br>EDTAVYYCARSDVDYFDYWGQGTLVTVSS | 48 |
| AB-63.14 | QVQLVQSGAEVKKPGSSVKVSCKASGYTFTDYNLHWVRQAPGQG<br>LEWIGFIYPSNGITGYAQKFQGRVTMTVDTSTSTVYMELSSLRS<br>EDTAVYYCARSDVDYFDYWGQGTLVTVSS | 49 |
| AB-63.15 | QVQLVQSGAEVKKPGASVKVSCKASGYTFTDYNYHWVRQAPGQG<br>LEWIGFIYPSNGITGYAQKFQGRVTMTVDTSTSTVYMELSSLRS<br>EDTAVYYCARSDVDYFDLWGQGTLVTVSS | 50 |
| AB-63.18 | QVQLVQSGAEVKKPGSSVKVSCKASGYTHTDYNLHWVRQAPGQG<br>LEWIGFIYPSNGITGYAQKFQGRVTMTVDTSTSTVYMELSSLRS<br>EDTAVYYCARSDVDYFDYWGQGTLVTVSS | 51 |
| AB-64.1; AB-64.4 | QVQLVQSGAEVKKPGASVKISCKASGYTFTDYNLHWVRQAPGQG<br>LEWIGFIYPSNGITGYAQKFQGRATLTVDNSTSTAYMELSSLRS<br>EDTAVYYCARSDVDYFDYWGQGTLLTVSS | 52 |
| AB-H64 and AB-64.2 | QVQLVQSGAEVKKPGASVKISCKASGYTFTDYNLHWVRQAPGQG<br>LEWIGFIYPSNGITGYAQKFQGRATLTVDNSTSTAYMELSSLRS<br>EDTAVYYCARSTVDYFDYWGQGTLLTVSS | 53 |
| AB-64.3 | QVQLVQSGAEVKKPGASVKISCKASGYTFTDYNLHWVRQAPGQG<br>LEWIGFIYPSNGITGYAEKFEGRATLTVDNSTSTAYMELSSLRS<br>EDTAVYYCARSFVDYFDYWGQGTLLTVSS | 54 |
| AB-64.5 | QVQLVQSGAEVKKPGASVKISCKASGYTFTDYNYHWVRQAPGQG<br>LEWIGFIYPSNGITGYAQKFFGRATLTVDNSTSTAYMELSSLRS<br>EDTAVYYCARSDVDYFDYWGQGTLLTVSS | 55 |
| AB-64.6 and AB-64.7 | QVQLVQSGAEVKKPGASVKISCKASGYTFTDYNYHWVRQAPGQG<br>LEWIGFIYPSNGITGYAQKFQGRATLTVDNSTSTAYMELSSLRS<br>EDTAVYYCARSDVDYFDYWGQGTLLTVSS | 56 |
| AB-64.8 | QVQLVQSGAEVKKPGASVKISCKASGYTFTDYNYHWVRQAPGQG<br>LEWIGFIYPSNGITGYAQKFQHRATLTVDNSTSTAYMELSSLRS<br>EDTAVYYCARSDVDYFDYWGQGTLLTVSS | 57 |
| AB-64.1.1 | QVQLVQSGAEVKKPGASVKISCKASGYTFTDYNLHWVRQAPGQG<br>LEWIGFIYPSNQITGYAQKFQGRATLTVDNSTSTAYMELSSLRS<br>EDTAVYYCARSDVDYFDYWGQGTLLTVSS | 58 |
| AB-64.1.2 | QVQLVQSGAEVKKPGASVKISCKASGYTFTDYNLHWVRQAPGQG<br>LEWIGFIYPSNRITGYAQKFQGRATLTVDNSTSTAYMELSSLRS<br>EDTAVYYCARSDVDYFDYWGQGTLLTVSS | 59 |
| AB-64.1.3 | QVQLVQSGAEVKKPGASVKISCKASGYTFTDYNLHWVRQAPGQG<br>LEWIGFIYPSNVITGYAQKFQGRATLTVDNSTSTAYMELSSLRS<br>EDTAVYYCARSDVDYFDYWGQGTLLTVSS | 60 |
| AB-64.1.4 | QVQLVQSGAEVKKPGASVKISCKASGYTFTDYNLHWVRQAPGQG<br>LEWIGFIYPSNGITGYAQKFQGRATLTVDTSTSTAYMELSSLRS<br>EDTAVYYCARSDVDYFDYWGQGTLLTVSS | 61 |
| AB-64.1.5 | QVQLVQSGAEVKKPGASVKISCKASGYTFTDYNLHWVRQAPGQG<br>LEWIGFIYPSNGITGYAQKFQGRATLTVDQSTSTAYMELSSLRS<br>EDTAVYYCARSDVDYFDYWGQGTLLTVSS | 62 |
| AB-64.1.6 | QVQLVQSGAEVKKPGASVKISCKASGYTFTDYNLHWVRQAPGQG<br>LEWIGFIYPSNGITGYAQKFQGRATLTVDNSASTAYMELSSLRS<br>EDTAVYYCARSDVDYFDYWGQGTLLTVSS | 63 |
| AB-64.1.7 | QVQLVQSGAEVKKPGASVKISCKASGYTFTDYNLHWVRQAPGQG<br>LEWIGFIYPSNGITGYAQKFQGRATLTVDNPTSTAYMELSSLRS<br>EDTAVYYCARSDVDYFDYWGQGTLLTVSS | 64 |
| AB-64.1.8 | QVQLVQSGAEVKKPGASVKISCKASGYTFTDYNLHWVRQAPGQG<br>LEWIGFIYPSNQITGYAQKFQGRATLTVDNSASTAYMELSSLRS<br>EDTAVYYCARSDVDYFDYWGQGTLLTVSS | 65 |
| AB-64.1.9 | QVQLVQSGAEVKKPGASVKISCKASGYTFTDYNLHWVRQAPGQG<br>LEWIGFIYPSNQITGYAQKFQGRATLTVDNPTSTAYMELSSLRS<br>EDTAVYYCARSDVDYFDYWGQGTLLTVSS | 66 |

TABLE 13-continued

EU or Kabat heavy chain variable region sequences of anti-CD33 antibodies

| Ab(s) | HCVR | SEQ ID NO: |
|---|---|---|
| AB-64.1.10 | QVQLVQSGAEVKKPGASVKISCKASGYTFTDYNLHWVRQAPGQGLEWIGFIYPSNRITGYAQKFQGRATLTVDTSTSTAYMELSSLRSEDTAVYYCARSDVDYFDYWGQGTLLTVSS | 67 |
| AB-64.1.11 | QVQLVQSGAEVKKPGASVKISCKASGYTFTDYNLHWVRQAPGQGLEWIGFIYPSNRITGYAQKFQGRATLTVDQSTSTAYMELSSLRSEDTAVYYCARSDVDYFDYWGQGTLLTVSS | 68 |
| AB-64.1.12 | QVQLVQSGAEVKKPGASVKISCKASGYTFTDYNLHWVRQAPGQGLEWIGFIYPSNRITGYAQKFQGRATLTVDNSASTAYMELSSLRSEDTAVYYCARSDVDYFDYWGQGTLLTVSS | 69 |
| AB-64.1.13 | QVQLVQSGAEVKKPGASVKISCKASGYTFTDYNLHWVRQAPGQGLEWIGFIYPSNVITGYAQKFQGRATLTVDTSTSTAYMELSSLRSEDTAVYYCARSDVDYFDYWGQGTLLTVSS | 70 |
| AB-64.1.14 | QVQLVQSGAEVKKPGASVKISCKASGYTFTDYNLHWVRQAPGQGLEWIGFIYPSNVITGYAQKFQGRATLTVDQSTSTAYMELSSLRSEDTAVYYCARSDVDYFDYWGQGTLLTVSS | 71 |
| AB-64.1.15 | QVQLVQSGAEVKKPGASVKISCKASGYTFTDYNLHWVRQAPGQGLEWIGFIYPSNVITGYAQKFQGRATLTVDNSASTAYMELSSLRSEDTAVYYCARSDVDYFDYWGQGTLLTVSS | 72 |
| AB-H9 and AB-H71 | QVQLVQSGAELKKPGASVKVSCKASGYTFTDYNLHWVRQAPGQRLEWIGFIYPSNGITGYSQKFQGKATLTVDTSASTAYMELSSLRSEDTAVYYCARSTVDYFDYWGQGTTVTVSS | 73 |
| AB-H3 and AB-H15 | QVQLVQSGAEVKKPGASVKISCKASGYTFTDYNLHWVRQAPGQGLEWIGFIYPSNGITGYAQKFQGRATLTVDTSTSTAYMELSSLRSEDTAVYYCARSTVDYFDYWGQGTLLTVSS | 74 |
| AB-H65 | QVQLVQSGAEVKKPGASVKVSCKASGYTFTDYNLHWVRQAPGQGLEWMGFIYPSNGITGYAQKFQGRVTMTRDTSTSTVYMELSSLRSEDTAVYYCARSTVDYFDYWGQGTTVTVSS | 75 |
| AB-H66 | QVQLVQSGAEVKKPGASVKISCKASGYTFTDYNLHWVRQAPGQGLEWIGFIYPSNGITGYAQKFQGRATLTVDTSTSTAYMELSSLRSEDTAVYYCARSTVDYFDYWGQGTTVTVSS | 76 |
| AB-H1 | QVQLVQSGAEVKKPGASVKVSCKASGYTFTDYNLHWVRQAPGQGLEWMGFIYPSNGITGYAQKFQGRVTMTRDTSTSTVYMELSSLRSEDTAVYYCARSTVDYFDYWGQGTLVTVSS | 170 |
| AB-H6 | QVQLVQSGAEVKKPGASVKVSCKASGYTFTDYNLHWVRQAPGQGLEWMGFIYPSNGITGYAQKFQGRVTMTVDTSTSTAYMELSSLRSEDTAVYYCARSTVDYFDYWGQGTTVTVSS | 171 |
| AB-H11 | QVQLVQSGAEVKKPGASVKVSCKASGYTFTDYNLHWVRQAPGQSLEWIGFIYPSNGITGYSQKFQGKATLTVDTSASTAYMELSSLRSEDTAVYYCARSTVDYFDYWGQGTTVTVSS | 172 |
| AB-H22 | QVQLVQSGAEVKKPGASVKISCKASGYTFTDYNLHWVRQAPGQRLEWIGFIYPSNGITGYNQKFKNKATLTVDTSASTAYMELSSLRSEDTAVYYCARSTVDYFDYWGQGTTVTVSS | 173 |
| AB-H24 | QVQLVQSGAEVKKPGASVKISCKASGYTFTDYNLHWVRQAPGQRLEWIGFIYPSNGITGYSQKFQGKATLTVDTSASTAYMELSSLRSEDTAVYYCARSTVDYFDYWGQGTTVTVSS | 174 |
| AB-H26 | QVQLVQSGAEVKKPGASVKVSCKASGYTFTDYNLHWVRQAPGQRLEWIGFIYPSNGITGYSQKFQGRATLTVDTSASTAYMELSSLRSEDTAVYYCARSTVDYFDYWGQGTTVTVSS | 175 |

TABLE 14

EU or Kabat light chain variable region
sequences of anti-CD33 antibodies

| Ab(s) | LCVR | SEQ ID NO: |
|---|---|---|
| AB-H14; AB-14.1; AB-H15; AB-22; AB-24; and AB-26 | DIQMTQSPSSLSASVGDRVTITCRASQSVSTSTYSYMHWYQQKPGKAPKLLIKYASNLESGVPSRFSGSGSGTDFTLTISSLQPEDFATYYCQHSWEIPLTFGQGTKLEIK | 77 |
| AB-14.2 | DIQMTQSPSSLSASVGDRVTITCRASQDVSTSTYSYMHWYQQKPGKAPKLLIKYASNLESGVPSRFSGSGSGTDFTLTISSLQPEDFATYYCQHSWEIPLTFGQGTKLEIK | 78 |
| AB-14.3; AB-14.4; and AB-14.11 | DIQMTQSPSSLSASVGDRVTITCRASQDVSTSTYSYMHWYQQKPGKAPKLLIKYVSNLESGVPSRFSGSGSGTDFTLTISSLQPEDFATYYCQHSWEIPLTFGQGTKLEIK | 79 |
| AB-14.5 | DIQMTQSPSSLSASVGDRVTITCRASQDVSTSTYSYMHWYQRKPGKAPKLLIKYASNLESGVPSRFSGSGSGTDFTLTISSLQPEDFATYYCQHSWEIPLTFGQGTKLEIK | 80 |
| AB-14.6 | DIQMTQSPSSLSASVGDRVTITCRASQSVGTSTYSYMHWYQQKPGKAPKLLIKYASALESGVPSRFSGSGSGTDFTLTISSLQPEDFATYYCQHSWEIPLTFGQGTKLEIK | 81 |
| AB-14.7 | DIQMTQSPSSLSASVGDRVTITCRASQSVGTSTYSYMHWYQQKPGKAPKLLIKYASNLESGVPSRFSGSGSGTDFTLTISSLQPEDFATYYCQHSWEIPLTFGQGTKLEIK | 82 |
| AB-14.8 | DIQMTQSPSSLPASVGDRVTITCRASQSVGTSTYSYMHWYQQKPGKAPKLLIKYASNLGSGVPSRFSGSGSGTDFTLTISSLQPEDFATYYCQHSWEIPLTFGQGTKLEIK | 83 |
| AB-14.9 | GIQMTQSPSSLSASVGDRVTITCRASQSVGTSTYSYMHWYQQKPGKAPKLLIKYAVNLESGVPSRFSGSGSGTDFTLTISSLQPEDFATYYCQHSWEIPLTFGQGTKLEIK | 84 |
| AB-14.10 | DIQMTQSPSSLSASVGDRVTITCRASQSVSASTYSYMHWYQQKPGKAPKLLIKYASNLESGVPSRFSGSGSGTDFTLTISSLQPEDLATYYCQHSWEIPLTFGQGTKLEIK | 85 |
| AB-H63; AB-63.4; AB-63.5; AB-H64; AB-64.1 AB-64.1.1; AB-64.1.2; AB-64.1.3; AB-64.1.4; AB-64.1.5; AB-64.1.6; AB-64.1.7; AB-64.1.8; AB-64.1.9; AB-64.1.10; AB-64.1.11; AB-64.1.12; AB-64.1.13 AB-64.1.14; AB-64.1.15; AB-H65, AB-H66; and AB-71 | DIVLTQSPDSLAVSLGERATINCRASQSVSTSTYSYMHWYQQKPGQPPKLLIKYASNLESGVPDRFSGSGSGTDFTLTISSLQAEDVAVYYCQHSWEIPLTFGQGTKLEIK | 86 |
| AB-63.6; AB-63.8; AB-63.11; and AB-64.8 | DIVLTQSPDSLAVSLGERATINCRASQDVSTSTYSYMHWYQQKPGQPPKLLIKYASNLESGVPDRFSGSGSGTDFTLTISSLQAEDVAVYYCQHSWEIPLTFGQGTKLEIK | 87 |
| AB-63.7 | DIVLTQSPDSLAVSLGERATINCRASQDVSTSTYSYMHWYQQKPGQPPKLLIKYAFNLESGVPDRFSGSGSGTDFTLTISSLQAEDVAVYYCQHSWEIPLEFGQGTKLEIK | 88 |
| AB-63.9; AB-64.3; and AB-64.4 | DIVLTQSPDSLAVSLGERATINCRASQDVSTSTYSYMHWYQQKPGQPPKLLIKYASYLESGVPDRFSGSGSGTDFTLTISSLQAEDVAVYYCEHSWEIPLTFGQGTKLEIK | 89 |
| AB-63.10 | DIVLTQSPDSLAVSLGERATINCRASQDVSTSTYSYMHWYQQKPGQPPKLLIKYASNLESGVPDRFSGSGSGTDFTLTISSLQAEDVAVYYCQHSWELPLTFGQGTKLEIK | 90 |
| AB-63.12 | DIVLTQSPDSLAVSLGERATINCRASQDVSTSTYSYMHWYQQKPGQPPKLLIKYASNVESGVPDRFSGSGSGTDFTLTISSLQAEDVAVYYCQHSWAIPLTFGQGTKLEIK | 91 |
| AB-63.13 | DIVLTQSPDSLAVSLGERATINCRASQSVSTSTYSYMHWYQQKPGQPPKLLIKYASNLESGVPDRFSGSGSGTDFTLTISSLQAEDVAVYYCQHSEEIPLTFGQGTKLEIK | 92 |

TABLE 14-continued

EU or Kabat light chain variable region sequences of anti-CD33 antibodies

| Ab(s) | LCVR | SEQ ID NO: |
|---|---|---|
| AB-63.14 | DIVLTQSPDSLAVSLGERATIDCKASQDVSTSTYSYMHWYQQKPGQPPKLLIKYASNLESGVPDRFSGSGSGTDFTLTISSLQAEDVAVYYCQHSWEIPLTFGQGTKLEIK | 93 |
| AB-63.15 | DIVLTQSPDSLAVSLGERATINCRASQDVSTSTYSYMHWYQQKPGQPPKLLIKYASNVESGVPDRFSGSGSGTDFTLTISSLQAEDVAVYYCQHSWEIPLTFGQGTKLEIE | 94 |
| AB-63.16 | DIVLTQSPDSLAVSLGERATINCRASQSVHTSTYSYMHWYQQKPGQPPKLLIKYASNLESGVPDRFSGSGSGTDFTLTISSLQAEDVAVYYCQHSWEIPLTFGQGTKLEIK | 95 |
| AB-63.17 | DIVLTQSPDSLAVSLGERATINCRGSQSVSTSTYSYMHWYQQKPGQPPKLLIKYESNLESGVPDRFSGSGSGTDFTLTISSLQAEDVAVYYCQHSWEIPLTFGQGTKLEIK | 96 |
| AB-63.18 | DIVLTQSPDSLAVSLGERATINCRASQSVSTSTYSYMHWYQQKPGQPPKLLIKYESNLESGVPDRFSGSGSGTDFTLTISSLQAEDVAVYYCQHSWEIPLTFGQGTKLEIK | 97 |
| AB-64.2 | DIVLTQSPDSLAVSLGERATINCRVSQDVSTSTYSYMHWYQQKPGQPPKLLIKYASNLESGVPDRFSGSGSGTDFTLTISSLQAEDVAVYYCQHSWEIPLTFGQGTKLEIK | 98 |
| AB-64.5 | DIVLTQSPDSLAVSLGERATINCRASQSVGTSTYSYMHWYQQKPGQPPKLLIKYASNLESGVPDRFSGSGSGTDFTLTISSLQAEDVAVYYCQHSWEIPLTFGQGTKLEIK | 99 |
| AB-64.6 | DIVLTQSPDSLAVSLGERATINCRASQDVSTSTYSYMHWYQQKPGQPPKLLIKYASFLESGVPDRFSGSGSGTDFTLTISSLQAEDVAVYYCQHSWEIPLTFGQGTKLEIK | 100 |
| AB-64.7 | DIVLTQSPDSLAVSLGERATINCRASQSVGTSTYSYMHWYQQKPGQPPKLLIKYASNLNSGVPDRFSGSGSGTDFTLTISSLQAEDVAVYYCQHSEEIPLTFGQGTKLEIK | 101 |
| AB-H1; AB-H2; AB-H3; AB-H6; AB-H9; and AB-H11 | DIQMTQSPSSLSASVGDRVTITCRASQSVSTSTYSYMHWYQQKPGKAPKLLIYYASNLESGVPSRFSGSGSGTDFTLTISSLQPEDFATYYCQHSWEIPLTFGQGTKLEIK | 102 |

Example 5: Affinity Maturation of AB-H14 and AB-H63

The affinities of AB-H14 and its affinity-matured variants (Table 15) and AB-H63 and its affinity-matured variants (Table 16), for human CD33 were measured by Fortebio assay according to the method described in Example 1 above.

TABLE 15 affinity measurements of humanized antibody AB-H14, and its variants, for human CD33

| Antibody | Monovalent affinity, $K_D$ (M): | Fold affinity improvement over parental Ab (AB-H14): | $k_{on}$ (1/Ms) | $k_{off}$ (1/s) |
|---|---|---|---|---|
| AB-H14 | 2.91E−09 | — | 3.97E+05 | 1.15E−03 |
| AB-14.1 | 2.99E−10 | 9.73 | 6.70E+05 | 2.00E−04 |
| AB-14.2 | 2.02E−10 | 14.39 | 9.91E+05 | 2.00E−04 |
| AB-14.3 | 2.36E−10 | 12.31 | 8.47E+05 | 2.00E−04 |
| AB-14.4 | 2.24E−10 | 13.00 | 8.95E+05 | 2.00E−04 |
| AB-14.5 | 2.12E−10 | 13.73 | 9.45E+05 | 2.00E−04 |
| AB-14.6 | 2.95E−10 | 9.83 | 8.94E+05 | 2.64E−04 |
| AB-14.7 | 2.46E−10 | 11.81 | 8.13E+05 | 2.00E−04 |
| AB-14.8 | 2.14E−10 | 13.57 | 9.35E+05 | 2.00E−04 |
| AB-14.9 | 2.17E−10 | 13.37 | 9.21E+05 | 2.00E−04 |
| AB-14.10 | 2.21E−10 | 13.15 | 9.06E+05 | 2.00E−04 |
| AB-14.11 | 2.05E−10 | 14.14 | 9.74E+05 | 2.00E−04 |

TABLE 16 affinity measurements of humanized antibody AB-H63, and its variants, for human CD33

| Antibody | Monovalent affinity, $K_D$ (M): | Fold affinity improvement over parental Ab (AB-H63): | $k_{on}$ (1/Ms) | $k_{off}$ (1/s) |
|---|---|---|---|---|
| AB-H63 | 2.72E−09 | — | 6.15E+05 | 1.68E−03 |
| AB-63.4 | 7.18E−10 | 3.79 | 6.02E+05 | 1.12E−03 |
| AB-63.5 | 6.19E−10 | 4.40 | 7.76E+05 | 1.55E−03 |
| AB-63.6 | 3.04E−10 | 8.96 | 6.79E+05 | 1.76E−03 |
| AB-63.7 | 9.17E−10 | 2.97 | 8.09E+05 | 5.81E−04 |
| AB-63.8 | 2.19E−10 | 12.43 | 8.47E+05 | 5.24E−04 |

TABLE 16-continued affinity measurements of humanized antibody AB-H63, and its variants, for human CD33

| Antibody | Monovalent affinity, $K_D$ (M): | Fold affinity improvement over parental Ab (AB-H63): | $k_{on}$ (1/Ms) | $k_{off}$ (1/s) |
|---|---|---|---|---|
| AB-63.9 | 2.71E−10 | 10.05 | 6.58E+05 | 2.00E−04 |
| AB-63.10 | 4.66E−10 | 5.84 | 5.96E+05 | 5.46E−04 |
| AB-63.11 | 3.84E−10 | 7.09 | 9.13E+05 | 2.00E−04 |
| AB-63.12 | 2.77E−10 | 9.84 | 7.38E+05 | 2.00E−04 |
| AB-63.13 | 2.25E−10 | 12.08 | 7.21E+05 | 3.36E−04 |
| AB-63.14 | 2.44E−10 | 11.15 | 8.39E+05 | 3.22E−04 |
| AB-63.15 | 2.25E−10 | 12.09 | 7.23E+05 | 2.00E−04 |
| AB-63.16 | 2.10E−10 | 12.97 | 1.02E+06 | 2.30E−04 |
| AB-63.17 | 2.95E−10 | 9.23 | 8.19E+05 | 2.00E−04 |
| AB-63.18 | 6.13E−10 | 4.44 | 9.03E+05 | 2.04E−04 |

Affinity matured antibodies derived from the humanized antibodies AB-H14 and AB-H63 showed 10- to 14-fold and 3- to 13-fold improvements in affinity, respectively.

The affinity matured antibodies were characterized for their ability to decrease cell-surface levels of CD33 on primary dendritic cells according to the method described in Example 2 above.

The half-maximal effective concentration ($EC_{50}$) and the maximal CD33 downregulation by AB-H14 and its variants and AB-H63 and its variants are shown in Table 17 and Table 18, respectively. The majority of the affinity matured antibodies exhibited substantial improvement in potency over the parental antibodies. However, surprisingly, as observed with the H64 lineage antibodies, the CD33 antibodies with the highest affinity were not necessarily the most effective in maximally reducing the levels of cell-surface CD33.

TABLE 17

CD33 cell surface downregulation with AB-H14 and its affinity matured variants

| Antibody | Receptor downregulation, ($EC_{50}$) (pM): | Maximal Downregulation (% CD33 remaining) |
|---|---|---|
| AB-H14 | 151.1 | 15.01 |
| AB-14.1 | 92.7 | 18.58 |
| AB-14.2 | 55.0 | 23.77 |
| AB-14.3 | 43.0 | 25.36 |
| AB-14.4 | 58.2 | 27.62 |
| AB-14.5 | 34.2 | 26.43 |
| AB-14.6 | 32.4 | 24.04 |
| AB-14.7 | 35.1 | 23.37 |
| AB-14.8 | 23.4 | 21.16 |
| AB-14.9 | 39.9 | 26.12 |
| AB-14.10 | 49.4 | 20.91 |
| AB-14.11 | 47.0 | 27.47 |

TABLE 18

CD33 cell surface downregulation with AB-H63 and its affinity matured variants

| Antibody | Receptor downregulation, ($EC_{50}$) (pM): | Maximal Downregulation (% CD33 remaining) |
|---|---|---|
| AB-H63 | 72.6 | 16.08 |
| AB-63.4 | 69.1 | 17.64 |
| AB-63.5 | 40.1 | 16.48 |
| AB-63.6 | 46.3 | 17.07 |
| AB-63.7 | 41.6 | 18.43 |
| AB-63.8 | 16.7 | 22.00 |
| AB-63.9 | 40.7 | 20.15 |
| AB-63.10 | 41.8 | 21.23 |
| AB-63.11 | 44.0 | 23.02 |
| AB-63.12 | 35.0 | 27.49 |
| AB-63.13 | 44.8 | 25.53 |
| AB-63.14 | 51.9 | 25.33 |
| AB-63.15 | 47.6 | 27.54 |
| AB-63.16 | 29.3 | 23.36 |
| AB-63.17 | 52.2 | 27.20 |
| AB-63.18 | 62.9 | 26.75 |

Example 6: Characterization of the Ability of CD33 Antibodies to Compete with CD33 Ligand for Binding to CD33

The purpose of this example was to test whether CD33 antibodies could recognize the ligand-binding site on CD33 and compete with ligand binding on CD33 receptors.

Figure 3:
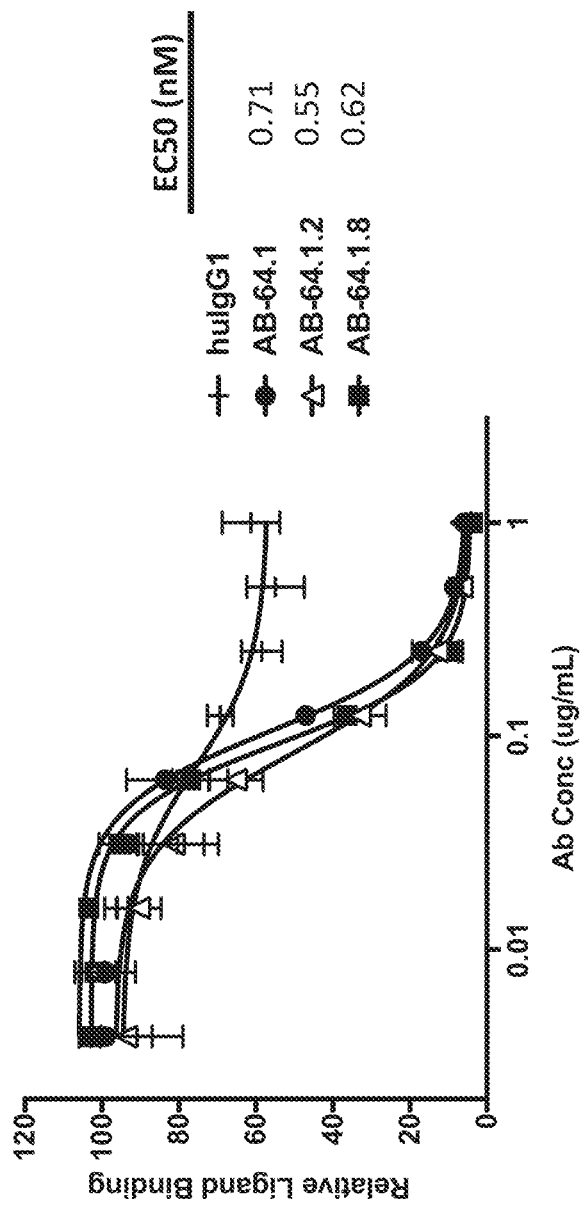
FIG. 3 depicts results from a ligand-blocking assay, where red blood cells containing sialic acid ligands for CD33 are evaluated for their ability to bind to CD33 in the presence of different concentrations of CD33 antibodies.

The affinity matured antibody, AB-64.1 and two of its variants, AB-64.1.2 and AB-64.1.8, were evaluated for their ability to compete with CD33 ligand for binding to CD33 using a red blood cell (RBC) solid adhesion assay, according to standard protocols (Kelm, et al. *Current Biology,* 1994). Red blood cells are highly decorated with glycoproteins containing sialic acids; therefore the ability of an antibody to block RBC binding to immobilized CD33 was used to determine ligand interference. Briefly, 96-well Immunolon plates were coated overnight with 5 μg/mL CD33-Fc, then were washed with PBS and blocked for one hour with binding buffer (PBS containing 0.25% BSA and 1 mM $CaCl_2$). CD33 antibodies were added and incubated for one hour at room temperature with gentle rocking. After removal of unbound antibody, RBCs were added to each well at $3.0 \times 10^6$ cells/mL and incubated at room temperature for one hour. Unbound RBCs were then carefully removed by washing three times with PBS, after which water was added to each well to induce hypotonic lysis of bound RBCs. The plate was transferred to −80° C. for 10 minutes, followed by 37° C. for 15 minutes. Quantification of bound RBCs was measured as peroxidase activity by adding TMB, followed by the addition of 2N sulfuric acid to stop the reaction. Signal was detected at 450 nm. Data was calculated as a percentage of RBC binding to plate-bound CD33-Fc in the absence of antibody. The results are shown in FIG. 3.

Example 7: Characterization of the Impact of the Fc Region on an Internalizing CD33 Antibody The purpose of this example was to evaluate the impact of the Fc on the ability of a CD33 antibody to decrease the cell surface level of CD33 on primary myeloid cells in vitro and in vivo.

The Fc region of an antibody can interact with Fcγ receptors expressed on the surface of cells, and myeloid cells that endogenously express CD33 also express multiple Fcγ receptors. Thus, the effect of different human IgG isotypes' interaction between the antibody's Fc and cell-surface Fcγ receptors, the clustering ability of the antibodies, and the impact the ability of the antibody to internalize the receptor was tested.

Figure 4:
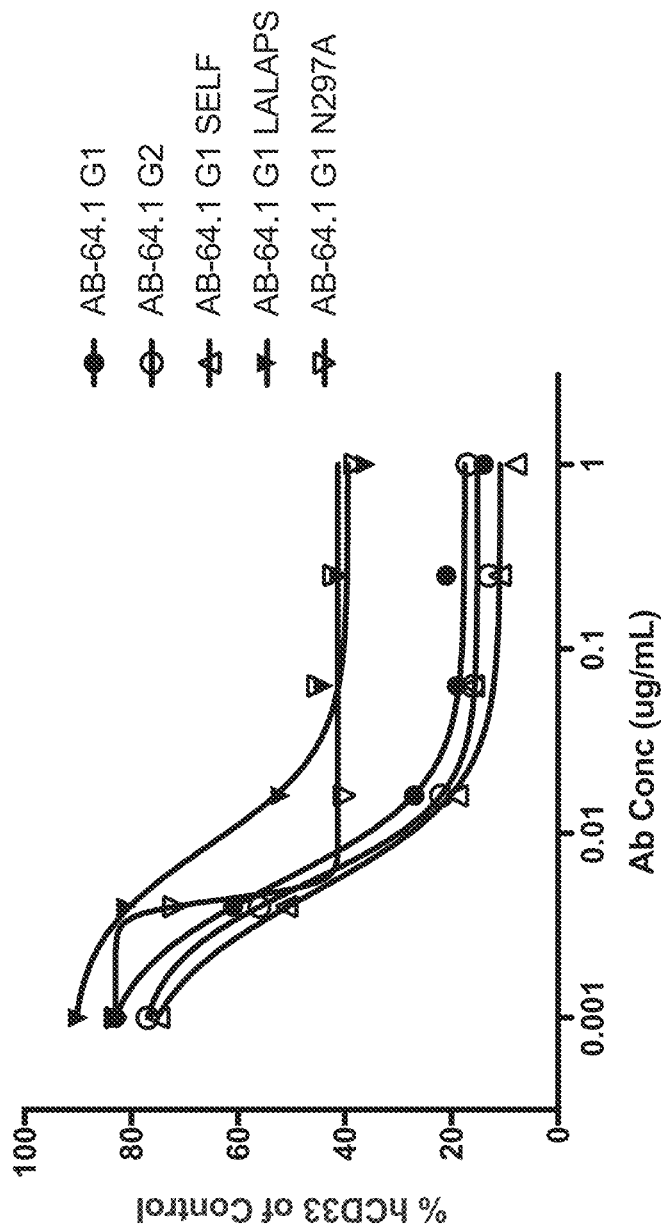
FIG. 4 depicts results from a flow cytometry assay measuring CD33 levels on the surface of primary human monocyte-derived dendritic cells after treatment with different concentrations of CD33 antibodies containing different Fc regions.

Antibodies containing the AB-64.1 variable region and different human IgG variants were generated. The Fc's tested included IgG1, which binds all Fcγ receptors; IgG1 SELF, which contains the S267E and L328F mutations and exhibits enhanced binding to CD32B and the R131 variant of CD32A; IgG2, which shows substantial binding only to CD32A; IgG1 LALAPS, which contains the L234A, L235A, and P331S mutations; and IgG1 N297A. The latter two Fc variants exhibit little or no binding to any of the Fcγ receptors. All five antibodies were evaluated for their ability to reduce the level of cell-surface CD33 on primary human dendritic cells, according to the method described in Example 1. The data are shown in FIG. 4, and Table 19 summarizes the half-maximal effective concentration ($EC_{50}$) and the maximal CD33 downregulation by the antibodies.

TABLE 19

CD33 cell surface downregulation with Fc variants of AB-64.1

| Antibody | Receptor downregulation, (pM, $EC_{50}$) | Maximal downregulation (% CD33 remaining) |
|---|---|---|
| AB-64.1 huIgG1 | 36.2 | 17.5 |
| AB-64.1 huIgG1 SELF | 31.9 | 10.9 |
| AB-64.1 huIgG2 | 35.6 | 15.1 |
| AB-64.1 huIgG1 N297A | 29.3 | 41.3 |
| AB-64.1 huIgG1 LALAPS | 57.1 | 39.4 |

All of the Fc variants tested reduced the levels of CD33 with $EC_{50}$'s within two-fold of each other. Moreover, human IgG1, human IgG2, and human IgG1 SELF exhibited similar maximal reduction of CD33. Unexpectedly, the two Fc's that do not bind to Fcγ receptors exhibited substantially reduced maximal receptor downregulation, suggesting that some Fcγ receptor interaction is necessary for maximal reduction in cell-surface CD33 levels on primary human dendritic cells.

The AB-64.1 Fc variants were also evaluated for their ability to reduce the levels of CD33 on myeloid cells in vivo. In one set of experiments, humanized NSG mice (hu-NSG) were used. These mice were engrafted with human CD34+ hematopoietic stem cells, were purchased from Jackson Laboratory and were used at 16 weeks after engraftment. Mice were administered a single intraperitoneal injection of AB-64.1 huIgG1, AB-64.1 huIgG2, AB-64.1 huIgG1 LALAPS, or a control antibody at 10 mg/kg on Day 0, and blood samples were collected on Day 1 (24 hours after dose), Day 6, Day 14, and Day 21, and processed for FACS analysis.

Briefly, blood samples were first incubated for 5 minutes in ACK lysis buffer to lyse red blood cells and then washed extensively with cold FACS buffer (PBS, 2% FBS, 2 mM EDTA). This procedure was repeated twice. Cells were then incubated in cold FACS buffer in the presence of anti-human-CD45-APC-Cy7, anti-mouse-CD45-FITC, anti-human-CD3-PE-Cy7, anti-human-CD14-Pacific Blue, anti-human-CD11b-PerCP-Cy5.5, anti-CD33-PE, anti-Siglec-7-APC, and a viability die (ThermoFisher, Cat # L34957) for 30 minutes on ice in the presence of Fc block solution, and then washed twice with cold FACS buffer. Cells were fixed with 4% paraformaldehyde in PBS. Stained cells were acquired on a BD FACS Fortessa cytometer (Becton Dickinson, San Jose, Calif.) and data were analyzed with FlowJo software (Ashland Oreg.). The level of CD33 expression was determined on the huCD45+ huCD14+ cell population, and CD33 levels were normalized to samples from mice dosed with the control antibody.

Figure 5:
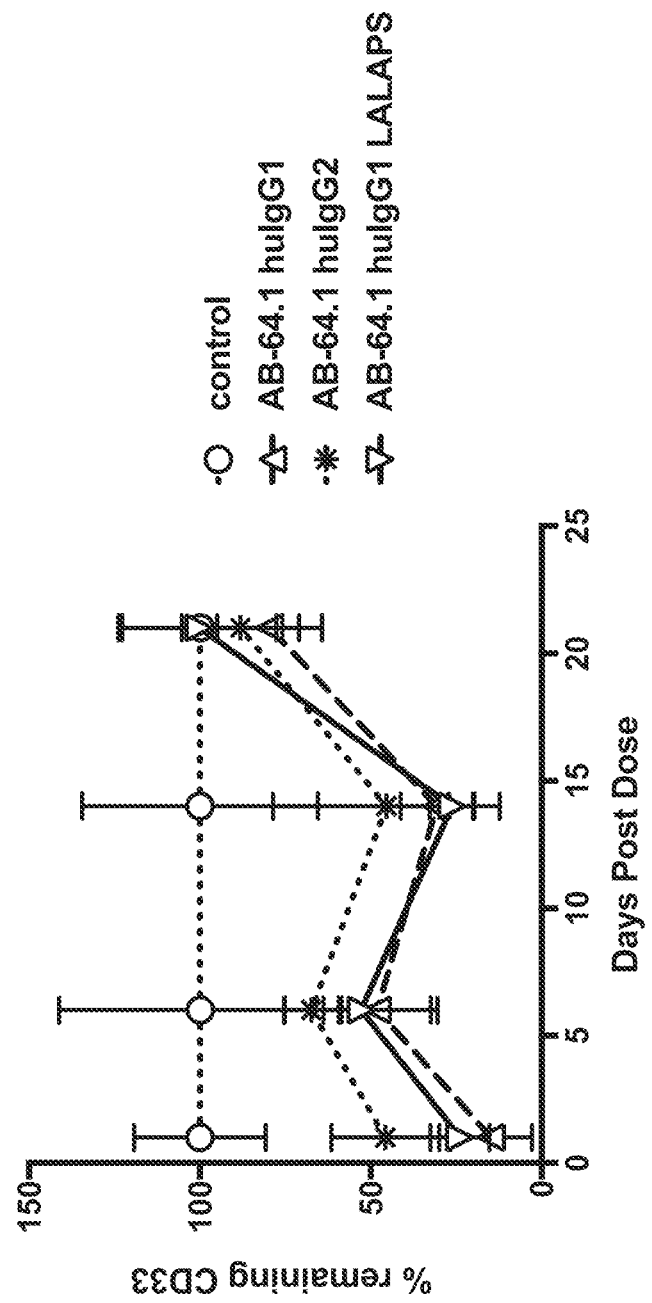
FIG. 5 depicts flow cytometry results measuring human CD33 levels on the surface of huCD45$^+$huCD14$^+$ cells in humanized NSG mice injected with CD33 antibodies.

In hu-NSG mice administered a single dose of AB-64.1 huIgG1, AB-64.1 huIgG2, or AB-64.1 huIgG1 LALAPS, CD33 levels on circulating myeloid cells were substantially reduced within 24 hours in all groups, as shown in FIG. 5. The CD33 levels were not statistically different between the AB-64.1 huIgG1, AB-64.1 huIgG2, or AB-64.1 huIgG1 LALAPS groups, and the reduction in CD33 was maintained for at least 2 weeks. By Day 21, the levels of CD33 in all groups had returned to control levels.

In a separate set of experiments, the ability of AB-64.1 Fc variants to reduce CD33 levels on immune cells in vivo was evaluated in immunocompetent C57BL/6 mice transgenic for human CD33. These mice express human CD33 on myeloid cells at levels similar to that observed on human immune cells. Mice were administered a single intraperitoneal injection of AB-64.1 huIgG1, AB-64.1 huIgG2, AB-64.1 huIgG1 LALAPS, or a control antibody at 10 mg/kg on Day 0, and blood samples were collected on Day 1 (24 hours after dose), Day 3, and Day 6, and were processed for FACS analysis. The mice were sacrificed on Day 21, and blood and spleen were processed for FACS analysis.

Briefly, blood samples were first incubated for 5 minutes in ACK lysis buffer to lyse red blood cells and then washed extensively with cold FACS buffer (PBS, 2% FBS, 2 mM EDTA). This procedure was repeated twice. Spleen samples were crushed through cell strainers and then red blood cells were lysed with ACK lysis buffer, followed by extensive washing with cold FACS buffer. Cells were then incubated in cold FACS buffer in the presence of anti-mouse CD3-Pacific Blue, anti-mouse-NK1.1-APC-Cy7, anti-mouse-CD11b-PerCP-Cy5.5, anti-mouse-Gr1-PE-Cy7, anti-CD33-PE, anti-Siglec-7-APC, and a viability die (ThermoFisher, Cat # L34957) for 30 minutes on ice in the presence of Fc block solution, and then washed twice with cold FACS buffer. Cells were fixed with 4% paraformaldehyde in PBS. Stained cells were acquired on a BD FACS Fortessa cytometer (Becton Dickinson, San Jose, Calif.) and data were analyzed with FlowJo software (Ashland Oreg.). The level of CD33 expression was determined on the mouse CD11b+ mouse Gr1+ cell population, and CD33 levels were normalized to samples from mice dosed with the control antibody.

Figure 6A:
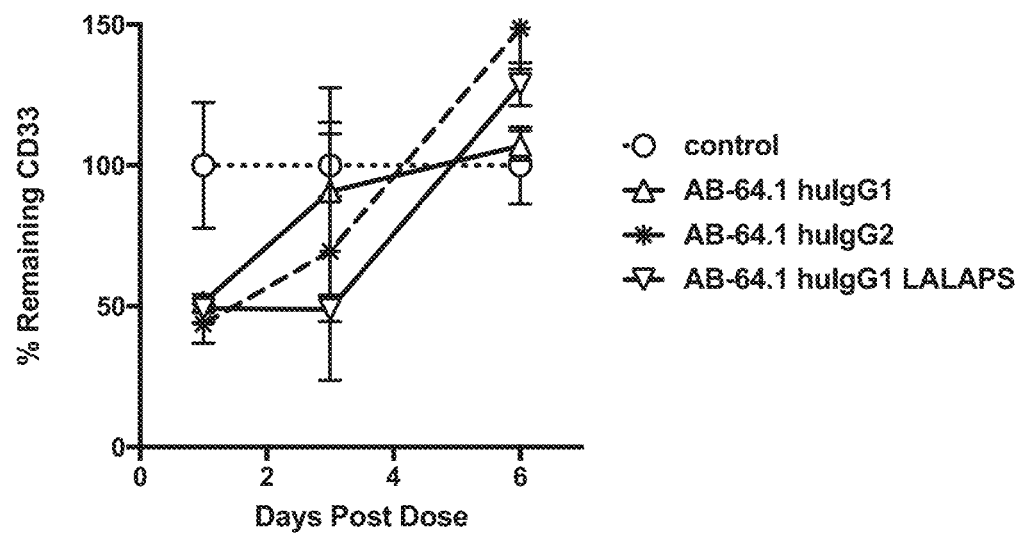
FIG. 6A depicts flow cytometry results measuring human CD33 levels on the surface of circulating CD11b$^+$Gr1$^+$ cells in mice transgenic for human CD33 that were injected with CD33 antibodies.
Figure 6B:
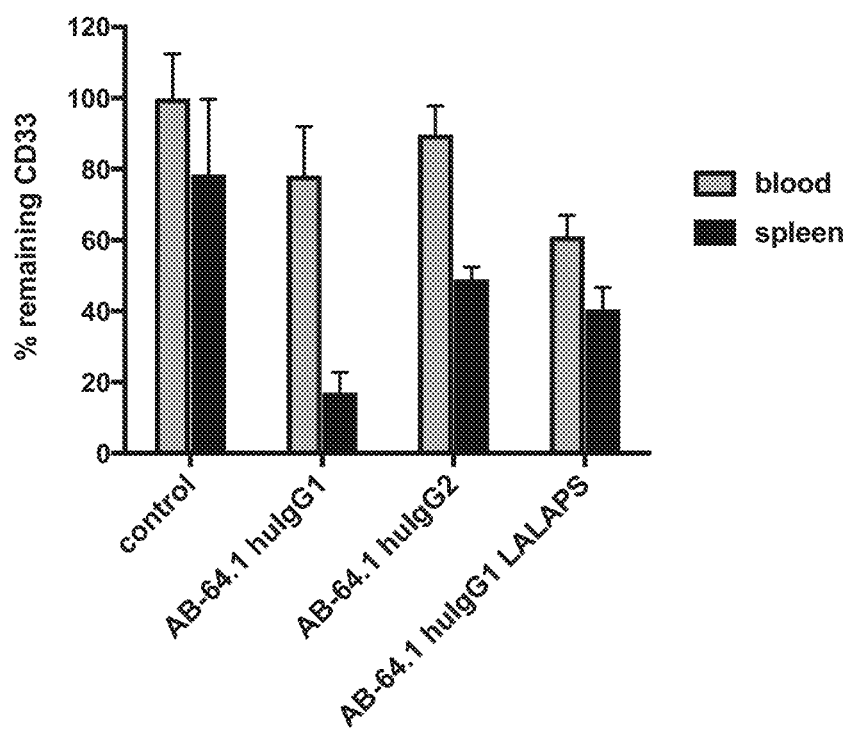
FIG. 6B depicts results from a flow cytometry assay measuring human CD33 levels on the surface of CD11b$^+$Gr1$^+$ cells in the blood or in the spleen in human CD33 transgenic mice transgenic injected with CD33 antibodies.

In human CD33 transgenic mice administered a single dose of AB-64.1 huIgG1, AB-64.1 huIgG2, or AB-64.1 huIgG1 LALAPS, CD33 levels on circulating myeloid cells were substantially reduced within 24 hours, as shown in FIG. 6A. The extent of the decrease was similar between the groups dosed with the CD33 antibodies. By Day 6, the levels of CD33 on circulating myeloid cells had returned to control levels in all groups. In contrast, on Day 21, while CD33 levels on circulating blood cells were at control levels, CD33 receptor levels on splenic myeloid cells was substantially decreased compared to control-treated mice, as shown in FIG. 6B. Thus, the recovery of CD33 expression on tissue-resident immune cells appears to be slower than that on circulating cells, suggesting a slower turnover of CD33 on tissue resident cells.

While Fc variants with little or no Fcγ receptor binding were less able to reduce CD33 levels on primary human dendritic cells in vitro, in vivo, both in humanized mice expressing both human and mouse Fcγ receptors and in immunocompetent mice transgenic for human CD33 expressing only mouse Fcγ receptors, the huIgG1 LALAPS reduced CD33 levels to a similar extent as Fcγ receptor binding-competent isotypes.

Example 8: ADCC Activity of a CD33 Antibody Harboring Different Fc Variants

The purpose of this example was to evaluate the ability of Fc variants of the AB-64.1 antibody to induce ADCC (antibody-dependent cellular cytotoxicity) on CD33-expressing cells. ADCC has been shown to be highly dependent on the interaction between an antibody's Fc region and the Fcγ receptors expressed on effector cells.

Figure 7:
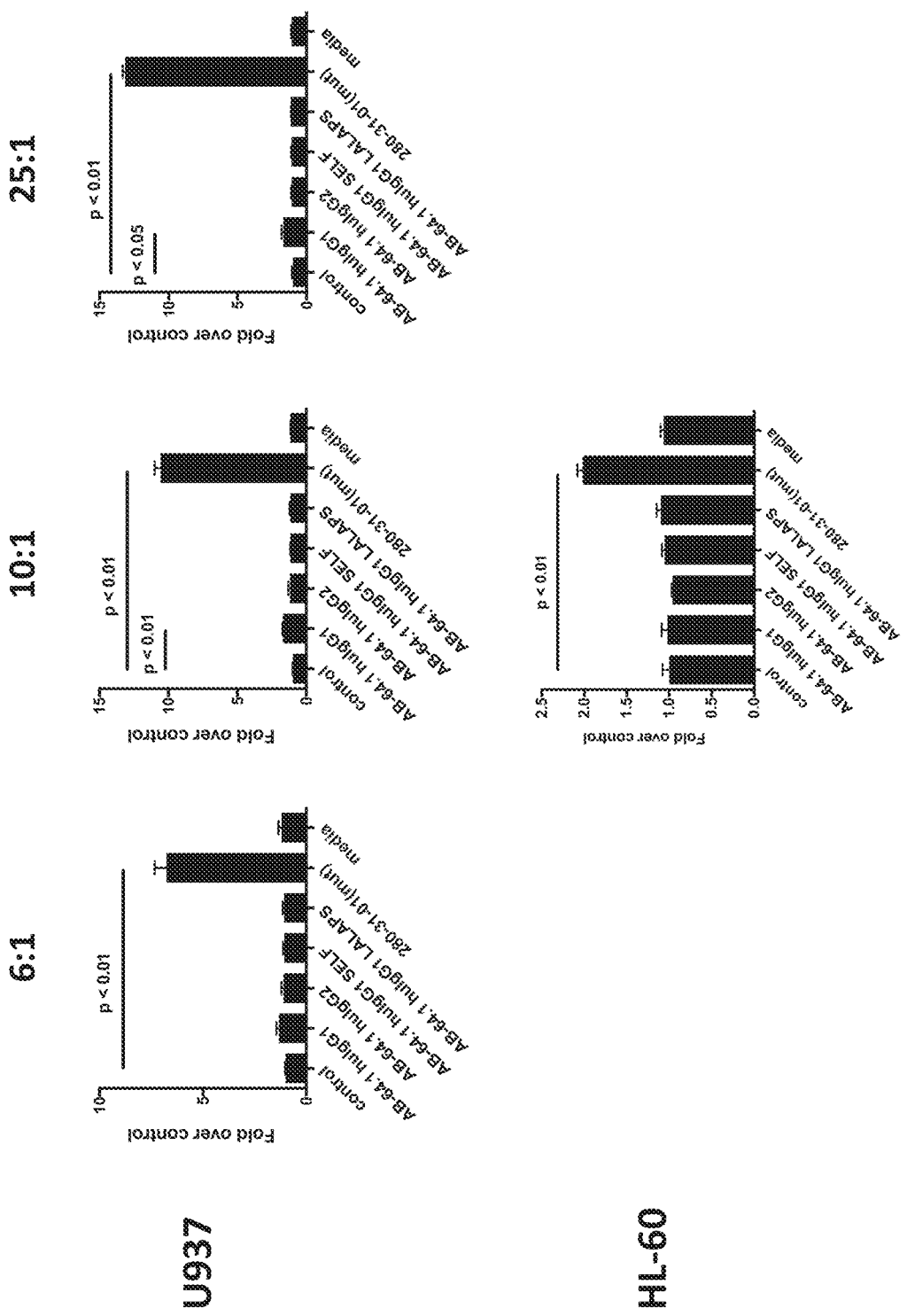
FIG. 7 depicts results from an assay to measure the ADCC activity of CD33 antibodies.

Four different human Fc variants of the AB-64.1 antibody were evaluated for ADCC: wild-type IgG1, IgG2, IgG1 SELF, and IgG1 LALAPS. ADCC was tested using two different target cell lines, HL60 cells and U937 cells. Both HL60 and U937 cells express CD33, with U937 cells expressing CD33 at higher levels than HL60 cells (data not shown). The ADCC assay was performed using the ADCC Reporter Bioassay (Promega), according to the manufacturer's instructions, using three different effector:target ratios, 6:1, 10:1, and 25:1. Briefly, target cells were first opsonized with the antibodies at 10 µg/ml, after which effector cells were added and incubated for 6 hours at 37° C. with 5% $CO_2$. ADCC activity was quantified by adding the luciferase assay reagent, and the plate was read on a luminometer (Biotek). Included as a positive control in the assay was a CD33 antibody, clone 280-31-01(mut), disclosed in WO2012/045752, which has been shown to have potent ADCC activity. The results from the ADCC assay are shown in FIG. 7.

On both HL60 cells and U937 cells and at all three effector:target ratios, the positive control antibody induced ADCC. Of the AB-64.1 Fc variant antibodies, only the wild-type human IgG1 Fc induced any statistically significant increase in ADCC, but only on the higher-expressing cell line, U937, only at the higher E:T ratios, and the induced ADCC levels were less than 2× background. Thus, AB-64.1 induces little or no ADCC.

Example 9: CDC Activity of a CD33 Antibody with Different Fc Variants

The purpose of this example was to evaluate the potential for Fc variants of the AB-64.1 antibody to induce CDC (complement-dependent cytotoxicity) on CD33-expressing cells. CDC is initiated by a target being opsonized by an antibody that can effectively bind and activate complement through its Fc region. Thus the ability of an antibody to induce CDC is dependent on its isotype: human IgG1 and IgG1 SELF are generally competent in inducing CDC, while IgG2 and IgG1 LALAPS are generally weaker in inducing CDC.

Figure 8:
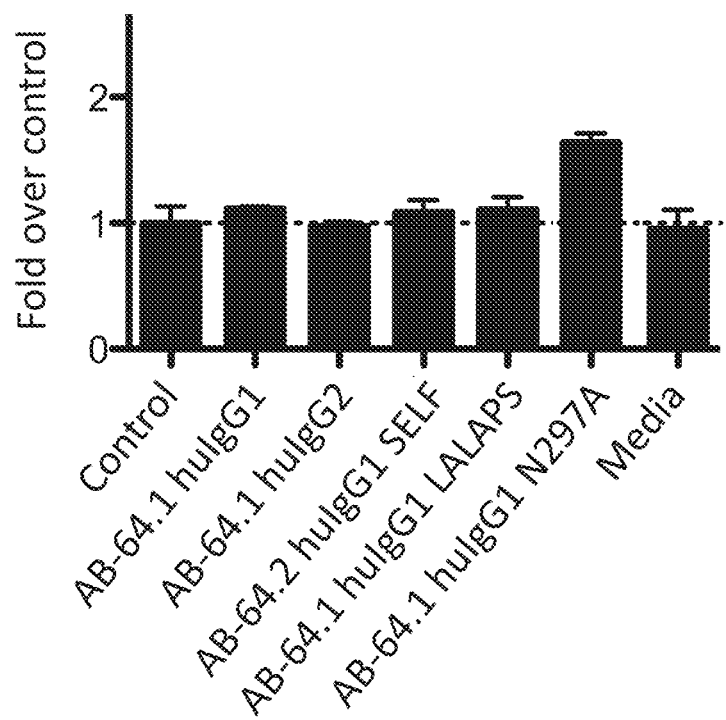
FIG. 8 depicts results from a CDC assay in the presence of CD33 antibodies.

Five different Fc variants of the AB-64.1 antibody were evaluated for the potential to induce CDC: wild-type human IgG1, human IgG2, human IgG1 SELF, human IgG1 LALAPS, and human IgG1 N297A. The potential for CDC was tested by measuring complement activation, C3b deposition, on the CD33-expressing cell line, U937. Briefly, U937 cells were incubated with 10 µg/ml of CD33 or control antibodies for 30 minutes on ice. Pooled complement human sera (Innovative Research) were added at a final concentration of 20% and cells were incubated for 2 hours at 37° C. Cells were washed once with cold FACS buffer (PBS, 2% FBS, 2 mM EDTA) and then incubated with anti-C3b-APC and a viability die (ThermoFisher, Cat # L34957) for 30 minutes on ice in the presence of Fc block solution. Cells were washed twice with cold FACS buffer and then fixed with 4% paraformaldehyde in PBS. Stained cells were acquired on a BD FACS Fortessa cytometer (Becton Dickinson, San Jose, Calif.) and data were analyzed with FlowJo software (Ashland Oreg.). The level of C3b deposition was determined by the MFI of C3b on U937 cells and deposition was normalized to samples from cells treated with the control antibody. The results are shown in FIG. 8.

Surprisingly, of the AB-64.1 variants tested, only the IgG1 N297A isotype induced significantly increased complement activation over the control-treated samples. Neither the IgG1 nor the IgG1 SELF isotypes induced CDC activity above background levels. Thus, AB-64.1 induced little or no CDC.

Example 10: Downregulation of CD33 Levels on Brain Microglia with a CD33 Internalizing Antibody The purpose of this Example was to test the ability of a CD33 antibody to reduce the levels of CD33 on microglia in the brain.

The AB-64.1.2 antibody on the human IgG2 Fc (AB-64.1.2-huG2) was generated and evaluated for its ability to downregulate CD33 on brain microglia and on circulating cells in human CD33 transgenic mice, described in Example 7. These mice are also transgenic for human Siglec-7. On Day 0, mice were administered a single dose of AB-64.1.2-huG2 (2 mg/kg, 10 mg/kg, or 40 mg/kg) or a control antibody (40 mg/kg), and on Day 1, Day 3, Day 6, Day 10, Day 14, Day 20, and Day 28, mice were sacrificed and blood and brains were harvested for analysis by flow cytometry.

Brains were placed into HBSS and were mechanically dissociated with a dounce homogenizer, after which Percoll (GE Healthcare) was added to 30%. The suspension was layered onto a 70% Percoll layer and was centrifuged at 550 g for 30 minutes. The enriched microglia were harvested from the interface of the two phases, then washed in HBSS and stained with anti-mouse CD11b Pacific Blue (BioLegend), anti-mouse CD45 PE-Cy7 (eBioscience), anti-human CD33 PE (eBioscience), anti-human Siglec-7 APC (BioLegend), and a viability dye in the presence of Fc block, then were analyzed by flow cytometry. Microglia were gated as $CD45^{int}CD11b^+$ cells. Blood was collected in heparinized tubes at the time of sacrifice and was centrifuged at 2,000 g for 10 minutes at 4° C. The cell pellet was resuspended in PBS with 3 mM EDTA by vortexing, after which red blood cells were lysed with 1 mL ACK buffer for 10 minutes on ice, followed by centrifugation at 500 g for 10 minutes. Cells were stained with anti-mouse CD11b Pacific Blue, anti-mouse Gr1 PE-Cy7 (BioLegend), anti-mouse Ly6G APC (BioLegend), anti-mouse Ly6C AF488 (BioLegend), anti-human CD33 PE, anti-human Siglec-7 APC, and a viability dye in the presence of Fc block, and were analyzed by flow cytometry. Neutrophils were gated as $CD11b^{high}Ly6G^+$ cells, and monocytes were gated as $Ly6C^{high}Ly6G^-CD33^+$ cells. The results are shown in FIGS. 9A-D.

Figure 9A:
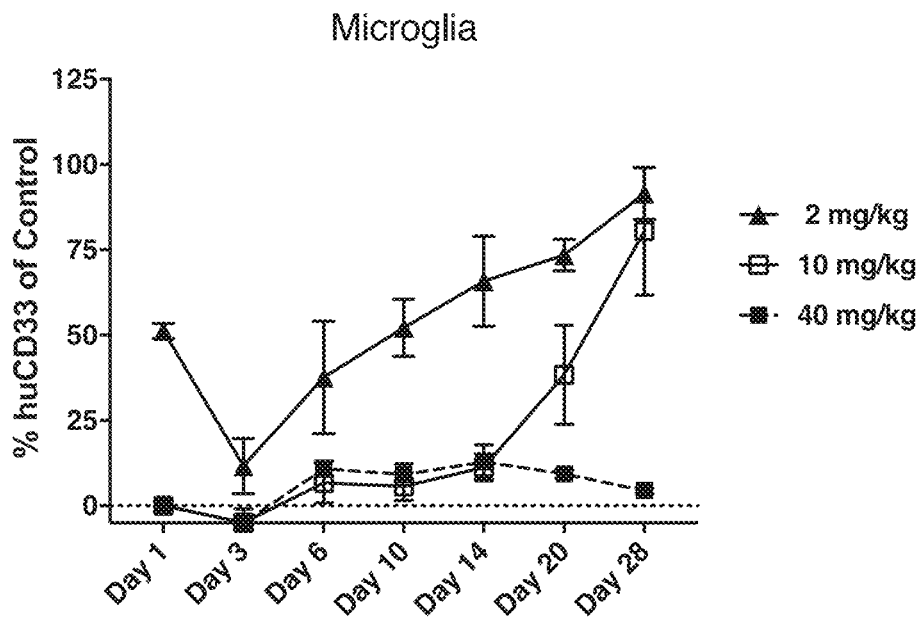
FIGS. 9A-D depicts flow cytometry results measuring human CD33 and human Siglec-7 levels on the surface of cells in mice transgenic for human CD33 and human Siglec-7 after treatment with different concentrations of a CD33 antibody.
Figure 9B:
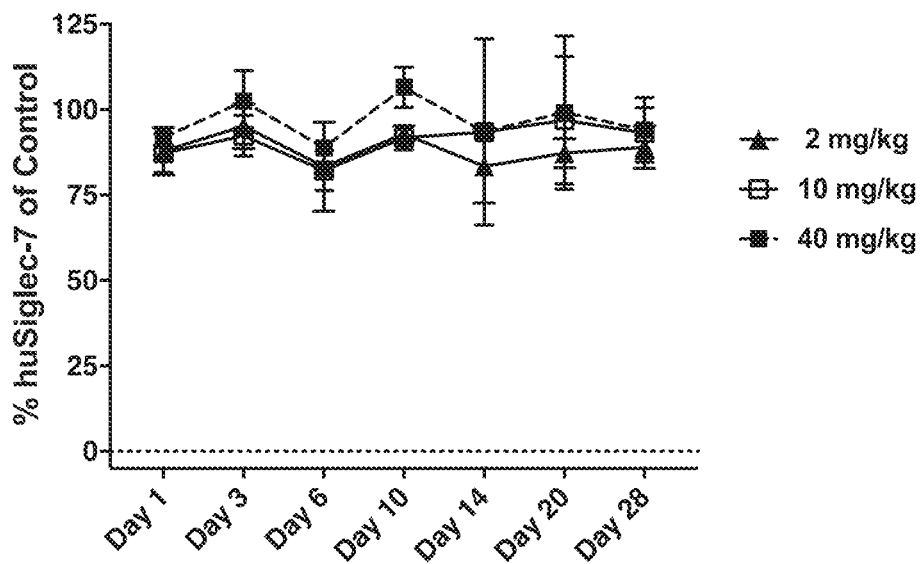
Figure 9C:
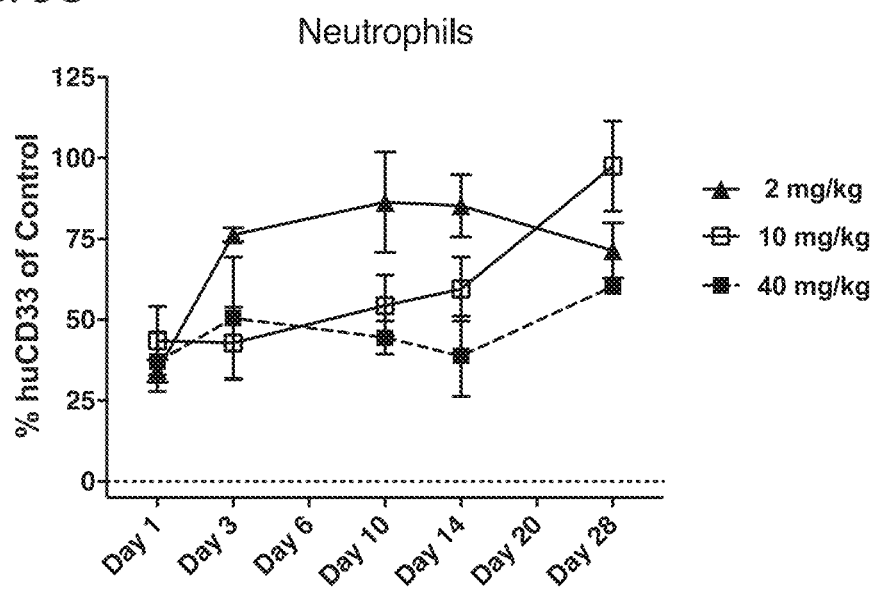
Figure 9D:
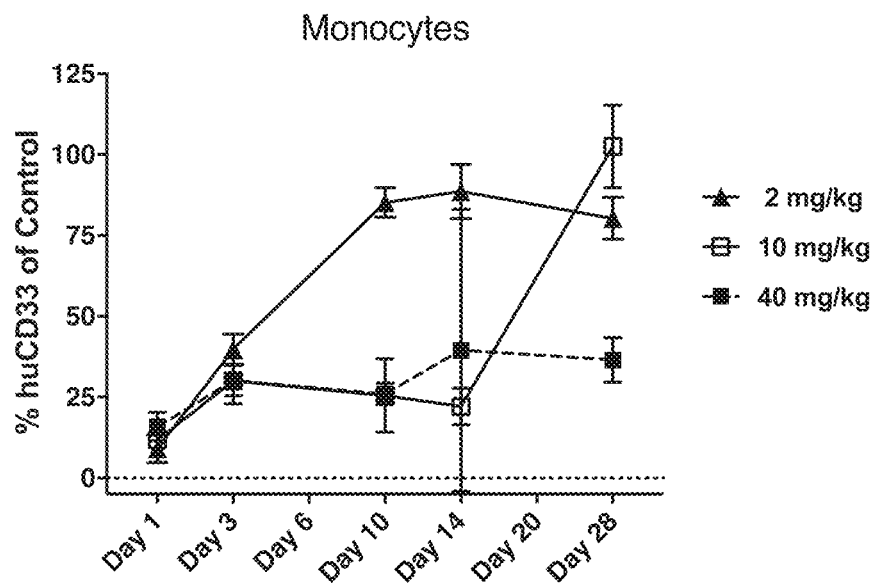

Administration of a single dose of AB-64.1.2-huG2 at 2 mg/kg, 10 mg/kg, or 40 mg/kg, resulted in substantial reductions of CD33 on microglia within 24 hours after dosing (Day 1). The most profound effects were observed at 10 mg/kg and 40 mg/kg, where the levels of CD33 on microglia were almost undetectable on Day 1 (FIG. 9A). In the 40 mg/kg dose group, the profound downregulation of CD33 persisted through Day 28, while in the 10 mg/kg group, receptor levels stayed low through Day 14, then returned to control levels by Day 28. Dosing at 2 mg/kg resulted in a reduction of CD33 expression, but the effect was milder and more transient than at the higher doses. The antibody had no effect on the level of human Siglec-7 on microglia at any dose level (FIG. 9B). On circulating neutrophils, administration of AB-64.1.2-huG2 at 2 mg/kg, 10 mg/kg, or 40 mg/kg, resulted in downregulation of CD33 by approximately 50% one day after dosing (FIG. 9C). On circulating monocytes, CD33 levels were almost completely ablated on Day 1 in all three dosing groups (FIG. 9D). Thus, on circulating neutrophils and monocytes, maximal downregulation was observed at the lowest dose tested, 2 mg/kg. On both cell types, CD33 receptor levels remained low through Day 28 in the 40 mg/kg group, CD33 levels returned to control levels by Day 28 in the 10 mg/kg group, and CD33 downregulation was more transient in the 2 mg/kg group. Thus, the durability of CD33 downregulation on monocytes and neutrophils exhibited a dose-response effect and was similar to that observed on microglia.

These results demonstrate that AB-64.1.2-huG2 potently reduced CD33 expression both on microglia in the brain and on circulating CD33-expressing cells. The observation that on microglia maximal CD33 downregulation was observed at the 10 mg/kg dose was unexpected, as only about 0.1% of circulating antibodies cross the blood-brain barrier (Pudoslo, et al. PNAS 1994). These results highlight the potency of this antibody to downregulate CD33. The durability of CD33 downregulation of CD33 by this antibody was also surprising, as after a single dose at 10 mg/kg or 40 mg/kg, CD33 levels on microglia, monocytes, and neutrophils did not recover for at least 14 or 28 days, respectively. In contrast, in these same mice treated with the parental antibody, AB-64.1, at 10 mg/kg, CD33 downregulation on circulating CD33+ cells persisted for fewer than 6 days after dosing (FIG. 6A). Thus, additional amino acid modifications, which did not affect affinity, may have impacted the durability of CD33 downregulation by the antibody in vivo.

SEQUENCES

All polypeptide sequences are presented N-terminal to C-terminal unless otherwise noted.

Parental Mouse Antibody Heavy Chain Variable Region:

(SEQ ID NO: 103)
EVQLQQSGPELVKPGASVKISCKASGYTFTDYNLHWVKLSHGKSLEWIGF

IYPSNGITGYNQKFKNKATLTVDNSSTAYMELRSLTSEDSAVYYCARST

VDYFDYWGQGTTLTVSS

Parental Mouse Antibody Light Chain Variable Region:

(SEQ ID NO: 104)
DIVLTQSPASLAVSLGQRATMSCRASQSVSTSTYSYMHWYQQKPGQPPKL

LIKYASNLESGVPARFSGSGSGTDFTLNIHPVEEEDTATYYCQHSWEIPL

TFGAGTKLELK

Receptor Motif:

(SEQ ID NO: 165)
D/Ex0-2YxxL/IX6-8YxxL/I

CH1 and Hinge Region of IGg2:

(SEQ ID NO: 166)
ASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVER

KCCVECPPCP

AB-64.1 huIgG1 Full-Length Antibody Sequence:

Heavy chain:
(SEQ ID NO: 176)
QVQLVQSGAEVKKPGASVKISCKASGYTFTDYNLHWVRQAPGQGLEWIGF

IYPSNGITGYAQKFQGRATLTVDNSTSTAYMELSSLRSEDTAVYYCARSD

VDYFDYWGQGTLLTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKVEPKSCDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK (SEQ ID NO: 197)
QVQLVQSGAEVKKPGASVKISCKASGYTFTDYNLHWVRQAPGQGLEWIGF

IYPSNGITGYAQKFQGRATLTVDNSTSTAYMELSSLRSEDTAVYYCARSD

VDYFDYWGQGTLLTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKVEPKSCDKTHTCPPCPAPELLGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPAPIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPG

Light chain:
(SEQ ID NO: 185)
DIVLTQSPDSLAVSLGERATINCRASQSVSTSTYSYMHWYQQKPGQPPKL

LIKYASNLESGVPDRFSGSGSGTDFTLTISSLQAEDVAVYYCQHSWEIPL

TFGQGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC

AB-64.1.2 huIgG1 Full-Length Antibody Sequence

Heavy chain:
(SEQ ID NO: 177)
QVQLVQSGAEVKKPGASVKISCKASGYTFTDYNLHWVRQAPGQGLEWIGF

IYPSNRITGYAQKFQGRATLTVDNSTSTAYMELSSLRSEDTAVYYCARSD

VDYFDYWGQGTLLTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKVEPKSCDKTHTCPPCPAPELLGGPSVFLFPPKPKDT

LMISRTPEVTCVVVDVSHEDPEVKFNWYVDGVEVHNAKTKPREEQYNSTY

-continued

RVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK (SEQ ID NO: 198)
QVQLVQSGAEVKKPGASVKISCKASGYTFTDYNLHWVRQAPGQGLEWIGF
IYPSNRITGYAQKFQGRATLTVDNSTSTAYMELSSLRSEDTAVYYCARSD
VDYFDYWGQGTLLTVSSASTKGPSVFPLAPSSKSTSGGTAALGCLVKDYF
PEPVTVSWNSGALTSGVHTFPAVLQSSGLYSLSSVVTVPSSSLGTQTYIC
NVNHKPSNTKVDKKVEPKSCDKTHTCPPCPAPELLGGPSVFLFPPKPKDT
LMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPG

Light chain:
(SEQ ID NO: 185)
DIVLTQSPDSLAVSLGERATINCRASQSVSTSTYSYMHWYQQKPGQPPKL
LIKYASNLESGVPDRFSGSGSGTDFTLTISSLQAEDVAVYYCQHSWEIPL
TFGQGTKLEIKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC AB-64.1.8 huIgG1 Full-Length Antibody Sequence Heavy chain:
(SEQ ID NO: 178)
QVQLVQSGAEVKKPGASVKISCKASGYTFTDYNLHWVRQAPGQGLEWIGF
IYPSNQITGYAQKFQGRATLTVDNSASTAYMELSSLRSEDTAVYYCARSD
VDYFDYWGQGTLLTVSSASTKGPSVFPLAPSSKSTSGGTAALGCLVKDYF
PEPVTVSWNSGALTSGVHTFPAVLQSSGLYSLSSVVTVPSSSLGTQTYIC
NVNHKPSNTKVDKKVEPKSCDKTHTCPPCPAPELLGGPSVFLFPPKPKDT
LMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK (SEQ ID NO: 199)
QVQLVQSGAEVKKPGASVKISCKASGYTFTDYNLHWVRQAPGQGLEWIGF
IYPSNQITGYAQKFQGRATLTVDNSASTAYMELSSLRSEDTAVYYCARSD
VDYFDYWGQGTLLTVSSASTKGPSVFPLAPSSKSTSGGTAALGCLVKDYF
PEPVTVSWNSGALTSGVHTFPAVLQSSGLYSLSSVVTVPSSSLGTQTYIC
NVNHKPSNTKVDKKVEPKSCDKTHTCPPCPAPELLGGPSVFLFPPKPKDT
LMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYT
LPPSRDELTKNQVSLTCLVKGFYPSDIAVEWESNGQPENNYKTTPPVLDS
DGSFFLYSKLTVDKSRWQQGNVFSCSVMHEALHNHYTQKSLSLSPG Light chain:
(SEQ ID NO: 185)
DIVLTQSPDSLAVSLGERATINCRASQSVSTSTYSYMHWYQQKPGQPPKL
LIKYASNLESGVPDRFSGSGSGTDFTLTISSLQAEDVAVYYCQHSWEIPL
TFGQGTKLEIKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC AB-64.1 huIgG2 Full-Length Antibody Sequence Heavy chain:
(SEQ ID NO: 179)
QVQLVQSGAEVKKPGASVKISCKASGYTFTDYNLHWVRQAPGQGLEWIGF
IYPSNGITGYAQKFQGRATLTVDNSTSTAYMELSSLRSEDTAVYYCARSD
VDYFDYWGQGTLLTVSSASTKGPSVFPLAPCSRSTSESTAALGCLVKDYF
PEPVTVSWNSGALTSGVHTFPAVLQSSGLYSLSSVVTVPSSNFGTQTYTC
NVDHKPSNTKVDKTVERKCCVECPPCPAPPVAGPSVFLFPPKPKDTLMIS
RTPEVTCVVVDVSHEDPEVQFNWYVDGVEVHNAKTKPREEQFNSTFRVVS
VLTVVHQDWLNGKEYKCKVSNKGLPAPIEKTISKTKGQPREPQVYTLPPS
REEMTKNQVSLTCLVKGFYPSDIAVEWESNGQPENNYKTTPPMLDSDGSF
FLYSKLTVDKSRWQQGNVFSCSVMHEALHNHYTQKSLSLSPGK (SEQ ID NO: 200)
QVQLVQSGAEVKKPGASVKISCKASGYTFTDYNLHWVRQAPGQGLEWIGF
IYPSNGITGYAQKFQGRATLTVDNSTSTAYMELSSLRSEDTAVYYCARSD
VDYFDYWGQGTLLTVSSASTKGPSVFPLAPCSRSTSESTAALGCLVKDYF
PEPVTVSWNSGALTSGVHTFPAVLQSSGLYSLSSVVTVPSSNFGTQTYTC
NVDHKPSNTKVDKTVERKCCVECPPCPAPPVAGPSVFLFPPKPKDTLMIS
RTPEVTCVVVDVSHEDPEVQFNWYVDGVEVHNAKTKPREEQFNSTFRVVS
VLTVVHQDWLNGKEYKCKVSNKGLPAPIEKTISKTKGQPREPQVYTLPPS
REEMTKNQVSLTCLVKGFYPSDIAVEWESNGQPENNYKTTPPMLDSDGSF
FLYSKLTVDKSRWQQGNVFSCSVMHEALHNHYTQKSLSLSPG Light chain:
(SEQ ID NO: 185)
DIVLTQSPDSLAVSLGERATINCRASQSVSTSTYSYMHWYQQKPGQPPKL
LIKYASNLESGVPDRFSGSGSGTDFTLTISSLQAEDVAVYYCQHSWEIPL
TFGQGTKLEIKRTVAAPSVFIFPPSDEQLKSGTASVVCLLNNFYPREAKV
QWKVDNALQSGNSQESVTEQDSKDSTYSLSSTLTLSKADYEKHKVYACEV
THQGLSSPVTKSFNRGEC AB-64.1.2 huIgG2 Full-Length Antibody Sequence Heavy chain:
(SEQ ID NO: 180)
QVQLVQSGAEVKKPGASVKISCKASGYTFTDYNLHWVRQAPGQGLEWIGF
IYPSNRITGYAQKFQGRATLTVDNSTSTAYMELSSLRSEDTAVYYCARSD
VDYFDYWGQGTLLTVSSASTKGPSVFPLAPCSRSTSESTAALGCLVKDYF
PEPVTVSWNSGALTSGVHTFPAVLQSSGLYSLSSVVTVPSSNFGTQTYTC
NVDHKPSNTKVDKTVERKCCVECPPCPAPPVAGPSVFLFPPKPKDTLMIS -continued

RTPEVTCVVVDVSHEDPEVQFNWYVDGVEVHNAKTKPREEQFNSTFRVVS

VLTVVHQDWLNGKEYKCKVSNKGLPAPIEKTISKTKGQPREPQVYTLPPS

REEMTKNQVSLTCLVKGFYPSDIAVEWESNGQPENNYKTTPPMLDSDGSF

FLYSKLTVDKSRWQQGNVFSCSVMHEALHNHYTQKSLSLSPGK (SEQ ID NO: 201)
QVQLVQSGAEVKKPGASVKISCKASGYTFTDYNLHWVRQAPGQGLEWIGF

IYPSNRITGYAQKFQGRATLTVDNSTSTAYMELSSLRSEDTAVYYCARSD

VDYFDYWGQGTLLTVSSASTKGPSVFPLAPCSRSTSESTAALGCLVKDYF

PEPVTVSWNSGALTSGVHTFPAVLQSSGLYSLSSVVTVPSSNFGTQTYTC

NVDHKPSNTKVDKTVERKCCVECPPCPAPPVAGPSVFLFPPKPKDTLMIS

RTPEVTCVVVDVSHEDPEVQFNWYVDGVEVHNAKTKPREEQFNSTFRVVS

VLTVVHQDWLNGKEYKCKVSNKGLPAPIEKTISKTKGQPREPQVYTLPPS

REEMTKNQVSLTCLVKGFYPSDIAVEWESNGQPENNYKTTPPMLDSDGSF

FLYSKLTVDKSRWQQGNVFSCSVMHEALHNHYTQKSLSLSPG

Light chain:
(SEQ ID NO: 185)
DIVLTQSPDSLAVSLGERATINCRASQSVSTSTYSYMHWYQQKPGQPPKL

LIKYASNLESGVPDRFSGSGSGTDFTLTISSLQAEDVAVYYCQHSWEIPL

TFGQGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC

AB-64.1.8 huIgG2 Full-Length Antibody Sequence

Heavy chain:
(SEQ ID NO: 181)
QVQLVQSGAEVKKPGASVKISCKASGYTFTDYNLHWVRQAPGQGLEWIGF

IYPSNQITGYAQKFQGRATLTVDNSASTAYMELSSLRSEDTAVYYCARSD

VDYFDYWGQGTLLTVSSASTKGPSVFPLAPCSRSTSESTAALGCLVKDYF

PEPVTVSWNSGALTSGVHTFPAVLQSSGLYSLSSVVTVPSSNFGTQTYTC

NVDHKPSNTKVDKTVERKCCVECPPCPAPPVAGPSVFLFPPKPKDTLMIS

RTPEVTCVVVDVSHEDPEVQFNWYVDGVEVHNAKTKPREEQFNSTFRVVS

VLTVVHQDWLNGKEYKCKVSNKGLPAPIEKTISKTKGQPREPQVYTLPPS

REEMTKNQVSLTCLVKGFYPSDIAVEWESNGQPENNYKTTPPMLDSDGSF

FLYSKLTVDKSRWQQGNVFSCSVMHEALHNHYTQKSLSLSPGK (SEQ ID NO: 202)
QVQLVQSGAEVKKPGASVKISCKASGYTFTDYNLHWVRQAPGQGLEWIGF

IYPSNQITGYAQKFQGRATLTVDNSASTAYMELSSLRSEDTAVYYCARSD

VDYFDYWGQGTLLTVSSASTKGPSVFPLAPCSRSTSESTAALGCLVKDYF

PEPVTVSWNSGALTSGVHTFPAVLQSSGLYSLSSVVTVPSSNFGTQTYTC

NVDHKPSNTKVDKTVERKCCVECPPCPAPPVAGPSVFLFPPKPKDTLMIS

RTPEVTCVVVDVSHEDPEVQFNWYVDGVEVHNAKTKPREEQFNSTFRVVS

VLTVVHQDWLNGKEYKCKVSNKGLPAPIEKTISKTKGQPREPQVYTLPPS

REEMTKNQVSLTCLVKGFYPSDIAVEWESNGQPENNYKTTPPMLDSDGSF

FLYSKLTVDKSRWQQGNVFSCSVMHEALHNHYTQKSLSLSPG

Light chain:
(SEQ ID NO: 185)
DIVLTQSPDSLAVSLGERATINCRASQSVSTSTYSYMHWYQQKPGQPPKL

LIKYASNLESGVPDRFSGSGSGTDFTLTISSLQAEDVAVYYCQHSWEIPL

TFGQGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC

AB-64.1 huIgG1 LALAPS Full-Length Antibody Sequence

Heavy chain:
(SEQ ID NO: 182)
QVQLVQSGAEVKKPGASVKISCKASGYTFTDYNLHWVRQAPGQGLEWIGF

IYPSNGITGYAQKFQGRATLTVDNSTSTAYMELSSLRSEDTAVYYCARSD

VDYFDYWGQGTLLTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKVEPKSCDKTHTCPPCPAPEAAGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPASIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK (SEQ ID NO: 203)
QVQLVQSGAEVKKPGASVKISCKASGYTFTDYNLHWVRQAPGQGLEWIGF

IYPSNGITGYAQKFQGRATLTVDNSTSTAYMELSSLRSEDTAVYYCARSD

VDYFDYWGQGTLLTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKVEPKSCDKTHTCPPCPAPEAAGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPASIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPG

Light chain:
(SEQ ID NO: 185)
DIVLTQSPDSLAVSLGERATINCRASQSVSTSTYSYMHWYQQKPGQPPKL

LIKYASNLESGVPDRFSGSGSGTDFTLTISSLQAEDVAVYYCQHSWEIPL

TFGQGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC

AB-64.1.2 huIgG1 LALAPS Full-Length Antibody Sequence

Heavy chain:
(SEQ ID NO: 183)
QVQLVQSGAEVKKPGASVKISCKASGYTFTDYNLHWVRQAPGQGLEWIGF

IYPSNRITGYAQKFQGRATLTVDNSTSTAYMELSSLRSEDTAVYYCARSD

-continued

VDYFDYWGQGTLLTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKVEPKSCDKTHTCPPCPAPEAAGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPASIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK (SEQ ID NO: 204)
QVQLVQSGAEVKKPGASVKISCKASGYTFTDYNLHWVRQAPGQGLEWIGF

IYPSNRITGYAQKFQGRATLTVDNSTSTAYMELSSLRSEDTAVYYCARSD

VDYFDYWGQGTLLTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKVEPKSCDKTHTCPPCPAPEAAGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPASIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPG

Light chain:
(SEQ ID NO: 185)
DIVLTQSPDSLAVSLGERATINCRASQSVSTSTYSYMHWYQQKPGQPPKL

LIKYASNLESGVPDRFSGSGSGTDFTLTISSLQAEDVAVYYCQHSWEIPL

TFGQGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC

AB-64.1.8 huIgG1 LALAPS Full-Length Antibody Sequence

Heavy chain:
(SEQ ID NO: 184)
QVQLVQSGAEVKKPGASVKISCKASGYTFTDYNLHWVRQAPGQGLEWIGF

IYPSNQITGYAQKFQGRATLTVDNSASTAYMELSSLRSEDTAVYYCARSD

VDYFDYWGQGTLLTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKVEPKSCDKTHTCPPCPAPEAAGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPASIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPGK (SEQ ID NO: 205)
QVQLVQSGAEVKKPGASVKISCKASGYTFTDYNLHWVRQAPGQGLEWIGF

IYPSNQITGYAQKFQGRATLTVDNSASTAYMELSSLRSEDTAVYYCARSD

VDYFDYWGQGTLLTVSSASTKGPSVFPLAPSSKSTSGGTAALGCLVKDYF

PEPVTVSWNSGALTSGVHTFPAVLQSSGLYSLSSVVTVPSSSLGTQTYIC

NVNHKPSNTKVDKKVEPKSCDKTHTCPPCPAPEAAGGPSVFLFPPKPKDT

LMISRTPEVTCVVVDVSHEDPEVKFNWYVDGVEVHNAKTKPREEQYNSTY

RVVSVLTVLHQDWLNGKEYKCKVSNKALPASIEKTISKAKGQPREPQVYT

LPPSRDELTKNQVSLTCLVKGFYPSDIAVEWESNGQPENNYKTTPPVLDS

DGSFFLYSKLTVDKSRWQQGNVFSCSVMHEALHNHYTQKSLSLSPG

Light chain:
(SEQ ID NO: 185)
DIVLTQSPDSLAVSLGERATINCRASQSVSTSTYSYMHWYQQKPGQPPKL

LIKYASNLESGVPDRFSGSGSGTDFTLTISSLQAEDVAVYYCQHSWEIPL

TFGQGTKLEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC

What is claimed is:

1. An antibody that binds to a CD33 protein, wherein the antibody comprises a heavy chain variable region comprising an HVR-H1, HVR-H2, and HVR-H3 and a light chain variable region comprising an HVR-L1, HVR-L2, and HVR-L3, wherein the HVR-H1 comprises the amino acid sequence of SEQ ID NO: 105, the HVR-H2 comprises the amino acid sequence of SEQ ID NO: 115, the HVR-H3 comprises the amino acid sequence of SEQ ID NO: 122, the HVR-L1 comprises the amino acid sequence of SEQ ID NO: 127, the HVR-L2 comprises the amino acid sequence of SEQ ID NO: 135, and the HVR-L3 comprises the amino acid sequence of SEQ ID NO: 146;

the HVR-H1 comprises the amino acid sequence of SEQ ID NO: 105, the HVR-H2 comprises the amino acid sequence of SEQ ID NO: 118, the HVR-H3 comprises the amino acid sequence of SEQ ID NO: 122, the HVR-L1 comprises the amino acid sequence of SEQ ID NO: 127, the HVR-L2 comprises the amino acid sequence of SEQ ID NO: 135, and the HVR-L3 comprises the amino acid sequence of SEQ ID NO: 146;

the HVR-H1 comprises the amino acid sequence of SEQ ID NO: 105, the HVR-H2 comprises the amino acid sequence of SEQ ID NO: 119, the HVR-H3 comprises the amino acid sequence of SEQ ID NO: 122, the HVR-L1 comprises the amino acid sequence of SEQ ID NO: 127, the HVR-L2 comprises the amino acid sequence of SEQ ID NO: 135, and the HVR-L3 comprises the amino acid sequence of SEQ ID NO: 146; or the HVR-H1 comprises the amino acid sequence of SEQ ID NO: 105, the HVR-H2 comprises the amino acid sequence of SEQ ID NO: 120, the HVR-H3 comprises the amino acid sequence of SEQ ID NO: 122, the HVR-L1 comprises the amino acid sequence of SEQ ID NO: 127, the HVR-L2 comprises the amino acid sequence of SEQ ID NO: 135, and the HVR-L3 comprises the amino acid sequence of SEQ ID NO: 146.

2. The antibody of claim 1, wherein the antibody comprises a heavy chain variable region comprising the amino acid sequence of SEQ ID NO: 58, and a light chain variable region comprising the amino acid sequence of SEQ ID NO: 86;

a heavy chain variable region comprising the amino acid sequence of SEQ ID NO: 59, and a light chain variable region comprising the amino acid sequence of SEQ ID NO: 86;

a heavy chain variable region comprising the amino acid sequence of SEQ ID NO: 60, and a light chain variable region comprising the amino acid sequence of SEQ ID NO: 86;

a heavy chain variable region comprising the amino acid sequence of SEQ ID NO: 61, and a light chain variable region comprising the amino acid sequence of SEQ ID NO: 86;

a heavy chain variable region comprising the amino acid sequence of SEQ ID NO: 62, and a light chain variable region comprising the amino acid sequence of SEQ ID NO: 86;

a heavy chain variable region comprising the amino acid sequence of SEQ ID NO: 63, and a light chain variable region comprising the amino acid sequence of SEQ ID NO: 86;

a heavy chain variable region comprising the amino acid sequence of SEQ ID NO: 64, and a light chain variable region comprising the amino acid sequence of SEQ ID NO: 86;

a heavy chain variable region comprising the amino acid sequence of SEQ ID NO: 65, and a light chain variable region comprising the amino acid sequence of SEQ ID NO: 86;

a heavy chain variable region comprising the amino acid sequence of SEQ ID NO: 66, and a light chain variable region comprising the amino acid sequence of SEQ ID NO: 86;

a heavy chain variable region comprising the amino acid sequence of SEQ ID NO: 67, and a light chain variable region comprising the amino acid sequence of SEQ ID NO: 86;

a heavy chain variable region comprising the amino acid sequence of SEQ ID NO: 68, and a light chain variable region comprising the amino acid sequence of SEQ ID NO: 86;

a heavy chain variable region comprising the amino acid sequence of SEQ ID NO: 69, and a light chain variable region comprising the amino acid sequence of SEQ ID NO: 86;

a heavy chain variable region comprising the amino acid sequence of SEQ ID NO: 70, and a light chain variable region comprising the amino acid sequence of SEQ ID NO: 86;

a heavy chain variable region comprising the amino acid sequence of SEQ ID NO: 71, and a light chain variable region comprising the amino acid sequence of SEQ ID NO: 86; or a heavy chain variable region comprising the amino acid sequence of SEQ ID NO: 72, and a light chain variable region comprising the amino acid sequence of SEQ ID NO: 86.

3. The antibody of claim 2, wherein:
the heavy chain variable region comprises the amino acid sequence of SEQ ID NO: 59, and the light chain variable region comprises the amino acid sequence of SEQ ID NO: 86.

4. The antibody of claim 1, wherein:
the HVR-H1 comprises the amino acid sequence GYTFTDYNLH (SEQ ID NO: 105), the HVR-H2 comprises the amino acid sequence FIYPSNRITG (SEQ ID NO: 119), the HVR-H3 comprises the amino acid sequence SDVDYFDY (SEQ ID NO: 122), the HVR-L1 comprises the amino acid sequence RASQSVSTSTYSYMH (SEQ ID NO: 127), the HVR-L2 comprises the amino acid sequence YASNLES (SEQ ID NO: 135), and the HVR-L3 comprises the amino acid sequence QHSWEIPLT (SEQ ID NO: 146).

5. The antibody of claim 1, wherein the antibody is of the IgG class, the IgM class, or the IgA class.

6. The antibody of claim 5, wherein the antibody is of the IgG class and has an IgG1, IgG2, IgG3, or IgG4 isotype.

7. The antibody of claim 6, wherein the antibody has an IgG4 isotype, and wherein the antibody comprises an S228P amino acid substitution at residue position 228, an F234A amino acid substitution at residue position 234, and an L235A amino acid substitution at residue position 235, wherein the numbering of the residue position is according to EU numbering.

8. The antibody of claim 6, wherein the antibody comprises one or more amino acid substitutions in the Fc region at a residue position selected from the group consisting of: C127S, L234A, L234F, L235A, L235E, S267E, K322A, L328F, A330S, P331S, E345R, E430G, S440Y, and any combination thereof, wherein the numbering of the residues is according to EU or Kabat numbering.

9. The antibody of claim 8, wherein:
the Fc region comprises an amino acid substitution at position E430G, wherein the numbering of the residue position is according to EU numbering;
the Fc region comprises an amino acid substitution at positions L243A, L235A, and P331A, wherein the numbering of the residue position is according to EU numbering;
the Fc region comprises an amino acid substitution at positions L243A, L235A, P331A, and E430G, wherein the numbering of the residue position is according to EU numbering;
the Fc region comprises an amino acid substitution at positions K322A and E430G, wherein the numbering of the residue position is according to EU numbering;
the Fc region comprises an amino acid substitution at positions P331S and E430G, wherein the numbering of the residue position is according to EU numbering;
the Fc region comprises an amino acid substitution at positions A330S, P331S, and E430G, wherein the numbering of the residue position is according to EU numbering;
the Fc region comprises an amino acid substitution at positions K322A, A330S, and P331S, wherein the numbering of the residue position is according to EU numbering;
the Fc region comprises an amino acid substitution at positions K322A, P331S, and E430G, wherein the numbering of the residue position is according to EU numbering;
the Fc region comprises an amino acid substitution at position E430G, wherein the numbering of the residue position is according to EU numbering;
the Fc region comprises an amino acid substitution at positions A330S, P331S, and E430G, wherein the numbering of the residue position is according to EU numbering;
the Fc region comprises an amino acid substitution at positions S267E and L328F, wherein the numbering of the residue position is according to EU numbering;
the Fc region comprises an amino acid substitution at position C127S, wherein the numbering of the residue position is according to EU numbering; or
the Fc region comprises an amino acid substitution at positions E345R, E430G and S440Y, wherein the numbering of the residue position is according to EU numbering.

10. The antibody of claim 5, wherein the antibody is of the IgG class and has an IgG2 isotype.

11. The antibody of claim 1, wherein the CD33 protein is expressed on one or more cells selected from the group consisting of human dendritic cells, human macrophages, human monocytes, human osteoclasts, human neutrophils, human T cells, human T helper cell, human cytotoxic T cells, human granulocytes, and human microglia.

12. The antibody of claim 1, wherein the antibody binds specifically to a human CD33 protein.

13. The antibody of claim 12, wherein the antibody is an antibody fragment that binds to one or more human proteins selected from the group consisting of human CD33, a naturally occurring variant of human CD33, and a disease variant of human CD33.

14. The antibody of claim 12, wherein the antibody is an antibody fragment that binds to an epitope comprising amino acid residues on human CD33.

15. The antibody of claim 14, wherein the antibody fragment is cross-linked to a second antibody fragment that binds to one or more human proteins selected from the group consisting of human CD33, a naturally occurring variant of human CD33, and a disease variant of human CD33.

16. The antibody of claim 14, wherein the fragment is an Fab, Fab', Fab'-SH, F(ab')$_2$, Fv, or scFv fragment.

17. The antibody of claim 1, wherein the antibody is a humanized antibody, a bispecific antibody, a monoclonal antibody, a multivalent antibody, a conjugated antibody, or a chimeric antibody.

18. The antibody of claim 17, wherein the antibody is a monoclonal antibody.

19. The antibody of claim 17, wherein the antibody is a bispecific antibody recognizing a first antigen and a second antigen.

20. The antibody of claim 19, wherein the first antigen is CD33 and the second antigen is:
(a) an antigen facilitating transport across the blood-brain-barrier;
(b) an antigen facilitating transport across the blood-brain-barrier selected from the group consisting of transferrin receptor (TR), insulin receptor (HIR), insulin-like growth factor receptor (IGFR), low-density lipoprotein receptor related proteins 1 and 2 (LPR-1 and 2), diphtheria toxin receptor, CRM197, a llama single domain antibody, TMEM 30(A), a protein transduction domain, TAT, Syn-B, penetratin, a poly-arginine peptide, an angiopep peptide, and ANG1005;
(c) a disease-causing agent selected from the group consisting of disease-causing peptides or proteins and disease-causing nucleic acids, wherein the disease-causing peptides or proteins are selected from the group consisting of amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), c9RAN protein, prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein Al, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and the disease-causing nucleic acids are antisense GGCCCC (G2C4) repeat-expansion RNA;
(d) ligands and/or proteins expressed on immune cells, wherein the ligands and/or proteins selected from the group consisting of CD40, OX40, ICOS, CD28, CD137/4-1BB, CD27, GITR, PD-L1, CTLA4, PD-L2, PD-1, B7-H3, B7-H4, HVEM, LIGHT, BTLA, CD38, TIGIT, VISTA, KIR, GAL9, TIM1, TIM3, TIM4, A2AR, LAG3, DR5, CD39, CD70, CD73, TREM1, TREM2, Siglec-5, Siglec-7, Siglec-9, Siglec-11, SirpA, CD47, CSF1-receptor, and phosphatidylserine; and
(e) a protein, lipid, polysaccharide, or glycolipid expressed on one or more tumor cells.

21. The antibody of claim 1, wherein the antibody has a dissociation constant ($K_D$) for human CD33 that ranges from about 2 nM to about 200 pM and wherein the $K_D$ is determined by BioLayer Interferometry.

22. The antibody of claim 1, wherein the antibody reduces cell surface levels of CD33.

23. The antibody of claim 22, wherein the CD33 is expressed on the surface of human dendritic cells.

24. The antibody of claim 22, wherein the antibody reduces cell surface levels of CD33 in vitro.

25. The antibody of claim 24, wherein the antibody reduces cell surface levels of CD33 in vitro with a half maximal effective concentration ($EC_{50}$) that is less than 150 pM, as measured by flow cytometry.

26. An isolated nucleic acid comprising a nucleic acid sequence encoding the antibody of claim 1.

27. A vector comprising the nucleic acid of claim 26.

28. An isolated host cell comprising the vector of claim 27.

29. A method of producing an antibody that binds to CD33, comprising culturing the cell of claim 28 so that the antibody is produced.

30. The method of claim 29, further comprising recovering the antibody produced by the cell.

31. An isolated antibody that binds to CD33 produced by the method of claim 30.

32. A pharmaceutical composition comprising the antibody of claim 1 and a pharmaceutically acceptable carrier.

33. A method of treating a disease selected from the group consisting of, Alzheimer's disease, acute lymphoblastic leukemia (ALL), acute myeloid leukemia (AML), chronic lymphocytic leukemia (CLL), chronic myeloid leukemia (CML), and multiple myeloma, comprising administering to an individual in need thereof a therapeutically effective amount of the antibody of claim 1.

34. The method of claim 33, wherein the disease is Alzheimer's disease.

35. The method of claim 34, wherein the method further comprises administering one or more antibodies that specifically bind a disease-causing agent selected from the group consisting of disease-causing peptides, disease-causing proteins, amyloid beta, oligomeric amyloid beta, amyloid beta plaques, amyloid precursor protein or fragments thereof, Tau, IAPP, alpha-synuclein, TDP-43, FUS protein, C9orf72 (chromosome 9 open reading frame 72), prion protein, PrPSc, huntingtin, calcitonin, superoxide dismutase, ataxin, ataxin 1, ataxin 2, ataxin 3, ataxin 7, ataxin 8, ataxin 10, Lewy body, atrial natriuretic factor, islet amyloid polypeptide, insulin, apolipoprotein AI, serum amyloid A, medin, prolactin, transthyretin, lysozyme, beta 2 microglobulin, gelsolin, keratoepithelin, cystatin, immunoglobulin light chain AL, S-IBM protein, Repeat-associated non-ATG (RAN) translation products, DiPeptide repeat (DPR) peptides, glycine-alanine (GA) repeat peptides, glycine-proline (GP) repeat peptides, glycine-arginine (GR) repeat peptides, proline-alanine (PA) repeat peptides, ubiquitin, and proline-arginine (PR) repeat peptides, and any combination thereof; or one or more antibodies that bind an immunomodulatory protein selected from the group consisting of: CD40, OX40, ICOS, CD28, CD137/4-1BB, CD27, GITR, PD-L1, CTLA4, PD-L2, PD-1, B7-H3, B7-H4, HVEM, LIGHT, BTLA, CD38, TIGIT, VISTA, KIR, GAL9, TIM1, TIM3, TIM4, A2AR3, DR5, CD39, CD70, CD73, LAG3, TREM1, TREM2, Siglec-5, Siglec-7, Siglec-9, Siglec-11, SirpA, CD47, CSF1-receptor, phosphatidylserine, disease-causing nucleic acids, antisense GGCCCC (G2C4) repeat-expansion RNA, and any combination thereof.

36. A monoclonal antibody that binds to a human CD33 protein, wherein the antibody comprises
a heavy chain variable region comprising the amino acid sequence of SEQ ID NO: 58, and a light chain variable region comprising the amino acid sequence of SEQ ID NO: 86;
a heavy chain variable region comprising the amino acid sequence of SEQ ID NO: 59, and a light chain variable region comprising the amino acid sequence of SEQ ID NO: 86;
a heavy chain variable region comprising the amino acid sequence of SEQ ID NO: 60, and a light chain variable region comprising the amino acid sequence of SEQ ID NO: 86;
a heavy chain variable region comprising the amino acid sequence of SEQ ID NO: 61, and a light chain variable region comprising the amino acid sequence of SEQ ID NO: 86;
a heavy chain variable region comprising the amino acid sequence of SEQ ID NO: 62, and a light chain variable region comprising the amino acid sequence of SEQ ID NO: 86;
a heavy chain variable region comprising the amino acid sequence of SEQ ID NO: 63, and a light chain variable region comprising the amino acid sequence of SEQ ID NO: 86;
a heavy chain variable region comprising the amino acid sequence of SEQ ID NO: 64, and a light chain variable region comprising the amino acid sequence of SEQ ID NO: 86;
a heavy chain variable region comprising the amino acid sequence of SEQ ID NO: 65, and a light chain variable region comprising the amino acid sequence of SEQ ID NO: 86;
a heavy chain variable region comprising the amino acid sequence of SEQ ID NO: 66, and a light chain variable region comprising the amino acid sequence of SEQ ID NO: 86;
a heavy chain variable region comprising the amino acid sequence of SEQ ID NO: 67, and a light chain variable region comprising the amino acid sequence of SEQ ID NO: 86;
a heavy chain variable region comprising the amino acid sequence of SEQ ID NO: 68, and a light chain variable region comprising the amino acid sequence of SEQ ID NO: 86;
a heavy chain variable region comprising the amino acid sequence of SEQ ID NO: 69, and a light chain variable region comprising the amino acid sequence of SEQ ID NO: 86;
a heavy chain variable region comprising the amino acid sequence of SEQ ID NO: 70, and a light chain variable region comprising the amino acid sequence of SEQ ID NO: 86;
a heavy chain variable region comprising the amino acid sequence of SEQ ID NO: 71, and a light chain variable region comprising the amino acid sequence of SEQ ID NO: 86; or
a heavy chain variable region comprising the amino acid sequence of SEQ ID NO: 72, and a light chain variable region comprising the amino acid sequence of SEQ ID NO: 86.

37. An antibody that binds to a CD33 protein, wherein the antibody comprises a heavy chain variable region comprising the amino acid sequence of SEQ ID NO: 58 and a light chain variable region comprising the amino acid sequence of SEQ ID NO: 86, a heavy chain variable region comprising the amino acid sequence of SEQ ID NO: 59 and a light chain variable region comprising the amino acid sequence of SEQ ID NO: 86, a heavy chain variable region comprising the amino acid sequence of SEQ ID NO: 65 and a light chain variable region comprising the amino acid sequence of SEQ ID NO: 86, a heavy chain variable region comprising the amino acid sequence of SEQ ID NO: 66 and a light chain variable region comprising the amino acid sequence of SEQ ID NO: 86, a heavy chain variable region comprising the amino acid sequence of SEQ ID NO: 67 and a light chain variable region comprising the amino acid sequence of SEQ ID NO: 86, a heavy chain variable region comprising the amino acid sequence of SEQ ID NO: 68 and a light chain variable region comprising the amino acid sequence of SEQ ID NO: 86, or a heavy chain variable region comprising the amino acid sequence of SEQ ID NO: 69 and a light chain variable region comprising the amino acid sequence of SEQ ID NO: 86.

38. An antibody that binds to a CD33 protein, wherein the antibody comprises
   (a) a heavy chain comprising the amino acid sequence of SEQ ID NO: 176 and a light chain comprising the amino acid sequence of SEQ ID NO: 185;
   (b) a heavy chain comprising the amino acid sequence of SEQ ID NO: 176 without the C-terminal lysine and a light chain comprising the amino acid sequence of SEQ ID NO: 185;
   (c) a heavy chain comprising the amino acid sequence of SEQ ID NO: 177 and a light chain comprising the amino acid sequence of SEQ ID NO: 185;
   (d) a heavy chain comprising the amino acid sequence of SEQ ID NO: 177 without the C-terminal lysine and a light chain comprising the amino acid sequence of SEQ ID NO: 185;
   (e) a heavy chain comprising the amino acid sequence of SEQ ID NO: 178 and a light chain comprising the amino acid sequence of SEQ ID NO: 185;
   (f) a heavy chain comprising the amino acid sequence of SEQ ID NO: 178 without the C-terminal lysine and a light chain comprising the amino acid sequence of SEQ ID NO: 185;
   (g) a heavy chain comprising the amino acid sequence of SEQ ID NO: 179 and a light chain comprising the amino acid sequence of SEQ ID NO: 185;
   (h) a heavy chain comprising the amino acid sequence of SEQ ID NO: 179 without the C-terminal lysine and a light chain comprising the amino acid sequence of SEQ ID NO: 185;
   (i) a heavy chain comprising the amino acid sequence of SEQ ID NO: 180 and a light chain comprising the amino acid sequence of SEQ ID NO: 185;
   (j) a heavy chain comprising the amino acid sequence of SEQ ID NO: 180 without the C-terminal lysine and a light chain comprising the amino acid sequence of SEQ ID NO: 185;
   (k) a heavy chain comprising the amino acid sequence of SEQ ID NO: 181 and a light chain comprising the amino acid sequence of SEQ ID NO: 185;
   (l) a heavy chain comprising the amino acid sequence of SEQ ID NO: 181 without the C-terminal lysine and a light chain comprising the amino acid sequence of SEQ ID NO: 185;
   (m) a heavy chain comprising the amino acid sequence of SEQ ID NO: 182 and a light chain comprising the amino acid sequence of SEQ ID NO: 185;
   (n) a heavy chain comprising the amino acid sequence of SEQ ID NO: 182 without the C-terminal lysine and a light chain comprising the amino acid sequence of SEQ ID NO: 185;
   (o) a heavy chain comprising the amino acid sequence of SEQ ID NO: 183 and a light chain comprising the amino acid sequence of SEQ ID NO: 185;
   (p) a heavy chain comprising the amino acid sequence of SEQ ID NO: 183 without the C-terminal lysine and a light chain comprising the amino acid sequence of SEQ ID NO: 185;
   (q) a heavy chain comprising the amino acid sequence of SEQ ID NO: 184 and a light chain comprising the amino acid sequence of SEQ ID NO: 185; or
   (r) a heavy chain comprising the amino acid sequence of SEQ ID NO: 184 without the C-terminal lysine and a light chain comprising the amino acid sequence of SEQ ID NO: 185.

39. An antibody that binds to a CD33 protein, wherein the antibody comprises:
   (a) a heavy chain variable region comprising an HVR-H1, HVR-H2, and HVR-H3 and a light chain variable region comprising an HVR-L1, HVR-L2, and HVR-L3, wherein the HVR-H1 comprises the amino acid sequence of SEQ ID NO:105, the HVR-H2 comprises the amino acid sequence of SEQ ID NO:119, the HVR-H3 comprises the amino acid sequence of SEQ ID NO:122, the HVR-L1 comprises the amino acid sequence of SEQ ID NO:127, the HVR-L2 comprises the amino acid sequence of SEQ ID NO:135, and the HVR-L3 comprises the amino acid sequence of SEQ ID NO:146;
   (b) a heavy chain variable region comprising the amino acid sequence of SEQ ID NO:59 and a light chain variable region comprising the amino acid sequence of SEQ ID NO:86;
   (c) a heavy chain comprising the amino acid sequence of SEQ ID NO:177, and a light chain comprising the amino acid sequence of SEQ ID NO:185;
   (d) a heavy chain comprising the amino acid sequence of SEQ ID NO:177 without the C-terminal lysine, and a light chain comprising the amino acid sequence of SEQ ID NO:185;
   (e) a heavy chain comprising the amino acid sequence of SEQ ID NO:180, and a light chain comprising the amino acid sequence of SEQ ID NO:185;
   (f) a heavy chain comprising the amino acid sequence of SEQ ID NO: 180 without the C-terminal lysine, and a light chain comprising the amino acid sequence of SEQ ID NO:185;
   (g) a heavy chain comprising the amino acid sequence of SEQ ID NO:183, and a light chain comprising the amino acid sequence of SEQ ID NO:185; or
   (h) a heavy chain comprising the amino acid sequence of SEQ ID NO: 183 without the C-terminal lysine, and a light chain comprising the amino acid sequence of SEQ ID NO:185.

40. An antibody that binds to a human CD33 protein, wherein the antibody comprises a heavy chain variable region comprising an HVR-H1, HVR-H2, and HVR-H3 and a light chain variable region comprising an HVR-L1, HVR-L2, and HVR-L3, wherein the HVR-H1 comprises the amino acid sequence of SEQ ID NO: 105, the HVR-H2 comprises the amino acid sequence of SEQ ID NO: 119, the HVR-H3 comprises the amino acid sequence of SEQ ID NO: 122, the HVR-L1 comprises the amino acid sequence of SEQ ID NO: 127, the HVR-L2 comprises the amino acid sequence of SEQ ID NO: 135, and the HVR-L3 comprises the amino acid sequence of SEQ ID NO: 146.

41. The antibody of claim 40, wherein the antibody is a monoclonal antibody.

42. The antibody of claim 40, wherein the antibody has an IgG2 isotype.

43. An isolated nucleic acid comprising a nucleic acid sequence encoding the antibody of claim 40.

44. A vector comprising the nucleic acid of claim 43.

45. An isolated host cell comprising the vector of claim 44.

46. A method of producing an antibody that binds to CD33, comprising culturing the cell of claim 45 so that the antibody is produced.

47. The method of claim 46, further comprising recovering the antibody produced by the cell.

48. An isolated antibody that binds to CD33, produced by the method of claim 47.

49. A pharmaceutical composition comprising the antibody of claim 40 and a pharmaceutically acceptable carrier.

50. An antibody that binds to a human CD33 protein, wherein the antibody comprises a heavy chain variable region comprising the amino acid sequence of SEQ ID NO: 59, and a light chain variable region comprising the amino acid sequence of SEQ ID NO: 86.

51. The antibody of claim 50, wherein the antibody is a monoclonal antibody.

52. The antibody of claim 50, wherein the antibody has an IgG2 isotype.

53. An isolated nucleic acid comprising a nucleic acid sequence encoding the antibody of claim 50.

54. A vector comprising the nucleic acid of claim 53.

55. An isolated host cell comprising the vector of claim 54.

56. A method of producing an antibody that binds to CD33, comprising culturing the cell of claim 55 so that the antibody is produced.

57. The method of claim 56, further comprising recovering the antibody produced by the cell.

58. An isolated antibody that binds to CD33, produced by the method of claim 57.

59. A pharmaceutical composition comprising the antibody of claim 50 and a pharmaceutically acceptable carrier.

60. An antibody that binds to a human CD33 protein, wherein the antibody comprises a heavy chain comprising the amino acid sequence of SEQ ID NO: 180 and a light chain comprising the amino acid sequence of SEQ ID NO: 185.

61. The antibody of claim 60, wherein the antibody is a monoclonal antibody.

62. An isolated nucleic acid comprising a nucleic acid sequence encoding the antibody of claim 60.

63. A vector comprising the nucleic acid of claim 62.

64. An isolated host cell comprising the vector of claim 63.

65. A method of producing an antibody that binds to CD33, comprising culturing the cell of claim 64 so that the antibody is produced.

66. The method of claim 65, further comprising recovering the antibody produced by the cell.

67. An isolated antibody that binds to CD33, produced by the method of claim 66.

68. A pharmaceutical composition comprising the antibody of claim 60 and a pharmaceutically acceptable carrier.

69. An antibody that binds to a human CD33 protein, wherein the antibody comprises a heavy chain comprising the amino acid sequence of SEQ ID NO: 180 without the C-terminal lysine and a light chain comprising the amino acid sequence of SEQ ID NO: 185.

70. The antibody of claim 69, wherein the antibody is a monoclonal antibody.

71. An isolated nucleic acid comprising a nucleic acid sequence encoding the antibody of claim 69.

72. A vector comprising the nucleic acid of claim 71.

73. An isolated host cell comprising the vector of claim 72.

74. A method of producing an antibody that binds to CD33, comprising culturing the cell of claim 73 so that the antibody is produced.

75. The method of claim 74, further comprising recovering the antibody produced by the cell.

76. An isolated antibody that binds to CD33, produced by the method of claim 75.

77. A pharmaceutical composition comprising the antibody of claim 69 and a pharmaceutically acceptable carrier.

\* \* \* \* \*

UNITED STATES PATENT AND TRADEMARK OFFICE
CERTIFICATE OF CORRECTION

PATENT NO. : 10,711,062 B2
APPLICATION NO. : 16/054840
DATED : July 14, 2020
INVENTOR(S) : Patricia Culp et al.

Page 1 of 1

It is certified that error appears in the above-identified patent and that said Letters Patent is hereby corrected as shown below:

In the Claims

In Claim 20, Column 356, Line 46, delete "apolipoprotein A1," and insert -- apolipoprotein Al, --, therefor.

In Claim 20, Column 356, Line 58, delete "wherein the ligands and/or proteins selected from the" and insert -- wherein the ligands and/or proteins are selected from the --, therefor.

In Claim 33, Column 357, Line 30, delete "consisting of, Alzheimer's disease," and insert -- consisting of Alzheimer's disease, --, therefor.

In Claim 35, Column 357, Line 49, delete "apolipoprotein AL," and insert -- apolipoprotein Al, --, therefor.

Signed and Sealed this
Tenth Day of November, 2020

Andrei Iancu
*Director of the United States Patent and Trademark Office*